US011920188B2

(12) United States Patent
Eggers et al.

(10) Patent No.: US 11,920,188 B2
(45) Date of Patent: Mar. 5, 2024

(54) COMBINATORIAL MICROARRAY ASSAY FOR CLADE VARIANT DETECTION

(71) Applicants: Frederick Henry Eggers, Sahuarita, AZ (US); Benjamin Alan Katchman, Tucson, AZ (US); Fushi Wen, Tucson, AZ (US); Candy Mavis Rivas, Tucson, AZ (US); Cory Scott Newland, Tucson, AZ (US); Michael Edward Hogan, Stony Brook, NY (US)

(72) Inventors: Frederick Henry Eggers, Sahuarita, AZ (US); Benjamin Alan Katchman, Tucson, AZ (US); Fushi Wen, Tucson, AZ (US); Candy Mavis Rivas, Tucson, AZ (US); Cory Scott Newland, Tucson, AZ (US); Michael Edward Hogan, Stony Brook, NY (US)

(*) Notice: Subject to any disclaimer, the term of this patent is extended or adjusted under 35 U.S.C. 154(b) by 259 days.

(21) Appl. No.: 17/332,837

(22) Filed: May 27, 2021

(65) Prior Publication Data

US 2022/0251635 A1 Aug. 11, 2022

Related U.S. Application Data

(60) Provisional application No. 63/147,613, filed on Feb. 9, 2021.

(51) Int. Cl.

| | |
|---|---|
| ***C12Q 1/68*** | (2018.01) |
| ***C12Q 1/6848*** | (2018.01) |
| ***C12Q 1/686*** | (2018.01) |
| ***C12Q 1/6865*** | (2018.01) |

(52) U.S. Cl.

CPC ........... *C12Q 1/6848* (2013.01); *C12Q 1/686* (2013.01); *C12Q 1/6865* (2013.01)

(58) Field of Classification Search

None

See application file for complete search history.

(56) References Cited

U.S. PATENT DOCUMENTS

| | | | | |
|---|---|---|---|---|
| 2022/0195539 A1* | 6/2022 | Hogan | ................... | C12Q 1/701 |
| 2022/0251635 A1* | 8/2022 | Eggers | ................... | C12Q 1/686 |
| 2022/0267829 A1* | 8/2022 | Eggers | ................. | C12Q 1/6837 |
| 2022/0267867 A1* | 8/2022 | Eggers | ................... | C12Q 1/701 |
| 2022/0364157 A1* | 11/2022 | Hogan | ................... | C12Q 1/686 |
| 2022/0403476 A1* | 12/2022 | Wen | ..................... | C12Q 1/6837 |

FOREIGN PATENT DOCUMENTS

| | | | | |
|---|---|---|---|---|
| WO | WO-2021195317 A1 * | 9/2021 | ............. | C12Q 1/701 |
| WO | WO-2021195322 A1 * | 9/2021 | ........... | C12Q 1/6816 |
| WO | WO-2022173707 A1 * | 8/2022 | | |
| WO | WO-2022266165 A1 * | 12/2022 | ........... | C12Q 1/6837 |

OTHER PUBLICATIONS

De Souza Luna et al., 2007. Generic detection of coronaviruses and differentiation at the prototype strain level by reverse transcription-PCR and nonfluorescent low-density microarray. Journal of clinical microbiology, 45(3), pp. 1049-1052. (Year: 2007).*

Graybill et al., 2018. Multiplexed microRNA expression profiling by combined asymmetric PCR and label-free detection using silicon photonic sensor arrays. Analytical methods, 10(14), pp. 1618-1623. (Year: 2018).*

Guo et al., 2014. Development of a single nucleotide polymorphism DNA microarray for the detection and genotyping of the SARS coronavirus. Journal of microbiology and biotechnology, 24(10), pp. 1445-1454. (Year: 2014).*

Guo et al., 2019. Fluorescence resonance energy transfer combined with asymmetric PCR for broad and sensitive detection of porcine reproductive and respiratory syndrome virus 2. Journal of virological methods, 272, 113710, pp. 1-8. (Year: 2019).*

Tao et al., 2009. Detection and differentiation of four poultry diseases using asymmetric reverse transcription polymerase chain reaction in combination with oligonucleotide microarrays. Journal of veterinary diagnostic investigation, 21(5), pp. 623-632. (Year: 2009).*

Zhang et al., 2005. Sensitive detection of SARS coronavirus RNA by a novel asymmetric multiplex nested RT-PCR amplification coupled with oligonucleotide microarray hybridization. Microarrays in Clinical Diagnostics, pp. 59-78. (Year: 2005).*

* cited by examiner

*Primary Examiner* — Teresa E Strzelecka

*Assistant Examiner* — Olayinka A Oyeyemi

(74) *Attorney, Agent, or Firm* — Benjamin Aaron Adler

(57) ABSTRACT

Provided herein is a method for detecting the presence of clade variants in the COVID-19 virus in a human sample and/or an environmental sample. Samples are processed to obtain total RNA. The RNA is used as a template in a combined reverse transcription and amplification reaction to obtain fluorescent COVID-19 virus amplicons. These amplicons are hybridized on a microarray with nucleic acid probes having sequences that discriminate among the various clade variants. The microarray is imaged to detect the clade variant. Also provided is a method of distinguishing each clade variant from others by generating an intensity distribution profile from the image, which is unique to each of the clade variants.

10 Claims, 48 Drawing Sheets

Specification includes a Sequence Listing.

COMBINATORIAL MICROARRAY ASSAY FOR CLADE VARIANT DETECTION

CROSS-REFERENCE TO RELATED APPLICATIONS

This non-provisional application claims the benefit of priority under 35 U.S.C. § 119(e) of provisional application U.S. Ser. No. 63/147,613, filed Feb. 9, 2021, hereby incorporated by reference in its entirety.

BACKGROUND OF THE INVENTION

Field of the Invention

The present invention relates to the field of multiplex based viral pathogen detection and analysis. More particularly, the present invention relates to detecting the presence of clade variants of SARS-COVID-2 virus in patient and environmental samples.

Description of the Related Art

The COVID-19 pandemic has increased awareness that viral infection can be an existential threat to health, public safety and the US economy. More fundamentally, there is a recognition that the viral risks are exceedingly dangerous and complex and require new approaches to diagnostics and screening.

The next pandemic wave is expected to have more pronounced flu-like symptoms (seasonal influenza A and/or B) coupled with the COVID-19, or COVID-19 variants that will coexist with the Coronavirus already responsible for the common cold. These complexities are expected to pose significant challenges to public health and the healthcare system in diagnosing multi-symptom conditions accurately and efficiently.

The COVID-19 pandemic has also led to the realization of an additional level of complexity that the realization that human health and environmental contamination are linked in a fundamental way that affects collection efficiency and increases risk to the healthcare workers (1, 2). Alternatives to nasopharyngeal collection methods such as for example, saliva collection are needed to enable scalability among millions of individuals.

Q-RT-PCR technology has dominated COVID-19 diagnostics and public health screening. Independent of the test developer, Q-RT-PCR has been shown to have an unusually high false negative rate (15% up to 30%). As of May 2020, the CDC has recorded 613, 041 COVID-19 tests. With a 15% false negative rate, approximately 91, 956 people would thus be falsely classified as free of infection. Meta-analysis has shown that the false negative rate for Q-RT-PCR is high below day 7 of infection when viral load is still low. This renders Q-RT-PCR ineffective as a tool for early detection of weak symptomatic carriers while also lessening its value in epidemiology.

As for other organisms, genetic variations in SARS-COVID-2 are grouped into clades. There are over 52, 600 complete and high-coverage genomes available on the Global Initiative on Sharing Avian Influenza Data (GISAID). Presently, WHO has identified 10, 022 SARS-COVID-2 genomes from 68 different countries and detected 65, 776 variants and 5, 775 distinct variants that comprised missense mutations, synonymous mutations, mutations in non-coding regions, non-coding deletions, in-frame deletions, non-coding insertions, stop-gained variants, frame-shift deletions and in-frame insertions among others. Identifying these clade variants in population and environmental samples while a daunting task, is critical for global public health management directed to controlling the pandemic.

When first identified, it was widely assumed that COVID-19 would mutate slowly, based on a relatively stable genome that would experience minimal genetic drift as the pandemic spread. Unfortunately, perhaps as a function of environmental selection pressure (crowding) physical selection pressure (PPE) and therapeutic selection pressure (vaccination) the original Wuhan clade has evolved into a very large number of clade variants. Consequently, in the past 3 months there has been an international effort to discover and track the full range of clade variant evolution.

Next Generation Sequencing (NGS), primarily Targeted Resequencing of the CoV-2 Spike gene, has been instrumental in elucidating the patterns of genetic variation which define the growing set of clade variants of present international concern (UK, South Africa, Brazil, India, US California, US NY, US Southern) with others emerging at an expanding rate. Whereas NGS is without equal as a discovery tool in genetic epidemiology, it is not ideally suited for field-deployed, public health screening at population scale due to complexities associated with purchasing and managing the kits supply chain, setting up and training personnel, especially when compared to Q-RT-PCR, which is the present standard for nucleic acid based COVID-19 screening. Conversely, while Q-RT-PCR (especially TaqMan) is now the clear standard in COVID-19 testing laboratories for simple positive/negative screening, its suitability for screening clade variants is limited. Deploying TaqMan for COVID-19 clade Identification requires running about 10-15 TaqMan kits on each sample to generate sequence content equivalent to Spike targeted NGS, thereby negating the benefits of costs and logistics with Q-RT-PCR.

Thus, there is a need in the art for superior tools to not only administer and stabilize sample collection for respiratory viruses from millions of samples in parallel obtained from diverse locations including, clinic, home, work, school and in transportation hubs, but also to detect and identify clade variants in the population at the highest levels of sensitivity and specificity. The present invention fulfills this longstanding need and desire in the art.

SUMMARY OF THE INVENTION

The present invention is directed to a method for detecting clade variants in the Coronavirus disease 2019 virus in a sample. The sample is obtained from which viruses are harvested. Total RNA is isolated from the harvested viruses. A combined reverse transcription and first amplification reaction is performed on the total RNA using at least one first primer pair selective for all COVID-19 viruses to generate COVID-19 virus cDNA amplicons. A second amplification is performed using the COVID-19 virus cDNA amplicons as template and at least one fluorescent labeled second primer pair selective for a target nucleotide sequence in the COVID-19 virus cDNA to generate at least one fluorescent labeled COVID-19 virus amplicon. The fluorescent labeled COVID-19 virus amplicons are hybridized to a plurality of nucleic acid probes. Each nucleic acid probe is attached to a solid microarray support, and has a sequence corresponding to a sequence determinant that discriminates among clade variants of the COVID-19 virus. After hybridization, the array is washed at least once and imaged to detect at least one fluorescent signal from the hybridized fluorescent labeled COVID-19 virus amplicons. The present invention is directed to a related method where prior to the harvesting step, the method further comprises mixing the sample with an RNA stabilizer.

The present invention is further directed to a method for detecting clade variants in the Coronavirus disease 2019 virus in a sample. The sample is obtained from which, viruses are harvested. Total RNA is isolated from the harvested viruses. A combined reverse transcription and first amplification reaction is performed on the total RNA using at least one fluorescent labeled primer pair comprising an unlabeled primer, and a fluorescently labeled primer, selective for a target sequence in all COVID-19 viruses to generate at least one fluorescent labeled COVID-19 virus amplicon. The fluorescent labeled COVID-19 virus amplicons are hybridized to a plurality of nucleic acid probes. Each nucleic acid probe is attached to a solid microarray support, and has a sequence corresponding to a sequence determinant that discriminates among clade variants of the COVID-19 virus. After hybridization, the array is washed at least once and imaged to detect at least one fluorescent signal from the hybridized fluorescent labeled COVID-19 virus amplicons. The present invention is directed to a related method where prior to the harvesting step, the method further comprises mixing the sample with an RNA stabilizer.

Other and further aspects, features, and advantages of the present invention will be apparent from the following description of the presently preferred embodiments of the invention. These embodiments are given for the purpose of disclosure.

BRIEF DESCRIPTION OF THE FIGURES

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 12A shows the multiplex analysis data normalized to Universal probe. FIG. 12B shows the multiplex analysis data normalized to Wild-type probe.

FIG. 13A shows the multiplex analysis data normalized to Universal probe. FIG. 13B shows the multiplex analysis data normalized to Wild-type probe.

FIG. 14A shows DETECTX-Cv analysis for the indicated variants corresponding to the Brazil region. FIG. 14Y shows DETECTX-Cv analysis for the indicated variants corresponding to the UK region.

FIG. 15A shows the analysis using synthetic Clade Variant standard corresponding to Brazil. FIG. 15B shows the analysis using synthetic Clade Variant standard corresponding to California 452 (CA 452). FIG. 15C shows the analysis using synthetic Clade Variant standard corresponding to India. FIG. 15D shows the analysis using synthetic Clade Variant standard corresponding to South Africa. FIG. 15E shows the analysis using synthetic Clade Variant standard corresponding to United Kingdom.

FIG. 18A shows a histogram analysis for the South Africa synthetic cocktail, D80A-, E484K, N501Y, A701V. FIG. 18B shows a histogram analysis for the California synthetic cocktail, W152C, L452R. FIG. 18C shows a histogram analysis for the India synthetic cocktail, N440K. FIG. 18D shows a histogram analysis for the Brazil P.1 synthetic cocktail, D138Y, E484K, N501Y. FIG. 18E shows a histogram analysis for the UK (B.1.1.7) synthetic cocktail, 69-70 deletion, N501Y, P681 H.

FIG. 19A shows a histogram analysis for a sample comprising Wuhan/European progenitor variants. FIG. 19B shows a histogram analysis for a sample comprising California variants, W152C AND L452R. FIG. 19C shows a histogram analysis for a sample comprising California variants, W152C and L452R. FIG. 19D shows a histogram analysis for a sample comprising UK variants, 69-70 deletion, N501Y and P681 H. FIG. 19E shows a histogram analysis for a sample comprising UK variants, 69-70 deletion, N501Y and P681 H. FIG. 19F shows a histogram analysis for a sample comprising, 69-70 deletion, and P681 H. FIG. 19G shows a histogram analysis for a sample comprising variant P681 H. FIG. 19H shows a histogram analysis for a sample comprising variant P681 H. FIG. 19I shows a histogram analysis for a sample comprising California variants, W152C and L452R. FIG. 19J shows a histogram analysis for a sample that did not pass QA/QC. FIG. 19K shows a histogram analysis for a sample that did not pass QA/QC.

FIG. 20A shows a histogram analysis for a sample comprising California variants W152C and L452R. FIG. 20B shows a histogram analysis for a sample comprising likely California variant L452R. FIG. 20C shows a histogram analysis for a sample comprising California variants, W152C and L452R. FIG. 20D shows a histogram analysis for a sample that did not pass QA/QC. FIG. 20E shows a histogram analysis for a sample comprising California variants W152C and L452R. FIG. 20F shows a histogram analysis for a sample comprising California variant, W152C and L452R. FIG. 20G shows a histogram analysis for a sample comprising California variants, W152C and L452R. FIG. 20H shows a histogram analysis for a sample comprising variant P681H. FIG. 20I shows a histogram analysis for a sample comprising variant P681H. FIG. 20J shows a histogram analysis for a sample comprising Wuhan/European progenitor variants.

DETAILED DESCRIPTION OF THE INVENTION

Figure 1:
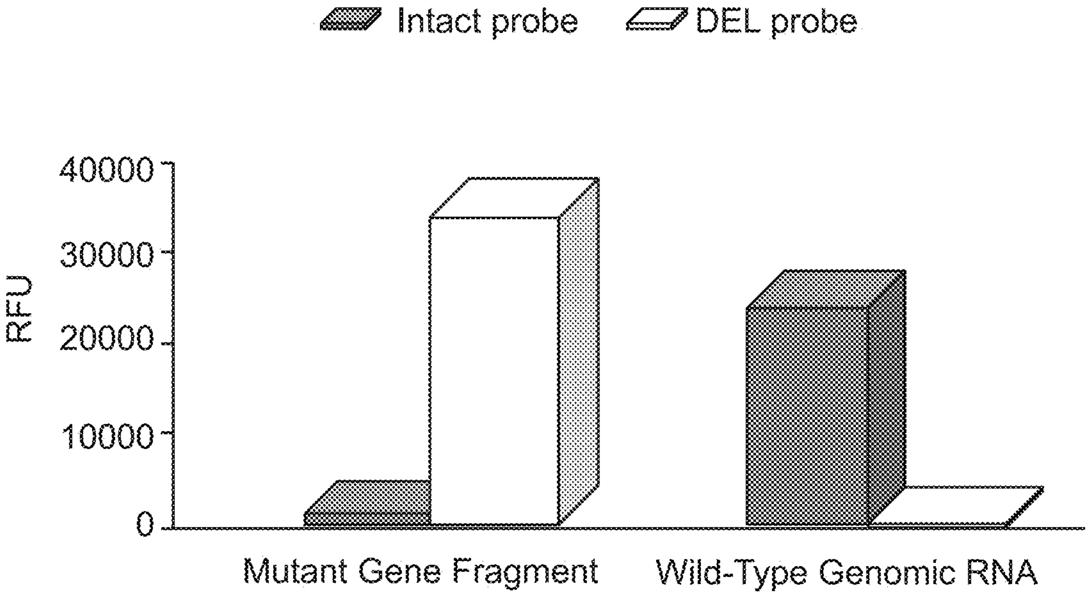
FIG. 1 shows Clade Chip target site performance data for the Spike 69-70 deletion.
Figure 2:
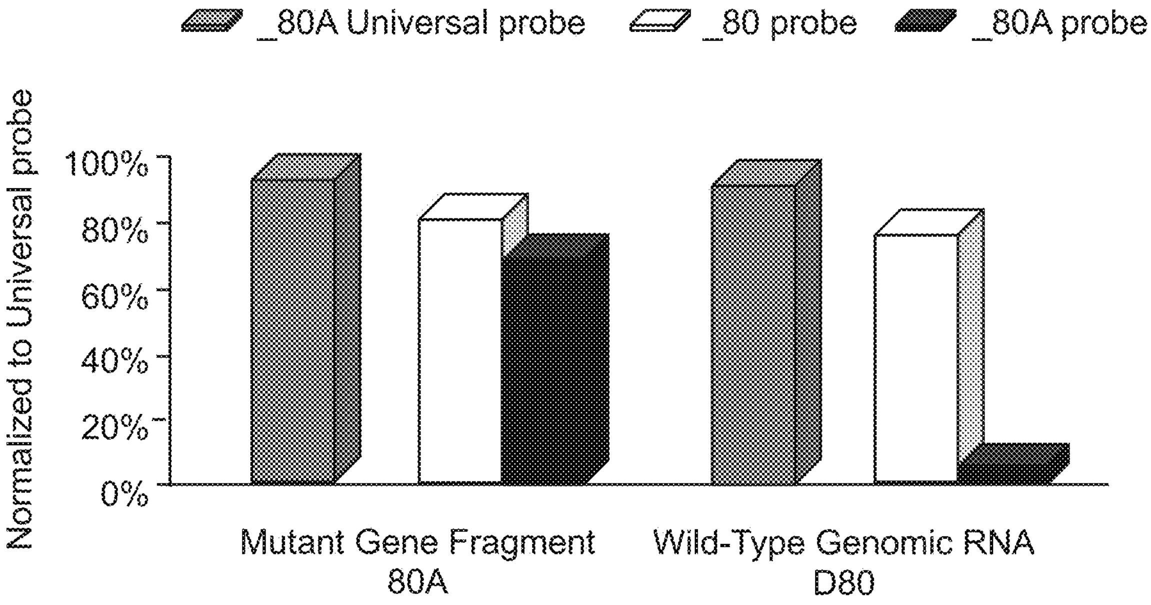
FIG. 2 shows Clade Chip target sites performance data normalized to a universal probe for the Spike D80A mutation.
Figure 3:
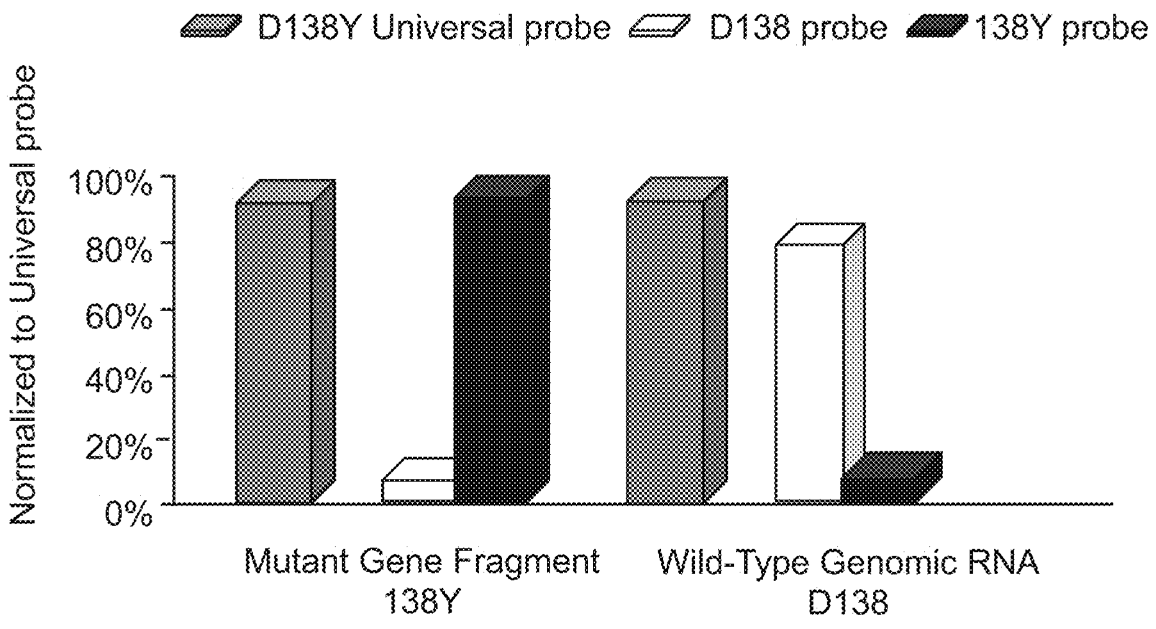
FIG. 3 shows Clade Chip target sites performance data normalized to a universal probe for the Spike D138Y mutation.
Figure 4:
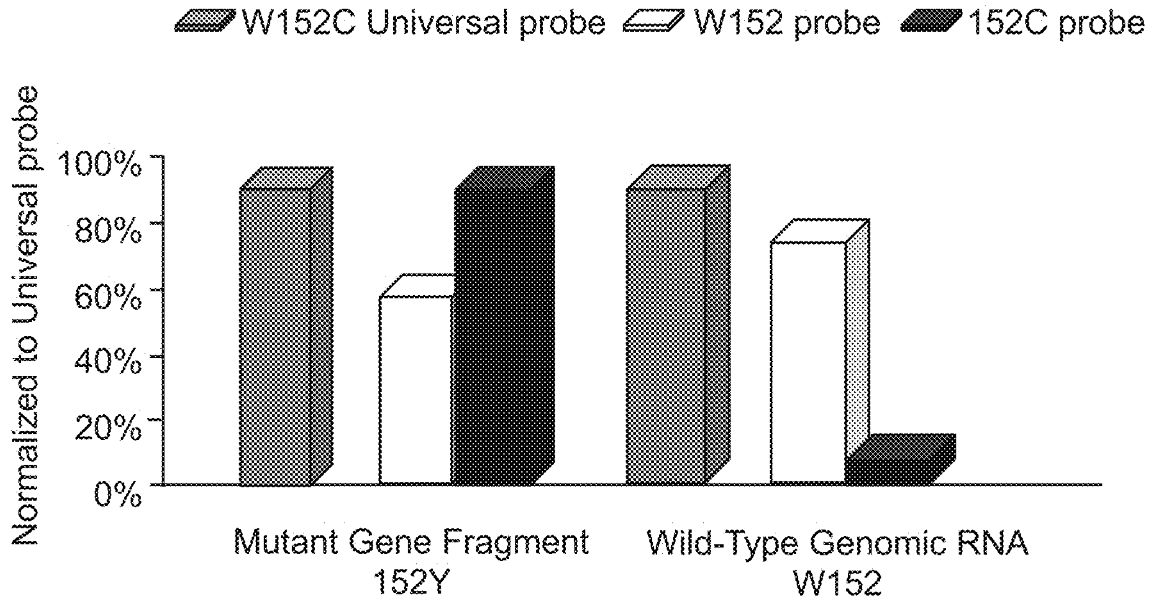
FIG. 4 shows Clade Chip target sites performance data normalized to a universal probe for the Spike W152C mutation.
Figure 5:
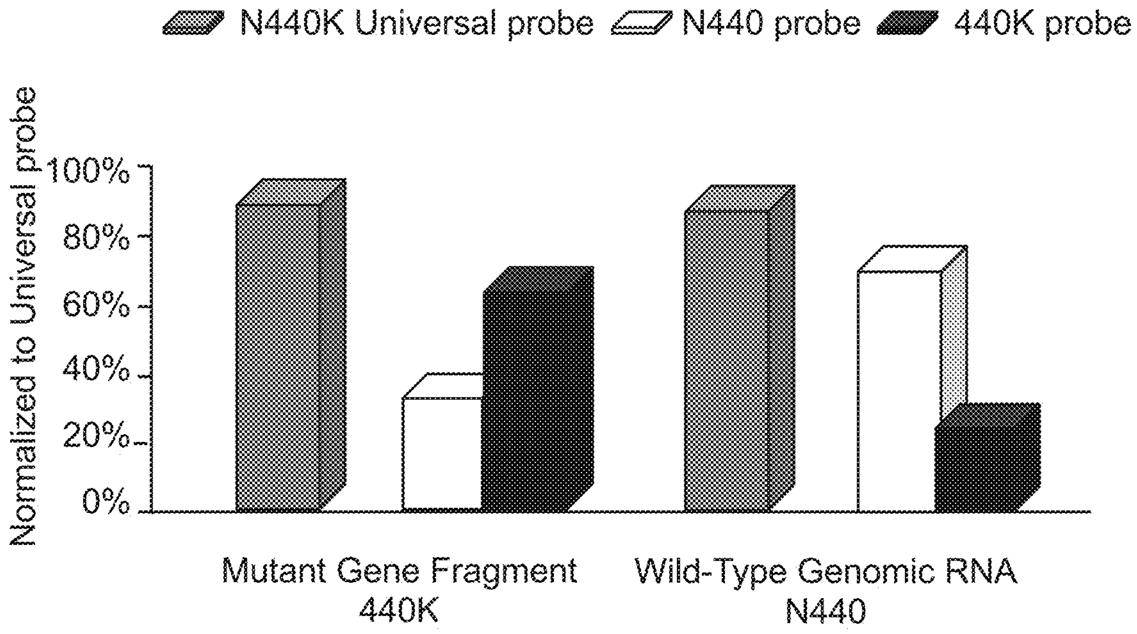
FIG. 5 shows Clade Chip target sites performance data normalized to a universal probe for the Spike N440K mutation.
Figure 6:
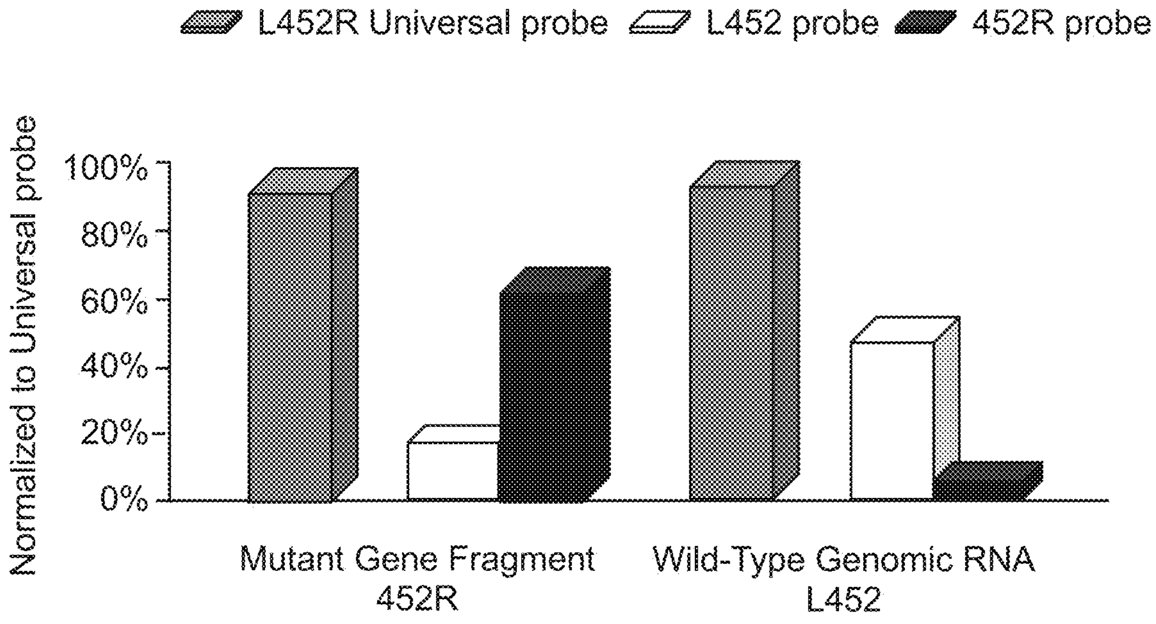
FIG. 6 shows Clade Chip target sites performance data normalized to a universal probe for the Spike L452R mutation.
Figure 7:
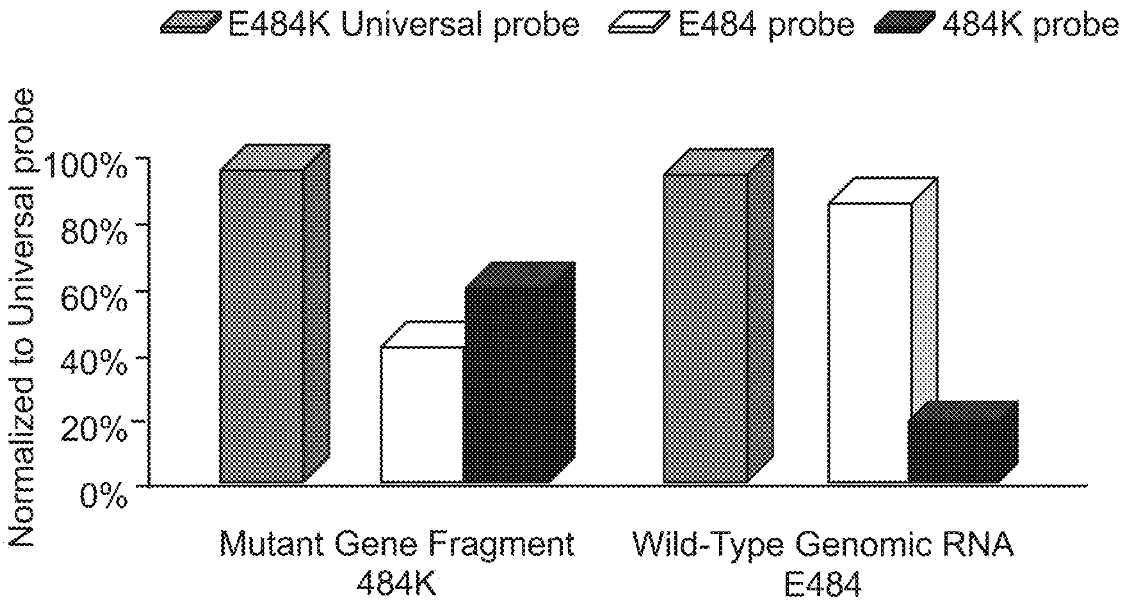
FIG. 7 shows Clade Chip target sites performance data normalized to a universal probe for the Spike E484K mutation.
Figure 8:
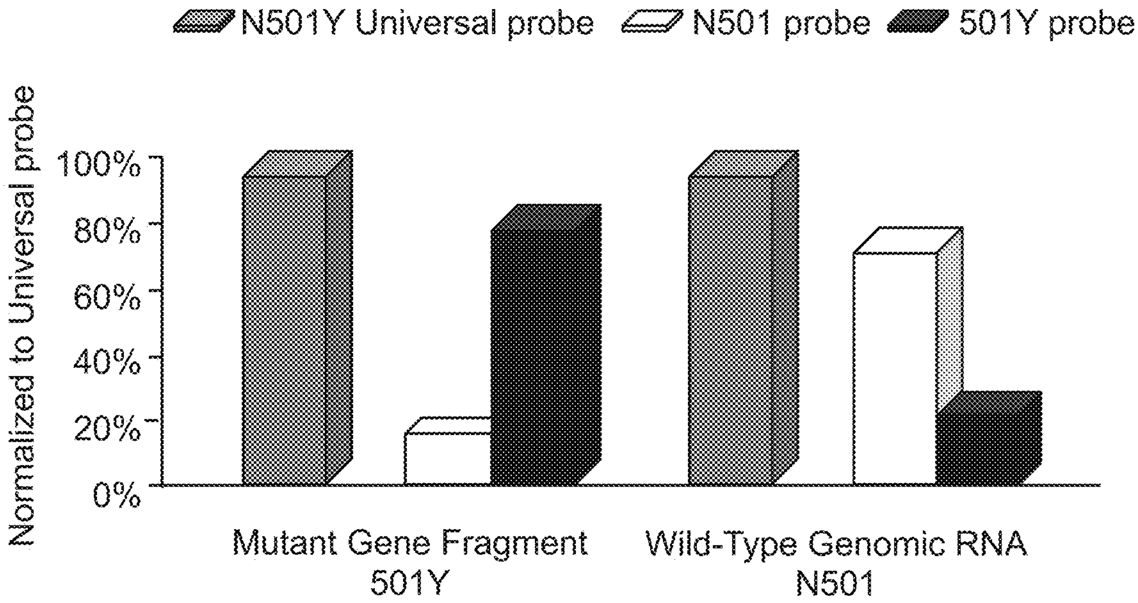
FIG. 8 shows Clade Chip target sites performance data normalized to a universal probe for the Spike N501Y mutation.
Figure 9:
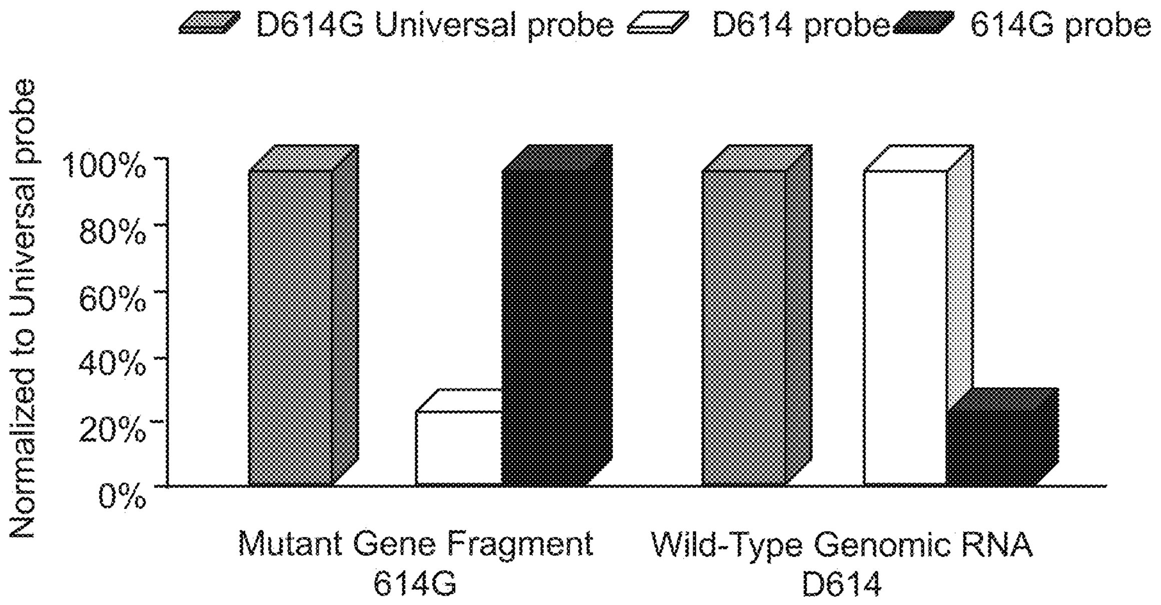
FIG. 9 shows Clade Chip target sites performance data normalized to a universal probe for the Spike D614G mutation.
Figure 10:
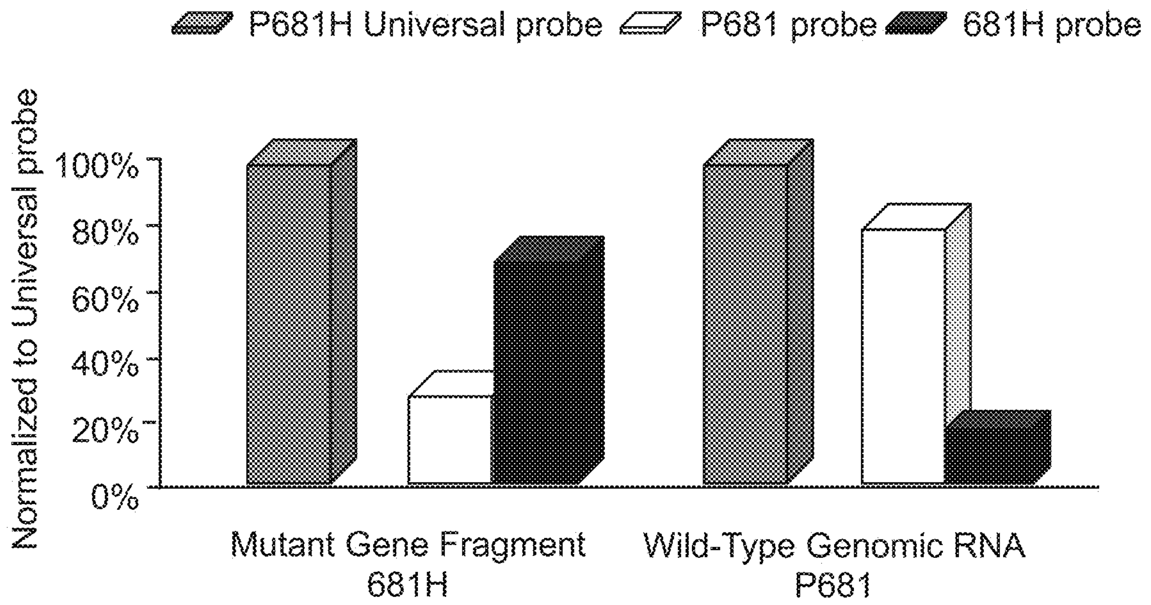
FIG. 10 shows Clade Chip target sites performance data normalized to a universal probe for the Spike P681 H mutation.
Figure 11:
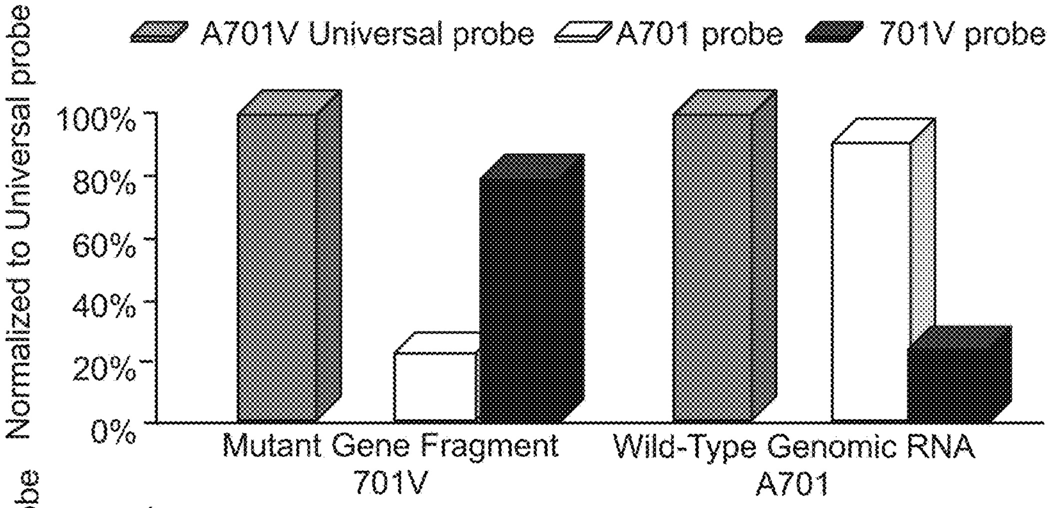
FIG. 11 shows Clade Chip target sites performance data normalized to a universal probe for the Spike A701V mutation.

As used herein, the term "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method described herein can be implemented with respect to any other method described herein.

As used herein, the term "or" in the claims is used to mean "and/or" unless explicitly indicated to refer to alternatives only or the alternatives are mutually exclusive, although the disclosure supports a definition that refers to only alternatives and "and/or".

As used herein, "comprise" and its variations, such as "comprises" and "comprising" will be understood to imply the inclusion of a stated item, element or step or group of items, elements or steps but not the exclusion of any other item, element or step or group of items, elements or steps unless the context requires otherwise. Similarly, "another" or "other" may mean at least a second or more of the same or different claim element or components thereof.

In one embodiment of the present invention there is provided a method for detecting clade variants in a Coronavirus disease 2019 virus (COVID-19) in a sample, comprising obtaining the sample; harvesting viruses from the sample; isolating a total RNA from the harvested viruses; performing a combined reverse transcription and first amplification reaction on the total RNA using at least one first primer pair selective for all COVID-19 viruses to generate COVID-19 virus cDNA amplicons; performing a second amplification using the COVID-19 virus cDNA amplicons as template and at least one fluorescent labeled second primer pair selective for a target nucleotide sequence in the COVID-19 virus cDNA to generate at least one fluorescent labeled COVID-19 virus amplicon; hybridizing the fluorescent labeled COVID-19 virus amplicons to a plurality of nucleic acid probes, each having a sequence corresponding to a sequence determinant that discriminates among the clade variants of the COVID-19 virus, where the nucleic acid probes are attached to a solid microarray support; washing the microarray at least once; and imaging the microarray to detect at least one fluorescent signal from the hybridized fluorescent labeled COVID-19 virus amplicons, thereby detecting the clade variants of the COVID-19 virus in the sample.

A total RNA potentially comprising RNA from COVID-19 virus and other contaminating pathogens and human cells is isolated from the sample. Commercially available RNA isolation kits such as for example, a Quick-DNA/RNA Viral MagBead Kit from Zymo Research are used for this purpose. The total RNA thus isolated is used without further purification. Alternatively, intact virus may be captured with magnetic beads, using kits such as that from Ceres Nanosciences (e.g., CERES NANOTRAP technology), or by first precipitating the virus with polyethylene glycol (PEG), followed by lysis of the enriched virus by heating with a "PCR-Friendly" lysis solution such as 1% NP40 in Tris-EDTA buffer and then used without additional purification.

The COVID-19 virus RNA in the total RNA isolate is used as a template for amplifying a COVID-19 virus specific sequence. This comprises first performing a combined reverse transcriptase enzyme catalyzed reverse transcription reaction and a first amplification reaction using a first primer pair selective for the virus to generate COVID-19 virus cDNA amplicons. In this embodiment, the first primer pairs have forward (odd numbers) and reverse (even number) sequences shown in SEQ ID NO: 1 to SEQ ID NO: 8 (Table 1).). Commercially available reverse transcriptase enzyme and buffers are used in this step. Controls including, but not limited to a RNAse P control having first primer pair (forward primer SEQ ID NO: 130, reverse primer SEQ ID NO: 131) are also used herein (Table 1). The COVID-19 virus cDNA amplicons generated in the first amplification reaction are used as a template for a second amplification that employs at least one fluorescent labeled second primer pair selective for a target nucleotide sequence in the COVID-19 virus cDNA to generate at least one fluorescent labeled COVID-19 virus amplicon.

The fluorescent labeled COVID-19 virus amplicons hybridize to the nucleic acid probes, which are attached at specific positions on a microarray support, for example, a 3-dimensional lattice microarray support. After hybridization, the microarray is washed at least once to remove unhybridized amplicons. Washed microarrays are imaged to detect a fluorescent signal from the hybridized fluorescent labeled COVID-19 virus amplicons to detect the Clade variants of the COVID-19 virus in the sample.

Further to this embodiment, prior to the harvesting step, the method comprises mixing the sample with an RNA stabilizer. A representative RNA stabilizer is a chemical stabilizer that protects the RNA from degradation during storage and transportation.

In both embodiments one or more of the at least one fluorescent labeled second primer pair is selective for a panel of target nucleotide sequences within a target region of a gene in the COVID-19 virus; and the nucleic acid probes are specific to the target region of the gene, whereby the at least one fluorescent labeled COVID-19 virus amplicon generated is hybridized to the nucleic acid probe thereby discriminating the clade variants of the COVID-19 virus in the sample. Further to this embodiment the method comprises detecting the at least one fluorescent signal from the hybridized at least one fluorescent labeled COVID-19 virus amplicons associated with the panel of target nucleotide sequences within the target region of the gene; and generating an intensity distribution profile unique to each of the clade variants, whereby each of the clade variants is distinguishable from others. Particularly, the gene may be a Spike gene.

In a non-limiting example, the target region may be in the Spike gene in the COVID-19 virus and the fluorescent labeled second primer pairs may have forward (odd numbers) and reverse (even number) sequences shown in SEQ ID NO: 9 to SEQ ID NO: 29 (Tables 2 and 11). Controls including, but not limited to a RNAse P control having

TABLE 1

Primer sequences used for the first amplification reaction

| SEQ ID NOS. | Amplimer # | Target | Gene | Primer Sequence (5' to 3') |
|---|---|---|---|---|
| SEQ ID NO: 1 | 1/2 | AA 00-103 | Spike | TTTAACAGAGTTGTTA TTTCTAGTGATG |
| SEQ ID NO: 2 | 1/2 | AA 00-103 | Spike | TTTTCTAAAGTAGTAC CAAAAATCCAGC |
| SEQ ID NO: 3 | 3/4 | AA 124-262 | Spike | TTTCCCTACTTATTGT TAATAACGCTAC |
| SEQ ID NO: 4 | 3/4 | AA 124-262 | Spike | TTTAGATAACCCACAT AATAAGCTGCAG |
| SEQ ID NO: 5 | 5/6 | AA 397-517 | Spike | TTTATCTCTGCTTTAC TAATGTCTATGC |
| SEQ ID NO: 6 | 5/6 | AA 397-517 | Spike | TTTACAAACAGTTGCT GGTGCATGTAGA |
| SEQ ID NO: 7 | 7/8 | AA 601-726 | Spike | TTTTGGTGTCAGTGTT ATAACACCAGGA |
| SEQ ID NO: 8 | 7/8 | AA 601-726 | Spike | TTTTGTCTTGGTCATA GACACTGGTAGA |
| SEQ ID: 130 | — | RNAse P control | RNAse P | TTTACTTCAGCATGG CGGTGTTTGCAGA |
| SEQ ID: 131 | — | RNAse P control | RNAse P | TTTTGATAGCAACAAC TGAATAGCCAAG |

primer pair (forward primer SEQ ID NO: 132, reverse primer SEQ ID NO: 133) are also used herein (Table 2).

Any fluorescent label may be used in the fluorescent labeled second primer pairs including, but not limited to, a CY3, a CY5, SYBR Green, a DYLIGHT™ DY647, a ALEXA FLUOR 647, a DYLIGHT™ DY547 and a ALEXA FLUOR 550.

Also in all embodiments the first primer pair may comprise the nucleotide sequences of SEQ ID NO: 1 and SEQ ID NO: 2, or SEQ ID NO: 3 and SEQ ID NO: 4, or SEQ ID NO: 5 and SEQ ID NO: 6, or SEQ ID NO: 7 and SEQ ID NO: 8, or a combination thereof. Sequences of the first primer pairs are shown in Table 1.

TABLE 2

Fluorescent labeled primer sequences used for amplification reactions

| SEQ ID NOS. | Amplimer # | Target | Gene | Primer Sequence (5' to 3') |
|---|---|---|---|---|
| SEQ ID NO: 9 | 2 | AA64-80 | Spike | ACCTTTCTTTTCCAATGT TACTTGGTTC |
| SEQ ID NO: 10 | 2 | AA64-80 | Spike | Cy3-TTTTATGTTAGA CTTCTCAGTGGAAGCA |
| SEQ ID NO: 11 | 3 | AA126-157 | Spike | TTTCTTATTGTTAATAAC GCTACTAATG |
| SEQ ID NO: 12 | 3 | AA126-157 | Spike | Cy3-TTTCATTCGCACT AGAATA AACTCTGAA |
| SEQ ID NO: 13 | 5 | AA408-456 | Spike | TGTAATTAGAGGTGATG AAGTCAGA |
| SEQ ID NO: 14 | 5 | AA408-456 | Spike | Cy3-TTTAAAGGTTTGA GATTAG ACTTCCTAA |
| SEQ ID NO: 15 | 6 | AA475-505 | Spike | TTTTATTTCAACTGAAAT YTATCAGGCC |
| SEQ ID NO: 16 | 6 | AA475-505 | Spike | Cy3-TTTAAAGTACTAC TACTCT GTATGGTTG |
| SEQ ID NO: 17 | 8 | AA677-707 | Spike | TTTTATATGCGCTAGTTA TCAGACTCAG |
| SEQ ID NO: 18 | 8 | AA677-707 | Spike | Cy3-TTTTGGTATGGC AATAGA GTTATTAGAG |
| SEQ ID NO: 19 | 1 | AA11-33 | Spike | TTTTTTTCTTGTTTTATTG CCACTAGTC |
| SEQ ID NO: 20 | 1 | AA11-33 | Spike | Cy3-TTTTTGTCAGGG TAATAAA CACCACGTG |
| SEQ ID NO: 21 | 4 | AA213-260 | Spike | TTTTAAGCACACGCCTA TTAATTTAGTG |
| SEQ ID NO: 22 | 4 | AA213-260 | Spike | Cy3-TTTCCACATAAT AAGCTGCAGCACCAGC |
| SEQ ID NO: 23 | 7 | AA603-618 | Spike | TTTAGTGTTATAACACCA GGAACAAATA |
| SEQ ID NO: 24 | 7 | AA603-618 | Spike | Cy3-TTTTGCATGAAT AGCAACAGGGACTTCT |
| SEQ ID NO: 132 | — | RNAse P control | RNAse P | TTTGTTTGCAGATTTGG ACCTGCGAGCG |
| SEQ ID NO: 133 | — | RNAse P control | RNAse P | Cy3-TTTAAGGTGAG CGGCTGTCTCCACAAGT |

In all embodiments the clade variants of the COVID-19 virus may be Denmark, UK (B.1.1.7), South African (B.1.351), Brazil/Japan (P1), Brazil (B1.1.28), California USA, L452R (1.429), India (N440K), or Wuhan, or a combination thereof. The COVID-19 virus is a Severe Acute Respiratory Syndrome Coronavirus 2 (SARS-CoV 2) or a mutated form thereof. A combination of these variants also may be detected simultaneously.

In addition in all embodiments the fluorescent labeled second primer pair may comprise the nucleotide sequences of SEQ ID NO: 9 and SEQ ID NO: 10, or SEQ ID NO: 11 and SEQ ID NO: 12, or SEQ ID NO: 13 and SEQ ID NO: 14, or SEQ ID NO: 15 and SEQ ID NO: 16, or SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO:

27 and SEQ ID NO: 28, SEQ ID NO: 29 and SEQ ID NO: 24, or a combination thereof. Sequences of the first primer pairs are shown in Table 2.

Furthermore, in all embodiments the nucleic acid probes may comprise at least one nucleotide sequence selected from the group consisting of SEQ ID NOS: 30-129. The nucleic acid probes may have a sequence corresponding to a sequence determinant that discriminates among the Clade variants of the COVID-19 virus. The nucleic acid probes are specific to the target region of the gene in the COVID-19 virus as discussed supra. This enables hybridization of the one fluorescent labeled COVID-19 virus amplicon generated to the Spike gene-specific nucleic acid probe thereby discriminating the Clade variants of the COVID-19 virus in the sample. In a non-limiting example, the target region is in a Spike gene in the COVID-19 virus and the nucleic acid probes have a sequence shown in SEQ ID NO: 30 to SEQ ID: 129 (Tables 3, 10 and 14). Controls including, but not limited to, a RNAse P control nucleic acid probe (SEQ ID NO: 68 and SEQ ID NO: 69) and a negative control nucleic acid probe (SEQ ID NO: 70) are also used herein (Table 3).

TABLE 3

Nucleic acid probe sequences used for hybridization

| SEQ ID NOS. | Amplimer # | Target | Probe Sequence (5' to 3') |
|---|---|---|---|
| SEQ ID NO: 31 | 2 | AA69-70 HV | TTTTTCCCATGCTATACATGTCTC TGTTTTTT |
| SEQ ID NO: 32 | 2 | AA69-70 DEL | TTTTTTTTTCCATGCTATCTCTGG GATTTTTT |
| SEQ ID NO: 33 | 2 | AA D80A | TTTTTCAGAGGTTTGMTAACCCTG TCTTTTTT |
| SEQ ID NO: 34 | 2 | AA D80_ | TTTTTTTGGTTTGATAACCCTGCTT TTTTT |
| SEQ ID NO: 35 | 2 | AA_80A | TTTTTTTGGTTTGCTAACCCTGCT TTTTTT |
| SEQ ID NO: 36 | 3 | AA D138Y | TTTTATTTTGTAATKATCCATTTTT GTTTT |
| SEQ ID NO: 37 | 3 | AA D138_ | TTTTTCTTTGTAATGATCCATTTTC TTTTT |
| SEQ ID NO: 38 | 3 | AA_138Y | TTTTTTTTTGTAATTATCCATTTTC TTTTT |
| SEQ ID NO: 39 | 3 | AA W152C | TTTTTAGTTGKATGGAAAGTGAGT TCTTTT |
| SEQ ID NO: 40 | 3 | AA W152_ | TTTCTCTAAAAGTTGGATGGAAAC TCTTCT |
| SEQ ID NO: 41 | 3 | AA_152C | TTTCTTCAAAGTTGTATGGAAAGC CTTCTT |
| SEQ ID NO: 42 | 5 | AA 439K + N440K | TTTTTAATTCTAAMAAKCTTGATTC TAATTTT |
| SEQ ID NO: 43 | 5 | AA N439_ + N440_ | TTTTTAATTCTAACAATCTTGATTT CTTTT |
| SEQ ID NO: 44 | 5 | AA N439_ + _440K | TTTTTTATTCTAACAAGCTTGATTT TTTTT |
| SEQ ID NO: 45 | 5 | AA_439K + N440_ | TTTTCTATTCTAAAAATCTTGATTT CTTTT |
| SEQ ID NO: 46 | 5 | AA L452R | TTTCTATAATTACCTGTATAGATTG TCTTT |
| SEQ ID NO: 47 | 5 | AA L452_ | TTTTTTTAATTACCTGTATAGATTT CTTTT |
| SEQ ID NO: 48 | 5 | AA_452R | TTTTTCATAATTACTGGTATAGATC TTTTT |
| SEQ ID NO: 49 | 6 | AA S477_ | TTTTTTCGCCGGTAGCACACCTCT TTTTTT |
| SEQ ID NO: 50 | 6 | AA_477N | TTTTCTTCCGGTAACACACCTTTT TTTTTT |

TABLE 3-continued

Nucleic acid probe sequences used for hybridization

| SEQ ID NOS. | Amplimer # | Target | Probe Sequence (5' to 3') |
|---|---|---|---|
| SEQ ID NO: 51 | 6 | AA V483A + E484K | TTTTTTAATGGTGTTRAAGGTTTTA ATTTTTT |
| SEQ ID NO: 52 | 6 | AA V483_ + E484_ | TTTTTTCTGGTGTTGAAGGTTTTA CTTTTT |
| SEQ ID NO: 53 | 6 | AA V483_ + _484K | TTTTTTTATGGTGTTAAAGGTTTTC TTTTT |
| SEQ ID NO: 54 | 6 | AA_483A + E484_ | TTTTTTTATGGTGCTGAAGGTTCT TTTTTT |
| SEQ ID NO: 55 | 6 | AA N501Y | TTTTTTTCCAACCCACTWATGGT GTTTTTTT |
| SEQ ID NO: 56 | 6 | AA N501_ | TTTTTTTTACCCACTAATGGTGTCT TTTTT |
| SEQ ID NO: 57 | 6 | AA N_501Y | TTTTTTTTACCCACTTATGGTGTCT TTTTT |
| SEQ ID NO: 58 | 8 | AA P681H | TTTTTCAGACTAATTCTCMTCGG CTTTTT |
| SEQ ID NO: 59 | 8 | AA P681_ | TTTTTTTCTAATTCTCCTCGGCGTT TTTTT |
| SEQ ID NO: 60 | 8 | AA_681H | TTTTTTTTTAATTCTCATCGGCGTT TTTTT |
| SEQ ID NO: 61 | 8 | AA A701V | TTTCACTTGGTGYAGAAAATTCA GTTTTT |
| SEQ ID NO: 62 | 8 | AA A701_ | TCTTCTTCTTGGTGCAGAAAATTA TTCTTT |
| SEQ ID NO: 63 | 8 | AA_701V | TCTTCTTCTTGGTGTAGAAAATTA TTCTTT |
| SEQ ID NO: 134 | — | RNAse P | TTTTTTTTCTGACCTGAAGGCTCT GCGCGTTTTT |
| SEQ ID NO: 135 | — | RNAse P | TTTTTCTTGACCTGAAGGCTCTGC TTTTTT |
| SEQ ID NO: 136 | — | Negative Control | TTTTTTCTACTACCTATGCTGATTC ACTCTTTTT |

Further still in all embodiments the sample may comprise at least one of a nasopharyngeal swab, a nasal swab, a mouth swab, a mouthwash, an aerosol, or a swab from a hard surface. In one aspect the sample may be any sample obtained from a subject including, but not limited to, a nasopharyngeal swab, a nasal swab, a mouth swab, and a mouthwash (sample obtained by rinsing the subject's buccal cavity). A pooled sample obtained by combining two or more of these samples or by combining samples from multiple subjects also may be used. In another aspect, the sample is an environmental sample obtain from inanimate sources including but is not limited to an aerosol and a hard surface. The aerosol samples may be obtained using commercial air samplers such as for example a Coriolis Micro Air Sampler. A sample from a hard surface may be obtained using a swab. In both aspects, the viruses from samples obtained on swabs are dispersed in a liquid such as phosphate buffered saline. Aerosol samples are transferred into a volume of a liquid such as phosphate buffered saline.

In another embodiment of the present invention, there is provided a method for detecting Clade variants in the Coronavirus disease 2019 virus (COVID-19) in a sample, comprising obtaining the sample; harvesting viruses from the sample; isolating total RNA from the harvested viruses; performing a combined reverse transcription and asymmetric PCR amplification reaction on the total RNA using at least one fluorescent labeled primer pair comprising an unlabeled primer, and a fluorescently labeled primer, selective for a target sequence in all COVID-19 viruses to generate at least one fluorescent labeled COVID-19 virus amplicon; hybridizing the fluorescent labeled COVID-19 virus amplicons to a plurality of nucleic acid probes, each having a sequence corresponding to a sequence determinant that discriminates among the clade variants of the COVID-19 virus, where the nucleic acid probes are attached to a solid microarray support; washing the microarray at least once; and imaging the microarray to detect at least one fluorescent signal from the hybridized fluorescent labeled COVID-19 virus amplicons, thereby detecting the clade variants of the COVID-19 virus in the sample.

The total RNA is isolated as described supra and any COVID-19 virus RNA in the total RNA isolate is used as a template in a combined reverse transcription/amplification reaction (RT-PCR). In this step, the nucleic acid sequences in the COVID-19 virus RNA are transcribed using a reverse transcriptase enzyme to generate COVID-19 complementary DNA (cDNA) that is amplified in the same reaction using COVID-19 virus selective fluorescent labeled primer pairs to generate fluorescent labeled COVID-19 virus amplicons. Each fluorescent labeled primer pair comprises an unlabeled primer and a fluorescently labeled primer in about 4-fold to about 8-fold excess of the unlabeled primer whereby, upon completion of the reaction, the fluorescently labelled amplicon is primarily single stranded (that is, the reaction is a type of "asymmetric PCR").

Hybridization of the fluorescent labeled COVID-19 virus amplicons to the plurality of nucleic acid probes attached at specific positions on a microarray support is performed as described supra. The nucleic acid probes may have a sequence corresponding to a sequence determinant that discriminates among the Clade variants of the COVID-19 virus and are specific to the target region of the gene in the COVID-19 virus, as discussed supra. This enables hybridization of the one fluorescent labeled COVID-19 virus amplicon generated to the Spike gene-specific nucleic acid probe thereby discriminating the Clade variants of the COVID-19 virus in the sample. In a non-limiting example, the target region is in a Spike gene in the COVID-19 virus and the nucleic acid probes have a sequence shown in SEQ ID NO: 31 to SEQ ID: 63 (Table 3). Controls are as described supra and shown in (Table 3).

Further to this embodiment, prior to the harvesting step, the method comprises mixing the sample with an RNA stabilizer. A representative RNA stabilizer is a chemical stabilizer, as described supra.

In both embodiments one or more of the at least one fluorescent labeled second primer pair is selective for a panel of target nucleotide sequences within a target region of a gene in the COVID-19 virus; and the nucleic acid probes are specific to the target region of the gene, whereby the at least one fluorescent labeled COVID-19 virus amplicon generated is hybridized to the nucleic acid probe thereby discriminating the clade variants of the COVID-19 virus in the sample. Further to this embodiment the method comprises detecting the at least one fluorescent signal from the hybridized at least one fluorescent labeled COVID-19 virus amplicons associated with the panel of target nucleotide sequences within the target region of the gene; and generating an intensity distribution profile unique to each of the clade variants, whereby each of the clade variants is distinguishable from others. Particularly, the gene may be the Spike gene.

In a non-limiting example, the target region may be in the Spike gene in the COVID-19 virus and the fluorescent labeled second primer pairs may have forward (odd numbers) and reverse (even number) sequences shown in SEQ ID NO: 9 to SEQ ID NO: 18 (Table 2). Controls including, but not limited to a RNAse P control having a primer pair with forward primer SEQ ID NO: 66 and reverse primer SEQ ID NO: 67 are also used herein (Table 2).

In all embodiments the COVID-19 gene, the clade variants of the COVID-19 virus, the at least one fluorescent labeled primer pair, the fluorescent label, the nucleic acid probes, and the samples are as described supra. Also in all embodiments the fluorescently labeled primer may be in an excess of about 4-fold to about 8-fold over the unlabeled primer in the fluorescent labeled primer pair. Exemplary nucleotide sequences for the fluorescent labeled primer pairs including, for example, RNAse P controls, are shown in Table 2. Exemplary nucleotide sequences for the nucleic acid probes, including, for example, RNAse P controls and negative controls, are shown in Table 3.

Provided herein are methods of nucleic acid analysis to detect stable genetic variation such as a clade variation in a viral pathogen which is based on simultaneous analysis of multiple sequence domains in a gene, such as for example the Spike gene in the RNA genome of CoV-2, to measure clade variation in SARS-CoV-2. In one method for detecting the stable genetic variation, total RNA from the harvested viruses is isolated and used in a combined reverse transcription and first amplification reaction (RT-PCR) to generate COVID-19 virus cDNA amplicons. These amplicons are used as template in a second amplification reaction that uses fluorescent labeled second primer pair selective for a panel of target nucleotide sequences within a target region of a gene in the COVID-19 virus such as for example, the gene for the Spike protein, to generate fluorescent labeled COVID-19 virus amplicons. In a second method, a combined reverse transcription and asymmetric PCR amplification reaction is performed using at least one fluorescent labeled primer pair selective for the panel of target nucleotide sequences within a target region of a gene in the COVID-19 virus to generate fluorescent labeled COVID-19 virus amplicons. In either method, the fluorescent labeled COVID-19 virus amplicons are hybridized to nucleic acid probes attached at specific positions on a microarray.

This method allows positive hybridization signals to be validated on each sample tested based on internal "mismatched" and "sequence specific" controls. Additionally, at least one fluorescent signal from the hybridized amplicons associated with the panel of target nucleotide sequences within the target region of the gene is detected and an intensity distribution profile unique to each of the Clade variants generated, whereby each of the Clade variants is distinguishable from others.

In the embodiments described supra, the solid microarray support is made of any suitable material known in the art including but not limited to borosilicate glass, a thermoplastic acrylic resin (e.g., poly(methyl methacrylate-VSUVT) a cycloolefin polymer (e.g. ZEONOR 1060R), a metal including, but not limited to gold and platinum, a plastic including, but not limited to polyethylene terephthalate, polycarbonate, nylon, a ceramic including, but not limited to $TiO_2$, and Indium tin oxide (ITO) and engineered carbon surfaces including, but not limited to graphene. A combination of these materials may also be used. The solid support has a front surface and a back surface and is activated on the front surface by chemically activatable groups for attachment of the nucleic acid probes. In this embodiment, the chemically activatable groups include but are not limited to epoxysilane, isocyanate, succinimide, carbodiimide, aldehyde and maleimide. These materials are well known in the art and one of ordinary skill in this art would be able to readily functionalize any of these supports as desired. In a preferred embodiment, the solid support is epoxysilane functionalized borosilicate glass support.

The nucleic acid probes are attached either directly to the solid microarray support, or indirectly attached to the support using bifunctional polymer linkers. In this embodiment, the bifunctional polymer linker has a top domain and a bottom end. On the bottom end is attached a first reactive moiety that allows covalent attachment to the chemically activatable groups in the solid support. Examples of first reactive moieties include but are not limited to an amine group, a thiol group and an aldehyde group. In one aspect the first reactive moiety is an amine group. On the top domain of the bifunctional polymer linker is provided a second reactive moiety that allows covalent attachment to the oligonucleotide probe. Examples of second reactive moieties include but are not limited to nucleotide bases like thymidine, adenine, guanine, cytidine, uracil and bromodeoxyuridine and amino acid like cysteine, phenylalanine, tyrosine glycine, serine, tryptophan, cystine, methionine, histidine, arginine and lysine. The bifunctional polymer linker may be an oligonucleotide such as OLIGOdT, an amino polysaccharide such as chitosan, a polyamine such as spermine, spermidine, cadaverine and putrescine, a polyamino acid, with a lysine or histidine, or any other polymeric compounds with dual functional groups which can be attached to the chemically activatable solid support on the bottom end, and the nucleic acid probes on the top domain. Preferably, the bifunctional polymer linker is OLIGOdT having an amine group at the 5' end.

The bifunctional polymer linker may be unmodified with a fluorescent label. Alternatively, the bifunctional polymer linker has a fluorescent label attached covalently to the top domain, the bottom end, or internally. The second fluorescent label is different from the fluorescent label in the fluorescent labeled primers. Having a fluorescent label (fluorescent tag) attached to the bifunctional polymer linker is beneficial since it allows the user to image and detect the position of the individual nucleic acid probes ("spot") printed on the microarray. By using two different fluorescent labels, one for the bifunctional polymer linker and the second for the amplicons generated from the viral RNA being queried, the user can obtain a superimposed image that allows parallel detection of those nucleic acid probes which have been hybridized with amplicons. This is advantageous since it helps in identifying the virus comprised in the sample using suitable computer and software, assisted by a database correlating nucleic acid probe sequence and microarray location of this sequence with a known RNA signature in viruses. Examples of fluorescent labels include, but are not limited to CY5, DYLIGHT™ DY647, ALEXA FLUOR 647, CY3, DYLIGHT™ DY547, or ALEXA FLUOR 550. The fluorescent labels may be attached to any reactive group including but not limited to, amine, thiol, aldehyde, sugar amido and carboxy on the bifunctional polymer linker. In one aspect, the bifunctional polymer linker is CY5-labeled OLIGOdT having an amino group attached at its 3'terminus for covalent attachment to an activated surface on the solid support.

Moreover, when the bifunctional polymer linker also is fluorescently labeled a second fluorescent signal image is detected in the imaging step. Superimposing the first fluorescent signal image and second fluorescent signal image allows identification of the virus by comparing the sequence of the nucleic acid probe at one or more superimposed signal positions on the microarray with a database of signature sequence determinants for a plurality of viral RNA. This embodiment is particularly beneficial since it allows identification of more than one type of virus in a single assay.

The following examples are given for the purpose of illustrating various embodiments of the invention and are not meant to limit the present invention in any fashion.

EXAMPLE 1

Microarray Assay for Clade Variant Detection

Provided herein is a method of nucleic acid analysis to detect stable genetic variation in a pathogen which is based on simultaneous analysis of multiple sequence domains in a gene, such as the Spike gene in the RNA genome of CoV-2, to measure clade variation in SARS-CoV-2. For CoV-2, the sequence domains are processed for nucleic acid analysis by converting them into a set of amplicons via a multiplex RT-PCR reaction. In a present preferred implementation, the sequence of those multiplex RT-PCR products is identified relative to that of the underlying CoV-2 Spike gene, by the Horizontal Black Bars in the bottom of Tables 4-8.

The product of that multiplex RT-PCR reaction is analyzed by hybridization to a matrix of synthetic oligonucleotide probes positioned as a microarray test (see the boxes in Tables 4-8). As seen in Tables 4-8, in a preferred implementation of the present invention for CoV-2, there are (15) such Spike Gene Target Regions containing meaningful local sequence variation. (See top Row of Tables 4-8 for their identification).

In terms of detailed test design, the oligonucleotide probes resident at each Target Region of the Spike surface protein are each produced as 3 closely related probe variants, which may be referred to as "Wild Type", "Mutant" and "Universal".

Wild Type Probes

In the present invention, a "Wild Type" probe refers to an oligonucleotide probe sequence, generally 14-25 bases long that is specific to the Wuhan progenitor Clade sequence. The pattern of Multiplex RT-PCR amplicon binding to such Wild Type Probes in the present invention are displayed as superscript "2" in Table 4 and as superscript "1" in Table 6.

Mutant Probes

"Mutant" probes correspond to an oligonucleotide probe sequence, also 15-25 bases long specific to the Sequence Change relative to the Wuhan progenitor manifest at the Spike gene location of interest are displayed as superscript "1" in Table 4 and as superscript "1" in Table 5.

Universal Probes

A "Universal" probe refers to an oligonucleotide probe sequence (15-30 bases long) which has been designed to bind to both "Wild Type" and "Mutant" sequences at each site with similar affinity. The patterns of Multiplex RT-PCR amplicon binding to such "Universal" Probes in the present invention are displayed are displayed as superscript "1" in Table 7.

TABLE 4

Combinatorial Analysis of CoV-2 Variants

| Spike Gene Target Region (Codon) Amino Acid Change | S13I | L18F | T20N | P26S | Δ69-70 | D80A | D138Y | Y144DEL | W152C | R190S |
|---|---|---|---|---|---|---|---|---|---|---|
| Mutation specific Probe coverage | ✓$^1$ | | ✓$^1$ | | ✓$^1$ | ✓$^1$ | ✓$^1$ | | ✓$^1$ | |
| Wuhan reference specific probe/s coverage | ✓$^2$ | | ✓$^2$ | | ✓$^2$ | ✓$^2$ | ✓$^2$ | | ✓$^2$ | |

TABLE 4-continued

Combinatorial Analysis of CoV-2 Variants

| | | | | | | | | | | | | |
|---|---|---|---|---|---|---|---|---|---|---|---|---|
| Locus specific Probe coverage | | | ✓ | | ✓ | | N/A | ✓ | ✓ | | ✓ | |
| REGION | LINEAGE DESIGNATION var | | | | | | | | | | | |
| Denmark | Mink V | B.1.1.298 | S[2] | L[3] | T[2] | P[3] | Δ[1] | D[2] | D[2] | Y[3] | W[2] | R[3] |
| UK | GR/501Y.V1 | B.1.1.7 | S[2] | L[3] | T[2] | P[3] | Δ[1] | D[2] | D[2] | Δ[3] | W[2] | R[3] |
| SA | GH/501Y.V2 | B.1.351 | S[2] | L[3] | T[2] | P[3] | HV[2] | A[1] | D[2] | Y[3] | W[2] | R[3] |
| Brazil/Japan | P.1 | | S[2] | F[3] | N[1] | S[3] | HV[2] | D[2] | Y[1] | Y[3] | W[2] | S[3] |
| Brazil | P.2 | | S[2] | L[3] | T[2] | P[3] | HV[2] | D[2] | D[2] | Y[3] | W[2] | R[3] |
| California | CAL.20C-GH/452R.V1 | B.1.429 | I[1] | L[3] | T[2] | P[3] | HV[2] | D[2] | D[2] | Y[3] | C[1] | R[3] |
| India | (Andhra Pradesh) | N440K | S[2] | L[3] | T[2] | P[3] | HV[2] | D[2] | D[2] | Y[3] | W[2] | R[3] |
| WUHAN | | WUHAN | S[2] | L[3] | T[2] | P[3] | HV[2] | D[2] | D[2] | Y[3] | W[2] | R[3] |
| PCR Amplimer length (bases) | | | | | (1) 101 | | (2) 104 | | | (3) 129 | | |

| Spike Gene Target Region (Codon) Amino Acid Change | | | D215G | A243del | R246I | K417N/T | N440K | L452R | Y453F |
|---|---|---|---|---|---|---|---|---|---|
| Mutation specific Probe coverage | | | ✓[1] | | | ✓[1] | ✓[1] | ✓[1] | |
| Wuhan reference specific probe/s coverage | | | ✓[2] | | | ✓[2] | ✓[2] | ✓[2] | |
| Locus specific Probe coverage | | | ✓ | | | ✓ | ✓ | ✓ | |
| REGION | LINEAGE DESIGNATION var | | | | | | | | |
| Denmark | Mink V | B.1.1.298 | D[2] | A[3] | R[3] | K[2] | N[2] | L[2] | F[3] |
| UK | GR/501Y.V1 | B.1.1.7 | D[2] | A[3] | R[3] | K[2] | N[2] | L[2] | Y[3] |
| SA | GH/501Y.V2 | B.1.351 | G[1] | Δ[3] | I[3] | N[1] | N[2] | L[2] | Y[3] |
| Brazil/Japan | P.1 | | D[2] | A[3] | R[3] | T[1] | N[2] | L[2] | Y[3] |
| Brazil | P.2 | | D[2] | A[3] | R[3] | K[2] | N[2] | L[2] | Y[3] |
| California | CAL.20C-GH/452R.V1 | B.1.429 | D[2] | A[3] | R[3] | K[2] | N[2] | R[1] | Y[3] |
| India | (Andhra Pradesh) | N440K | D[2] | A[3] | R[3] | K[2] | K[1] | L[2] | Y[3] |
| WUHAN | | WUHAN | D[2] | A[3] | R[3] | K[2] | N[2] | L[2] | Y[3] |
| PCR Amplimer length (bases) | | | | (4) 160 | | | (5) 199 | | |

| Spike Gene Target Region (Codon) Amino Acid Change | | | E484K | N501Y | A570D | D614G | H655Y | P681H | I692V | A701V |
|---|---|---|---|---|---|---|---|---|---|---|
| Mutation specific Probe coverage | | | ✓[1] | ✓[1] | | ✓[1] | | ✓[1] | | ✓[1] |
| Wuhan reference specific probe/s coverage | | | ✓[2] | ✓[2] | | ✓[2] | | ✓[2] | | ✓[2] |
| Locus specific Probe coverage | | | ✓ | ✓ | | ✓ | | ✓ | | ✓ |
| REGION | LINEAGE DESIGNATION var | | | | | | | | | |
| Denmark | Mink V | B.1.1.29 | E[2] | N[2] | A[3] | G[1] | H[3] | P[2] | V | A[2] |
| UK | GR/501Y.V1 | B.1.1.7 | E[2] | Y[1] | D[3] | G[1] | H[3] | H[1] | I | A[2] |
| SA | GH/501Y.V2 | B.1.351 | K[1] | Y[1] | A[3] | G[1] | H[3] | P[2] | I | V[1] |
| Brazil/Japan | P.1 | | K[1] | Y[1] | A[3] | G[1] | Y[3] | P[2] | I | A[2] |
| Brazil | P.2 | | K[1] | N[2] | A[3] | G[1] | H[3] | P[2] | I | A[2] |
| California | CAL.20C-GH/452R.V1 | B.1.429 | E[2] | N[2] | A[3] | G[1] | H[3] | P[2] | I | A[2] |
| India | (Andhra Pradesh) | N440K | E[2] | N[2] | A[3] | G[1] | H[3] | P[2] | I | A[2] |
| WUHAN | | WUHAN | E[2] | N[2] | A[3] | D[2] | H[3] | P[2] | I | A[2] |
| PCR Amplimer length (bases) | | | (6) 151 | | | (7) 88 | | | (8) 135 | |

| Spike Gene Target Region (Codon) Amino Acid Change | | | T716I | S982A | T1027I | D1118H | V1176F | M1229I |
|---|---|---|---|---|---|---|---|---|
| Mutation specific Probe coverage | | | | | | | | |
| Wuhan reference specific probe/s coverage | | | | | | | | |
| Locus specific Probe coverage | | | | | | | | |
| REGION | LINEAGE DESIGNATION var | | | | | | | |
| Denmark | Mink V | B.1.1.29 | T[3] | S[3] | T[3] | D[3] | V[3] | I[3] |
| UK | GR/501Y.V1 | B.1.1.7 | I[3] | A[3] | T[3] | H[3] | V[3] | M[3] |
| SA | GH/501Y.V2 | B.1.351 | T[3] | S[3] | T[3] | D[3] | V[3] | M[3] |
| Brazil/Japan | P.1 | | T[3] | S[3] | I[3] | D[3] | F[3] | M[3] |
| Brazil | P.2 | | T[3] | S[3] | T[3] | D[3] | F[3] | M[3] |
| California | CAL.20C-GH/452R.V1 | B.1.429 | T[3] | S[3] | T[3] | D[3] | V[3] | M[3] |
| India | (Andhra Pradesh) | N440K | T[3] | S[3] | T[3] | D[3] | V[3] | M[3] |
| WUHAN | | WUHAN | T[3] | S[3] | T[3] | D[3] | V[3] | M[3] |
| PCR Amplimer length (bases) | | | | | | | | |

[1]AA mutation - hybridizes to mutation specific probe

[2]AA identical to hCoV-19/Wuhan/WIV04/2019 (WIV04) - official reference sequence employed by GISAID (EPI_ISL_402124) Hybridizes to reference specific probe

[3]Potential probe target

TABLE 5

Combinatorial Analysis of CoV-2 Variants - Mutant Probes

| Spike Gene Target Region (Codon) Amino Acid Change | | | S13I | L18F | T20N | P26S | Δ69-70 | D80A | D138Y | Y144DEL | W152C | R190S |
|---|---|---|---|---|---|---|---|---|---|---|---|---|
| Mutation specific Probe coverage | | | ✓[1] | | ✓[1] | | ✓[1] | ✓[1] | ✓[1] | | ✓[1] | |
| REGION | LINEAGE DESIGNATION var | | | | | | | | | | | |
| Denmark | Mink V | B.1.1.298 | S | L | T | P | Δ[1] | D | D | Y | W | R |
| UK | GR/501Y.V1 | B.1.1.7 | S | L | T | P | Δ[1] | D | D | Δ | W | R |
| SA | GH/501Y.V2 | B.1.351 | S | L | T | P | HV | A | D | Y | W | R |
| Brazil/Japan | P.1 | | S | F | N[1] | S | HV | D | Y[1] | Y | W | S |
| Brazil | P.2 | | S | L | T | P | HV | D | D | Y | W | R |
| California | CAL.20C-GH/452R.V1 | B.1.429 | I[1] | L | T | P | HV | D | D | Y | C[1] | R |
| India | (Andhra Pradesh) | N440K | S | L | T | P | HV | D | D | Y | W | R |
| WUHAN | | WUHAN | S | L | T | P | HV | D | D | Y | W | R |
| PCR Amplimer length (bases) | | | | (1) 101 | | | | (2) 104 | | (3) 129 | | |

| Spike Gene Target Region (Codon) Amino Acid Change | | | D215G | A243del | R246I | K417N/T | N440K | L452R | Y453F |
|---|---|---|---|---|---|---|---|---|---|
| Mutation specific Probe coverage | | | ✓[1] | | | ✓[1] | ✓[1] | ✓[1] | |
| REGION | LINEAGE DESIGNATION var | | | | | | | | |
| Denmark | Mink V | B.1.1.298 | D | A | R | K | N | L | F |
| UK | GR/501Y.V1 | B.1.1.7 | D | A | R | K | N | L | Y |
| SA | GH/501Y.V2 | B.1.351 | G[1] | Δ | I | N[1] | N | L | Y |
| Brazil/Japan | P.1 | | D | A | R | T[1] | N | L | Y |
| Brazil | P.2 | | D | A | R | K | N | L | Y |
| California | CAL.20C-GH/452R.V1 | B.1.429 | D | A | R | K | N | R[1] | Y |
| India | (Andhra Pradesh) | N440K | D | A | R | K | K[1] | L | Y |
| WUHAN | | WUHAN | D | A | R | K | N | L | Y |
| PCR Amplimer length (bases) | | | | (4) 160 | | | | (5) 199 | |

| Spike Gene Target Region (Codon) Amino Acid Change | | | E484K | N501Y | A570D | D614G | H655Y | P681H | I692V | A701V |
|---|---|---|---|---|---|---|---|---|---|---|
| Mutation specific Probe coverage | | | ✓[1] | ✓[1] | | ✓[1] | | ✓[1] | | ✓[1] |
| REGION | LINEAGE DESIGNATION var | | | | | | | | | |
| Denmark | Mink V | B.1.1.298 | E | N | A | G[1] | H | P | V | A |
| UK | GR/501Y.V1 | B.1.1.7 | E | Y[1] | D | G[1] | H | H[1] | I | A |
| SA | GH/501Y.V2 | B.1.351 | K[1] | Y[1] | A | G[1] | H | P | I | V[1] |
| Brazil/Japan | P.1 | | K[1] | Y[1] | A | G[1] | Y | P | I | A |
| Brazil | P.2 | | K[1] | N | A | G[1] | H | P | I | A |
| California | CAL.20C-GH/452R.V1 | B.1.429 | E | N | A | G[1] | H | P | I | A |
| India | (Andhra Pradesh) | N440K | E | N | A | G[1] | H | P | I | A |
| WUHAN | | WUHAN | E | N | A | D | H | P | I | A |
| PCR Amplimer length (bases) | | | (6) 151 | | | (7) 88 | | | (8) 135 | |

| Spike Gene Target Region (Codon) Amino Acid Change | | | T716I | S982A | T1027I | D1118H | V1176F | M1229I |
|---|---|---|---|---|---|---|---|---|
| Mutation specific Probe coverage | | | | | | | | |
| REGION | LINEAGE DESIGNATION var | | | | | | | |
| Denmark | Mink V | B.1.1.298 | T | S | T | D | V | I |
| UK | GR/501Y.V1 | B.1.1.7 | I | A | T | H | V | M |
| SA | GH/501Y.V2 | B.1.351 | T | S | T | D | V | M |
| Brazil/Japan | P.1 | | T | S | I | D | F | M |
| Brazil | P.2 | | T | S | T | D | F | M |
| California | CAL.20C-GH/452R.V1 | B.1.429 | T | S | T | D | V | M |
| India | (Andhra Pradesh) | N440K | T | S | T | D | V | M |
| WUHAN | | WUHAN | T | S | T | D | V | M |
| PCR Amplimer length (bases) | | | | | | | | |

[1]AA mutation - hybridizes to mutation specific probe

TABLE 6

Combinatorial Analysis of CoV-2 Variants - Wild Type Probes

| Spike Gene Target Region (Codon) Amino Acid Change | | | S13I | L18F | T20N | P26S | Δ69-70 | D80A | D138Y | Y144DEL | W152C | R190S |
|---|---|---|---|---|---|---|---|---|---|---|---|---|
| Wuhan reference specific probe/s coverage | | | ✓[1] | | ✓[1] | | ✓[1] | ✓[1] | ✓[1] | | ✓[1] | |
| REGION | LINEAGE DESIGNATION var | | | | | | | | | | | |
| Denmark | Mink V | B. 1.1.298 | S[1] | L | T[1] | P | Δ | D[1] | D[1] | Y | W[1] | R |
| UK | GR/501Y.V1 | B.1.1.7 | S[1] | L | T[1] | P | Δ | D[1] | D[1] | Δ | W[1] | R |
| SA | GH/501Y.V2 | B.1.351 | S[1] | L | T[1] | P | HV | A | D[1] | Y | W[1] | R |
| Brazil/Japan | P.1 | | S[1] | F | N | S | HV | D[1] | Y | Y | W[1] | S |
| Brazil | P.2 | | S[1] | L | T[1] | P | HV | D[1] | D[1] | Y | W[1] | R |
| California | CAL.20C-GH/452R.V1 | B.1.429 | I | L | T[1] | P | HV | D[1] | D[1] | Y | C | R |
| India | (Andhra Pradesh) | N440K | S[1] | L | T[1] | P | HV | D[1] | D[1] | Y | W[1] | R |
| WUHAN | | WUHAN | S[1] | L | T[1] | P | HV | D[1] | D[1] | Y | W[1] | R |
| PCR Amplimer length (bases) | | | | | (1) 101 | | | (2) 104 | | (3) 129 | | |

| Spike Gene Target Region (Codon) Amino Acid Change | | | D215G | A243del | R246I | K417N/T | N440K | L452R | Y453F |
|---|---|---|---|---|---|---|---|---|---|
| Wuhan reference specific probe/s coverage | | | ✓[1] | | | ✓[1] | ✓[1] | ✓[1] | |
| REGION | LINEAGE DESIGNATION var | | | | | | | | |
| Denmark | Mink V | B. 1.1.298 | D[1] | A | R | K[1] | N[1] | L[1] | F |
| UK | GR/501Y.V1 | B.1.1.7 | D[1] | A | R | K[1] | N[1] | L[1] | Y |
| SA | GH/501Y.V2 | B.1.351 | G | Δ | I | N | N[1] | L[1] | Y |
| Brazil/Japan | P.1 | | D[1] | A | R | T | N[1] | L[1] | Y |
| Brazil | P.2 | | D[1] | A | R | K[1] | N[1] | L[1] | Y |
| California | CAL.20C-GH/452R.V1 | B.1.429 | D[1] | A | R | K[1] | N[1] | R | Y |
| India | (Andhra Pradesh) | N440K | D[1] | A | R | K[1] | K | L[1] | Y |
| WUHAN | | WUHAN | D[1] | A | R | K[1] | N[1] | L[1] | Y |
| PCR Amplimer length (bases) | | | | (4) 160 | | | (5) 199 | | |

| Spike Gene Target Region (Codon) Amino Acid Change | | | E484K | N501Y | A570D | D614G | H655Y | P681H | I692V | A701V |
|---|---|---|---|---|---|---|---|---|---|---|
| Wuhan reference specific probe/s coverage | | | ✓[1] | ✓[1] | | ✓[1] | | ✓[1] | | ✓[1] |
| REGION | LINEAGE DESIGNATION var | | | | | | | | | |
| Denmark | Mink V | B.1.1.298 | E[1] | N[1] | A | G | H | P[1] | V | A[1] |
| UK | GR/501Y.V1 | B.1.1.7 | E[1] | Y | D | G | H | H | I | A[1] |
| SA | GH/501Y.V2 | B.1.351 | K | Y | A | G | H | P[1] | I | V |
| Brazil/Japan | P.1 | | K | Y | A | G | Y | P[1] | I | A[1] |
| Brazil | P.2 | | K | N[1] | A | G | H | P[1] | I | A[1] |
| California | CAL.20C-GH/452R.V1 | B.1.429 | E[1] | N[1] | A | G | H | P[1] | I | A[1] |
| India | (Andhra Pradesh) | N440K | E[1] | N[1] | A | G | H | P[1] | I | A[1] |
| WUHAN | | WUHAN | E[1] | N[1] | A | D[1] | H | P[1] | I | A[1] |
| PCR Amplimer length (bases) | | | (6) 151 | | | (7) 88 | | | (8) 135 | |

| Spike Gene Target Region (Codon) Amino Acid Change | | | T716I | S982A | T1027I | D1118H | V1176F | M1229I |
|---|---|---|---|---|---|---|---|---|
| Wuhan reference specific probe/s coverage | | | | | | | | |
| REGION | LINEAGE DESIGNATION var | | | | | | | |
| Denmark | Mink V | B.1.1.298 | T | S | T | D | V | I |
| UK | GR/501Y.V1 | B.1.1.7 | I | A | T | H | V | M |
| SA | GH/501Y.V2 | B.1.351 | T | S | T | D | V | M |
| Brazil/Japan | P.1 | | T | S | I | D | F | M |
| Brazil | P.2 | | T | S | T | D | F | M |
| California | CAL.20C-GH/452R.V1 | B.1.429 | T | S | T | D | V | M |
| India | (Andhra Pradesh) | N440K | T | S | T | D | V | M |
| WUHAN | | WUHAN | T | S | T | D | V | M |
| PCR Amplimer length (bases) | | | | | | | | |

[1]AA identical to hCoV-19/Wuhan/WIV04/2019 (WIV04) - official reference sequence employed by GISAID (EPI_ISL_402124) Hybridizes to reference specific probe

TABLE 7

Combinatorial Analysis of CoV-2 Variants - Universal Probes

| Spike Gene Target Region (Codon) Amino Acid Change | | | S13I | L18F | T20N | P26S | Δ69-70 | D80A | D138Y | Y144DEL | W152C | R190S |
|---|---|---|---|---|---|---|---|---|---|---|---|---|
| Locus specific Probe coverage | | | ✓[1] | | ✓ | | N/A | ✓[1] | ✓[1] | | ✓[1] | |
| REGION | LINEAGE DESIGNATION var | | | | | | | | | | | |
| Denmark | Mink V | B.1.1.298 | S[1] | L | T[1] | P | Δ | D[1] | D[1] | Y | W[1] | R |
| UK | GR/501Y.V1 | B.1.1.7 | S[1] | L | T[1] | P | Δ | D[1] | D[1] | Δ | W[1] | R |
| SA | GH/501Y.V2 | B.1.351 | S[1] | L | T[1] | P | HV | A[1] | D[1] | Y | W[1] | R |
| Brazil/Japan | P.1 | | S[1] | F | N[1] | S | HV | D[1] | Y[1] | Y | W[1] | S |
| Brazil | P.2 | | S[1] | L | T[1] | P | HV | D[1] | D[1] | Y | W[1] | R |
| California | CAL.20C-GH/452R.V1 | B.1.429 | I[1] | L | T[1] | P | HV | D[1] | D[1] | Y | C[1] | R |
| India | (Andhra Pradesh) | N440K | S[1] | L | T[1] | P | HV | D[1] | D[1] | Y | W[1] | R |
| WUHAN | | WUHAN | S[1] | L | T[1] | P | HV | D[1] | D[1] | Y | W[1] | R |
| PCR Amplimer length (bases) | | | | | (1) 101 | | | (2) 104 | | (3) 129 | | |

| Spike Gene Target Region (Codon) Amino Acid Change | | | D215G | A243del | R246I | K417N/T | N440K | L452R | Y453F |
|---|---|---|---|---|---|---|---|---|---|
| Locus specific Probe coverage | | | ✓[1] | | | ✓[1] | ✓[1] | ✓[1] | |
| REGION | LINEAGE DESIGNATION var | | | | | | | | |
| Denmark | Mink V | B.1.1.298 | D[1] | A | R | K[1] | N[1] | L[1] | F |
| UK | GR/501Y.V1 | B.1.1.7 | D[1] | A | R | K[1] | N[1] | L[1] | Y |
| SA | GH/501Y.V2 | B.1.351 | G[1] | Δ | I | N[1] | N[1] | L[1] | Y |
| Brazil/Japan | P.1 | | D[1] | A | R | T[1] | N[1] | L[1] | Y |
| Brazil | P.2 | | D[1] | A | R | K[1] | N[1] | L[1] | Y |
| California | CAL.20C-GH/452R.V1 | B.1.429 | D[1] | A | R | K[1] | N[1] | R[1] | Y |
| India | (Andhra Pradesh) | N440K | D[1] | A | R | K[1] | K[1] | L[1] | Y |
| WUHAN | | WUHAN | D[1] | A | R | K[1] | N[1] | L[1] | Y |
| PCR Amplimer length (bases) | | | | (4) 160 | | | (5) 199 | | |

| Spike Gene Target Region (Codon) Amino Acid Change | | | E484K | N501Y | A570D | D614G | H655Y | P681H | I692V | A701V |
|---|---|---|---|---|---|---|---|---|---|---|
| Locus specific Probe coverage | | | ✓ | ✓ | | ✓ | | ✓ | | ✓ |
| REGION | LINEAGE DESIGNATION var | | | | | | | | | |
| Denmark | Mink V | B.1.1.298 | E[1] | N[1] | A | G[1] | H | P[1] | V | A[1] |
| UK | GR/501Y.V1 | B.1.1.7 | E[1] | Y[1] | D | G[1] | H | H[1] | I | A[1] |
| SA | GH/501Y.V2 | B.1.351 | K[1] | Y[1] | A | G[1] | H | P[1] | I | V[1] |
| Brazil/Japan | P.1 | | K[1] | Y[1] | A | G[1] | Y | P[1] | I | A[1] |
| Brazil | P.2 | | K[1] | N[1] | A | G[1] | H | P[1] | I | A[1] |
| California | CAL.20C-GH/452R.V1 | B.1.429 | E[1] | N[1] | A | G[1] | H | P[1] | I | A[1] |
| India | (Andhra Pradesh) | N440K | E[1] | N[1] | A | G[1] | H | P[1] | I | A[1] |
| WUHAN | | WUHAN | E[1] | N[1] | A | D[1] | H | P[1] | I | A[1] |
| PCR Amplimer length (bases) | | | (6) 151 | | | (7) 88 | | | (8) 135 | |

| Spike Gene Target Region (Codon) Amino Acid Change | | | T716I | S982A | T1027I | D1118H | V1176F | M1229I |
|---|---|---|---|---|---|---|---|---|
| Locus specific Probe coverage | | | | | | | | |
| REGION | LINEAGE DESIGNATION var | | | | | | | |
| Denmark | Mink V | B.1.1.298 | T | S | T | D | V | I |
| UK | GR/501Y.V1 | B.1.1.7 | I | A | T | H | V | M |
| SA | GH/501Y.V2 | B.1.351 | T | S | T | D | V | M |
| Brazil/Japan | P.1 | | T | S | I | D | F | M |
| Brazil | P.2 | | T | S | T | D | F | M |
| California | CAL.20C-GH/452R.V1 | B.1.429 | T | S | T | D | V | M |
| India | (Andhra Pradesh) | N440K | T | S | T | D | V | M |
| WUHAN | | WUHAN | T | S | T | D | V | M |
| PCR Amplimer length (bases) | | | | | | | | |

[1]Both Mutant and Wuhan reference sequence virus hybridize to Locus specific probe

TABLE 8

Combinatorial Analysis of CoV-2 Variants

| | | | Spike_S13I | Spike_L18F | Spike_T20N | Spike_P26S | Spike_Δ69-70 |
|---|---|---|---|---|---|---|---|
| Mutation specific Probe coverage | | | ✓$^{3}$ | | ✓$^{3}$ | | ✓$^{3}$ |
| Wuhan reference specific probe/s coverage | | | ✓$^{1}$ | | ✓$^{1}$ | | ✓$^{1}$ |
| Locus specific Probe coverage | | | ✓$^{4}$ | | ✓$^{4}$ | | N/A |
| REGION | LINEAGE DESIGNATION var | | | | | | |
| Denmark | Mink V | B.1.1.298 | $S^{2}$ | $L^{4}$ | $T^{2}$ | $P^{4}$ | $\Delta^{3}$ |
| UK | GR/501Y.V1 | B.1.1.7 | $S^{2}$ | $L^{4}$ | $T^{2}$ | $P^{4}$ | $\Delta^{3}$ |
| SA | GH/501Y.V2 | B.1.351 | $S^{2}$ | $L^{4}$ | $T^{2}$ | $P^{4}$ | HV |
| Brazil/Japan | P.1 | | $S^{2}$ | $F^{5}$ | $N^{3}$ | $S^{5}$ | HV |
| Brazil | P.2 | | S | $L^{4}$ | $T^{2}$ | $P^{4}$ | HV |
| California | CAL.20C-GH/452R.V1 | B.1.429 | $I^{3}$ | $L^{4}$ | $T^{2}$ | $P^{4}$ | HV |
| India | (Andhra Pradesh) | N440K | $S^{2}$ | $L^{4}$ | $T^{2}$ | $P^{4}$ | HV |
| WUHAN | | WUHAN | $S^{1}$ | $L^{4}$ | $T^{1}$ | $P^{4}$ | $HV^{1}$ |
| | | | | | AMP 1<br>101 BASE | | AMP 2<br>104 BASE |

| | | | Spike_D80A | Spike_D138Y | Spike_Y144DE | Spike_W152C |
|---|---|---|---|---|---|---|
| Mutation specific Probe coverage | | | ✓$^{3}$ | ✓$^{3}$ | | ✓$^{3}$ |
| Wuhan reference specific probe/s coverage | | | ✓$^{1}$ | ✓$^{1}$ | | ✓$^{1}$ |
| Locus specific Probe coverage | | | ✓$^{4}$ | ✓$^{4}$ | | ✓$^{4}$ |
| REGION | LINEAGE DESIGNATION var | | | | | |
| Denmark | Mink V | B.1.1.298 | $D^{2}$ | $D^{2}$ | $Y^{4}$ | $W^{2}$ |
| UK | GR/501Y.V1 | B.1.1.7 | $D^{2}$ | $D^{2}$ | $\Delta^{5}$ | $W^{2}$ |
| SA | GH/501Y.V2 | B.1.351 | $A^{3}$ | $D^{2}$ | $Y^{4}$ | $W^{2}$ |
| Brazil/Japan | P.1 | | $D^{2}$ | $Y^{3}$ | $Y^{4}$ | $W^{2}$ |
| Brazil | P.2 | | $D^{2}$ | $D^{2}$ | $Y^{4}$ | $W^{2}$ |
| California | CAL.20C-GH/452R.V1 | B.1.429 | $D^{2}$ | $D^{2}$ | $Y^{4}$ | $C^{3}$ |
| India | (Andhra Pradesh) | N440K | $D^{2}$ | $D^{2}$ | $Y^{4}$ | $W^{2}$ |
| WUHAN | | WUHAN | $D^{1}$ | $D^{1}$ | $Y^{4}$ | $W^{1}$ |
| | | | AMP 2<br>104 BASE | | AMP 3<br>129 BASE | |

| | | | Spike_R190S | Spike_D215G | Spike_A243del | Spike_R246I |
|---|---|---|---|---|---|---|
| Mutation specific Probe coverage | | | | ✓$^{3}$ | | |
| Wuhan reference specific probe/s coverage | | | | ✓$^{1}$ | | |
| Locus specific Probe coverage | | | | ✓$^{4}$ | | |
| REGION | LINEAGE DESIGNATION var | | | | | |
| Denmark | Mink V | B.1.1.298 | $R^{4}$ | $D^{2}$ | $A^{4}$ | $R^{4}$ |
| UK | GR/501Y.V1 | B.1.1.7 | $R^{4}$ | $D^{2}$ | $A^{4}$ | $R^{4}$ |
| SA | GH/501Y.V2 | B.1.351 | $R^{4}$ | $G^{3}$ | $\Delta^{5}$ | $I^{5}$ |
| Brazil/Japan | P.1 | | $S^{5}$ | $D^{2}$ | $A^{4}$ | $R^{4}$ |
| Brazil | P.2 | | $R^{4}$ | $D^{2}$ | $A^{4}$ | $R^{4}$ |
| California | CAL.20C-GH/452R.V1 | B.1.429 | $R^{4}$ | $D^{2}$ | $A^{4}$ | $R^{4}$ |
| India | (Andhra Pradesh) | N440K | $R^{4}$ | $D^{2}$ | $A^{4}$ | $R^{4}$ |
| WUHAN | | WUHAN | $R^{4}$ | $D^{1}$ | $A^{4}$ | $R^{4}$ |
| | | | | | AMP 4<br>160 BASE | |

| | | | Spike_K417N | Spike_N440K | Spike_L452R | Spike_Y453F |
|---|---|---|---|---|---|---|
| Mutation specific Probe coverage | | | ✓$^{3}$ | ✓$^{3}$ | ✓$^{3}$ | |
| Wuhan reference specific probe/s coverage | | | ✓$^{1}$ | ✓$^{1}$ | ✓$^{1}$ | |
| Locus specific Probe coverage | | | ✓$^{4}$ | ✓$^{4}$ | ✓$^{4}$ | |
| REGION | LINEAGE DESIGNATION var | | | | | |
| Denmark | Mink V | B.1.1.298 | $K^{2}$ | $N^{2}$ | $L^{2}$ | $F^{5}$ |
| UK | GR/501Y.V1 | B.1.1.7 | $K^{2}$ | $N^{2}$ | $L^{2}$ | $Y^{4}$ |
| SA | GH/501Y.V2 | B.1.351 | $N^{3}$ | $N^{2}$ | $L^{2}$ | $Y^{4}$ |
| Brazil/Japan | P.1 | | $T^{3}$ | $N^{2}$ | $L^{2}$ | $Y^{4}$ |
| Brazil | P.2 | | $K^{2}$ | $N^{2}$ | $L^{2}$ | $Y^{4}$ |
| California | CAL.20C-GH/452R.V1 | B.1.429 | $K^{2}$ | $N^{2}$ | $R^{3}$ | $Y^{4}$ |
| India | (Andhra Pradesh) | N440K | $K^{2}$ | $K^{3}$ | $L^{2}$ | $Y^{4}$ |
| WUHAN | | WUHAN | $K^{1}$ | $N^{1}$ | $L^{1}$ | $Y^{4}$ |
| | | | | AMP 5<br>199 BASE | | |

TABLE 8-continued

Combinatorial Analysis of CoV-2 Variants

| | | | Spike_E484K | Spike_N501Y | Spike_A570D | Spike_D614G | Spike_H655Y |
|---|---|---|---|---|---|---|---|
| Mutation specific Probe coverage | | | ✓[3] | ✓[3] | | ✓[3] | |
| Wuhan reference specific probe/s coverage | | | ✓[1] | ✓[1] | | ✓[1] | |
| Locus specific Probe coverage | | | ✓[4] | ✓[4] | | ✓[4] | |
| REGION | LINEAGE DESIGNATION var | | | | | | |
| Denmark | Mink V | B.1.1.298 | E[2] | N[2] | A[4] | G[3] | H[4] |
| UK | GR/501Y.V1 | B.1.1.7 | E[2] | Y[3] | D[5] | G[3] | H[4] |
| SA | GH/501Y.V2 | B.1.351 | K[3] | Y[3] | A[4] | G[3] | H[4] |
| Brazil/Japan | P.1 | | K[3] | Y[3] | A[4] | G[3] | Y[5] |
| Brazil | P.2 | | K[3] | N[2] | A[4] | G[3] | H[4] |
| California | CAL.20C-GH/452R.V1 | B.1.429 | E[2] | N[2] | A[4] | G[3] | H[4] |
| India | (Andhra Pradesh) | N440K | E[2] | N[2] | A[4] | G[3] | H[4] |
| WUHAN | | WUHAN | E[1] | N[1] | A[4] | D[1] | H[4] |
| | | | AMP 6 151 BASE | | | AMP 7 88 BASE | |

| | | | Spike_P681H | Spike_I692V | Spike_A701V | Spike_T716I | Spike_S982A |
|---|---|---|---|---|---|---|---|
| Mutation specific Probe coverage | | | ✓[3] | | ✓[3] | | |
| Wuhan reference specific probe/s coverage | | | ✓[1] | | ✓[1] | | |
| Locus specific Probe coverage | | | ✓[4] | | ✓[4] | | |
| REGION | LINEAGE DESIGNATION var | | | | | | |
| Denmark | Mink V | B.1.1.298 | P[2] | V[5] | A[2] | T[4] | S[4] |
| UK | GR/501Y.V1 | B.1.1.7 | H[3] | I[4] | A[2] | I[5] | A[5] |
| SA | GH/501Y.V2 | B.1.351 | P[2] | I[4] | V[3] | T[4] | S[4] |
| Brazil/Japan | P.1 | | P[2] | I[4] | A[2] | T[4] | S[4] |
| Brazil | P.2 | | P[2] | I[4] | A[2] | T[4] | S[4] |
| California | CAL.20C-GH/452R.V1 | B.1.429 | P[2] | I[4] | A[2] | T[4] | S[4] |
| India | (Andhra Pradesh) | N440K | P[2] | I[4] | A[2] | T[4] | S[4] |
| WUHAN | | WUHAN | P[1] | I[4] | A[1] | T[4] | S[4] |
| | | | | AMP 8 135 BASE | | | |

| | | | Spike_T1027I | Spike_D1118H | Spike_V1176F | Spike_M1229I |
|---|---|---|---|---|---|---|
| Mutation specific Probe coverage | | | | | | |
| Wuhan reference specific probe/s coverage | | | | | | |
| Locus specific Probe coverage | | | | | | |
| REGION | LINEAGE DESIGNATION var | | | | | |
| Denmark | Mink V | B.1.1.298 | T[4] | D[4] | V[4] | I[5] |
| UK | GR/501Y.V1 | B.1.1.7 | T[4] | H[5] | V[4] | M[4] |
| SA | GH/501Y.V2 | B.1.351 | T[4] | D[4] | V[4] | M[4] |
| Brazil/Japan | P.1 | | I[5] | D[4] | F[5] | M[4] |
| Brazil | P.2 | | T[4] | D[4] | F[5] | M[4] |
| California | CAL.20C-GH/452R.V1 | B.1.429 | T[4] | D[4] | V[4] | M[4] |
| India | (Andhra Pradesh) | N440K | T[4] | D[4] | V[4] | M[4] |
| WUHAN | | WUHAN | T[4] | D[4] | V[4] | M[4] |

[1]AA of hCoV-19/Wuhan/WIV04/2019 (WIV04) - official reference sequence employed by GISAID (EPI_ISL_402124)
[2]AA Identical to (WIV04) - hybridizes to Wuhan reference probe
[3]AA mutation - hybridizes to mutation specific probe
[4]Potential probe target identical to (WIV04)
[5]Potential AA mutation probe target

EXAMPLE 2

Biological Rationale for the Design of the Present Invention

The oligonucleotide probes of the microarray and the PCR primers to generate RT-PCR amplicons were developed to accommodate a specific CoV-2 Clade Variant set of international interest in 2021, as specified in the Left-most Column in Tables 4-8. But, as can already be seen among the Clade Variant strain these tables, the pattern of local sequence change manifest in each Clade Variant comprises a unique combination derived from a larger set of specific local sequence variation chosen at discrete sites in the Spike gene.

For the Spike protein of the CoV-2 virus and for pathogens more universally, spontaneous local mutation in a surface protein such as Spike is likely to inactivate the protein, thus disabling the pathogen. As such, most spontaneous mutations in surface proteins do not propagate and hence go undetected.

On occasion, however, such random mutation produces a surface protein change that confers a selective advantage to a pathogen, such as enhanced infectivity, better resistance to vaccination or drug therapy and thus the mutation propagates in an infection and ultimately be detected at population scale. Such positively selected local mutational changes are generally rare and thus localized to a relatively small number of discrete segments within a pathogen surface protein such as Spike, often localized to specific sites where the protein contacts host cells, or sites which present peptides for interaction with a protective host antibody or sites where a drug might bind. In many cases such altered surface protein features may function in an additive way (enhanced cell binding+diminished neutralizing antibody binding may be selected for, concurrently) to produce a Clade Variant presenting a combination derived from the set of available local sequence changes that confer functional superiority to the pathogen.

The present invention takes advantage of the fundamental matrix-like character of such selectable (discrete, local) surface protein changes and the ability of a matrix of hybridization probes (as in a microarray) to query many sites of local surface protein sequence change simultaneously (Tables 4-7). As such, this oligonucleotide probe set can interrogate (at the nucleic acid level) many possible combinations of such surface protein change as a single combinatorial test.

Based on the core design test design embodied in Tables 4-7, new, as-yet unknown, functionally relevant local sequence change can be added, once known, as new probes to the microarray (cells with superscript "3" in Table 4). It is expected that many other CoV-2 Clades could be detected and discriminated, in a similar combinatorial fashion, via such relatively minor expansion of the core invention depicted in Table 4.

EXAMPLE 3

Test Manufacturing Considerations

The present implementation of such an oligonucleotide probe panel for analysis of the CoV-2 Spike gene is based upon detection of 15 positively selected local mutational changes in the Spike gene, i.e. Tables 4-7, each with 3 probe sequence variants at each site, "Mutant", "Wild Type", "Universal", thus generating a set of 15×3=45 oligonucleotide probes to be used for the purpose of combinatorial Clade Variant Analysis.

In the present implementation, if that set of 45 probes is manufactured in triplicate, a 3×45=135 probe microarray is thus generated, which when printed along with positive and negative controls appropriate for CoV-2 testing (such as RNAse P) the present Clade Chip Assay consumes the full microarray content capacity presented by the standard 150 probe, 96-Well format described in applications U.S. Ser. No. 16/950,171 and U.S. Ser. No. 16/950,210, both hereby incorporated by reference in their entireties.

It is useful to note that the information content of such a 150-probe microarray becomes resident in a single well of the 96-well microarray format and thus generates information content similar to that of re-sequencing of the entire gene and content that is equivalent to that obtained from 150 q-RT-PCR assays performed in parallel. As seen below, a first preferred implementation of such a Clade Chip prototype has been fabricated via standard mass production methods described in the above-referenced patent applications.

Performance

In a first preferred implementation, the sample preparation methods of the Clade Chip are optimized for both NP-Swab and Saliva collection and designed to detect CoV-2 at 5 virus/RT-PCR reaction sensitivity (500 cp/ml) and resolve multiple CoV-2 Clade variants of present international concern (Denmark, UK, S Africa, Brazil/Japan, India, CA L452R, Wuhan), as depicted in Tables 4-7.

So long as any new CoV-2 Clade may be detected and discriminated via its pattern of Spike gene gRNA sequence change, that additional Clade sequence content (cells with superscript "3" in Table 4) can be designed and added to the manufacture of the present invention in less than 2-weeks, as the need for new or broader-range CoV-2 Clade Variant detection emerges.

The Clade-Chip Assay in the present preferred implementation is based on a standard 96-well plate microarray processing workflow already described in applications having U.S. Ser. No. 16/950,171 and U.S. Ser. No. 16/950,210 both hereby incorporated by reference in their entireties and is deployed in that standard 96-well format as a manual or automated test. However, the matrix of oligonucleotide probes of the present invention to detect CoV-2 Clade Variants via Combinatorial Analysis could, in principle, be implemented by other methods of microarray manufacture or via alternative methods of bead-based solution phase nucleic acid hybridization. Additionally, the same principles of Combinatorial Analysis could be used to develop analogous tests for clade variation in other viruses, bacterial and fungi in the microarray or other hybridization formats.

EXAMPLE 4

Clade Array Manufacturing Quality and Functional Characterization

The Clade Chip Test Design summary is shown in Table 9 and is suited for combinatorial analysis among multiple Spike Targets. The following are its features;

1. Core Content, Completed (11) Target Sites, >3 Probes Each (Universal, Mutant, Wild Type)=11×3×3=99 probe spots
2. Additional (Future Clade) Content Array Real-estate,
    a. Up to 8 additional Target sites can be added to current Clade Array
    b. 9×3×3=81 additional probe spots.

Clade Variant Content as Printed

A Clade Chip Probe layout was set up in duplicate. The probe content included three (3) probes for each Spike target site (Universal, Mutant, Wild Type). Validation testing was used to pick the best" of the two closely related "redundant" lead designs for each of the three probes. In addition to the core set of 11 spike targets, new probe designs were included to expand the content of the assay. The full set of redundant probe content was printed in duplicate as a 12 x 16 probe array in a 96-well format (Table 10). The forward (odd numbers) and reverse (even numbers) primer sequences for each amplimer employed in this assay are shown in Table 11.

TABLE 9

Validation of test design for the five prevalent Clade variants

| Spike Gene Target Region (Codon) Amino Acid Change | | | S13I | L18F | T20N | P26S | Δ69-70 | D80A | D138Y | Y144D |
|---|---|---|---|---|---|---|---|---|---|---|
| Mutation specific Probe coverage | | | | | | | ✓[1] | ✓[1] | ✓[1] | |
| Wuhan reference specific probe/s coverage | | | | | | | ✓[2] | ✓[2] | ✓[2] | |
| Locus specific Probe coverage | | | | | | | N/A | ✓ | ✓ | |
| Region | Lineage Designation Var | | | | | | | | | |
| Denmark | Mink V | B.1.1.298 | S[3] | L[3] | T[3] | P[3] | Δ[1] | D[2] | D[2] | Y[3] |
| UK | GR/501Y.V1 | B.1.1.7 | S[3] | L[3] | T[3] | P[3] | Δ[1] | D[2] | D[2] | Δ[3] |
| SA | GH/501Y.V2 | B.1.351 | S[3] | L[3] | T[3] | P[3] | HV[2] | A[1] | D[2] | Y[3] |
| Brazil/Japan | P.1 | | S[3] | F[3] | N[3] | S[3] | HV[2] | D[2] | Y[1] | Y[3] |
| Brazil | P.2 | | S[3] | L[3] | T[3] | P[3] | HV[2] | D[2] | D[2] | Y[3] |
| California | CAL.20C-GH/452R.V1 | B.1.429 | I[3] | L[3] | T[3] | P[3] | HV[2] | D[2] | D[2] | Y[3] |
| India | (Andhra Pradesh) | N440K | S[3] | L[3] | T[3] | P[3] | HV[2] | D[2] | D[2] | Y[3] |
| S. US | 20G/B.1.2 | Q677P/H | S[3] | L[3] | T[3] | P[3] | HV[2] | D[2] | D[2] | Y[3] |
| WUHAN | | WUHAN | S[3] | L[3] | T[3] | P[3] | HV[2] | D[2] | D[2] | Y[3] |
| | | | | | | | ✓[4] | ✓[5] | ✓[4] | |
| | | | | (1) 101 | | | | (2) | (3)129 | |

| Spike Gene Target Region (Codon) Amino Acid Change | | | W152C | R190S | D215G | A243del | R246I | K417N | N440K | L452R |
|---|---|---|---|---|---|---|---|---|---|---|
| Mutation specific Probe coverage | | | ✓[1] | | | | | | ✓[1] | ✓[1] |
| Wuhan reference specific probe/s coverage | | | ✓[2] | | | | | | ✓[2] | ✓[2] |
| Locus specific Probe coverage | | | ✓ | | | | | | ✓ | ✓ |
| Region | Lineage Designation Var | | | | | | | | | |
| Denmark | Mink V | B.1.1.298 | W[2] | R[3] | D[3] | A[3] | R[3] | K[3] | N[2] | L[2] |
| UK | GR/501Y.V1 | B.1.1.7 | W[2] | R[3] | D[3] | A[3] | R[3] | K[3] | N[2] | L[2] |
| SA | GH/501Y.V2 | B.1.351 | W[2] | R[3] | G[3] | Δ[3] | I[3] | N[3] | N[2] | L[2] |
| Brazil/Japan | P.1 | | W[2] | S[3] | D[3] | A[3] | R[3] | T[3] | N[2] | L[2] |
| Brazil | P.2 | | W[2] | R[3] | D[3] | A[3] | R[3] | K[3] | N[2] | L[2] |
| California | CAL.20C-GH/452R.V1 | B.1.429 | C[1] | R[3] | D[3] | A[3] | R[3] | K[3] | N[2] | R[1] |
| India | (Andhra Pradesh) | N440K | W[2] | R[3] | D[3] | A[3] | R[3] | K[3] | K[1] | L[2] |
| S. US | 20G/B.1.2 | Q677P/H | W[2] | R[3] | D[3] | A[3] | R[3] | K[3] | N[2] | L[2] |
| WUHAN | | WUHAN | W[2] | R[3] | D[3] | A[3] | R[3] | K[3] | N[2] | L[2] |
| | | | ✓[4] | | | | | | ✓[4] | ✓[4] |
| | | | (3)129 | | | (4) 160 | | | (5) 199 | |

| Spike Gene Target Region (Codon) Amino Acid Change | | | Y453F | E484K | N501Y | A570D | D614G | H655Y | Q677P/H | P681H |
|---|---|---|---|---|---|---|---|---|---|---|
| Mutation specific Probe coverage | | | | ✓[1] | ✓[1] | | ✓[1] | | | ✓[1] |
| Wuhan reference specific probe/s coverage | | | | ✓[2] | ✓[2] | | ✓[2] | | | ✓[2] |
| Locus specific Probe coverage | | | | ✓ | ✓ | | ✓ | | | ✓ |
| Region | Lineage Designation Var | | | | | | | | | |
| Denmark | Mink V | B.1.1.298 | F[3] | E[2] | N[2] | A[3] | G[1] | H[3] | Q[3] | P[2] |
| UK | GR/501Y.V1 | B.1.1.7 | Y[3] | E[2] | Y[1] | D[3] | G[1] | H[3] | Q[3] | H[1] |
| SA | GH/501Y.V2 | B.1.351 | Y[3] | K[1] | Y[1] | A[3] | G[1] | H[3] | Q[3] | P[2] |
| Brazil/Japan | P.1 | | Y[3] | K[1] | Y[1] | A[3] | G[1] | Y[3] | Q[3] | P[2] |
| Brazil | P.2 | | Y[3] | K[1] | N[2] | A[3] | G[1] | H[3] | Q[3] | P[2] |
| California | CAL.20C-GH/452R.V1 | B.1.429 | Y[3] | E[2] | N[2] | A[3] | G[1] | H[3] | Q[3] | P[2] |
| India | (Andhra Pradesh) | N440K | Y[3] | E[2] | N[2] | A[3] | G[1] | H[3] | Q[3] | P[2] |
| S. US | 20G/B.1.2 | Q677P/H | Y[3] | E[2] | N[2] | A[3] | G[1] | H[3] | P/H | P[2] |
| WUHAN | | WUHAN | Y[3] | E[2] | N[2] | A[3] | D[2] | H[3] | Q[3] | P[2] |
| | | | | ✓[5] | ✓[4] | | ✓[4] | | | ✓[4] |
| | | | (5) 199 | (6) 151 | | | (7) 88 | | (8) 135 | |

| Spike Gene Target Region (Codon) Amino Acid Change | | | I692V | A701V | T716I | S982A | T1027I | D1118 | V1176 | M1229I |
|---|---|---|---|---|---|---|---|---|---|---|
| Mutation specific Probe coverage | | | | ✓[1] | | | | | | |
| Wuhan reference specific probe/s coverage | | | | ✓[2] | | | | | | |
| Locus specific Probe coverage | | | | ✓ | | | | | | |
| Region | Lineage Designation Var | | | | | | | | | |
| Denmark | Mink V | B.1.1.298 | V[3] | A[2] | T[3] | S[3] | T[3] | D[3] | V[3] | I[3] |
| UK | GR/501Y.V1 | B.1.1.7 | I[3] | A[2] | I[3] | A[3] | T[3] | H[3] | V[3] | M[3] |
| SA | GH/501Y.V2 | B.1.351 | I[3] | V[1] | T[3] | S[3] | T[3] | D[3] | V[3] | M[3] |
| Brazil/Japan | P.1 | | I[3] | A[2] | T[3] | S[3] | I[3] | D[3] | F[3] | M[3] |
| Brazil | P.2 | | I[3] | A[2] | T[3] | S[3] | T[3] | D[3] | F[3] | M[3] |
| California | CAL.20C-GH/452R.V1 | B.1.429 | I[3] | A[2] | T[3] | S[3] | T[3] | D[3] | V[3] | M[3] |

TABLE 9-continued

| Validation of test design for the five prevalent Clade variants | | | | | | | | | | |
|---|---|---|---|---|---|---|---|---|---|---|
| India | (Andhra Pradesh) | N440K | I[3] | A[2] | T[3] | S[3] | T[3] | D[3] | V[3] | M[3] |
| S. US | 20G/B.1.2 | Q677P/H | I[3] | A[2] | T[3] | S[3] | T[3] | D[3] | V[3] | M[3] |
| WUHAN | | WUHAN | I[3] | A[2] | T[3] | S[3] | T[3] | D[3] | V[3] | M[3] |
| | | | | ✓[4] | | | | | | |
| | | | (8) 135 | | | | | | | |

[1]AA mutation - hybridizes to mutation specific probe
[2]AA identical to hCoV-19/Wuhan/WIV04/2019 (WIV04) - official reference sequence employed by GISAID (EPI_ISL_402124). Hybridizes to reference specific probe
[3]Potential probe target
[4]No Probe Adjustment Necessary
[5]Minor Probe Adjustment Necessary

TABLE 10

Clade chip probe layout

| Row | Col. | SEQ ID NOS. | Amplimer # | Target | Probe Sequence (5' to 3') |
|---|---|---|---|---|---|
| 1 | 1 | SEQ ID NO: 30 | 1 | AA S13I | TTTTTCTAGTCTCTAKTCAGTGTGTTTTTT |
| 1 | 2 | SEQ ID NO: 64 | 1 | AA S13_ (1) | TTTTTTTGTCTCTAGTCAGTGTTTTTTTTT |
| 1 | 3 | SEQ ID NO: 65 | 1 | AA S13_ (2) | TTTTTTTAGTCTCTAGTCAGTGTTTTTTTT |
| 1 | 4 | SEQ ID NO: 66 | 1 | AA_13I (1) | TTTTTTAGTCTCTATTCAGTGTTTTTTTTT |
| 1 | 5 | SEQ ID NO: 67 | 1 | AA_13I (2) | TTTTTTTAGTCTCTATTCAGTGTTTTTTTT |
| 1 | 6 | SEQ ID NO: 68 | 1 | AA T20N | TTTTTTAATYTTACAAMCAGAACTCTTTTT |
| 1 | 7 | SEQ ID NO: 69 | 1 | AA T20_ (1) | TTTTTTTATCTTACAACCAGAACCTTTTTT |
| 1 | 8 | SEQ ID NO: 70 | 1 | AA T20_ (2) | TTTTTTTATCTTACAACCAGAACTTTTTTT |
| 1 | 9 | SEQ ID NO: 71 | 1 | AA_20N (1) | TTTTTTATTTTACAAACAGAACTTTTTTTT |
| 1 | 10 | SEQ ID NO: 72 | 1 | AA_20N (2) | TTTTTCAATTTTACAAACAGAACTTTTTTT |
| 1 | 11 | SEQ ID NO: 68 | | RNAse P control | TTTTTTTTCTGACCTGAAGGCTCTGCGCGTTTTT |
| 1 | 12 | SEQ ID NO: 73 | 2 | AA69-70 HV (1) | TTTTTTATGCTATACATGTCTCTGTTTTTT |
| 2 | 1 | SEQ ID NO: 31 | 2 | AA69-70 HV (2) | TTTTTCCCATGCTATACATGTCTCTGTTTTTT |
| 2 | 2 | SEQ ID NO: 74 | 2 | AA69-70 DEL (1) | TTTTTTACCATGCTATCTCTGGGATTTTTT |
| 2 | 3 | SEQ ID NO: 32 | 2 | AA69-70 DEL (2) | TTTTTTTTTCCATGCTATCTCTGGGATTTTTT |
| 2 | 4 | SEQ ID NO: 33 | 2 | AA D80A | TTTTTCAGAGGTTTGMTAACCCTGTCTTTTTT |
| 2 | 5 | SEQ ID NO: 34 | 2 | AA D80_ (1) | TTTTTTTGGTTTGATAACCCTGCTTTTTTT |
| 2 | 6 | SEQ ID NO: 75 | 2 | AA D80_ (2) | TTTTTCTAGGTTTGATAACCCTGCTTTTTT |
| 2 | 7 | SEQ ID NO: 76 | 2 | AA_80A (1) | TTTTTTTAGGTTTGCTAACCCTCTTTTTTT |
| 2 | 8 | SEQ ID NO: 35 | 2 | AA_80A (2) | TTTTTTTGGTTTGCTAACCCTGCTTTTTTT |
| 2 | 9 | SEQ ID NO: 36 | 3 | AA D138Y | TTTTATTTTGTAATKATCCATTTTTGTTTT |
| 2 | 10 | SEQ ID NO: 37 | 3 | AA D138_ (1) | TTTTTCTTTGTAATGATCCATTTTCTTTTT |
| 2 | 11 | SEQ ID NO: 77 | 3 | AA D138_ (2) | TTTTTTCTTTGTAATGATCCATTTCTTTTT |
| 2 | 12 | SEQ ID NO: 38 | 3 | AA_138Y (1) | TTTTTTTTTGTAATTATCCATTTTCTTTTT |
| 3 | 1 | SEQ ID NO: 78 | 3 | AA_138Y (2) | TTTTTCTTTGTAATTATCCATTTTCTTTTT |
| 3 | 2 | SEQ ID NO: 39 | 3 | AA W152C | TTTTTAGTTGKATGGAAAGTGAGTTCTTTT |
| 3 | 3 | SEQ ID NO: 40 | 3 | AA W152_ (1) | TTTCTCTAAAAGTTGGATGGAAACTCTTCT |
| 3 | 4 | SEQ ID NO: 79 | 3 | AA W152_ (2) | TTTTCTTCAAAGTTGGATGGAAACTCTTTT |
| 3 | 5 | SEQ ID NO: 41 | 3 | AA_152C (1) | TTTCTTCAAAGTTGTATGGAAAGCCTTCTT |

TABLE 10-continued

Clade chip probe layout

| Row | Col. | SEQ ID NOS. | Amplimer # | Target | Probe Sequence (5' to 3') |
|---|---|---|---|---|---|
| 3 | 6 | SEQ ID NO: 80 | 3 | AA_152C (2) | TTTCTCTAAAAGTTGTATGGAAACTCTTCT |
| 3 | 7 | SEQ ID NO: 81 | 4 | AA D215G | TTTTTTAGTGCGTGRTCTCCCTCATTTTTT |
| 3 | 8 | SEQ ID NO: 82 | 4 | AA D215_ (1) | TTTTTTCTGCGTGATCTCCCTCATTTTTTT |
| 3 | 9 | SEQ ID NO: 83 | 4 | AA D215_ (2) | TTTTTTTCTGCGTGATCTCCCTCTTTTTTT |
| 3 | 10 | SEQ ID NO: 84 | 4 | AA_215G (1) | TTTTTTTTGCGTGGTCTCCCTCTTTTTTTT |
| 3 | 11 | SEQ ID NO: 85 | 4 | AA_215G (2) | TTTTTTTTTGCGTGGTCTCCCTTTTTTTTT |
| 3 | 12 | SEQ ID NO: 86 | 5 | AA K417N | TTTTAACTGGAAAKATTGCTGATTATTTTT |
| 4 | 1 | SEQ ID NO: 87 | 5 | AA K417_ (1) | TTTCTTCTCTGGAAAGATTGCTGCTTTTTT |
| 4 | 2 | SEQ ID NO: 88 | 5 | AA K417_ (2) | TTCTTCTCTGGAAAGATTGCTGACTTTTTT |
| 4 | 3 | SEQ ID NO: 89 | 5 | AA_417N (1) | TTTTTCTCTGGAAATATTGCTGACTTTTTT |
| 4 | 4 | SEQ ID NO: 90 | 5 | AA_417N (2) | TTTTCTCTGGAAATATTGCTGATCTTTTTT |
| 4 | 5 | SEQ ID NO: 91 | 5 | AA_417T (1) | TTTTTTTACTGGAACGATTGCTTTTTTTTT |
| 4 | 6 | SEQ ID NO: 92 | 5 | AA_417T (2) | TTTTTTCCTGGAACGATTGCTGTTTTTTTT |
| 4 | 7 | SEQ ID NO: 42 | 5 | AA N439K + N440K | TTTTTAATTCTAAMAAKCTTGATTCTAATTTT |
| 4 | 8 | SEQ ID NO: 93 | 5 | AA N439_ + N440_ (1) | TTTTTTATTCTAACAATCTTGATTTCTTTT |
| 4 | 9 | SEQ ID NO: 43 | 5 | AA N439_ + N440_ (2) | TTTTTAATTCTAACAATCTTGATTTCTTTT |
| 4 | 10 | SEQ ID NO: 94 | 5 | AA N439_ + _440K (1) | TTTTTTTTTCTAACAAGCTTGATTTTTTTT |
| 4 | 11 | SEQ ID NO: 44 | 5 | AA N439_ + _440K (2) | TTTTTTATTCTAACAAGCTTGATTTTTTTT |
| 4 | 12 | SEQ ID NO: 45 | 5 | AA_439K + N440_ (1) | TTTTCTATTCTAAAAATCTTGATTTCTTTT |
| 5 | 1 | SEQ ID NO: 95 | 5 | AA_439K + N440_ (2) | TTCTTAATTCTAAAAATCTTGATTTCTTTT |
| 5 | 2 | SEQ ID NO: 46 | 5 | AA L452R | TTTCTATAATTACCTGTATAGATTGTCTTT |
| 5 | 3 | SEQ ID NO: 96 | 5 | AA L452_ (1) | TTTTTCATAATTACCTGTATAGACTTTCTT |
| 5 | 4 | SEQ ID NO: 47 | 5 | AA L452_ (2) | TTTTTTTAATTACCTGTATAGATTTCTTTT |
| 5 | 5 | SEQ ID NO: 48 | 5 | AA_452R (1) | TTTTTCATAATTACTGGTATAGATCTTTTT |
| 5 | 6 | SEQ ID NO: 97 | 5 | AA_452R (2) | TTTTTTCAATTACCGGTATAGATCTTTTTT |
| 5 | 7 | SEQ ID NO: 49 | 6 | AA S477_ | TTTTTTCGCCGGTAGCACACCTCTTTTTTT |
| 5 | 8 | SEQ ID NO: 98 | 6 | AA_478I (1) | TTTTTTTTGGTAGCATACCTTGTTTTTTTT |
| 5 | 9 | SEQ ID NO: 99 | 6 | AA_478I (2) | TTTTTTTCGGTAGCATACCTTGTTTTTTT |
| 5 | 10 | SEQ ID NO: 50 | 6 | AA_477N (1) | TTTTCTTCCGGTAACACACCTTTTTTTTTT |
| 5 | 11 | SEQ ID NO: 100 | 6 | AA_477N (2) | TTTTTTCGCCGGTAACACACCTCTTTTTTT |
| 5 | 12 | SEQ ID NO: 101 | 6 | AA_476S (1) | TTTTTTTTCAGGCCAGTAGCACTTTTTTTT |
| 6 | 1 | SEQ ID NO: 51 | 6 | AA V483A + E484K | TTTTTTAATGGTGTTRAAGGTTTTAATTTTTT |
| 6 | 2 | SEQ ID NO: 52 | 6 | AA V483_ + E484_ (1) | TTTTTTCTGGTGTTGAAGGTTTTACTTTTT |
| 6 | 3 | SEQ ID NO: 102 | 6 | AA V483_ + E484_ (2) | TTTTTCTGGTGTTGAAGGTTTTATCTTTTT |
| 6 | 4 | SEQ ID NO: 103 | 6 | AA V483_ + _484K (1) | TTTTTTCTGGTGTTAAAGGTTTTACTTTTT |
| 6 | 5 | SEQ ID NO: 53 | 6 | AA V483_ + _484K (2) | TTTTTTTATGGTGTTAAAGGTTTTCTTTTT |
| 6 | 6 | SEQ ID NO: 54 | 6 | AA_483A + E484_ (1) | TTTTTTTATGGTGCTGAAGGTTCTTTTTTT |

TABLE 10-continued

Clade chip probe layout

| Row | Col. | SEQ ID NOS. | Amplimer # | Target | Probe Sequence (5' to 3') |
|---|---|---|---|---|---|
| 6 | 7 | SEQ ID NO: 104 | 6 | AA_483A + E484_ (2) | TTTTTTCAATGGTGCTGAAGGTTCTTTTTT |
| 6 | 8 | SEQ ID NO: 55 | 6 | AA N501Y | TTTTTTTTCCAACCCACTWATGGTGTTTTTTTT |
| 6 | 9 | SEQ ID NO: 56 | 6 | AA N501_ (1) | TTTTTTTTACCCACTAATGGTGTCTTTTTT |
| 6 | 10 | SEQ ID NO: 105 | 6 | AA N501_ (2) | TTTTTTTAACCCACTAATGGTGTCTTTTTT |
| 6 | 11 | SEQ ID NO: 57 | 6 | AA_501Y (1) | TTTTTTTTACCCACTTATGGTGTCTTTTTT |
| 6 | 12 | SEQ ID NO: 106 | 6 | AA_501Y (2) | TTTTTTTAACCCACTTATGGTGTCTTTTTT |
| 7 | 1 | SEQ ID NO: 107 | 7 | AA D614G | TTTTTCTCTTTATCARGRTGTTAACTGCTTTTTT |
| 7 | 2 | SEQ ID NO: 108 | 7 | AA D614_ | TTTTTCTTATCAGGATGTTAACTTTTTTTT |
| 7 | 3 | SEQ ID NO: 109 | 7 | AA_614G + 613 (CAG) | TTTTTTCCTATCAGGGTGTTAACTTTTTTT |
| 7 | 4 | SEQ ID NO: 110 | 7 | AA_614G + 613 (CAA) | TTTTTTCCTATCAAGGTGTTAACTTTTTTT |
| 7 | 5 | SEQ ID NO: 111 | 7 | AA_614G | TTTTTTCCTATCARGGTGTTAACTTTTTTT |
| 7 | 6 | SEQ ID NO: 58 | 8 | AA P681H | TTTTTTCAGACTAATTCTCMTCGGCTTTTT |
| 7 | 7 | SEQ ID NO: 112 | 8 | AA P681_ (1) | TTTTTTTTAATTCTCCTCGGCGTTTTTTTT |
| 7 | 8 | SEQ ID NO: 59 | 8 | AA P681_ (2) | TTTTTTTCTAATTCTCCTCGGCGTTTTTTT |
| 7 | 9 | SEQ ID NO: 60 | 8 | AA_681H (1) | TTTTTTTTTAATTCTCATCGGCGTTTTTTT |
| 7 | 10 | SEQ ID NO: 113 | 8 | AA_681H (2) | TTTTTTTCTAATTCTCATCGGCGTTTTTTT |
| 7 | 11 | SEQ ID NO: 61 | 8 | AA A701V | TTTTCACTTGGTGYAGAAAATTCAGTTTTT |
| 7 | 12 | SEQ ID NO: 62 | 8 | AA A701_ (1) | TCTTCTTCTTGGTGCAGAAAATTATTCTTT |
| 8 | 1 | SEQ ID NO: 114 | 8 | AA A701_ (2) | TTCTTCTACTTGGTGCAGAAAATTATTCTT |
| 8 | 2 | SEQ ID NO: 63 | 8 | AA_701V (1) | TCTTCTTCTTGGTGTAGAAAATTATTCTTT |
| 8 | 3 | SEQ ID NO: 115 | 8 | AA_701V (2) | TTTCTTTCTTGGTGTAGAAAATTCTTTTTT |
| 8 | 4 | SEQ ID NO: 116 | | N2 | TTTTTTACAATTTGCCCCCAGCGTCTTTTT |
| 8 | 5 | SEQ ID NO: 117 | | SARS-2003 N2 | TTTTTTTTTGCTCCRAGTGCCTCTTTTTTT |
| 8 | 6 | SEQ ID NO: 70 | | Negative Control | TTTTTTCTACTACCTATGCTGATTCACTCTTTTT |
| 8 | 7 | EMPTY | | | |
| 8 | 8 | EMPTY | | | |
| 8 | 9 | EMPTY | | | |
| 8 | 10 | EMPTY | | | |
| 8 | 11 | EMPTY | | | |
| 8 | 12 | EMPTY | | | |

TABLE 11

Amplimer primer sequences

| SEQ ID NOS. | Amplimer # | Target | Gene | Primer Sequence (5' to 3') |
|---|---|---|---|---|
| SEQ ID NO: 25 | 2 | AA66-85 | Spike | TTCTTTTCCAATGTTACTTGGTT CCATG |
| SEQ ID NO: 26 | 2 | AA66-85 | Spike | Cy3-TTTCAAAATAAACACCATC ATTAAATGG |
| SEQ ID NO: 11 | 3 | AA126-157 | Spike | TTTCTTATTGTTAATAACGCTAC TAATG |
| SEQ ID NO: 12 | 3 | AA126-157 | Spike | Cy3-TTTCATTCGCACTAGAATA AACTCTGAA |
| SEQ ID NO: 27 | 5 | AA413-458 | Spike | TTTGATGAAGTCAGACAAATCG CTCCAG |
| SEQ ID NO: 28 | 5 | AA413-458 | Spike | Cy3-TTTCTCTCAAAAGGTTTGA GATTAGACT |
| SEQ ID NO: 15 | 6 | AA475-506 | Spike | TTTTATTTCAACTGAAATYTATCA GGCC |
| SEQ ID NO: 16 | 6 | AA475-506 | Spike | Cy3-TTTAAAGTACTACTACTCT GTATGGTTG |
| SEQ ID NO: 29 | 7 | AA610-618 | Spike | TTTCAAATACTTCTAACCAGGTT GCTGT |
| SEQ ID NO: 24 | 7 | AA610-618 | Spike | Cy3-TTTTGCATGAATAGCAACA GGGACTTCT |
| SEQ ID NO: 17 | 8 | AA677-707 | Spike | TTTTATATGCGCTAGTTATCAGA CTCAG |
| SEQ ID NO: 18 | 8 | AA677-707 | Spike | Cy3-TTTTGGTATGGCAATAGAG TTATTAGAG |

EXAMPLE 5

Clade Array Functional Characterization

Experiment 1

Samples Used for Testing. Analysis was performed with a highly characterized, purified Wuhan gRNA standard (Quantitative Standard obtained from ATCC-BEI) or with synthetic "mutant" targets designed by PDx, obtained by SGI fabrication (IDT).

RT-PCR Conditions. RT-PCR was performed using the [UNG+One-Step RT-PCR] protocol. As is customary in optimization of multiplex RT-PCR, the data presented comprise the use of Single PCR primer pairs as a single reaction. Based on these data multiplex RT-PCR conditions are optimized.

Clade Array Hybridization & Imaging. Conditions of Hybridization, Washing and Imaging were exactly as described. Following the completion of the multiplex RT-PCR, the DNA microarray was prepared for hybridization with brief water washes, and an incubation in prehybridization buffer (0.6M NaCl, 0.06M sodium citrate solution, 0.1% Ficoll, 0.1% Polyvinylpyrrolidone 0.1% Bovine Serum Albumin). Following aspiration of the prehybridization buffer, a mixture of amplicon and hybridization buffer (0.6M NaCl, 0.06M sodium citrate solution, 0.1% Ficoll, 0.1% Polyvinylpyrrolidone 0.1% Bovine Serum Albumin) was added to the DNA microarray and allowed to incubate for 2 hours. The microarray was prepared for imaging with one quick wash of wash buffer (22.5 mM NaCl, 2.25 mM sodium citrate solution) and a 10-minute incubation (22.5 mM NaCl, 2.25 mM sodium citrate solution). The microarray plate was then spun dry for 5 minutes at 2200 rpm. The underside of the plate was wiped clean with 70% ethanol and lens tissue until all dust particles were removed. The plate was scanned on the Sensospot utilizing Sensovation software. Cy5 exposure time was set at 312 ms, and the Cy3 exposure times at 115 ms and 578 ms. Upon image scanning completion, the folder containing all of the scanned data was saved to a thumb drive and uploaded to Dropbox for Augury Analysis.

Data Analysis. Data for all (11) Core Spike Target Sites are presented in FIGS. 1-11. For all Spike Target sites, data is presented as a bar graph, where the ratio of hybridization signal strength for Wild Type vs Mutant Probes define the specificity of analysis.

a) Left Side of each bar graph shows hybridization data derived from analysis of the "Mutant" synthetic CoV-2 target sequence appropriate for that site.
b) Right Side of each bar graph displays the corresponding data obtained for the "Wild Type" Wuhan gRNA reference sequence.
c) In the analysis of each bar graph at each target site, the parameter of analytical importance is the hybridization signal strength (RFU) ratio obtained by comparison of RT-PCR amplimer hybridization to the Mutant-Specific vs Wild-Type specific probe which can be presented as $[RFU_{wt}/RFU_{mt}]$.

i. Criterion #1. Primary Data. The $[RFU_{wt}/RFU_{mt}]$ ratio should differ significantly (>5×) upon comparison of "Wild Type" CoV2 genome hybridization at that site, vs "Mutant" Template hybridization measured at that same site.

ii. Criterion #2. Optimal but not necessarily. The [$RFU_{wt}$/$RFU_{mt}$] ratio should change qualitatively upon CoV2 hybridization analysis of a "Wild Type" CoV2 genome at that site, vs a "Mutant" Template measured at that site. i.e.

Wild-Type Template 4→[$RFU_{wt}$/$RFU_{mt}$]>1

Mutant Template 4→[$RFU_{wt}$/$RFU_{mt}$]<1

Clade Array Results a) The Data, Presented in FIGS. 1-11 demonstrate that all (11) Spike Target sites show generally excellent hybridization-based discrimination between Wild Type vs Mutant Sequence Variants by the primary Criterion #1 listed above.

b) For (9) of the 11, Both Criterion #1 and Criterion #2 have been met. All such sites are thus marked among FIGS. 1-11 as "No Additional Probe Optimization Required" and are marked by a "*" below their location in the probe matrix of Table 9.

c) For two of the 11 Spike Target sites (D80A and E484K, FIGS. 2 and 7), Criterion #2 was not met adequately.

d) Only two Probes need Optimization. In two cases (Target Sites D80A and E484K) although the Wild Type (Wuhan gRNA) is easily distinguished from the Mutant based on significant differences in relative hybridization (Criterion #1, above), the Mutant/Wild Type distinction does not change sign (Criterion #2). Thus, although the data obtained at those (2) sites (D80A, E484K) is adequate at present to make accurate "Clade Calls", modest Optimization (1 Probe at each site) can be deployed quickly to enhance the quality of the data obtained there.

e) Experience and general understanding of nucleic acid biophysics suggest that the needed optimization (Target Sites D80A and E484K) was obtainable by simply reducing the length of one probe at each site by 2 bases. As soon as the need for such.

SUMMARY

The Clade Array Probe Content was found to be fully functional. An optimized shorter probe was seen to improve Cov-2 mutant analysis at target sites D80A and E484K.

Experiment 2

A second 15 Plate Manufacturing Run (#2) of DETECTX-Cv, similar to the one described in Experiment 1 above was implemented to complete validation of the Multiplex assay. In this assessment, print quality passed the test for all 96 (160 probe) arrays among all 15 plates.

The second set of validation tests sought to evaluate the preferred method of multiplexing of the RT-PCR reaction, using the UNG combined with One Step RT-PCR condition. The primary goal was to deliver a first RT-PCR Multiplex capable of distinguishing the five prevalent Clade Variants—UK (B.1.1.7), S Africa (B.1.351) Brazil (P.1) Brazil (P.2) US California (B.1.429) shown in Table 12. The validation materials comprised a purified Wuhan gRNA reference (ATCC-BEI). The data obtained subsequent to RT-PCR, hybridization and washing revealed that an initial deployment of a specific 4-plex RT-PCR reaction, comprising amplimers [2, 3, 6, 8] was sufficient to distinguish, as a single multiplex assay, these five prevalent Clade variants (FIGS. 12A-12B).

Figure 12A:
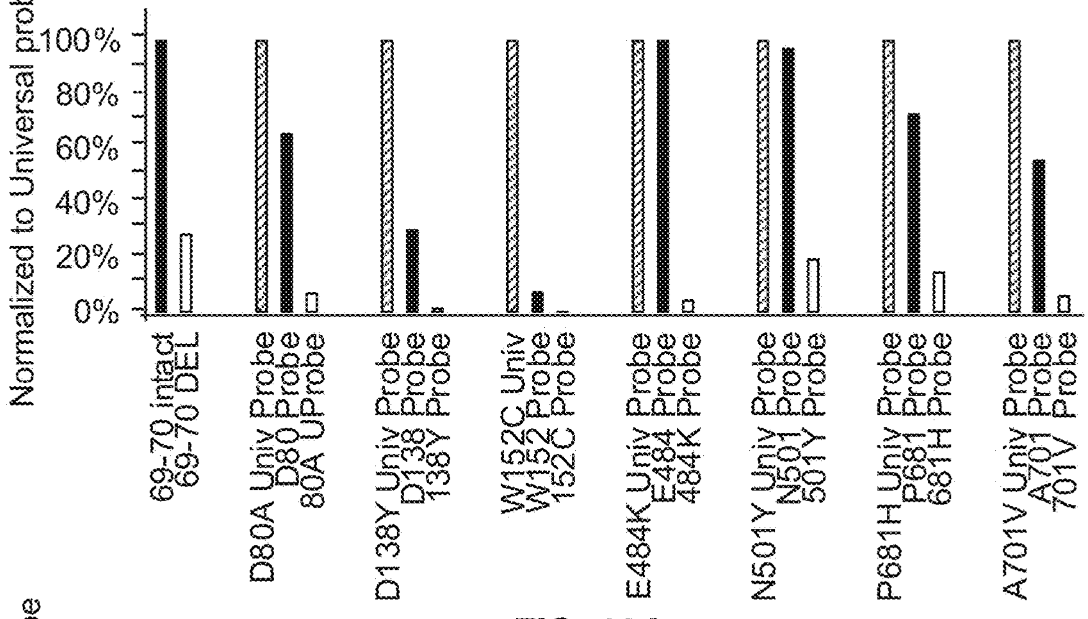
FIGS. 12A-12B shows the results of DETECTX-Cv analysis using a multiplex of Amplimers 2, 3, 6, 8.
Figure 12B:
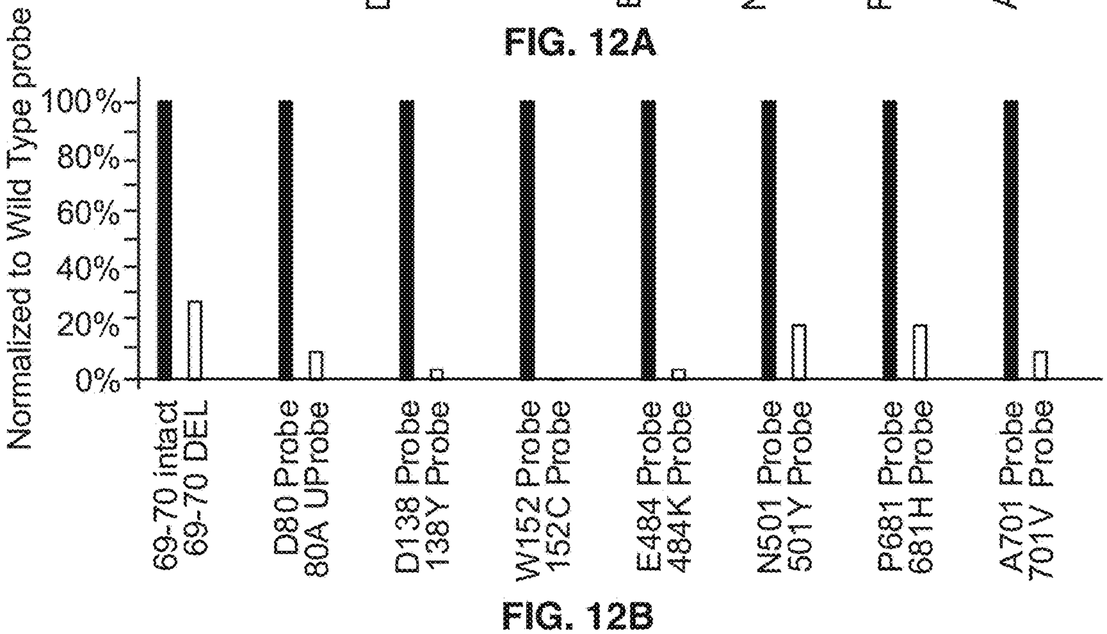

FIG. 12A shows the raw microarray hybridization data for the eight (8) target sites covered by amplimer sets 2, 3, 6 and 8 with data normalized to the Universal Probe at "100%" to emphasize the sensitivity of Universal vs Wild-Type/Mutant Target Detection. FIG. 12B shows the same raw hybridization data for the eight (8) target sites covered by the amplimer sets 2, 3, 6 and 8, but normalized to the Wild-Type probe signal, to emphasize the specificity of discrimination between Wild-Type vs Mutant target sequence.

Experiment 3

Fully Multiplexed DETECTX-Cv

A third round of validation was performed to evaluate the preferred method of multiplexing of the RT-PCR reaction, using the UNG combined with One Step RT-PCR condition. The primary goal was to deliver a second (N=5) RT-PCR Multiplex capable of distinguishing the six (6) prevalent US Clade Variants—UK (B.1.1.7), S Africa (B.1.351) Brazil (P.1) Brazil (P.2) a second redundant target in US California (B.1.429) and India N440K. shown in Table 12. The validation materials comprised a purified Wuhan gRNA reference (ATCC-BEI). The data obtained subsequent to RT-PCR, hybridization and washing revealed that a second deployment of a specific 5-plex RT-PCR reaction, comprising a N=5 multiplex of amplimers [2, 3, 5, 6, 8] was sufficient to distinguish, as a single multiplex assay, these six prevalent Clade Variants (FIGS. 13A-13B).

Figure 13A:
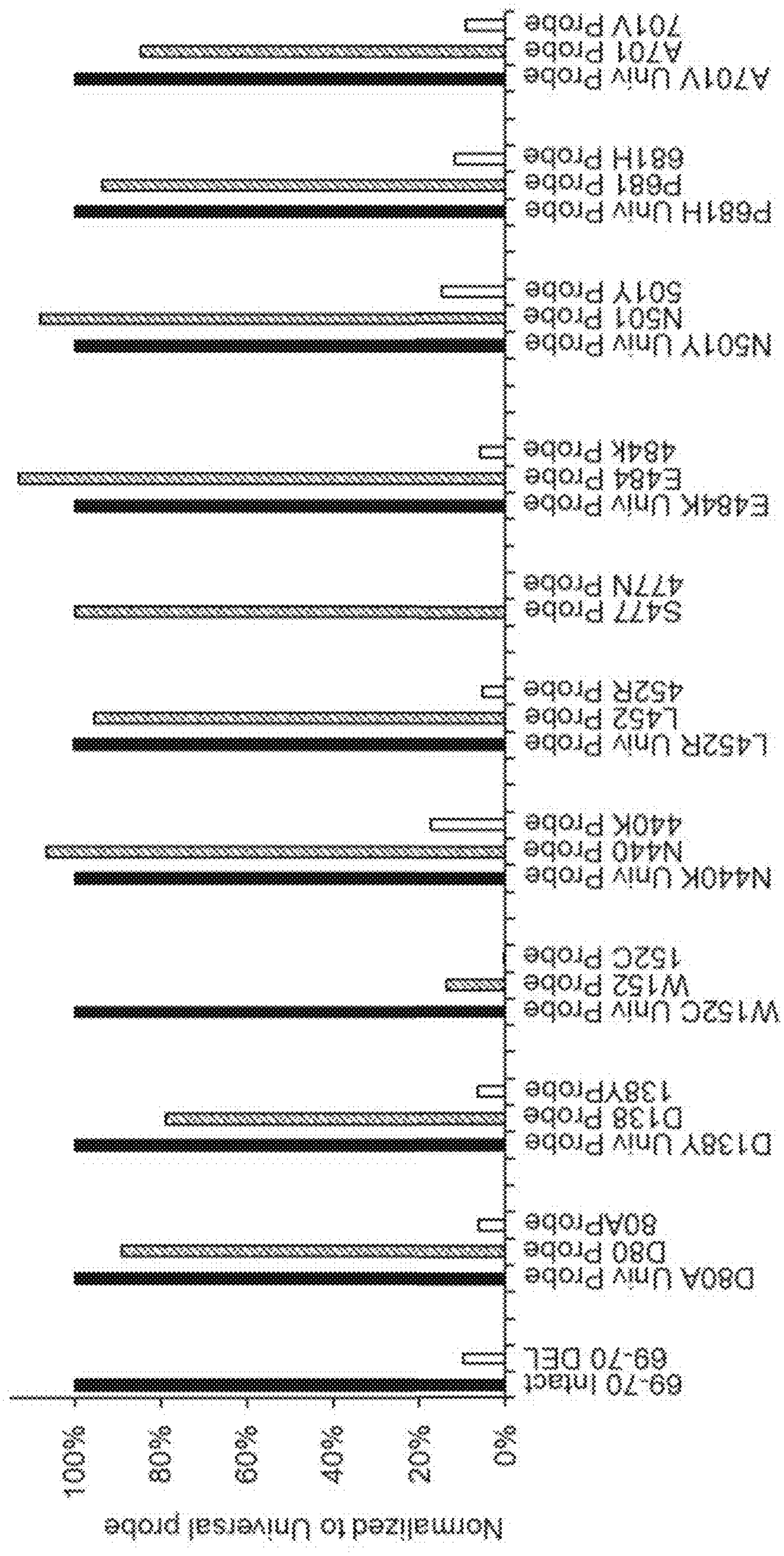
FIGS. 13A-13B shows the results of DETECTX-Cv analysis using a multiplex of Amplimers 2, 3, 5, 6, 8.
Figure 13B:
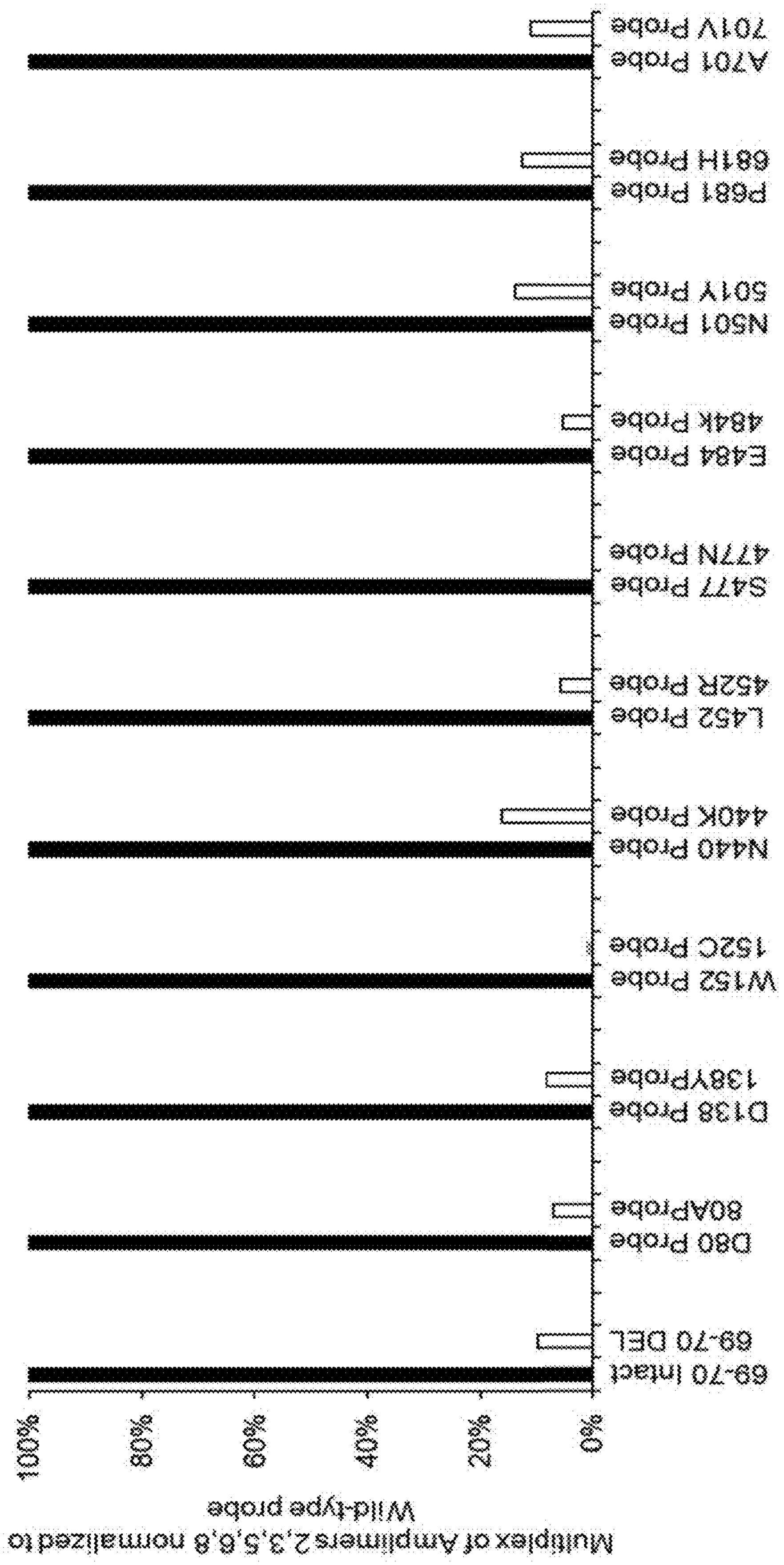

FIG. 13A shows the raw microarray hybridization data for the eleven (11) target sites covered by amplimer sets 2, 3, 5, 6 and 8 with data normalized to the Universal Probe at "100%" to emphasize the sensitivity of Universal vs Wild-Type/Mutant Target Detection. FIG. 13B shows the same raw hybridization data for the eleven (11) target sites covered by the amplimer sets 2, 3, 5, 6 and 8, but normalized to the Wild-Type probe signal, to emphasize the specificity of discrimination between Wild-Type vs Mutant target sequence.

TABLE 12

Validation of test design for the five prevalent Clade variants

| Spike Gene Target Region (Codon) Amino Acid Change | S13I | L18F | T20N | P26S | Δ69-70 | D80A | T95I | D138Y | Y144D |
|---|---|---|---|---|---|---|---|---|---|
| Mutation specific Probe coverage | | | | | ✓[1] | ✓[1] | | ✓[1] | |
| Wuhan reference specific probe/s coverage | | | | | ✓[2] | ✓[2] | | ✓[2] | |
| Locus specific Probe coverage | | | | | N/A | ✓ | | ✓ | |
| Region Lineage Designation Var | | | | | | | | | |

TABLE 12-continued

Validation of test design for the five prevalent Clade variants

| | | | | | | | | | | | |
|---|---|---|---|---|---|---|---|---|---|---|---|
| Denmark | Mink V | B.1.1.298 | $S^3$ | $L^3$ | $T^3$ | $P^3$ | $\Delta^1$ | $D^2$ | $T^3$ | $D^2$ | $Y^3$ |
| UK | GR/501Y.V1 | B.1.1.7 | $S^3$ | $L^3$ | $T^3$ | $P^3$ | $\Delta^1$ | $D^2$ | $T^3$ | $D^2$ | $\Delta^3$ |
| SA | GH/501Y.V2 | B.1.351 | $S^3$ | $L^3$ | $T^3$ | $P^3$ | $HV^2$ | $A^1$ | $T^3$ | $D^2$ | $Y^3$ |
| Brazil | P.1 | | $S^3$ | $F^3$ | $N^3$ | $S^3$ | $HV^2$ | $D^2$ | $T^3$ | $Y^1$ | $Y^3$ |
| Brazil | P.2 | | $S^3$ | $L^3$ | $T^3$ | $P^3$ | $HV^2$ | $D^2$ | $T^3$ | $D^2$ | $Y^3$ |
| California | CAL.20C-GH/452R.V1 | B.1.429 | $I^3$ | $L^3$ | $T^3$ | $P^3$ | $HV^2$ | $D^2$ | $T^3$ | $D^2$ | $Y^3$ |
| India | (Andhra Pradesh) | N440K | $S^3$ | $L^3$ | $T^3$ | $P^3$ | $HV^2$ | $D^2$ | $T^3$ | $D^2$ | $Y^3$ |
| S. US | B.1.596/B.1.2 | Q677P/H | $S^3$ | $L^3$ | $T^3$ | $P^3$ | $HV^2$ | $D^2$ | $T^3$ | $D^2$ | $Y^3$ |
| NY | Ho et al. | B.1.526a | $S^3$ | $L^3$ | $T^3$ | $P^3$ | $HV^2$ | $D^2$ | $I^3$ | $D^2$ | $Y^3$ |
| | | B.1.526b | $S^3$ | $L^3$ | $T^3$ | $P^3$ | $HV^2$ | $D^2$ | $I^3$ | $D^2$ | $Y^3$ |
| WUHAN | | WUHAN | $S^3$ | $L^3$ | $T^3$ | $P^3$ | $HV^2$ | $D^2$ | $T^3$ | $D^2$ | $Y^3$ |
| | | | | | | | ✓$^4$ | ✓$^5$ | | ✓$^4$ | |
| PCR Amplimer length (bases) | | | | | (1) 101 | | | $(2_B)$150 | | (3)129 | |

| Spike Gene Target Region (Codon) Amino Acid Change | | | W152C | R190S | D215G | A243del | R246I | D253G | K417N | N440K | L452R |
|---|---|---|---|---|---|---|---|---|---|---|---|
| Mutation specific Probe coverage | | | ✓$^1$ | | | ✓$^1$ | ✓$^1$ | ✓$^1$ | ✓$^1$ | ✓$^1$ | ✓$^1$ |
| Wuhan reference specific probe/s coverage | | | ✓$^2$ | | | ✓$^2$ | ✓$^2$ | ✓$^2$ | ✓$^2$ | ✓$^2$ | ✓$^2$ |
| Locus specific Probe coverage | | | ✓ | | | ✓ | ✓ | ✓ | ✓ | ✓ | ✓ |
| Region | Lineage | Designation Var | | | | | | | | | |
| Denmark | Mink V | B.1.1.298 | $W^2$ | $R^3$ | $D^3$ | $A^2$ | $R^2$ | $D^2$ | $K^2$ | $N^2$ | $L^2$ |
| UK | GR/501Y.V1 | B.1.1.7 | $W^2$ | $R^3$ | $D^3$ | $A^2$ | $R^2$ | $D^2$ | $K^2$ | $N^2$ | $L^2$ |
| SA | GH/501Y.V2 | B.1.351 | $W^2$ | $R^3$ | $G^3$ | $\Delta^1$ | $I^1$ | $D^2$ | $N^1$ | $N^2$ | $L^2$ |
| Brazil | P.1 | | $W^2$ | $S^3$ | $D^3$ | $A^2$ | $R^2$ | $D^2$ | $T^1$ | $N^2$ | $L^2$ |
| Brazil | P.2 | | $W^2$ | $R^3$ | $D^3$ | $A^2$ | $R^2$ | $D^2$ | $K^2$ | $N^2$ | $L^2$ |
| California | CAL.20C-GH/452R.V1 | B.1.429 | $C^1$ | $R^3$ | $D^3$ | $A^2$ | $R^2$ | $D^2$ | $K^2$ | $N^2$ | $R^1$ |
| India | (Andhra Pradesh) | N440K | $W^2$ | $R^3$ | $D^3$ | $A^2$ | $R^2$ | $D^2$ | $K^2$ | $K^1$ | $L^2$ |
| S. US | B.1.596/B.1.2 | Q677P/H | $W^2$ | $R^3$ | $D^3$ | $A^2$ | $R^2$ | $D^2$ | $K^2$ | $N^2$ | $L^2$ |
| NY | Ho et al. | B.1.526a | $W^2$ | $R^3$ | $D^3$ | $A^2$ | $R^2$ | $G^1$ | $K^2$ | $N^2$ | $L^2$ |
| | | B.1.526b | $W^2$ | $R^3$ | $D^3$ | $A^2$ | $R^2$ | $G^1$ | $K^2$ | $N^2$ | $L^2$ |
| WUHAN | | WUHAN | $W^2$ | $R^3$ | $D^3$ | $A^2$ | $R^2$ | $D^2$ | $K^2$ | $N^2$ | $L^2$ |
| | | | ✓$^4$ | | | | | | | ✓$^4$ | ✓$^4$ |
| PCR Amplimer length (bases) | | | (3)129 | | | | $(4_B)$ 160 | | | (5) 199 | |

| Spike Gene Target Region (Codon) Amino Acid Change | | | Y453F | S477N | E484K | N501Y | A570D | D614G | H655Y | Q677P/H | P681H |
|---|---|---|---|---|---|---|---|---|---|---|---|
| Mutation specific Probe coverage | | | | ✓$^1$ | ✓$^1$ | ✓$^1$ | | ✓$^1$ | | ✓$^1$ | ✓$^1$ |
| Wuhan reference specific probe/s coverage | | | | ✓$^2$ | ✓$^2$ | ✓$^2$ | | ✓$^2$ | | ✓$^2$ | ✓$^2$ |
| Locus specific Probe coverage | | | | ✓ | ✓ | ✓ | | ✓ | | ✓ | ✓ |
| Region | Lineage | Designation Var | | | | | | | | | |
| Denmark | Mink V | B.1.1.298 | $F^3$ | $S^2$ | $E^2$ | $N^2$ | $A^3$ | $G^1$ | $H^3$ | $Q^2$ | $P^2$ |
| UK | GR/501Y.V1 | B.1.1.7 | $Y^3$ | $S^2$ | $E^2$ | $Y^1$ | $D^3$ | $G^1$ | $H^3$ | $Q^2$ | $H^1$ |
| SA | GH/501Y.V2 | B.1.351 | $Y^3$ | $S^2$ | $K^1$ | $Y^1$ | $A^3$ | $G^1$ | $H^3$ | $Q^2$ | $P^2$ |
| Brazil | P.1 | | $Y^3$ | $S^2$ | $K^1$ | $Y^1$ | $A^3$ | $G^1$ | $Y^3$ | $Q^2$ | $P^2$ |
| Brazil | P.2 | | $Y^3$ | $S^2$ | $K^1$ | $N^2$ | $A^3$ | $G^1$ | $H^3$ | $Q^2$ | $P^2$ |
| California | CAL.20C-GH/452R.V1 | B.1.429 | $Y^3$ | $S^2$ | $E^2$ | $N^2$ | $A^3$ | $G^1$ | $H^3$ | $Q^2$ | $P^2$ |
| India | (Andhra Pradesh) | N440K | $Y^3$ | $S^2$ | $E^2$ | $N^2$ | $A^3$ | $G^1$ | $H^3$ | $Q^2$ | $P^2$ |
| S. US | B.1.596/B.1.2 | Q677P/H | $Y^3$ | $S^2$ | $E^2$ | $N^2$ | $A^3$ | $G^1$ | $H^3$ | P/ $H^1$ | $P^2$ |
| NY | Ho et al. | B.1.526a | $Y^3$ | $S^2$ | $K^1$ | $N^2$ | $A^3$ | $G^1$ | $H^3$ | $Q^2$ | $P^2$ |
| | | B.1.526b | $Y^3$ | $N^1$ | $E^2$ | $N^2$ | $A^3$ | $G^1$ | $H^3$ | $Q^2$ | $P^2$ |
| WUHAN | | WUHAN | $Y^3$ | $S^2$ | $E^2$ | $N^2$ | $A^3$ | $D^2$ | $H^3$ | $Q^2$ | $P^2$ |
| | | | | | ✓$^5$ | ✓$^4$ | | ✓$^4$ | | | ✓$^4$ |
| PCR Amplimer length (bases) | | | (5) 199 | | (6) 151 | | | (7)88 | | (8) 135 | |

| Spike Gene Target Region (Codon) Amino Acid Change | | | I692V | A701V | T716I | S982A | T1027I | D1118 | V1176 | M1229I |
|---|---|---|---|---|---|---|---|---|---|---|
| Mutation specific Probe coverage | | | | ✓$^1$ | | | | | | |
| Wuhan reference specific probe/s coverage | | | | ✓$^2$ | | | | | | |
| Locus specific Probe coverage | | | | ✓ | | | | | | |
| Region | Lineage | Designation Var | | | | | | | | |
| Denmark | Mink V | B.1.1.298 | $V^3$ | $A^2$ | $T^3$ | $S^3$ | $T^3$ | $D^3$ | $V^3$ | $I^3$ |
| UK | GR/501Y.V1 | B.1.1.7 | $I^3$ | $A^2$ | $I^3$ | $A^3$ | $T^3$ | $H^3$ | $V^3$ | $M^3$ |
| SA | GH/501Y.V2 | B.1.351 | $I^3$ | $V^1$ | $T^3$ | $S^3$ | $T^3$ | $D^3$ | $V^3$ | $M^3$ |

TABLE 12-continued

Validation of test design for the five prevalent Clade variants

| | | | | | | | | | | |
|---|---|---|---|---|---|---|---|---|---|---|
| Brazil | P.1 | | I[3] | A[2] | T[3] | S[3] | I[3] | D[3] | F[3] | M[3] |
| Brazil | P.2 | | I[3] | A[2] | T[3] | S[3] | T[3] | D[3] | F[3] | M[3] |
| California | CAL.20C-GH/452R.V1 | B.1.429 | I[3] | A[2] | T[3] | S[3] | T[3] | D[3] | V[3] | M[3] |
| India | (Andhra Pradesh) | N440K | I[3] | A[2] | T[3] | S[3] | T[3] | D[3] | V[3] | M[3] |
| S. US | B.1.596/B.1.2 | Q677P/H | I[3] | A[2] | T[3] | S[3] | T[3] | D[3] | V[3] | M[3] |
| NY | Ho et al. | B.1.526a | I[3] | V[1] | T[3] | S[3] | T[3] | D[3] | V[3] | M[3] |
| | | B.1.526b | I[3] | A/V | T[3] | S[3] | T[3] | D[3] | V[3] | M[3] |
| WUHAN | | WUHAN | I[3] | A[2]<br>✓[4] | T[3] | S[3] | T[3] | D[3] | V[3] | M[3] |
| PCR Amplimer length (bases) | | | (8) 135 | | | | | | | |

[1]AA mutation - hybridizes to mutation specific probe

[2]AA identical to hCoV-19/Wuhan/WIV04/2019 (WIV04) - official reference sequence employed by GISAID (EPI_ISL_402124)

[3]Potential probe target

[4]No Probe Adjustment Necessary

[5]Minor Probe Adjustment Necessary

Table 13 shows the information content for the fully multiplexed (2, 3, 5, 6, 8) data obtained via the multiplex RT-PCR reaction in this DETECTX-Cv assay, which is sufficient to discriminate the five clade variants (superscript "1"). It was determined that including Amplimer 5 to the multiplex adds redundancy (superscript "2") thereby allowing unambiguous discrimination of the India Mutant (B.1.36.29). Similarly, addition of amplimer 4 (for NY B.1.526) and Q677P/H probes (for Southern US B.1.596/13.1.2) to the multiplex enabled discrimination of Southern US and NY Clade variants (superscript "3"). Importantly, the emerging Southern US Clade variants (B.1.596/1.1.2) does not require modification of the present multiplex reaction since inclusion of probes at Q677P/H would be sufficient. Analytical specificity was established as described earlier via analysis of both wild type (Wuhan) gRNA and synthetic, Clade specific fragments.

Augury Software Modification

Current deployment of Augury software was modified to include automated capacity for determining "Wild-Type" vs "Mutant" at each of the (11) Spike target sites of the present DETECTX-Cv assay described above (the columns in Table 12. As modified, Augury is capable of calling the identity of the clade variant, based on the pattern of mutant presentation among the sites (that is, a "look-up" table comprising the pattern of each row of Table 12). Coding to enable such autonomous calling is based on allelotyping methods previously developed for HLA allelotyping. In the present case, the clade variant test is also an exercise in spike gene allelotyping. Such spike gene allelotypes (the rows in Table 12) have already been determined as being the preferred marker for CoV-2 Clade Variation.

Information content obtained by addition of amplimers

| Region | Lineage Designation Var | | Information obtained with Amplimers 2, 3, 6, 8 | Information obtained by adding Amplimer 5 | Information obtained by adding Amplimer 4 + New Clade variant probes |
|---|---|---|---|---|---|
| Denmark | Mink V | B.1.1.298 | ✓[1] | | |
| UK | GR/501Y.V1 | B.1.1.7 | ✓[1] | | |
| SA | GH/501Y.V2 | B.1.351 | ✓[1] | ✓[2] | ✓[3] |
| Brazil/Japan | P.1 | | ✓[1] | ✓[2] | |
| Brazil | P.2 | | ✓[1] | | |
| California | CAL.20C-GH/452R.V1 | B.1.429 | ✓[1] | ✓[2] | |
| India | (Andhra Pradesh) | N440K | | ✓[2] | |
| S. US | B.1.596/B.1.2 | Q677P/H | | | ✓[3] |
| NY | Ho et al. | B.1.526 | | | ✓[3] |
| | | B.1.526.2 | | | ✓[3] |
| WUHAN | | | ✓[1] | ✓[2] | ✓[3] |

TABLE 14

| New Clade variant probe" sequences | | | |
|---|---|---|---|
| SEQ ID NOS. | Amplimer # | Target | Probe Sequence (5' to 3') |
| SEQ ID NO: 118 | 4 | AA_A243_ | TTTTTTTTCAAACTTTACTTGCTTTACTCTTT |
| SEQ ID NO: 119 | 4 | AA_243DEL | TTTTTTTTCAAACTTTACATAGAAGCCTTTTT |
| SEQ ID NO: 120 | 4 | AA_R246_ | TTTTCTACATAGAAGTTATTTGACTCCCTTTT |
| SEQ ID NO: 121 | 4 | AA_246I | TTTTCTGCTTTACATATGACTCCTGGTTTTTT |
| SEQ ID NO: 122 | 4 | AA_D253G | TTTCTACTCCTGGTGRTTCTTCTTCATTTT |
| SEQ ID NO: 123 | 4 | AA_D253_ | TTTTTTCCCTGGTGATTCTTCTTTCTTTTT |
| SEQ ID NO: 124 | 4 | AA_253G | TTTTTTCCCTGGTGGTTCTTCTTTTTTTTT |
| SEQ ID NO: 125 | 8 | AA_Q677P/H | TTTTTTATCAGACTCMGACTAATTCTCTTTTT |
| SEQ ID NO: 126 | 8 | AA_Q677_ | TTTTTTCCAGACTCAGACTAATTTCTTTTT |
| SEQ ID NO: 127 | 8 | AA_677P | TTTTTCTTCAGACTCCGACTAATCTTTTTT |
| SEQ ID NO: 128 | 8 | AA_677H1 | TTTTTTCCAGACTCATACTAATTTCTTTTT |
| SEQ ID NO: 129 | 8 | AA_677H2 | TTTTTTCCAGACTCACACTAATTTCTTTTT |

EXAMPLE 6

Augury Modification with Clade ID Module

The current deployment of the Augury software for wild type COV-2 was modified to include automated capacity for determining "Wild-Type" vs "Mutant" at each of the Spike target sites of the DETECTX-Cv assay (the columns in Table 15) and to identify the Clade variant based on the pattern of mutant presentation among the sites (the rows in Tables 15 and 16). Coding for the software is based on allelotyping formalism previously developed for HLA allelotyping.

Augury Software for DETECTX-Cv

All DETECTX-Cv probe sequences and their information content were added to a database ("Dot Score" file) within Augury. This database defined the DETECTX-Cv probe content (Mutant, Wild Type, Universal) at each of the eleven (11) Spike target regions (the columns in Table 15).

Establishment of DETECTX-Cv Version Control

The Augury Software is configured to read the bar code associated with each 96-well plate of microarrays for DETECTX-Cv and use the information in the bar code to create a "Dot Score" file for the probe content introduced into DETECTX-Cv. Further, Augury is configured to incorporate a new "Dot Score" file as appropriate for any new Clade Variant content with additional probes in the array (Table 15). Additionally, Augury is intrinsically cloud enabled and configured to deploy software modification downloaded from the cloud. When useful for analysis of DETECTX-Cv, data such as those from the RADx Rosalind initiative can also be introduced directly into Augury autonomously, to update the list of prevalent clade variants.

Manual Deployment Version of Augury for DETECTX-Cv

The core functionality of Augury has been used as a manual product for deployment at TriCore. This version of Augury automatically is enabled to read DETECTX-Cv plate bar codes, perform microarray image analysis, create "Dot Score" files and present the resulting averaged, background subtracted DETECTX-Cv data as a spread sheet matrix, which can be compared to the Clade Variant Hybridization patterns such as described in Table 15. This manual deployment version has been tested on DETECTX-Cv synthetic Clade variant standards.

Clade Variant "Look up Table"

All prevalent Cov-2 Clades have been programmed into Augury to generate a "Look-up Table" (equivalent in content to the pattern of boxes having superscript 1 and 2 in Table 15). The Augury internal "Lookup Table" is formatted to function as part of a Boolean pattern search as developed previously for allelotype analysis of all genes.

TABLE 15

Validation of Clade variants

| Spike Gene Target Region (Codon) Amino Acid Change | | S13I | L18F | T20N | P26S | Q52R | A67V/ Δ69-70 | D80A | T95I | D138Y | Y144DEL | W152C |
|---|---|---|---|---|---|---|---|---|---|---|---|---|
| Mutation specific Probe coverage | | | | | | | ✓[1] | ✓[1] | | ✓[1] | ✓[1] | ✓[1] |
| Wuhan reference specific probe/s coverage | | | | | | | ✓[2] | ✓[2] | | ✓[2] | ✓[2] | ✓[2] |
| Locus specific Probe coverage | | | | | | | N/A | ✓ | | ✓ | ✓ | ✓ |
| Street name | Pango lineage - (Clade Nexstrain) | | | | | | | | | | | |
| UK | B.1.1.7 - (20I/501Y.V1) | S[3] | L[3] | T[3] | P[3] | Q[3] | Δ[1] | D[2] | T[3] | D[2] | Δ[1] | W[2] |
| SA | B.1.351 - (20H/501Y.V2) | S[3] | L[3] | T[3] | P[3] | Q[3] | HV[2] | A[1] | T[3] | D[2] | Y[2] | W[2] |
| US | B.1.375 | S[3] | L[3] | T[3] | P[3] | Q[3] | Δ[1] | D[2] | T[3] | D[2] | Y[2] | W[2] |
| Brazil | P.1 - (20J/501Y.V3) | S[3] | F | N | S | Q[3] | HV[2] | D[2] | T[3] | Y[1] | Y[2] | W[2] |
| Cal L452R | B.1.429/427 - (20C/S:452R) | I | L[3] | T[3] | P[3] | Q[3] | HV[2] | D[2] | T[3] | D[2] | Y[2] | C[1] |
| Rio de Jan. | B.1.1.28 | S[3] | L[3] | T[3] | P[3] | Q[3] | HV[2] | D[2] | T[3] | D[2] | Y[2] | W[2] |
| Andrah Pradesh | B.1.36.29 | S[3] | L[3] | T[3] | P[3] | Q[3] | HV[2] | D[2] | T[3] | D[2] | Y[2] | W[2] |
| S. US/Q677P/H | (S:677P.B.1.596) (S:677H.B.1.2) | S[3] | L[3] | T[3] | P[3] | Q[3] | HV[2] | D[2] | T[3] | D[2] | Y[2] | W[2] |
| NYC (Ho etal) | B.1.526a - (20C/S:484K) | S[3] | L[3] | T[3] | P[3] | Q[3] | HV[2] | D[2] | I | D[2] | Y[2] | W[2] |
| | B.1.526b | S[3] | L[3] | T[3] | P[3] | Q[3] | HV[2] | D[2] | I | D[2] | Y[2] | W[2] |
| NYC | B.1.525 - (20A/S:484K) | S[3] | L[3] | T[3] | P[3] | R | V/Δ[1] | D | T[3] | D | Δ[1] | W |
| | A.23.1 | S[3] | L[3] | T[3] | P[3] | Q[3] | HV[2] | D[2] | T[3] | D[2] | Y[2] | W[2] |
| | B.1.258 - (20A/S:439K) | S[3] | L[3] | T[3] | P[3] | Q[3] | Δ[1] | D[2] | T[3] | D[2] | Y[2] | W[2] |
| | B.1.1.33 | S[3] | L[3] | T[3] | P[3] | Q[3] | HV[2] | D[2] | T[3] | D[2] | Y[2] | W[2] |
| | B.1.177 - (20E (EU1)(S:A222V)) | S[3] | L[3] | T[3] | P[3] | Q[3] | HV[2] | D[2] | T[3] | D[2] | Y[2] | W[2] |
| | B.1.1.207 | S[3] | L[3] | T[3] | P[3] | Q[3] | HV[2] | D[2] | T[3] | D[2] | Y[2] | W[2] |
| Mink/Cluster V | B.1.1.298 (S:Y453F) | S[3] | L[3] | T[3] | P[3] | Q[3] | Δ[1] | D[2] | T[3] | D[2] | Y[2] | W[2] |
| WUHAN | WUHAN | S[3] | L[3] | T[3] | P[3] | Q[3] | HV[2] | D[2] | T[3] | D[2] | Y[2] | W[2] |
| | | | | | | | ✓[4] | ✓[5] | | ✓[4] | | ✓[4] |
| PCR Amplimer length (bases) | | | (1) 101 | | | | | $(2_B)$ 150 | | | (3) 129 | |

| Spike Gene Target Region (Codon) Amino Acid Change | | F157L | R190S | D215G | A222V | A243del | R246I | D253G | V367F |
|---|---|---|---|---|---|---|---|---|---|
| Mutation specific Probe coverage | | | | | | ✓[1] | ✓[1] | ✓[1] | |
| Wuhan reference specific probe/s coverage | | | | | | ✓[2] | ✓[2] | ✓[2] | |
| Locus specific Probe coverage | | | | | | ✓ | ✓ | ✓ | |
| Street name | Pango lineage - (Clade Nexstrain) | | | | | | | | |
| UK | B.1.1.7 - (20I/501Y.V1) | F[3] | R[3] | D[3] | A[3] | A[2] | R[2] | D[2] | V[3] |
| SA | B.1.351 - (20H/501Y.V2) | F[3] | R[3] | G | A[3] | Δ[1] | I[1] | D[2] | V[3] |
| US | B.1.375 | F[3] | R[3] | D[3] | A[3] | A[2] | R[2] | D[2] | V[3] |
| Brazil | P.1 - (20J/501Y.V3) | F[3] | S | D[3] | A[3] | A[2] | R[2] | D[2] | V[3] |
| Cal L452R | B.1.429/427 - (20C/S:452R) | F[3] | R[3] | D[3] | A[3] | A[2] | R[2] | D[2] | V[3] |
| Rio de Jan. | B.1.1.28 | F[3] | R[3] | D[3] | A[3] | A[2] | R[2] | D[2] | V[3] |
| Andrah Pradesh | B.1.36.29 | F[3] | R[3] | D[3] | A[3] | A[2] | R[2] | D[2] | V[3] |
| S. US/Q677P/H | (S:677P.B.1.596) (S:677H.B.1.2) | F[3] | R[3] | D[3] | A[3] | A[2] | R[2] | D[2] | V[3] |
| NYC (Ho etal) | B.1.526a - (20C/S:484K) | F[3] | R[3] | D[3] | A[3] | A[2] | R[2] | G[1] | V[3] |
| | B.1.526b | F[3] | R[3] | D[3] | A[3] | A[2] | R[2] | G[1] | V[3] |
| NYC | B.1.525 - (20A/S:484K) | F[3] | R[3] | D[3] | A[3] | A | R | D | V[3] |
| | A.23.1 | L | R[3] | D[3] | A[3] | A[2] | R[2] | D[2] | F |
| | B.1.258 - (20A/S:439K) | F[3] | R[3] | D[3] | A[3] | A[2] | R[2] | D[2] | V[3] |
| | B.1.1.33 | F[3] | R[3] | D[3] | A[3] | A[2] | R[2] | D[2] | V[3] |
| | B.1.177 - (20E (EU1)(S:A222V)) | F[3] | R[3] | D[3] | V | A[2] | R[2] | D[2] | V[3] |
| | B.1.1.207 | F[3] | R[3] | D[3] | A[3] | A[2] | R[2] | D[2] | V[3] |
| Mink/Cluster V | B.1.1.298 (S:Y453F) | F[3] | R[3] | D[3] | A[3] | A[2] | R[2] | D[2] | V[3] |
| WUHAN | WUHAN | F[3] | R[3] | D[3] | A[3] | A[2] | R[2] | D[2] | V[3] |
| PCR Amplimer length (bases) | | | | | | | $(4_B)$ 160 | | |

| Spike Gene Target Region (Codon) Amino Acid Change | | K417N/T | N439K | N440K | L452R | Y453F | S477N | E484K | N501Y |
|---|---|---|---|---|---|---|---|---|---|
| Mutation specific Probe coverage | | ✓[1] | ✓[1] | ✓[1] | ✓[1] | ✓[1] | ✓[1] | ✓[1] | ✓[1] |
| Wuhan reference specific probe/s coverage | | ✓[2] | ✓[2] | ✓[2] | ✓[2] | ✓[2] | ✓[2] | ✓[2] | ✓[2] |
| Locus specific Probe coverage | | ✓ | ✓ | ✓ | ✓ | ✓ | N/A | ✓ | ✓ |
| Street name | Pango lineage - (Clade Nexstrain) | | | | | | | | |
| UK | B.1.1.7 - (20I/501Y.V1) | K[2] | N[2] | N[2] | L[2] | Y[2] | S[2] | E[2] | Y[1] |
| SA | B.1.351 - (20H/501Y.V2) | N[1] | N[2] | N[2] | L[2] | Y[2] | S[2] | K[1] | Y[1] |
| US | B.1.375 | K[2] | N[2] | N[2] | L[2] | Y[2] | S[2] | E[2] | N[2] |
| Brazil | P.1 - (20J/501Y.V3) | T[1] | N[2] | N[2] | L[2] | Y[2] | S[2] | K[1] | Y[1] |
| Cal L452R | B.1.429/427 - (20C/S:452R) | K[2] | N[2] | N[2] | R[1] | Y[2] | S[2] | E[2] | N[2] |
| Rio de Jan. | B.1.1.28 | K[2] | N[2] | N[2] | L[2] | Y[2] | S[2] | K[1] | N[2] |
| Andrah Pradesh | | K[2] | N[2] | K[1] | L[2] | Y[2] | S[2] | E[2] | N[2] |
| S. US/Q677P/H | (S:677P.P.B.1.596) (S:677H.B.1.2) | K[2] | N[2] | N[2] | L[2] | Y[2] | S[2] | E[2] | N[2] |
| NYC (Ho etal) | B.1.526a - (20C/S:484K) | K[2] | N[2] | N[2] | L[2] | Y[2] | S[2] | K[1] | N[2] |
| | B.1.526b | K[2] | N[2] | N[2] | L[2] | Y[2] | N[1] | E[2] | N[2] |

TABLE 15-continued

Validation of Clade variants

| | | | | | | | | | |
|---|---|---|---|---|---|---|---|---|---|
| NYC | B.1.525 - (20A/S:484K) | K | N | N | L | Y | S | K[1] | N |
| | A.23.1 | K[2] | N[2] | N[2] | L[2] | Y[2] | S[2] | E[2] | N[2] |
| | B.1.258 - (20A/S:439K) | K[2] | K[1] | N[2] | L[2] | Y[2] | S[2] | E[2] | N[2] |
| | B.1.1.33 | K[2] | N[2] | N[2] | L[2] | Y[2] | S[2] | K | N[2] |
| | B.1.177 - (20E (EU1)(S:A222V)) | K[2] | N[2] | N[2] | L[2] | Y[2] | S[2] | E[2] | N[2] |
| | (22.5 mM NaCl, 2.25 mM sodium citrate) | K[2] | N[2] | N[2] | L[2] | Y[2] | S[2] | E[2] | N[2] |
| Mink/Cluster V | B.1.1.298 (S:Y453F) | K[2] | N[2] | N[2] | L[2] | F | S[2] | E[2] | N[2] |
| WUHAN | WUHAN | K[2] | N[2] | N[2] | L[2] | Y[2] | S[2] | E[2] | N[2] |
| | | | | ✓[4] | ✓[4] | | | ✓[5] | ✓[4] |
| PCR Amplimer length (bases) | | | | (5) 199 | | | | (6) 151 | |

| Spike Gene Target Region (Codon) Amino Acid Change | | A570D | Q613H | D614G | H655Y | Q677P/H | P681H | I692V | A701V |
|---|---|---|---|---|---|---|---|---|---|
| Mutation specific Probe coverage | | | ✓[1] | ✓[1] | | ✓[1] | ✓[1] | ✓[1] | ✓[1] |
| Wuhan reference specific probe/s coverage | | | ✓[2] | ✓[2] | | ✓[2] | ✓[2] | ✓[2] | ✓[2] |
| Locus specific Probe coverage | | | ✓ | ✓ | | ✓ | ✓ | ✓ | ✓ |
| Street name | Pango lineage - (Clade Nexstrain) | | | | | | | | |
| UK | B.1.1.7 - (20I/501Y.V1) | D | Q[2] | G[1] | H[3] | Q[2] | H[1] | I[2] | A[2] |
| SA | B.1.351 - (20H/501Y.V2) | A[3] | Q[2] | G[1] | H[3] | [3]Q[2] | P[2] | I[2] | V[1] |
| US | B.1.375 | A[3] | Q[2] | G[1] | H[3] | Q[2] | P[2] | I[2] | A[2] |
| Brazil | P.1 - (20J/501Y.V3) | A[3] | Q[2] | G[1] | Y | Q[2] | P[2] | I[2] | A[2] |
| Cal L452R | B.1.429/427 - (20C/S:452R) | A[3] | Q[2] | G[1] | H[3] | Q[2] | P[2] | I[2] | A[2] |
| Rio de Jan. | B.1.1.28 | A[3] | Q[2] | G[1] | H[3] | Q[2] | P[2] | I[2] | A[2] |
| Andrah Pradesh | | A[3] | Q[2] | G[1] | H[3] | Q[2] | P[2] | I[2] | A[2] |
| S. US/Q677P/H | (S:677P.P.B.1.596) (S:677H.B.1.2) | A[3] | Q[2] | G[1] | H[3] | P/H[1] | P[2] | I[2] | A[2] |
| NYC (Ho etal) | B.1.526a - (20C/S:484K) | A[3] | Q[2] | G[1] | H[3] | Q[2] | P[2] | I[2] | V[1] |
| | B.1.526b | A[3] | Q[2] | G[1] | H[3] | Q[2] | P[2] | I[2] | A/V[1] |
| NYC | B.1.525 - (20A/S:484K) | A[3] | Q | G[1] | H[3] | H[1] | P | I | A |
| | A.23.1 | A[3] | H[1] | D[2] | H[3] | Q[2] | R[1] | I[2] | A[2] |
| | B.1.258 - (20A/S:439K) | A[3] | Q[2] | G[1] | H[3] | Q[2] | P[2] | I[2] | A[2] |
| | B.1.1.33 | A[3] | Q[2] | G | H[3] | Q[2] | P[2] | I[2] | A[2] |
| | B.1.177 - (20E (EU1)(S:A222V)) | A[3] | Q[2] | G | H[3] | Q[2] | P[2] | I[2] | A[2] |
| | (22.5 mM NaCl, 2.25 mM sodium citrate) | A[3] | Q[2] | G | H[3] | Q[2] | H | I[2] | A[2] |
| Mink/Cluster V | B.1.1.298 (S:Y453F) | A[3] | Q[2] | G | H[3] | Q[2] | P[2] | V | A[2] |
| WUHAN | WUHAN | A[3] | Q[2] | D[2] | H[3] | Q[2] | P[2] | I[2] | A[2] |
| | | | | ✓[4] | | | ✓[4] | | ✓[4] |
| PCR Amplimer length (bases) | | | (7) 88 | | | | (8) 135 | | |

| Spike Gene Target Region (Codon) Amino Acid Change | | T716I | F888L | S982A | T1027I | D1118H | V1176F | M1229I |
|---|---|---|---|---|---|---|---|---|
| Mutation specific Probe coverage | | | | | | | | |
| Wuhan reference specific probe/s coverage | | | | | | | | |
| Locus specific Probe coverage | | | | | | | | |
| Street name | Pango lineage - (Clade Nexstrain) | | | | | | | |
| UK | B.1.1.7 - (20I/501Y.V1) | I | F[3] | A | T | H | V[3] | M[3] |
| SA | B.1.351 - (20H/501Y.V2) | T[3] | F[3] | S[3] | T[3] | D[3] | V[3] | M[3] |
| US | B.1.375 | T[3] | F[3] | S[3] | T[3] | D[3] | V[3] | M[3] |
| Brazil | P.1 - (20J/501Y.V3) | T[3] | F[3] | S[3] | I | D[3] | F | M[3] |
| Cal L452R | B.1.429/427 - (20C/S:452R) | T[3] | F[3] | S[3] | T[3] | D[3] | V[3] | M[3] |
| Rio de Jan. | B.1.1.28 | T[3] | F[3] | S[3] | T[3] | D[3] | F | M[3] |
| Andrah Pradesh | | T[3] | F[3] | S[3] | T[3] | D[3] | V[3] | M[3] |
| S. US/Q677P/H | (S:677P.P.B.1.596) (S:677H.B.1.2) | T[3] | F[3] | S[3] | T[3] | D[3] | V[3] | M[3] |
| NYC (Ho etal) | B.1.526a - (20C/S:484K) | T[3] | F[3] | S[3] | T[3] | D[3] | V[3] | M[3] |
| | B.1.526b | T[3] | F[3] | S[3] | T[3] | D[3] | V[3] | M[3] |
| NYC | B.1.525 - (20A/S:484K) | T[3] | L | S[3] | T[3] | D[3] | V[3] | M[3] |
| | A.23.1 | T[3] | F[3] | S[3] | T[3] | D[3] | V[3] | M[3] |
| | B.1.258 - (20A/S:439K) | T[3] | F[3] | S[3] | T[3] | D[3] | V[3] | M[3] |
| | B.1.1.33 | T[3] | F[3] | S[3] | T[3] | D[3] | V[3] | M[3] |
| | B.1.177 - (20E (EU1)(S:A222V)) | T[3] | F[3] | S[3] | T[3] | D[3] | V[3] | M[3] |
| | (22.5 mM NaCl, 2.25 mM sodium citrate) | T[3] | F[3] | S[3] | T[3] | D[3] | V[3] | M[3] |
| Mink/Cluster V | B.1.1.298 (S:Y453F) | T[3] | F[3] | S[3] | T[3] | D[3] | V[3] | I |
| WUHAN | WUHAN | T[3] | F[3] | S[3] | T[3] | D[3] | V[3] | M[3] |
| PCR Amplimer length (bases) | | | | | | | | |

[1]AA mutation - hybridizes to mutation specific probe

[2]AA identical to hCoV-19/Wuhan/WIV04/2019 (WIV04) - official reference sequence employed by GISAID (EPI_ISL_402124)

[3]Potential probe target

[4]No Probe Adjustment Necessary

[5]Minor Probe Adjustment Necessary

TABLE 16

Information content obtained by addition of amplimers

| Street Name | Pango lineage (Clade Nextstrain open-source toolkit) | Amplimers 2, 3, 6, 8 | Amplimer 5 | Potential Probe content as described in Table 14 | Amplimer 4 + New Clade variant probes |
|---|---|---|---|---|---|
| UK | B.1.1.7 - (20I/501Y.V1) | ✓[1] | | ✓[3] | |
| SA | B.1.351 - (20H/501Y.V2) | ✓[1] | ✓[2] | | ✓[4] |
| US | B.1.375 | ✓[1] | | | |
| Brazil | P.1 - (20J/501Y.V3) | ✓[1] | ✓[2] | | |
| California L452R | B.1.429/427 - (20C/S:452R) | ✓[1] | ✓[2] | | |
| Rio de Janeiro | B.1.1.28 | ✓[1] | | | |
| Andhra Pradesh | | | ✓[2] | | |
| S.US/Q677P/H | (S: 677P.Pelican) (S:677H.Robin1) | | | ✓[3] | |
| NYC (Ho et al.) | B.1.526a - (20C/S:484K) | | | | ✓[4] |
| | B.1.526a - (20C/S:484K) | | | | ✓[4] |
| NYC | B.1.525 - (20A/S:484K) | | | ✓[3] | |
| Mink/Cluster V | (S:Y453F) | ✓[1] | | ✓[3] | |
| WUHAN | | ✓[1] | ✓[2] | ✓[3] | ✓[4] |

[1]Information obtained by adding Amplimers 2, 3, 6 and 8
[2]Information obtained by adding Amplimer 5
[3]Information obtained by adding Potential probe content
[4]Information obtained by adding Amplimer 4 + New Clade variant probes

Analytical Threshold Values

Multiplex RT-PCR [2, 3, 5, 6, 8] were performed in the absence of template (0 copies/reaction) to obtain the mean and STD from the mean for LoB signals. This "blank" data collection data is used by Augury to obtain the analytical threshold for each probe (3.2×STD+Mean) to yield Mutant threshold (Tm), Wild Type threshold (Tw) and Universal threshold (Tu) values for all thirty-three (33) probes comprising the content of DETECTX-Cv.

Deployment of Automatic Mutant Vs Wild Type Detection ("Delta")

Threshold values were introduced as constants into Augury for autonomous Mutant vs Wild Type determination at all eleven (11) sites. This was performed using the following relationship analytical approach;

$$Delta=([RFU_m-T_m]/T_m)-([RFU_w-T_w]/T_w) \quad \text{(Equation 1)}$$

where, $RFU_m$=mutant probe RFU signal in a sample $RFU_w$=wild type probe RFU signal in a sample $T_m$=mutant probe RFU Threshold–a constant obtained from CLSI (LoB) analysis $T_w$=wild type probe RFU Threshold–a constant obtained from CLSI (LoB) analysis $[RFU_m-T_m]$=Mutant Probe Signal strength above Threshold. By definition, this is a non-zero value.

$[RFU_w-T_w]$=Wild Type Signal strength above Threshold. By definition, this is a non-zero value.

Delta=Difference in Signal Strength above Threshold normalized to Threshold

If Delta>0, within experimental accuracy, then "Mutant" (i.e. boxes having superscript 1 in Table 15). If Delta<0, within experimental accuracy, then "Wild Type" (i.e. boxes having superscript 2 in Table 15).

EXAMPLE 7

Clade Variant Array Deployment-1

1. Analytical LoD Determination. A first determination of analytical LoD was performed for DETECTX-Cv, among all eleven (11) Spike target sites deployed using the [UNG+One Step RT-PCR] conditions. For this analysis, validation materials comprised a purified Wuhan gRNA reference (ATCC-BEI) and a cocktail of five (5) synthetic fragments designed by PathogenDx and fabricated by Integrated DNA Technologies, Inc. (IDT, Coralville, Iowa), comprising each region targeted for amplification via the [2, 3, 5, 6, 8] multiplex RT-PCR reaction (deployed as N=5 multiplex).

To support the multiplex reaction, all 5 synthetic CoV-2 fragments were mixed [1:1:1:1:1] in strand equivalents. Copy number values listed in Table 15 refer to the copy number of each fragment (in the equimolar mix) applied to the RT-PCR reaction. The primary goal here is to deploy the (N=5) RT-PCR multiplex to obtain a preliminary analytical LoD in units of copies/reaction for each of the probes comprising the set associated with each of the (n) target sites—$LoD_n$ (Universal), $LoD_n$ (Wild Type), $LoD_n$ (Mutant). The analytical LoD associated with the Universal probes ($LoD_n$) were lower than that of either $LoD_n$ or $LoD_n$, due to the intentionally longer probe sequence for the universal probe, which is associated with a higher affinity for its complementary amplicon sequence.

Results

Subsequent to RT-PCR the DNA microarray was prepared for hybridization with brief water washes, and an incubation in prehybridization buffer (0.6M NaCl, 0.06M sodium citrate solution, 0.1% Ficoll, 0.1% Polyvinylpyrrolidone 0.1% Bovine Serum Albumin). Following aspiration of the prehybridization buffer, a mixture of amplicon and hybridization buffer (0.6M NaCl, 0.06M sodium citrate, 0.1% Ficoll, 0.1% Polyvinylpyrrolidone 0.1% Bovine Serum Albumin) was added to the DNA microarray and allowed to incubate for 2 hours. The microarray is then washed with wash buffer (22.5 mM NaCl, 2.25 mM sodium citrate) and dried via centrifugation. The glass portion of the microarray was cleaned with lens tissue and 70% ethanol and images were acquired on the Sensospot. Images were then uploaded for Augury analysis. Following image acquisition and upload to Augury, it was found that the 5-plex RT-PCR reaction, comprising a N=5 multiplex of amplimers [2, 3, 5, 6, 8] was sufficient to obtain a first determination of analytical LODs [$LoD_n$ (Universal), $LoD_n$ (Wild Type), and $LoD_n$ (Mutant)].

Figure 14A:
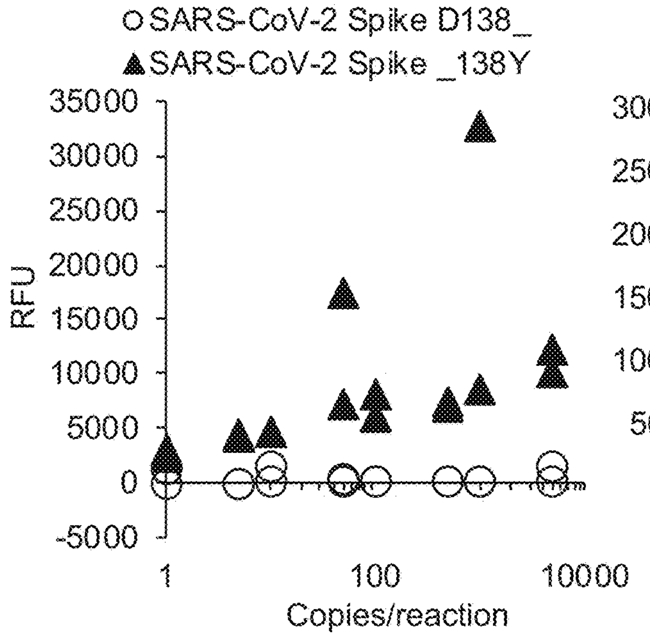
FIGS. 14A-14Y shows analytical LoD data for a series of synthetic G-block fragments, used as "synthetic clade variant standards", corresponding to domains 2-8.
Figure 14B:
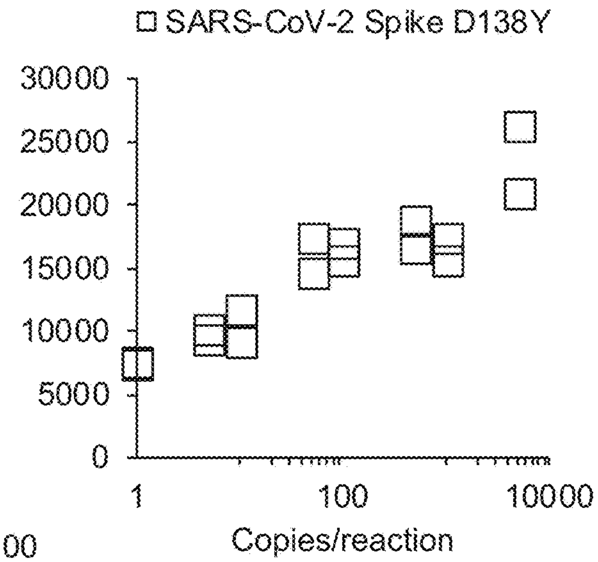
FIG. 14B shows DETECTX-Cv analysis for the indicated variants corresponding to the Brazil region.
Figure 14C:
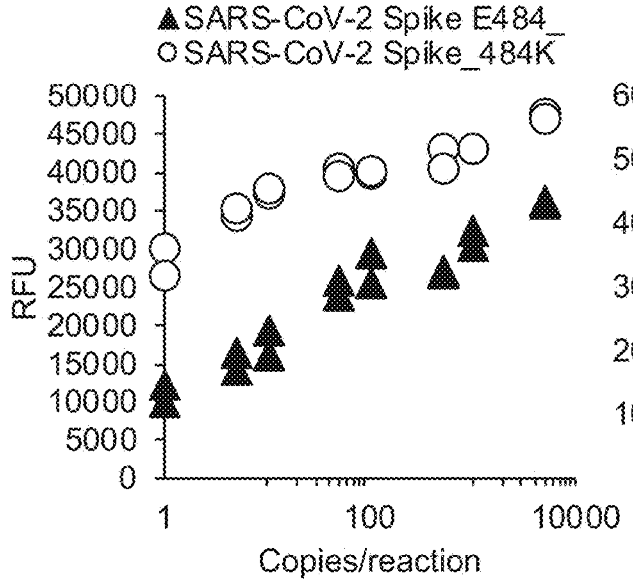
FIG. 14C shows DETECTX-Cv analysis for the indicated variants corresponding to the Brazil region.
Figure 14D:
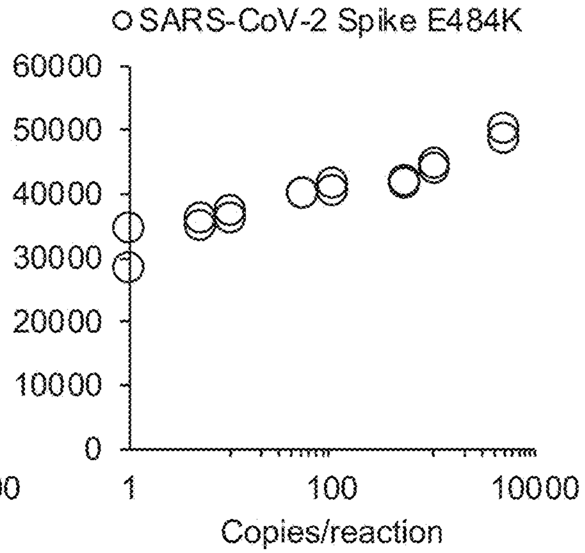
FIG. 14D shows DETECTX-Cv analysis for the indicated variants corresponding to the Brazil region.
Figure 14E:
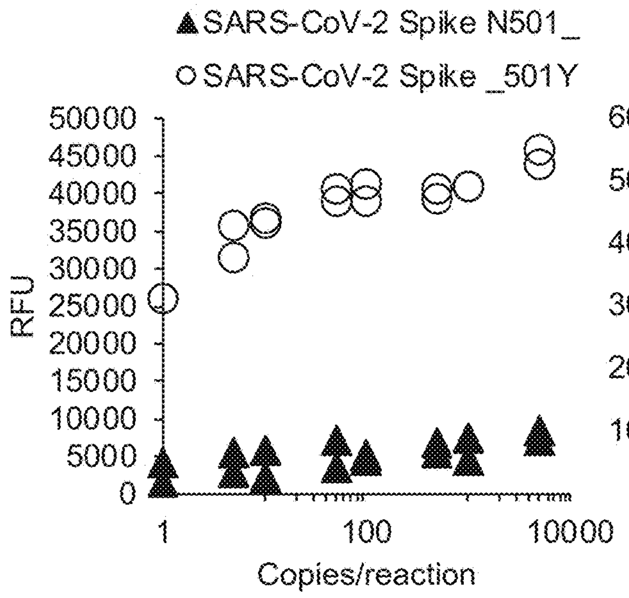
FIG. 14E shows DETECTX-Cv analysis for the indicated variants corresponding to the Brazil region.
Figure 14F:
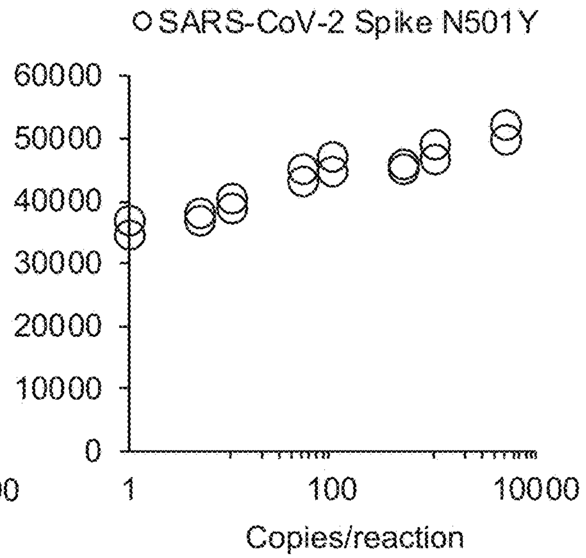
FIG. 14F shows DETECTX-Cv analysis for the indicated variants corresponding to the Brazil region.
Figure 14G:
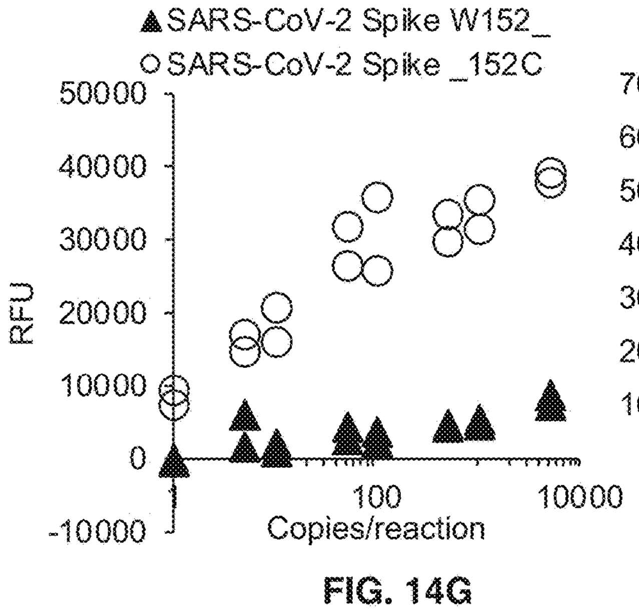
FIG. 14G shows DETECTX-Cv analysis for the indicated variants corresponding to the California region.
Figure 14H:
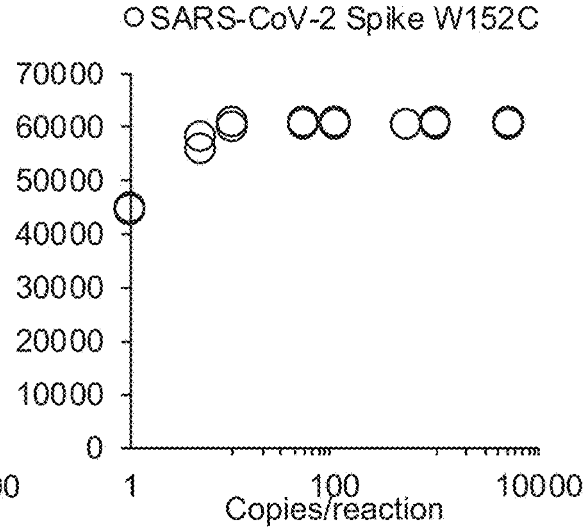
FIG. 14H shows DETECTX-Cv analysis for the indicated variants corresponding to the California region.
Figure 14I:
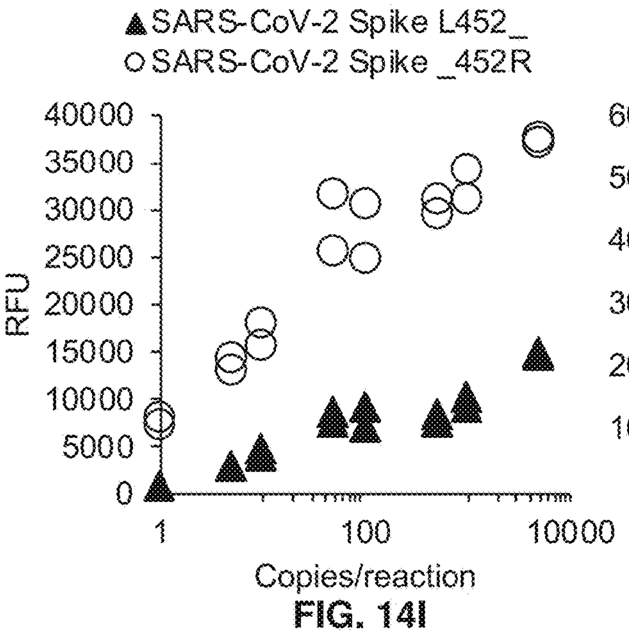
FIG. 14I shows DETECTX-Cv analysis for the indicated variants corresponding to the California region.
Figure 14J:
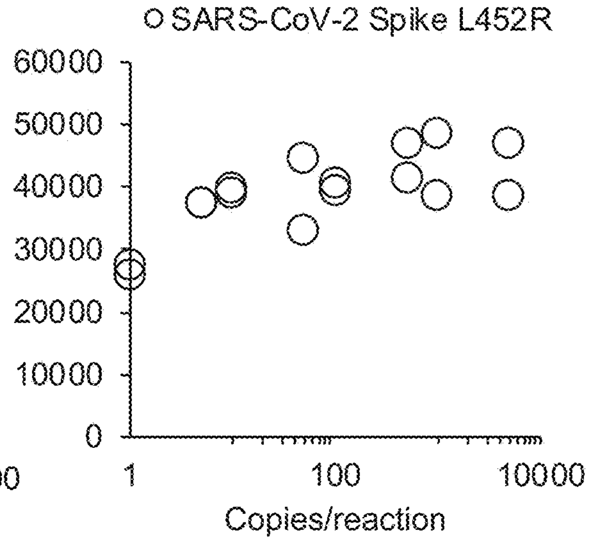
FIG. 14J shows DETECTX-Cv analysis for the indicated variants corresponding to the California region.
Figure 14K:
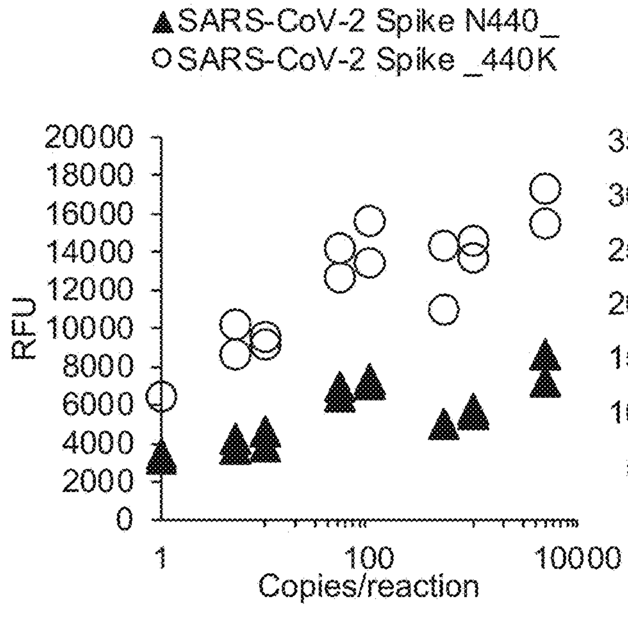
FIG. 14K shows DETECTX-Cv analysis for the indicated variants corresponding to the Indian region.
Figure 14L:
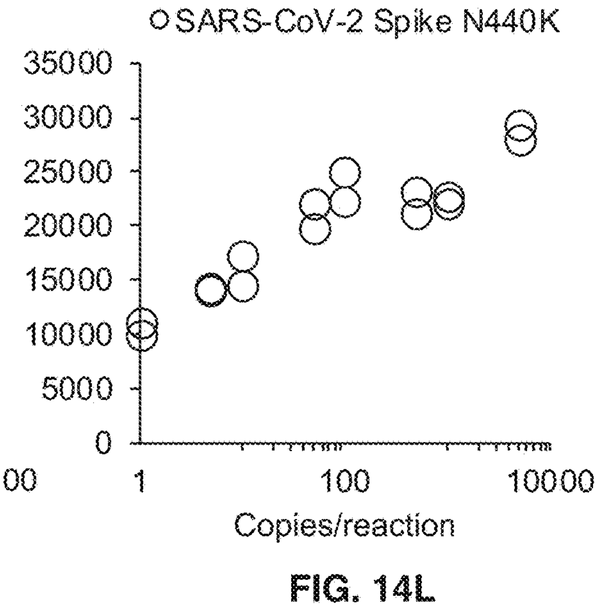
FIG. 14L shows DETECTX-Cv analysis for the indicated variants corresponding to the Indian region.
Figure 14M:
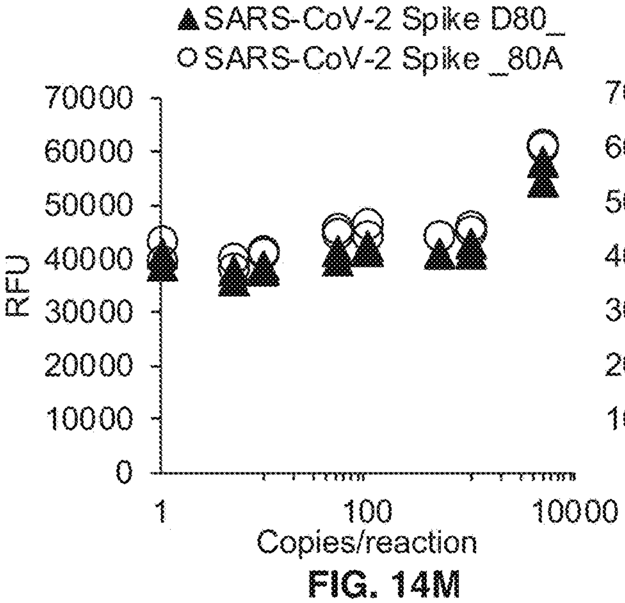
FIG. 14M shows DETECTX-Cv analysis for the indicated variants corresponding to the South Africa region.
Figure 14N:
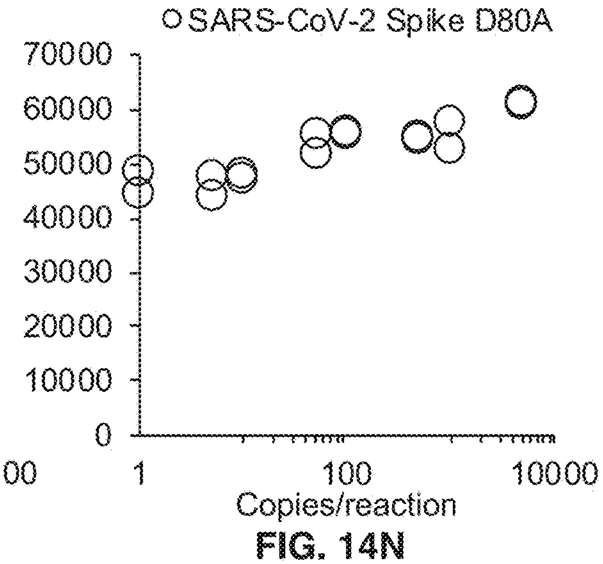
FIG. 14N shows DETECTX-Cv analysis for the indicated variants corresponding to the South Africa region.
Figure 14O:
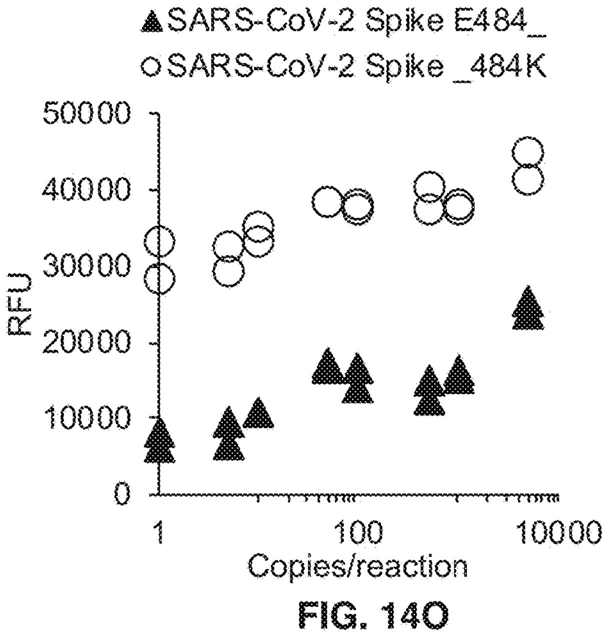
FIG. 14O shows DETECTX-Cv analysis for the indicated variants corresponding to the South Africa region.
Figure 14P:
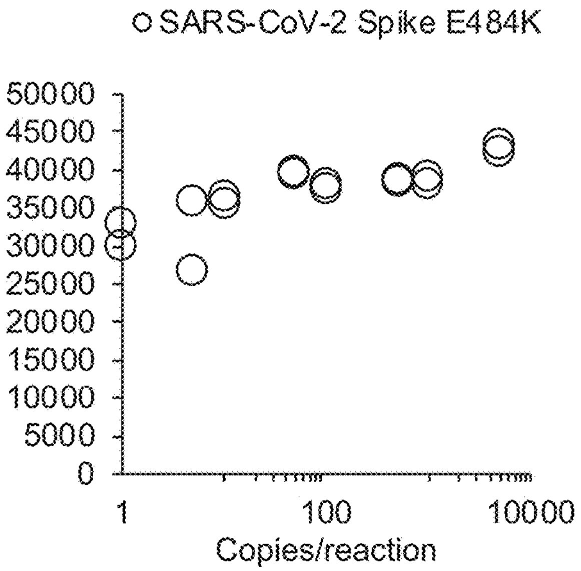
FIG. 14P shows DETECTX-Cv analysis for the indicated variants corresponding to the South Africa region.
Figure 14Q:
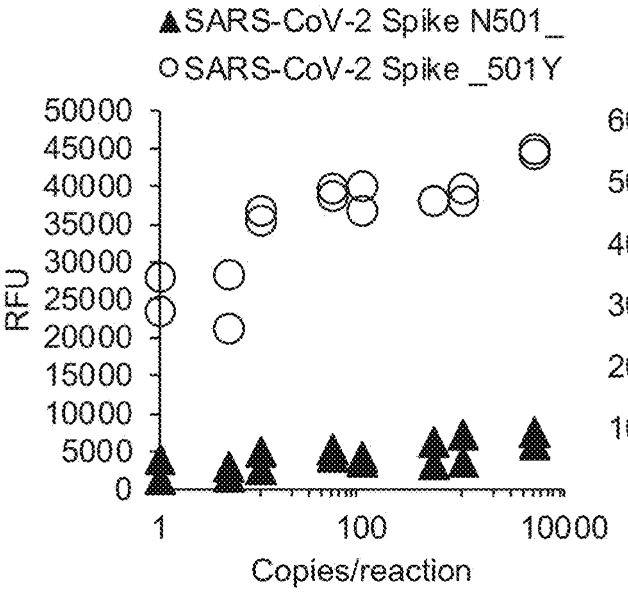
FIG. 14Q shows DETECTX-Cv analysis for the indicated variants corresponding to the South Africa region.
Figure 14R:
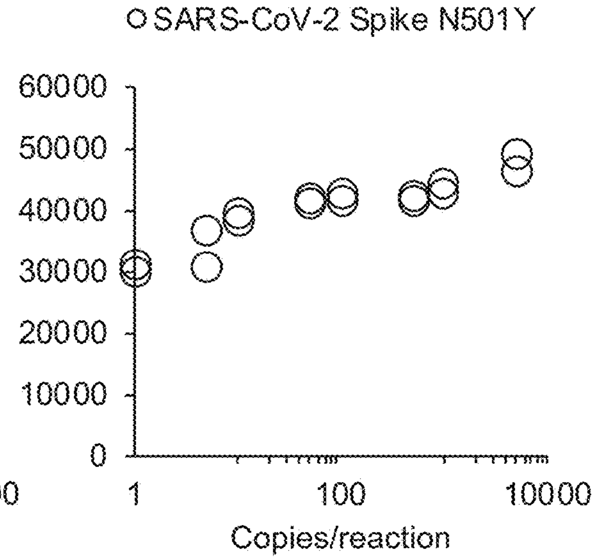
FIG. 14R shows DETECTX-Cv analysis for the indicated variants corresponding to the South Africa region.
Figure 14S:
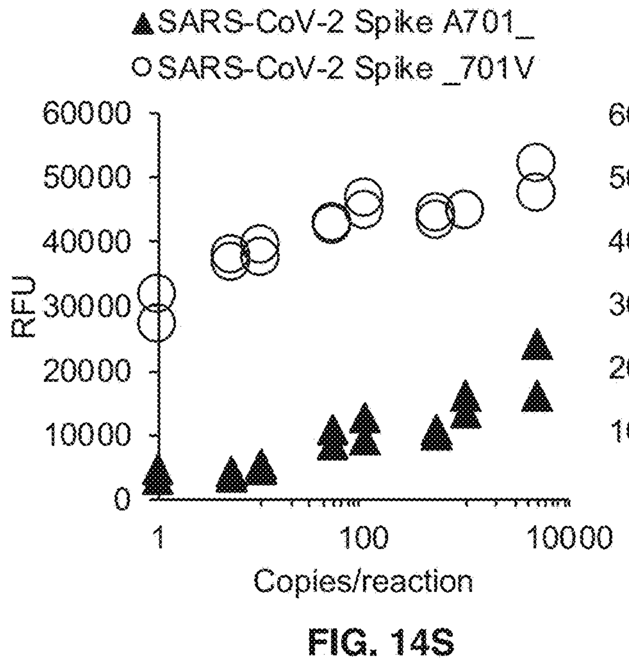
FIG. 14S shows DETECTX-Cv analysis for the indicated variants corresponding to the South Africa region.
Figure 14T:
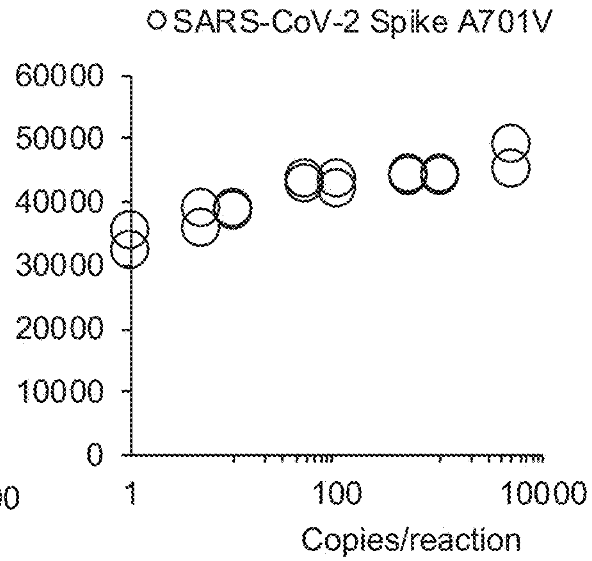
FIG. 14T shows DETECTX-Cv analysis for the indicated variants corresponding to the South Africa region.
Figure 14U:
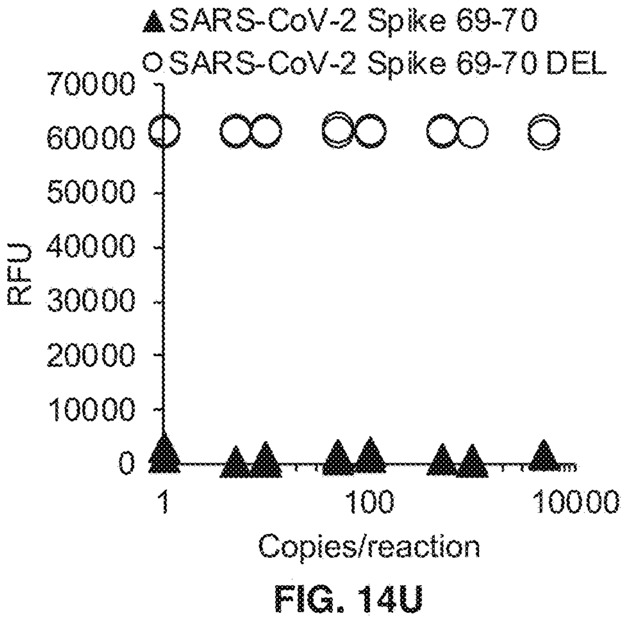
FIG. 14U shows DETECTX-Cv analysis for the indicated variants corresponding to the UK region.
Figure 14V:
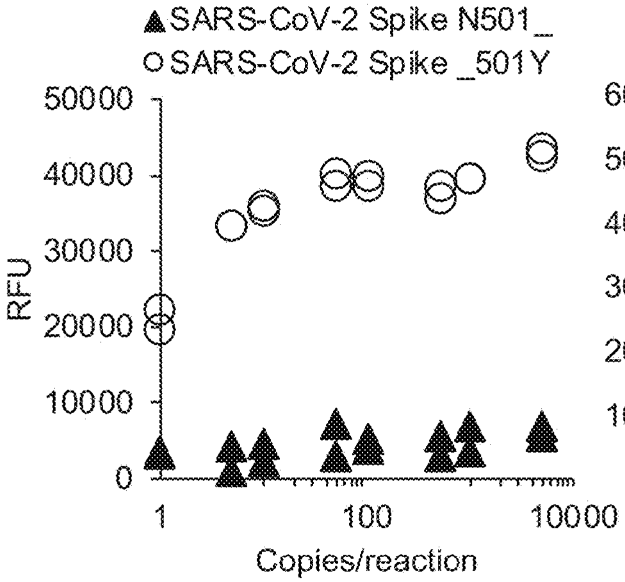
FIG. 14V shows DETECTX-Cv analysis for the indicated variants corresponding to the UK region.
Figure 14W:
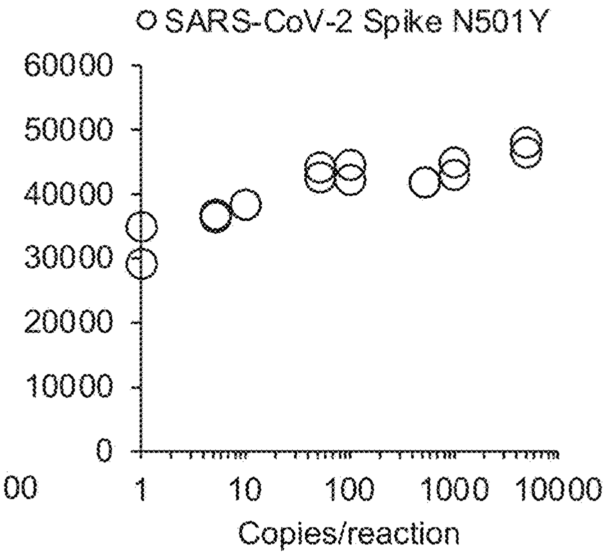
FIG. 14W shows DETECTX-Cv analysis for the indicated variants corresponding to the UK region.
Figure 14X:
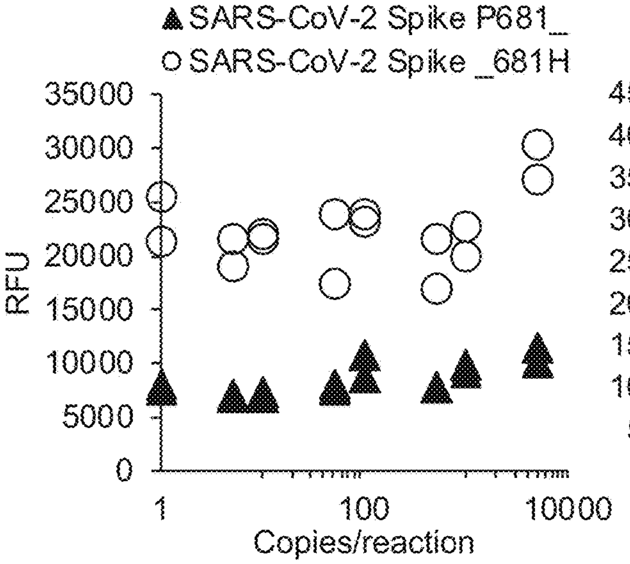
FIG. 14X shows DETECTX-Cv analysis for the indicated variants corresponding to the UK region.
Figure 14Y:
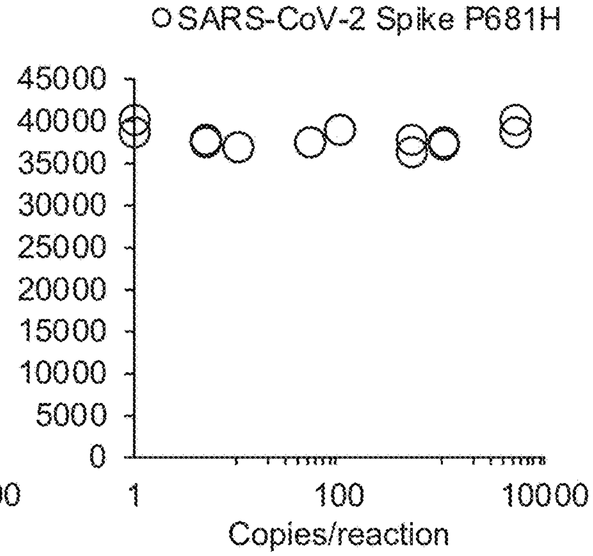
Figure 15A:
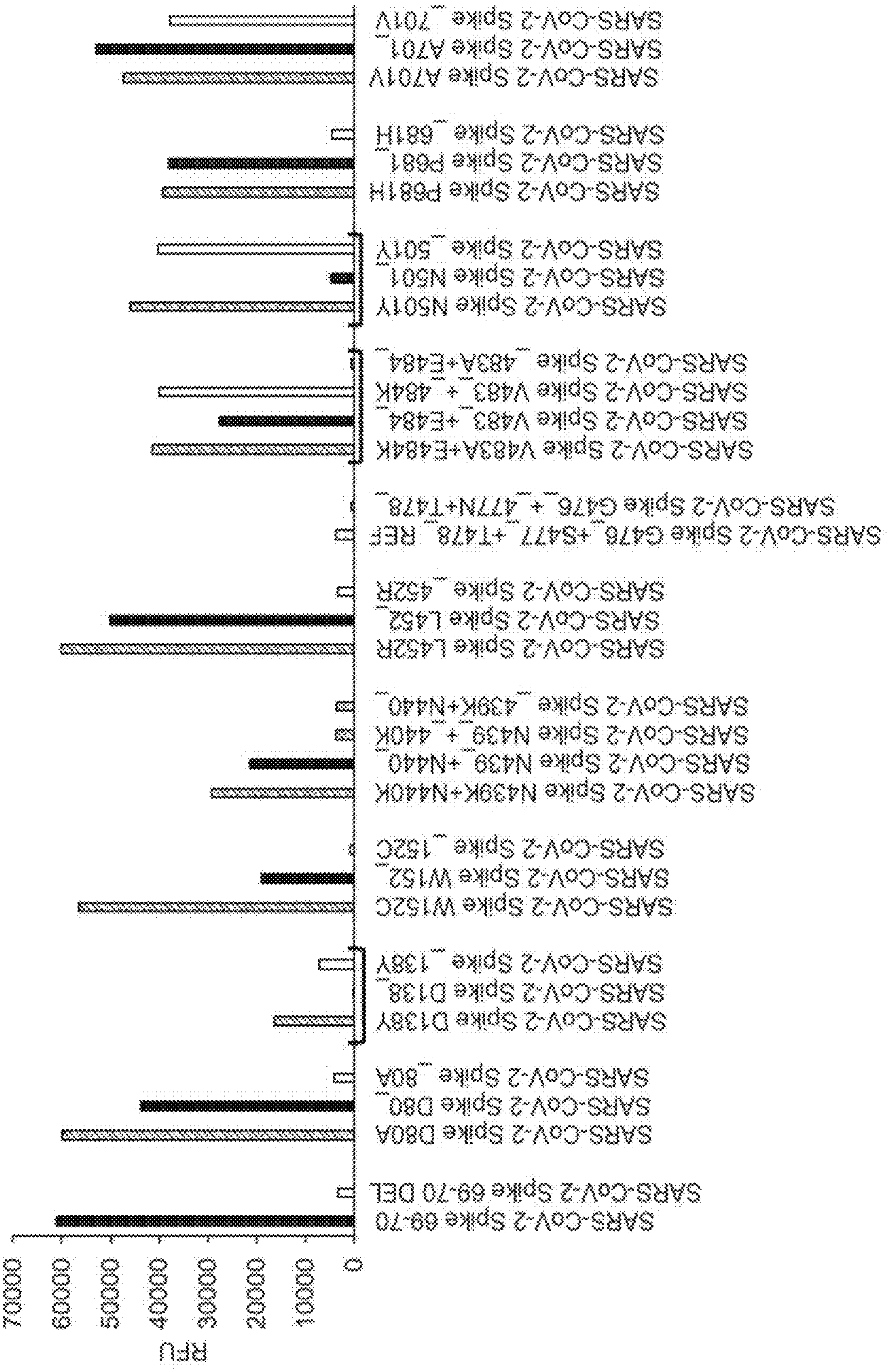
FIGS. 15A-15E shows DETECTX-Cv analysis using synthetic Clade Variant standards.
Figure 15B:
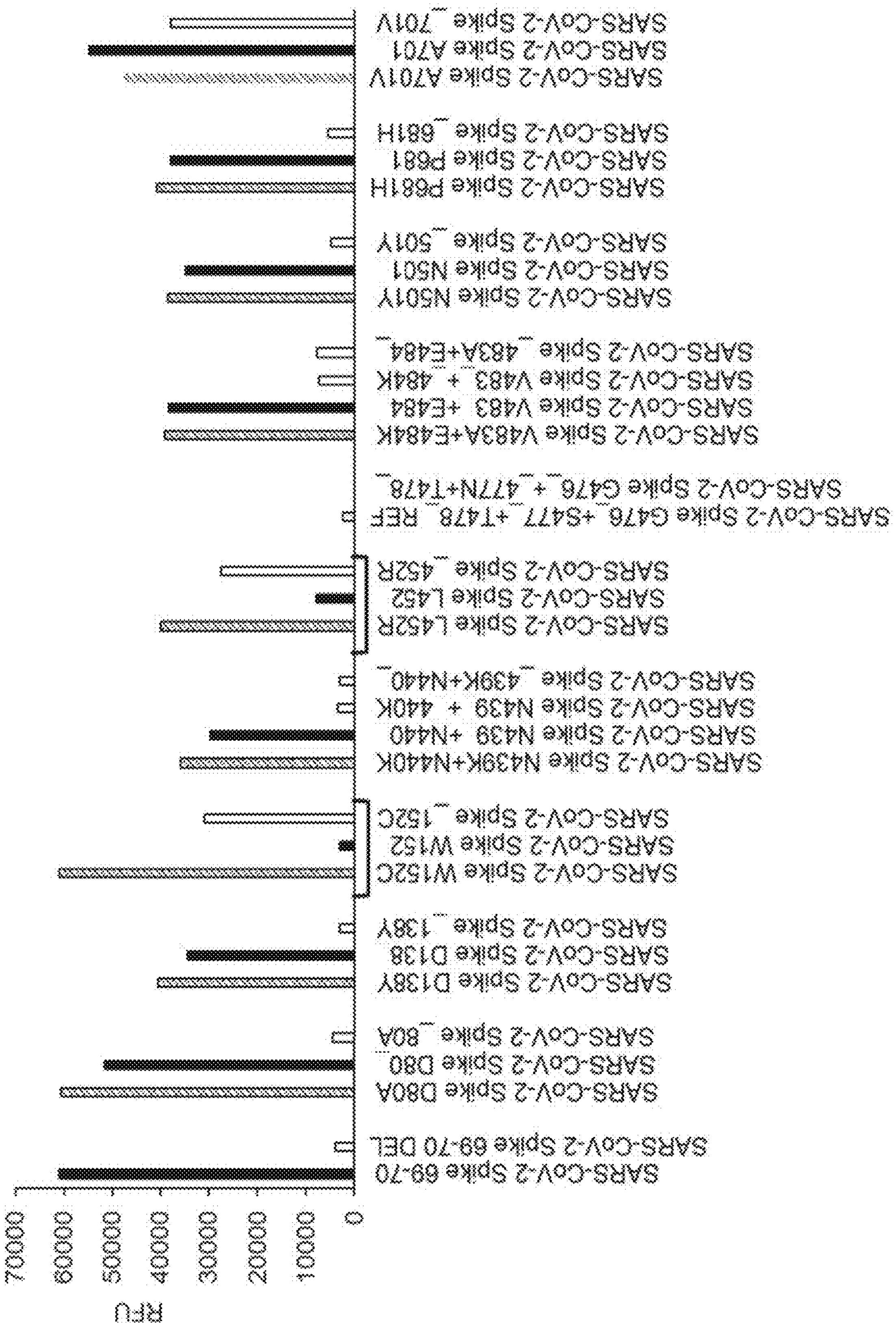
Figure 15C:
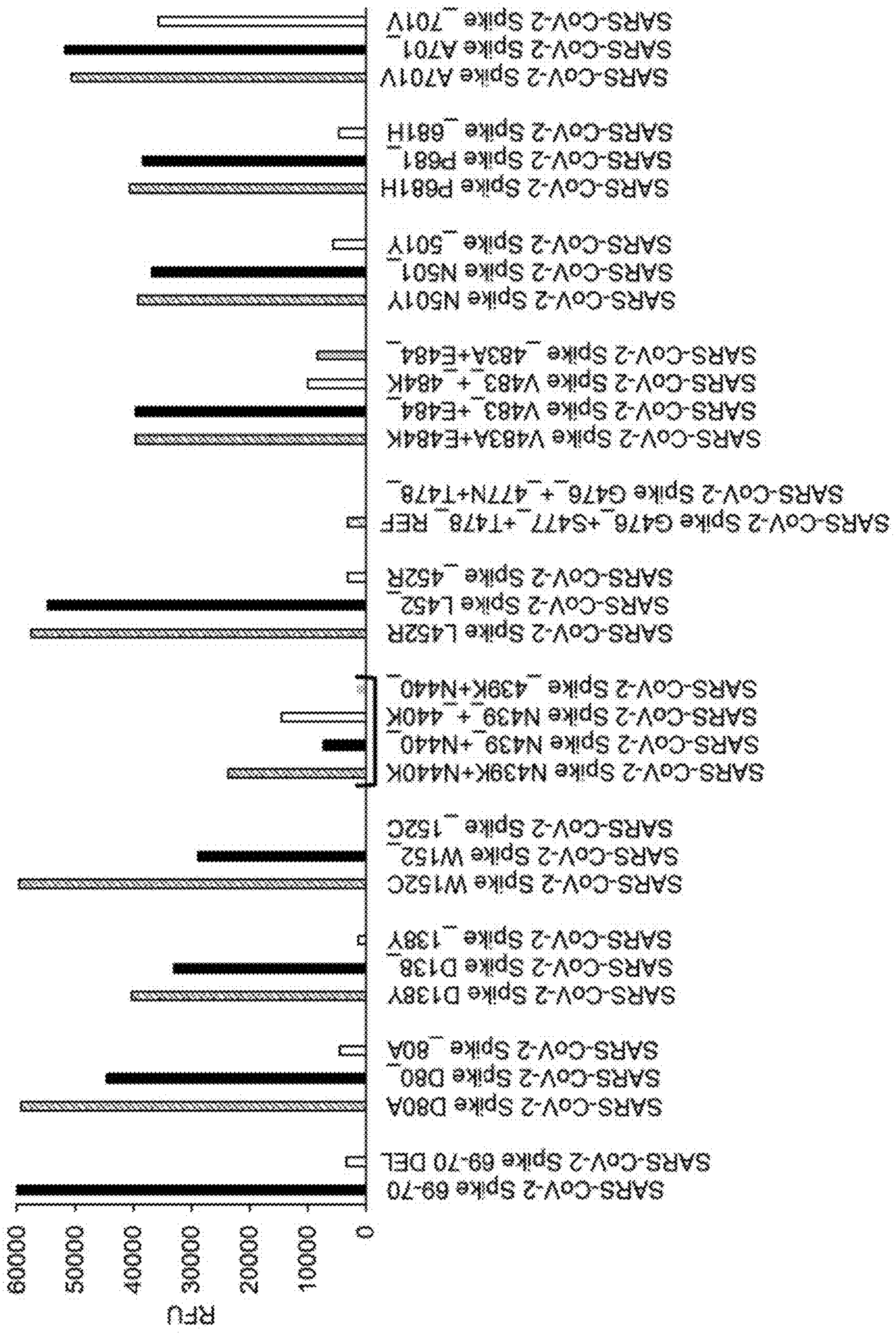
Figure 15D:
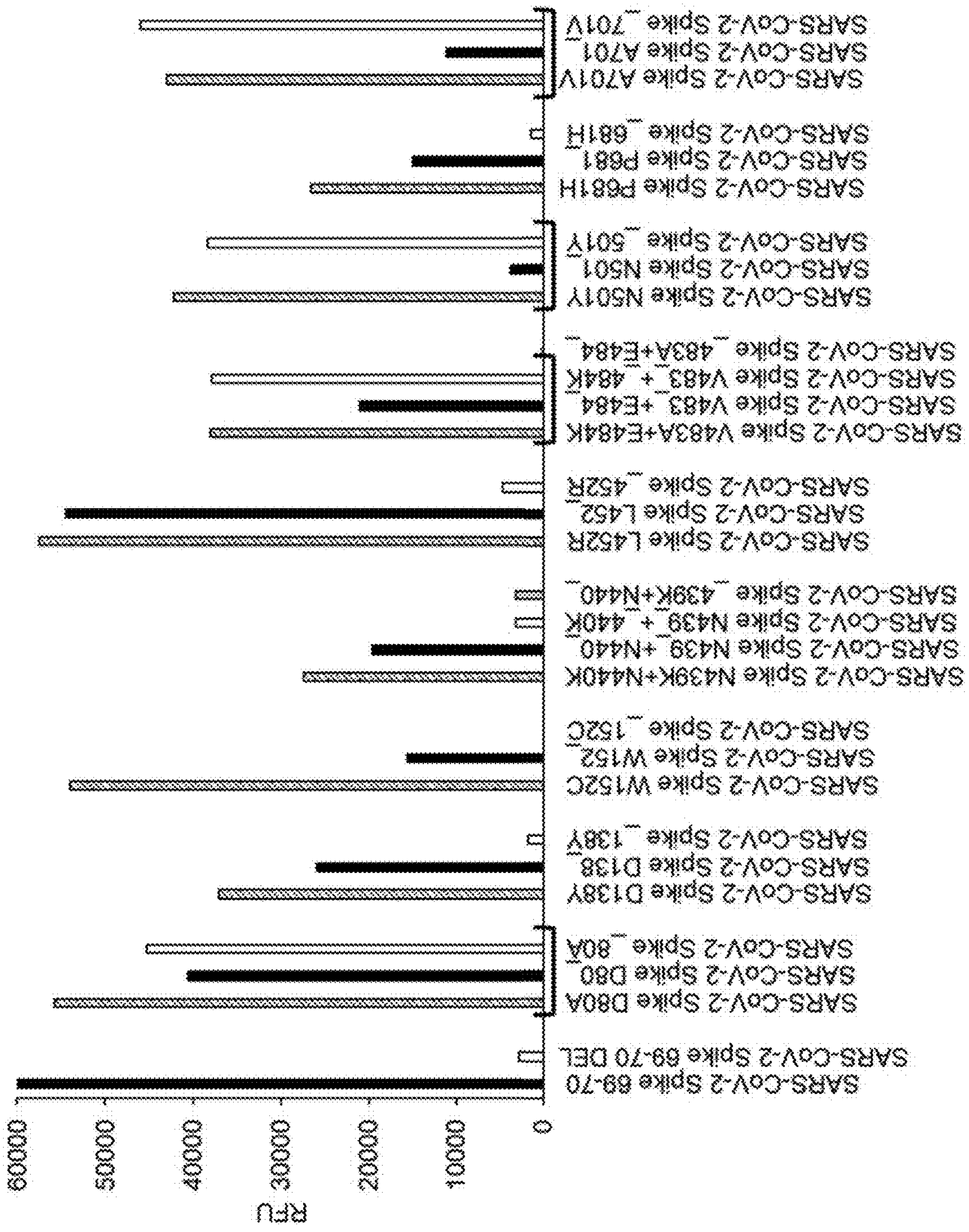
Figure 15E:
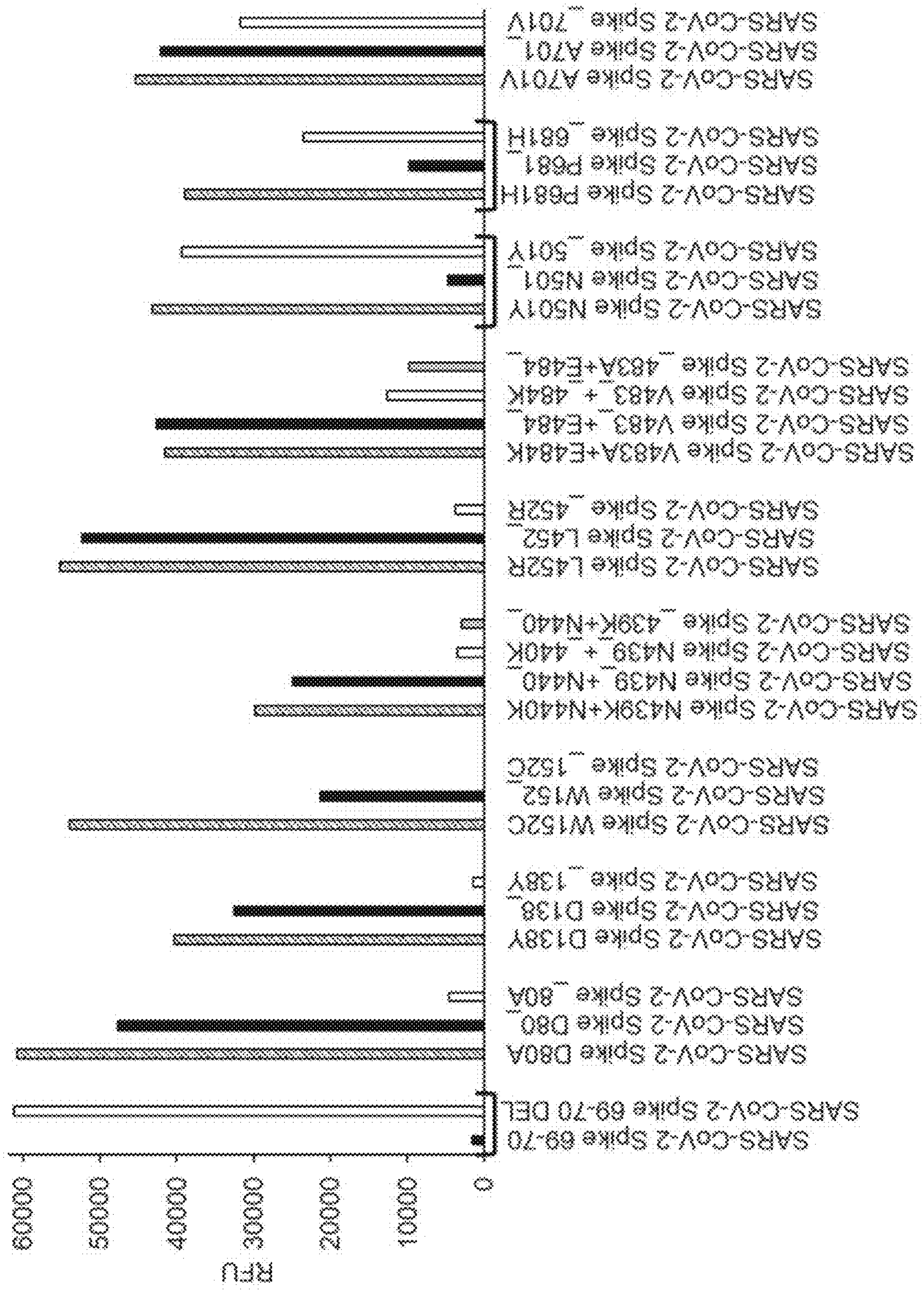

FIGS. 14A-14Y shows analytical LoD data for a series of synthetic G-block fragments corresponding to domains 2-8. The synthetic copy number was determined by IDT and used as such, in subsequent dilutions. Fragments fabricated to display "signature" mutations as defined in boxes showing superscript 1 in Table 15 were mixed into a series of "cocktails" to emulate different clade variant types.

FIGS. 14A, 14C, 14E, 14G, 14I, 14K, 14M, 14O, 14Q, 14S, 14U, 14V and 14X FIGS. 4(*a-q*) show a comparison of signals for Mutant (Synthetic) Cov-2, followed by hybridization to DETECTX-Cv to yield Wild-Type Probe (open circle) vs Mutant Probe (closed triangle) to emphasize the specificity of discrimination between Wild-Type vs Mutant target sequence. The signals were derived from microarray hybridization data (N=2 Repeats) for the N=5 multiplex RT-PCR amplification of Mutant (Synthetic) Cov-2, followed by hybridization to DETECTX-Cv. Table 17 summarizes the analytical $LoD_n$ (Wild Type) and $LoD_n$ (Mutant) values. FIGS. 14B, 14D, 14F, 14H, 14J, 14L, 14N, 14P, 14R, 14T, 14W and 14Y FIGS. 4(*a-q*) show microarray hybridization data (N=2 Repeats) for the N=5 multiplex RT-PCR amplification of Mutant (Synthetic) Cov-2, followed by hybridization to DETECTX-Cv, to yield Universal Probe Hybridization probe signals (open square). These data emphasize the high sensitivity of analysis obtained via hybridization to the (longer) Universal Probe, generally manifested as a lower $LoD_n$ (Universal).

TABLE 17

Summary of analytical LoD values measured for each of the eleven Spike gene target sites, for Universal, Wild-Type and Mutant probes.

| Target Site (n) | Amplicon | $LoD_n$* (Universal) WT | $LoD_n$* (Universal) MT | $LoD_n$§ (Wild Type) | $LoD_n$¶ (Mutant) |
|---|---|---|---|---|---|
| 69-70(del) | 2 | NA | NA | 50 | <10 ** |
| D80A | 2 | 50 | <10 | 50 | <10 |
| D138Y | 3 | 100 | <10 | 100 | <10 |
| W152C | 3 | 100 | <10 | 500 | <10 |
| N440K | 5 | 50 | <10 | 50 | <10 |
| L452R | 5 | 50 | <10 | 50 | <10 |
| S477N | 6 | 10 | <10 | 50 | <10 |
| E484K | 6 | 10 | <10 | 10 | <10 |
| N501Y | 6 | 100 | <10 | 100 | <10 |
| P681H | 8 | 10 | <10 | 10 | <10 |
| A701V | 8 | 10 | <10 | 50 | <10 |

*$LoD_n$ (Universal). Analytical LoD Values for Universal Probes as defined from the input target density (in copies per RT-PCR reaction) at which the signal obtained from the Universal probe becomes indistinguishable from the present estimate of background. There are two related values obtained for $LoD_n$ (Universal). One value is obtained upon titration with Wild Type (Wuhan) genomic gRNA ($LoD_n$ (Universal) and the other obtained upon titration with Mutant Synthetic Fragments ($LoD_n$ (Universal) MT)

§$LoD_n$ (Wild Type). Analytical LoD Values for Analysis of Wild Type (Wuhan) as defined from the input target density (measured in copies per RT-PCR reaction) at which the signal obtained from the Wild Type probe becomes indistinguishable from background.

¶$LoD_n$ (Mutant). Analytical LoD Values for Analysis of Mutant (Synthetic Fragment) as defined from the input target density (measured in copies per RT-PCR reaction) at which the signal obtained from the Mutant probe becomes indistinguishable from background.

EXAMPLE 8

Analysis of "Synthetic Clade Variant" Standards for Deployment to TriCore and Other Labs 1. Synthetic Clade Variant Analysis.

The (N=5) RT-PCR Multiplex (2, 3, 5, 6, 8) described in Example 7 was deployed to obtain a full eleven (11) site Clade variant profile using standard hybridization and wash procedures described above.

2. Synthetic Clade Variant Cocktails.

A set of five (5) different "Synthetic Clade Variant Standards" corresponding to UK (B.1.1.7), SA (B.1.351), CA452 (B.1.429), Brazil (P.1) and India N440K (B.1.36.29) were prepared each containing a synthetic gene fragment (IDT, Coralville, Iowa) identical to each of the Spike domains amplified by the present RT-PCR multiplex.

3. Synthetic Clade Variant Data Analysis.

Data were obtained at 100 copies/reaction for each of the five (5) synthetic cocktails. Hybridization analysis was performed, and the hybridization data thus obtained was plotted as described above.

4. Results.

Raw data from this analysis presented in FIGS. 15A-15E shows that the ratio of Mutant (open bars) to Wild Type signal (black bars) readily identify the state of each of the eleven (11) target domains. Spike target sites expected to display a "Mutant" Signal (i.e. open bars>black bars) are marked with brackets.

EXAMPLE 9

CoV-2 Detection and Pooling Via (Oasis) Pure-SAL Saliva Collection

Clinical LoD Range Finding and Clinical LoD analysis were performed on contrived samples, comprising clinical negatives from healthy volunteers, collected in PURE-SAL™ collection device (OASIS DIAGNOSTICS® Corporation, WA). The samples were contrived with heat attenuated CoV-2 (Wuhan, BEI).

Contrived samples were subjected to viral gRNA capture and purification on Zymo silica magnetic beads or Ceres magnetic beads. Five microliters of purified RNA was added to the RT-PCR mix in a PCR plate. The plate was sealed and placed in a thermocycler to undergo 20 minutes of reverse transcription and 45 cycles of asymmetric PCR. Upon PCR completion, the DNA microarray was prepared for hybridization with brief water washes, and an incubation in prehybridization buffer (0.6M NaCl, 0.06M sodium citrate solution, 0.1% Ficoll, 0.1% Polyvinylpyrrolidone 0.1% Bovine Serum Albumin). Following aspiration of the prehybridization buffer, a mixture of amplicon and hybridization buffer (0.6M NaCl, 0.06M sodium citrate, 0.1% Ficoll, 0.1% Polyvinylpyrrolidone 0.1% Bovine Serum Albumin) was added to the DNA microarray and allowed to incubate for 2 hours. The microarray is then washed with wash buffer (22.5 mM NaCl, 2.25 mM sodium citrate) and dried via centrifugation. The glass portion of the microarray was cleaned with lens tissue and 70% ethanol and images were acquired on the Sensospot. Images were then uploaded for Augury analysis.

Figure 16:
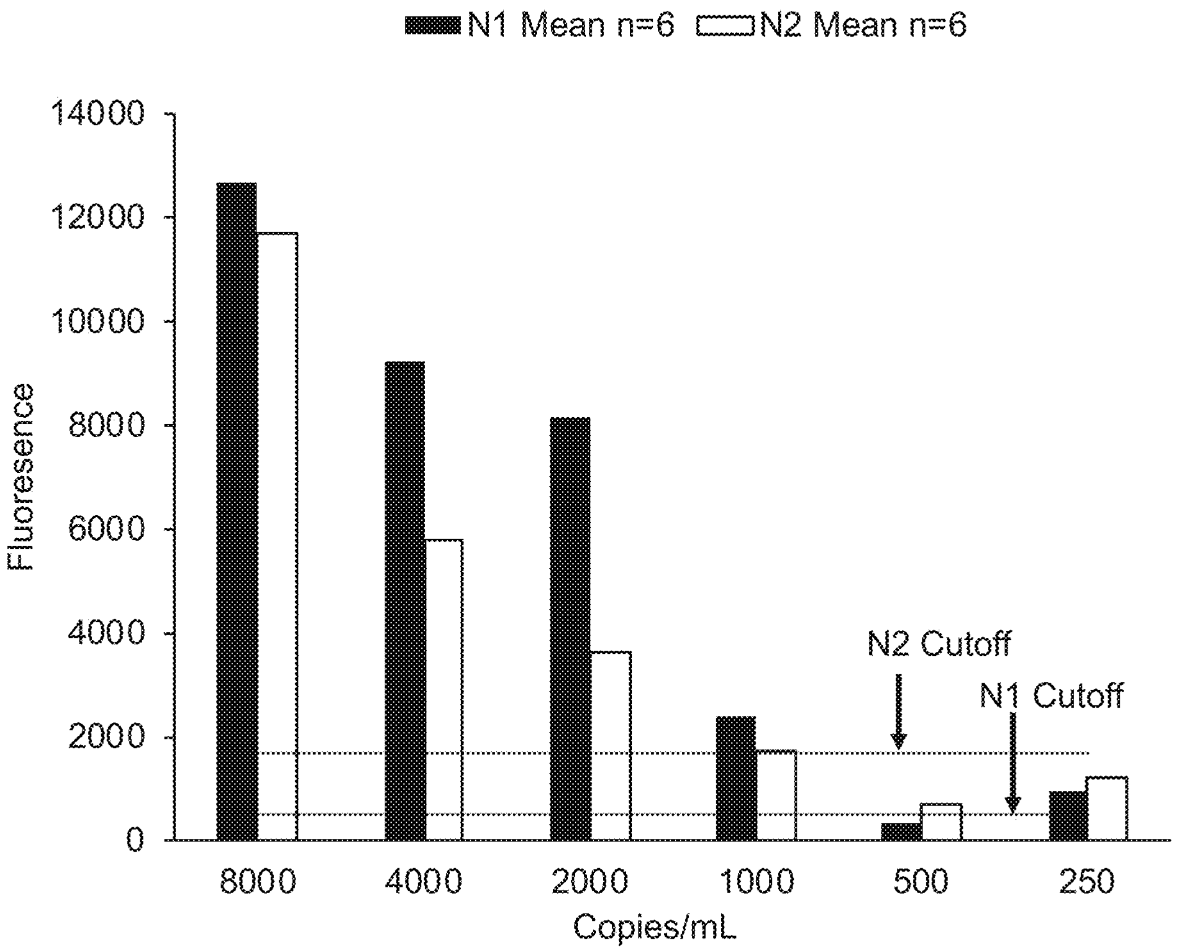
FIG. 16 shows LoD range finding DETECTX-Cv analysis for clinical samples processed using Zymo bead capture.

Clinical LoD Results: Clinical LoD range finding was performed as described above (N=6 repeats) using clinically negative saliva samples (PURE-SAL™) to which were added heat inactivated CoV-2 that were processed using Zymo bead capture. FIG. 16 shows that the clinical LoD is close to 1000 copies/ml. A follow-up experiment was performed at N=20, where the resulting clinical LoD is defined as the point at which nineteen of the twenty (19/20) repeated samples produced positive detection (Table 18), which corresponds to a clinical LoD of 1000 copies/ml, a value that is identical within experimental accuracy to that obtained via the same DETECTX-Cv assay of contrived NP-VTM samples with Ceres bead collection as follows. Twenty microliters of beads were added to 400 μL of clinical sample and 800 μL of viral DNA/RNA buffer and mixed on a shaker at 1200 rpm for 10 minutes. The samples were placed on the magnet and supernatant was removed before the addition and pipette-mixing of Zymo Wash Buffer 1. This was repeated for Zymo Wash Buffer 2 and two washes with 100% ethanol. All washes were performed at a volume of 500 μL. The beads were dried at 55° C. Once completely dried, 50 μL of water was added to the beads and mixed well. After placing the samples on the magnet, the supernatant was transfer to another plate for RNA storage. Five microliters of purified RNA were added to the RT-PCR mix in a PCR plate. The plate was sealed and placed in a thermocycler to undergo 20 minutes of reverse transcription and 45 cycles of asymmetric PCR. Upon PCR completion, the DNA microarray was prepared for hybridization with brief water washes, and an incubation in prehybridization buffer (0.6M NaCl, 0.06M sodium citrate solution, 0.1% Ficoll, 0.1% Polyvinylpyrrolidone 0.1% Bovine Serum Albumin). Following aspiration of the prehybridization buffer, a mixture of amplicon and hybridization buffer (0.6M NaCl, 0.06M sodium citrate solution, 0.1% Ficoll, 0.1% Polyvinylpyrrolidone 0.1% Bovine Serum Albumin) was added to the DNA microarray and allowed to incubate for 2 hours. The microarray is then washed with wash buffer (22.5 mM NaCl, 2.25 mM sodium citrate) and dried via centrifugation. The glass portion of the microarray was cleaned with lens tissue and 70% ethanol and images were acquired on the Sensospot. Images were then uploaded for Augury analysis.

TABLE 18

Summary of LoD Experiment Results

| Input Concentration | SARS-CoV-2 N1 | SARS-CoV-2 N2 | Positive Final Call | % Positive Final Call |
|---|---|---|---|---|
| 1500 cp/mL | 20/20 | 19/20 | 20/20 | 100% |
| 1000 cp/mL | 19/20 | 13/20 | 19/20 | 95% |
| | | Final LoD | | |
| 1000 cp/mL | 19/20 | 13/20 | 19/20 | 95% |

Pure-SAL Saliva. Pooling Range Finding

Figure 17:
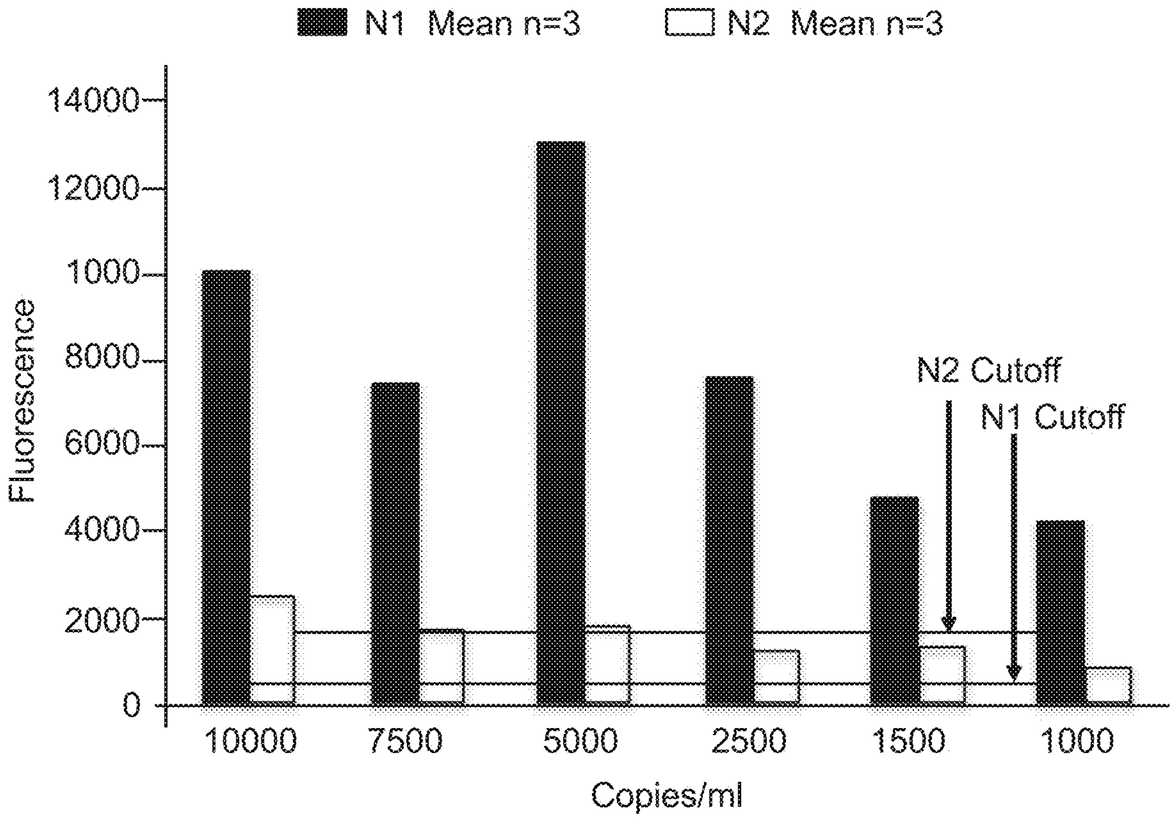
FIG. 17 shows LoD range finding DETECTX-Cv analysis for clinical negative saliva samples processed using Zymo bead capture.

The ability to pool CoV-2 contrived clinical negative PURE-SAL™ saliva samples was tested. Contrived clinical negative samples were pooled at (1) Positive Clinical Sample (100 L)+(4) Clinical samples (100 (L each), to yield a final pooled sample where the viral complement of the original contrived clinical positive is diluted 5×. The entire pooled specimen was then subjected to Zymo magnetic bead purification, RT-PCR and Hybridization to DETECTX-Cv as described above. The results shown in FIG. 17 suggest that subsequent to 5× pooling, the LoD is reduced less than the full 5× expected from a simple 5× dilution, thus demonstrating feasibility of the N=5 PURE-SAL™ pooling.

EXAMPLE 10

Autonomous Analysis

DETECTX-Cv analysis was performed by hands-free, autonomous analysis of raw DETECTX-microarray data obtained from Sensovation Scans to generate "Mutant" vs "Wild Type" calls among the ten (10) Spike target sites Table 19. These calls were subsequently used for Clade identification. The autonomous analysis is presented here along with manual Augury analysis.

The following multiple functional modules were added to Augury to enable autonomous analysis of DETECTX-Cv data as follows;

(1) Look-Up Table. A database (a "Look-Up Table") directly related to a Clade Variant vs Mutation data matrix (Table 19) was programmed into Augury. The database is flexible, resident within Augury and can be increased in size as needed to include a larger number of Spike Gene Targets (i.e. more columns as in Table 19) or Clade Variant Targets (i.e. more Rows as in Table 19). Augury is intrinsically linked to the cloud. Further, the Clade Variant Look-Up Table in Augury can be updated in real time via secure inputs such as those which could be provided by Rosalind (San Diego, CA).

(2) Comparison among probe data sets. Augury was modified to compare probe information to be used for data quality (QA/QC) and for interpretation of the RFU data (Clade ID):

a) QA/QC based on signal strength (signal intensity). The universal probes described earlier were used to measure data quality. If universal probe signals were <10,000 (resulting from sample degradation or low concentration), the data associated with the corresponding Mutant and Wild type data at a Spike Target Site are not used by Augury for Clade variant identification.

b) Data Interpretation: Primary. "Wild Type" and "Mutant" Probe data (RFU) were compared automatically, along with clinical threshold data stored in Augury to generate a "Delta" value (see Example 6). A Delta value greater than 0 returns a "Mutant" call, whereas a Delta value less than 0 returns a "Wild Type" call at each Spike Target Site.

c) Data Interpretation: Secondary. The pattern of Wild Type vs Mutant calls (i.e. the rows in Table 19) obtained from the Primary Data Interpretation were automatically compared to patterns associated with known Clade variants. The most likely Clade variant pattern is automatically reported. A statistical probability is also assignable to the Clade Variant call and alternative calls based on DETECTX-Cv analysis of multiple Clade Variant samples.

d) Data Reports. A Standard Report Format was chosen.

DETECTX-Cv Analysis of Synthetic Clade Variant Standards at TriCore

Five (5) synthetic Clade variant standards described earlier (UK, SA, CA452, Brazil P.1, India, Examples 8 and 9) were used for on-site validation. Each standard contained a synthetic gene fragment (IDT) identical to each of the Spike domains amplified by the RT-PCR multiplex. DETECTX-Cv data were obtained at TriCore at 100 copies/reaction for each of the five (5) synthetic cocktails. Analysis of the hybridization data were plotted as described previously. Table 20 shows a plate map, PCR recipe and cycling conditions for this analysis. DNA fragment cocktails were utilized as reference.

TABLE 19

| | | | | | Spike Gene Target Region (Codon) Amino Acid Change | | | | | | |
|---|---|---|---|---|---|---|---|---|---|---|---|
| | | | | | L5F | S13I | L18F | T20N | P26S | Q52R | A67V |
| | Street name | Pango lineage | CDC % Mar. 14-27, 2021 (US) | Incidence % Gisaid March 2021 | Signal (1-13) | | S1 subunit (14-685) N-terminal domain (14-305) | | | | |
| VOC | UK | B.1.1.7 | 44.10% | 49.81% | $L^3$ | $S^2$ | $L^3$ | $T^2$ | $P^3$ | $Q^3$ | $A^3$ |
| VOC | California L452R | B.1.427 | 6.90% | 2.08% | $L^3$ | $I^1$ | $L^3$ | $T^2$ | $P^3$ | $Q^3$ | $A^3$ |
| VOC | | B.1.427 | 2.90% | 0.90% | $L^3$ | $S/I^1$ | $L^3$ | $T^2$ | $P^3$ | $Q^3$ | $A^3$ |
| VOC | Brazil | P.1 | 1.40% | 0.39% | $L^3$ | $S^2$ | F | $N^1$ | S | $Q^3$ | $A^3$ |
| VOC | SA | B.1.351 | 0.70% | 1.13% | $L^3$ | $S^2$ | $L^3$ | $T^2$ | $P^3$ | $Q^3$ | $A^3$ |
| VOC | NYC (Ho et al.) | B.1.526 | 9.20% | 0.82% | L/F | $S^2$ | $L^3$ | $T^2$ | $P^3$ | $Q^3$ | $A^3$ |
| VOC | NYC | B.1.525 | 0.50% | 0.10% | $L^3$ | $S^2$ | $L^3$ | $T^2$ | $P^3$ | R | V |
| VOC | Rio de Janeiro | P.2 | 0.30% | 0.36% | $L^3$ | $S^2$ | $L^3$ | $T^2$ | $P^3$ | $Q^3$ | $A^3$ |
| | | B.1.2 | 10.00% | 7.83% | $L^3$ | $S^2$ | $L^3$ | $T^2$ | $P^3$ | $Q^3$ | $A^3$ |
| | | B.1, B.1.1, B.1.234 | 2.4%/ 0.9%/ 0.5% | 2.6%/ 1.5%/ 0.5% | $L^3$ | $S^2$ | $L^3$ | $T^2$ | $P^3$ | $Q^3$ | $A^3$ |
| | | B.1.1.519 | 4.10% | 1.50% | $L^3$ | $S^2$ | $L^3$ | $T^2$ | $P^3$ | $Q^3$ | $A^3$ |
| | | B.1.526.1 | 3.90% | 0.35% | F | $S^2$ | $L^3$ | $T^2$ | $P^3$ | $Q^3$ | $A^3$ |
| | | B.1.526.2 | 2.90% | 0.18% | F | $S^2$ | $L^3$ | $T^2$ | $P^3$ | $Q^3$ | $A^3$ |
| | | B.1.596 | 1.70% | 1.04% | $L^3$ | $S^2$ | $L^3$ | $T^2$ | $P^3$ | $Q^3$ | $A^3$ |
| | | R.1 | 1.20% | 0.20% | $L^3$ | $S^2$ | $L^3$ | $T^2$ | $P^3$ | $Q^3$ | $A^3$ |
| | | B.1.575 | 1.10% | 0.19% | $L^3$ | $S^2$ | $L^3$ | $T^2$ | $P^3$ | $Q^3$ | $A^3$ |
| | | B.1.243, B.1.1.207 | 0.60% | 0.84% | $L^3$ | $S^2$ | $L^3$ | $T^2$ | $P^3$ | $Q^3$ | $A^3$ |
| | US | B.1.375 | <1% | 0.03% | $L^3$ | $S^2$ | $L^3$ | $T^2$ | $P^3$ | $Q^3$ | $A^3$ |
| | | B.1.1.1, B.1.416, B.1.1.33, B.1.311, B.1.1.122 | <1% | 0.50% | $L^3$ | $S^2$ | $L^3$ | $T^2$ | $P^3$ | $Q^3$ | $A^3$ |
| | Brazil (Original) | B.1.1.28 | <1% | 0.10% | $L^3$ | $S^2$ | $L^3$ | $T^2$ | $P^3$ | $Q^3$ | $A^3$ |
| | Andhra Pradesh | B.1.36.29 | <1% | 0.08% | $L^3$ | $S^2$ | F | $T^2$ | $P^3$ | $Q^3$ | $A^3$ |
| | | A.23.1 | <1% | 0.05% | $L^3$ | $S^2$ | $L^3$ | $T^2$ | $P^3$ | $Q^3$ | $A^3$ |
| | | A.27 | <1% | 0.05% | $L^3$ | $S^2$ | F | $T^2$ | $P^3$ | $Q^3$ | $A^3$ |
| | | A.28 | <1% | 0.02% | $L^3$ | $S^2$ | $L^3$ | $T^2$ | $P^3$ | $Q^3$ | $A^3$ |
| | Mink/Cluster V | B.1.1.298 | <1% | 0.00% | $L^3$ | $S^2$ | $L^3$ | $T^2$ | $P^3$ | $Q^3$ | $A^3$ |
| | | B.1.1.318 | <1% | 0.01% | $L^3$ | $S^2$ | $L^3$ | $T^2$ | $P^3$ | $Q^3$ | $A^3$ |
| | | B.1.160 | <1% | 1.76% | $L^3$ | $S^2$ | $L^3$ | $T^2$ | $P^3$ | $Q^3$ | $A^3$ |
| | | B.1.177 | <1% | 3.19% | $L^3$ | $S^2$ | F | $T^2$ | $P^3$ | $Q^3$ | $A^3$ |
| | | B.1.177.80 | <1% | 0.04% | $L^3$ | $S^2$ | F | $T^2$ | $P^3$ | $Q^3$ | $A^3$ |
| | | B.1.258 | <1% | 1.15% | $L^3$ | $S^2$ | $L^3$ | $T^2$ | $P^3$ | $Q^3$ | $A^3$ |
| | | B.1.258.14 | <1% | 0.06% | $L^3$ | $S^2$ | $L^3$ | $T^2$ | $P^3$ | $Q^3$ | $A^3$ |
| | | B.1.258.17 | <1% | 1.02% | $L^3$ | $S^2$ | $L^3$ | $T^2$ | $P^3$ | $Q^3$ | $A^3$ |
| | | B.1.517 | <1% | 0.25% | $L^3$ | $S^2$ | $L^3$ | $T^2$ | $P^3$ | $Q^3$ | $A^3$ |
| | WUHAN | WUHAN | — | — | $L^3$ | $S^2$ | $L^3$ | $T^2$ | $P^3$ | $Q^3$ | $A^3$ |
| PCR Amplimer length (bases) | | | | | | | | (1) 101 | | | $(2_B)$ 150 |

| | | | | | Δ69-70 | D80A/G | T95I | D138Y | Y144DEL | W152C | F157L/S |
|---|---|---|---|---|---|---|---|---|---|---|---|
| | Street name | Pango lineage | CDC % Mar. 14-27, 2021 (US) | Incidence % Gisaid March 2021 | | | S1 subunit (14-685) N-terminal domain (14-305) | | | | |
| VOC | UK | B.1.1.7 | 44.10% | 49.81% | $Δ^1$ | $D^2$ | $T^3$ | $D^2$ | $Δ^1$ | $W^2$ | $F^3$ |
| VOC | California L452R | B.1.427 | 6.90% | 2.08% | $HV^2$ | $D^2$ | $T^3$ | $D^2$ | $Y^2$ | $C^1$ | $F^3$ |
| VOC | | B.1.427 | 2.90% | 0.90% | $HV^2$ | $D^2$ | $T^3$ | $D^2$ | $Y^2$ | $W/C^2$ | $F^3$ |
| VOC | Brazil | P.1 | 1.40% | 0.39% | $HV^2$ | $D^2$ | $T^3$ | $Y^1$ | $Y^2$ | $W^2$ | $F^3$ |
| VOC | SA | B.1.351 | 0.70% | 1.13% | $HV^2$ | $A^1$ | $T^3$ | $D^2$ | $Y^2$ | $W^2$ | $F^3$ |
| VOC | NYC (Ho et al.) | B.1.526 | 9.20% | 0.82% | $HV^2$ | $D^2$ | I | $D^2$ | $Y^2$ | $W^2$ | $F^3$ |
| VOC | NYC | B.1.525 | 0.50% | 0.10% | $Δ^1$ | $D^2$ | $T^3$ | $D^2$ | $Δ^1$ | $W^2$ | $F^3$ |
| VOC | Rio de Janeiro | P.2 | 0.30% | 0.36% | $HV^2$ | $D^2$ | $T^3$ | $D^2$ | $Y^2$ | $W^2$ | $F^3$ |
| | | B.1.2 | 10.00% | 7.83% | $HV^2$ | $D^2$ | $T^3$ | $D^2$ | $Y^2$ | $W^2$ | $F^3$ |
| | | B.1, B.1.1, B.1.234 | 2.4%/ 0.9%/ 0.5% | 2.6%/ 1.5%/ 0.5% | $HV^2$ | $D^2$ | $T^3$ | $D^2$ | $Y^2$ | $W^2$ | $F^3$ |
| | | B.1.1.519 | 4.10% | 1.50% | $HV^2$ | $D^2$ | $T^3$ | $D^2$ | $Y^2$ | $W^2$ | $F^3$ |
| | | B.1.526.1 | 3.90% | 0.35% | $HV^2$ | G | I | $D^2$ | $Δ^1$ | $W^2$ | S |
| | | B.1.526.2 | 2.90% | 0.18% | $HV^2$ | $D^2$ | $T^3$ | $D^2$ | $Y^2$ | $W^2$ | $F^3$ |
| | | B.1.596 | 1.70% | 1.04% | $HV^2$ | $D^2$ | $T^3$ | $D^2$ | $Y^2$ | $W^2$ | $F^3$ |

TABLE 19-continued

| | | | | | Spike Gene Target Region (Codon) Amino Acid Change | | | | | | |
|---|---|---|---|---|---|---|---|---|---|---|---|
| | | R.1 | 1.20% | 0.20% | $HV^2$ | $D^2$ | $T^3$ | $D^2$ | $Y^2$ | L | $F^3$ |
| | | B.1.575 | 1.10% | 0.19% | $HV^2$ | $D^2$ | $T^3$ | $D^2$ | $Y^2$ | $W^2$ | $F^3$ |
| | | B.1.243, B.1.1.207 | 0.60% | 0.84% | $HV^2$ | $D^2$ | $T^3$ | $D^2$ | $Y^2$ | $W^2$ | $F^3$ |
| | US | B.1.375 | <1% | 0.03% | $\Delta^1$ | $D^2$ | $T^3$ | $D^2$ | $Y^2$ | $W^2$ | $F^3$ |
| | | B.1.1.1, B.1.416, B.1.1.33, B.1.311, B.1.1.122 | <1% | 0.50% | $HV^2$ | $D^2$ | $T^3$ | $D^2$ | $Y^2$ | $W^2$ | $F^3$ |
| | Brazil (Original) | B.1.1.28 | <1% | 0.10% | $HV^2$ | $D^2$ | $T^3$ | $D^2$ | $Y^2$ | $W^2$ | $F^3$ |
| | Andhra Pradesh | B.1.36.29 | <1% | 0.08% | $HV^2$ | $D^2$ | $T^3$ | $D^2$ | $Y^2$ | $W^2$ | $F^3$ |
| | | A.23.1 | <1% | 0.05% | $HV^2$ | $D^2$ | $T^3$ | $D^2$ | $Y^2$ | $W^2$ | L |
| | | A.27 | <1% | 0.05% | $HV^2$ | $D^2$ | $T^3$ | $D^2$ | $Y^2$ | $W^2$ | $F^3$ |
| | | A.28 | <1% | 0.02% | $\Delta^1$ | $D^2$ | $T^3$ | $D^2$ | $Y^2$ | $W^2$ | $F^3$ |
| | Mink/Cluster V | B.1.1.298 | <1% | 0.00% | $\Delta^1$ | $D^2$ | $T^3$ | $D^2$ | $Y^2$ | $W^2$ | $F^3$ |
| | | B.1.1.318 | <1% | 0.01% | $HV^2$ | $D^2$ | $T^3$ | $D^2$ | $\Delta^1$ | $W^2$ | $F^3$ |
| | | B.1.160 | <1% | 1.76% | $HV^2$ | $D^2$ | $T^3$ | $D^2$ | $Y^2$ | $W^2$ | $F^3$ |
| | | B.1.177 | <1% | 3.19% | $HV^2$ | $D^2$ | $T^3$ | $D^2$ | $Y^2$ | $W^2$ | $F^3$ |
| | | B.1.177.80 | <1% | 0.04% | $HV^2$ | $D^2$ | $T^3$ | $D^2$ | $\Delta/Y^1$ | $W^2$ | $F^3$ |
| | | B.1.258 | <1% | 1.15% | $HV/\Delta^1$ | $D^2$ | $T^3$ | $D^2$ | $Y^2$ | $W^2$ | $F^3$ |
| | | B.1.258.14 | <1% | 0.06% | $HV^2$ | $D^2$ | $T^3$ | $D^2$ | $Y^2$ | $W^2$ | $F^3$ |
| | | B.1.258.17 | <1% | 1.02% | $\Delta^1$ | $D^2$ | $T^3$ | $D^2$ | $Y^2$ | $W^2$ | $F^3$ |
| | | B.1.517 | <1% | 0.25% | $HV^2$ | $D^2$ | $T^3$ | $D^2$ | $Y^2$ | $W^2$ | $F^3$ |
| | WUHAN | WUHAN | — | — | $HV^2$ | $D^2$ | $T^3$ | $D^2$ | $Y^2$ | $W^2$ | $F^3$ |
| PCR Amplimer length (bases) | | | | | $(2_B)$ 150 | | | | (3) 129 | | |
| | | | | | L189F | R190S | D215G | A222V | A243del | G252V | D253G |
| | Street name | Pango lineage | CDC % Mar. 14-27, 2021 (US) | Incidence % Gisaid March 2021 | S1 subunit (14-685) N-terminal domain (14-305) | | | | | | |
| VOC | UK | B.1.1.7 | 44.10% | 49.81% | $L^3$ | $R^3$ | $D^3$ | $A^3$ | $A^2$ | $G^3$ | $D^2$ |
| VOC | California L452R | B.1.427 | 6.90% | 2.08% | $L^3$ | $R^3$ | $D^3$ | $A^3$ | $A^2$ | $G^3$ | $D^2$ |
| VOC | | B.1.427 | 2.90% | 0.90% | $L^3$ | $R^3$ | $D^3$ | $A^3$ | $A^2$ | $G^3$ | $D^2$ |
| VOC | Brazil | P.1 | 1.40% | 0.39% | $L^3$ | S | $D^3$ | $A^3$ | $A^2$ | $G^3$ | $D^2$ |
| VOC | SA | B.1.351 | 0.70% | 1.13% | $L^3$ | $R^3$ | G | $A^3$ | $\Delta^1$ | $G^3$ | $D^2$ |
| VOC | NYC (Ho et al.) | B.1.526 | 9.20% | 0.82% | $L^3$ | $R^3$ | $D^3$ | $A^3$ | $A^2$ | $G^3$ | $G^1$ |
| VOC | NYC | B.1.525 | 0.50% | 0.10% | $L^3$ | $R^3$ | $D^3$ | $A^3$ | $A^2$ | $G^3$ | $D^2$ |
| VOC | Rio de Janeiro | P.2 | 0.30% | 0.36% | $L^3$ | $R^3$ | $D^3$ | $A^3$ | $A^2$ | $G^3$ | $D^2$ |
| | | B.1.2 | 10.00% | 7.83% | $L^3$ | $R^3$ | $D^3$ | $A^3$ | $A^2$ | $G^3$ | $D^2$ |
| | | B.1, B.1.1, B.1.234 | 2.4%/ 0.9%/ 0.5% | 2.6%/ 1.5%/ 0.5% | $L^3$ | $R^3$ | $D^3$ | $A^3$ | $A^2$ | $G^3$ | $D^2$ |
| | | B.1.1.519 | 4.10% | 1.50% | $L^3$ | $R^3$ | $D^3$ | $A^3$ | $A^2$ | $G^3$ | $D^2$ |
| | | B.1.526.1 | 3.90% | 0.35% | $L^3$ | $R^3$ | $D^3$ | $A^3$ | $A^2$ | $G^3$ | $D/G^1$ |
| | | B.1.526.2 | 2.90% | 0.18% | $L^3$ | $R^3$ | $D^3$ | $A^3$ | $A^2$ | $G^3$ | $G^1$ |
| | | B.1.596 | 1.70% | 1.04% | $L^3$ | $R^3$ | $D^3$ | $A^3$ | $A^2$ | $G^3$ | $D^2$ |
| | | R.1 | 1.20% | 0.20% | $L^3$ | $R^3$ | $D^3$ | $A^3$ | $A^2$ | $G^3$ | $D^2$ |
| | | B.1.575 | 1.10% | 0.19% | $L^3$ | $R^3$ | $D^3$ | $A^3$ | $A^2$ | $G^3$ | $D^2$ |
| | | B.1.243, B.1.1.207 | 0.60% | 0.84% | $L^3$ | $R^3$ | $D^3$ | $A^3$ | $A^2$ | $G^3$ | $D^2$ |
| | US | B.1.375 | <1% | 0.03% | $L^3$ | $R^3$ | $D^3$ | $A^3$ | $A^2$ | $G^3$ | $D^2$ |
| | | B.1.1.1, B.1.416, B.1.1.33, B.1.311, B.1.1.122 | <1% | 0.50% | $L^3$ | $R^3$ | $D^3$ | $A^3$ | $A^2$ | $G^3$ | $D^2$ |
| | Brazil (Original) | B.1.1.28 | <1% | 0.10% | $L^3$ | $R^3$ | $D^3$ | $A^3$ | $A^2$ | $G^3$ | $D^2$ |
| | Andhra Pradesh | B.1.36.29 | <1% | 0.08% | $L^3$ | $R^3$ | $D^3$ | $A^3$ | $A^2$ | $G^3$ | $D^2$ |
| | | A.23.1 | <1% | 0.05% | $L^3$ | $R^3$ | $D^3$ | $A^3$ | $A^2$ | $G^3$ | $D^2$ |
| | | A.27 | <1% | 0.05% | $L^3$ | $R^3$ | $D^3$ | $A^3$ | $A^2$ | $G^3$ | $D^2$ |
| | | A.28 | <1% | 0.02% | $L^3$ | $R^3$ | $D^3$ | $A^3$ | $A^2$ | $G^3$ | $D^2$ |
| | Mink/Cluster V | B.1.1.298 | <1% | 0.00% | $L^3$ | $R^3$ | $D^3$ | $A^3$ | $A^2$ | $G^3$ | $D^2$ |
| | | B.1.1.318 | <1% | 0.01% | $L^3$ | $R^3$ | $D^3$ | $A^3$ | $A^2$ | $G^3$ | $D^2$ |
| | | B.1.160 | <1% | 1.76% | $L^3$ | $R^3$ | $D^3$ | $A^3$ | $A^2$ | $G^3$ | $D^2$ |
| | | B.1.177 | <1% | 3.19% | $L^3$ | $R^3$ | $D^3$ | V | $A^2$ | $G^3$ | $D^2$ |
| | | B.1.177.80 | <1% | 0.04% | $L^3$ | $R^3$ | $D^3$ | V | $A^2$ | $G^3$ | $D^2$ |
| | | B.1.258 | <1% | 1.15% | $L^3$ | $R^3$ | $D^3$ | $A^3$ | $A^2$ | $G^3$ | $D^2$ |
| | | B.1.258.14 | <1% | 0.06% | $L^3$ | $R^3$ | $D^3$ | $A^3$ | $A^2$ | $G^3$ | $D^2$ |
| | | B.1.258.17 | <1% | 1.02% | F | $R^3$ | $D^3$ | $A^3$ | $A^2$ | $G^3$ | $D^2$ |
| | | B.1.517 | <1% | 0.25% | $L^3$ | $R^3$ | $D^3$ | $A^3$ | $A^2$ | G/V | $D^2$ |
| | WUHAN | WUHAN | — | — | $L^3$ | $R^3$ | $D^3$ | $A^3$ | $A^2$ | $G^3$ | $D^2$ |
| PCR Amplimer length (bases) | | | | | | | | | | $(4_B)$ 160 | |

TABLE 19-continued

| | | | | | Spike Gene Target Region (Codon) Amino Acid Change | | | | | | |
|---|---|---|---|---|---|---|---|---|---|---|---|
| | | | | | V367F | K417N/T | N439K | N440K | L452R | Y453F | S477N |
| | Street name | Pango lineage | CDC % Mar. 14-27, 2021 (US) | Incidence % Gisaid March 2021 | S1 subunit (14-685) RBD (319-541) | | | | | | |
| VOC | UK | B.1.1.7 | 44.10% | 49.81% | $V^3$ | $K^2$ | $N^2$ | $N^2$ | $L^2$ | $Y^2$ | $S^2$ |
| VOC | California L452R | B.1.427 | 6.90% | 2.08% | $V^3$ | $K^2$ | $N^2$ | $N^2$ | $R^1$ | $Y^2$ | $S^2$ |
| VOC | | B.1.429 | 2.90% | 0.90% | $V^3$ | $K^2$ | $N^2$ | $N^2$ | $R^1$ | $Y^2$ | $S^2$ |
| VOC | Brazil | P.1 | 1.40% | 0.39% | $V^3$ | $K^2$ | $N^2$ | $N^2$ | $L^2$ | $Y^2$ | $S^2$ |
| VOC | SA | B.1.351 | 0.70% | 1.13% | $V^3$ | $K^2$ | $N^2$ | $N^2$ | $L^2$ | $Y^2$ | $S^2$ |
| VOC | NYC (Ho et al.) | B.1.526 | 9.20% | 0.82% | $V^3$ | $K^2$ | $N^2$ | $N^2$ | $L^2$ | $Y^2$ | $S/N^1$ |
| VOC | NYC | B.1.525 | 0.50% | 0.10% | $V^3$ | $K^2$ | $N^2$ | $N^2$ | $L^2$ | $Y^2$ | $S^2$ |
| VOC | Rio de Janeiro | P.2 | 0.30% | 0.36% | $V^3$ | $K^2$ | $N^2$ | $N^2$ | $L^2$ | $Y^2$ | $S^2$ |
| | | B.1.2 | 10.00% | 7.83% | $V^3$ | $K^2$ | $N^2$ | $N^2$ | $L^2$ | $Y^2$ | $S^2$ |
| | | B.1, B.1.1, B.1.234 | 2.4%/ 0.9%/ 0.5% | 2.6%/ 1.5%/ 0.5% | $V^3$ | $K^2$ | $N^2$ | $N^2$ | $L^2$ | $Y^2$ | $S^2$ |
| | | B.1.1.519 | 4.10% | 1.50% | $V^3$ | $K^2$ | $N^2$ | $N^2$ | $L^2$ | $Y^2$ | $S^2$ |
| | | B.1.526.1 | 3.90% | 0.35% | $V^3$ | $K^2$ | $N^2$ | $N^2$ | $R^1$ | $Y^2$ | $S^2$ |
| | | B.1.526.2 | 2.90% | 0.18% | $V^3$ | $N/T^1$ | $N^2$ | $N^2$ | $L^2$ | $Y^2$ | $N^1$ |
| | | B.1.596 | 1.70% | 1.04% | $V^3$ | $N^1$ | $N^2$ | $N^2$ | $L^2$ | $Y^2$ | $S^2$ |
| | | R.1 | 1.20% | 0.20% | $V^3$ | $K^2$ | $N^2$ | $N^2$ | $L^2$ | $Y^2$ | $S^2$ |
| | | B.1.575 | 1.10% | 0.19% | $V^3$ | $K^2$ | $N^2$ | $N^2$ | $L^2$ | $Y^2$ | $S^2$ |
| | | B.1.243, B.1.1.207 | 0.60% | 0.84% | $V^3$ | $K^2$ | $N^2$ | $N^2$ | $L^2$ | $Y^2$ | $S^2$ |
| | US | B.1.375 | <1% | 0.03% | $V^3$ | $K^2$ | $N^2$ | $N^2$ | $L^2$ | $Y^2$ | $S^2$ |
| | | B.1.1.1, B.1.416, B.1.1.33, B.1.311, B.1.1.122 | <1% | 0.50% | $V^3$ | $K^2$ | $N^2$ | $N^2$ | $L^2$ | $Y^2$ | $S^2$ |
| | Brazil Original | B.1.1.28 | <1% | 0.10% | $V^3$ | $K^2$ | $N^2$ | $N^2$ | $L^2$ | $Y^2$ | $S^2$ |
| | Andhra Pradesh | B.1.36.29 | <1% | 0.08% | $V^3$ | $K^2$ | $N^2$ | $K^1$ | $L^2$ | $Y^2$ | $S^2$ |
| | | A.23.1 | <1% | 0.05% | F | $K^2$ | $N^2$ | $N^2$ | $L^2$ | $Y^2$ | $S^2$ |
| | | A.27 | <1% | 0.05% | $V^3$ | $K^2$ | $N^2$ | $N^2$ | $R^1$ | $Y^2$ | $S^2$ |
| | | A.28 | <1% | 0.02% | $V^3$ | $K^2$ | $N^2$ | $N^2$ | $L^2$ | $Y^2$ | $S^2$ |
| | Mink/ Cluster V | B.1.1.298 | <1% | 0.00% | $V^3$ | $K^2$ | $N^2$ | $N^2$ | $L^2$ | $F^1$ | $S^2$ |
| | | B.1.1.318 | <1% | 0.01% | $V^3$ | $K^2$ | $N^2$ | $N^2$ | $L^2$ | $Y^2$ | $S^2$ |
| | | B.1.160 | <1% | 1.76% | $V^3$ | $K^2$ | $N^2$ | $N^2$ | $L^2$ | $Y^2$ | $N^1$ |
| | | B.1.177 | <1% | 3.19% | $V^3$ | $K^2$ | $N^2$ | $N^2$ | $L^2$ | $Y^2$ | $S^2$ |
| | | B.1.177.80 | <1% | 0.04% | $V^3$ | $K^2$ | $N^2$ | $N^2$ | $L^2$ | $Y^2$ | $S^2$ |
| | | B.1.258 | <1% | 1.15% | $V^3$ | $K^2$ | $K^1$ | $N^2$ | $L^2$ | $Y^2$ | $S^2$ |
| | | B.1.258.14 | <1% | 0.06% | $V^3$ | $K^2$ | $K^1$ | $N^2$ | $L^2$ | $Y^2$ | $S^2$ |
| | | B.1.258.17 | <1% | 1.02% | $V^3$ | $K^2$ | $K^1$ | $N^2$ | $L^2$ | $Y^2$ | $S^2$ |
| | | B.1.517 | <1% | 0.25% | $V^3$ | $K^2$ | $N^2$ | $N^2$ | $L^2$ | $Y^2$ | $S^2$ |
| | WUHAN | WUHAN | — | — | $V^3$ | $K^2$ | $N^2$ | $N^2$ | $L^2$ | $Y^2$ | $S^2$ |
| PCR Amplimer length (bases) | | | | | | | | (5) 199 | | | (6) 151 |

| | | | | | V483A | E484K | S494P | N501Y/T | A570D | Q613H | D614G |
|---|---|---|---|---|---|---|---|---|---|---|---|
| | Street name | Pango lineage | CDC % Mar. 14-27, 2021 (US) | Incidence % Gisaid March 2021 | S1 subunit (14-685) RBD (319-541) | | | | | | |
| VOC | UK | B.1.1.7 | 44.10% | 49.81% | $V^2$ | $E/K^1$ | S/P | $Y^1$ | D | $Q^2$ | $G^1$ |
| VOC | California L452R | B.1.427 | 6.90% | 2.08% | $V^2$ | $E^2$ | $S^3$ | $N^2$ | $A^3$ | $Q^2$ | $G^1$ |
| VOC | | B.1.429 | 2.90% | 0.90% | $V^2$ | $E^2$ | $S^3$ | $N^2$ | $A^3$ | $Q^2$ | $G^1$ |
| VOC | Brazil | P.1 | 1.40% | 0.39% | $V^2$ | $K^1$ | $S^3$ | $Y^1$ | $A^3$ | $Q^2$ | $G^1$ |
| VOC | SA | B.1.351 | 0.70% | 1.13% | $V^2$ | $K^1$ | $S^3$ | $Y^1$ | $A^3$ | $Q^2$ | $G^1$ |
| VOC | NYC (Ho et al.) | B.1.526 | 9.20% | 0.82% | $V^2$ | $E/K^1$ | $S^3$ | $N^2$ | $A^3$ | $Q^2$ | $G^1$ |
| VOC | NYC | B.1.525 | 0.50% | 0.10% | $V^2$ | $K^1$ | $S^3$ | $N^2$ | $A^3$ | $Q^2$ | $G^1$ |
| VOC | Rio de Janeiro | P.2 | 0.30% | 0.36% | $V^2$ | $K^1$ | $S^3$ | $N^2$ | $A^3$ | $Q^2$ | $G^1$ |
| | | B.1.2 | 10.00% | 7.83% | $V^2$ | $E^2$ | $S^3$ | $Y^1$ | $A^3$ | $Q^2$ | $G^1$ |
| | | B.1, B.1.1, B.1.234 | 2.4%/ 0.9%/ 0.5% | 2.6%/ 1.5%/ 0.5% | $V^2$ | $E^2$ | $S^3$ | $N^2$ | $A^3$ | $Q^2$ | $G^1$ |
| | | B.1.1.519 | 4.10% | 1.50% | $V^2$ | $E^2$ | $S^3$ | $N^2$ | $A^3$ | $Q^2$ | $G^1$ |
| | | B.1.526.1 | 3.90% | 0.35% | $V^2$ | $K^1$ | $S^3$ | $N^2$ | $A^3$ | $Q^2$ | $G^1$ |

TABLE 19-continued

| | | | | | Spike Gene Target Region (Codon) Amino Acid Change | | | | | | |
|---|---|---|---|---|---|---|---|---|---|---|---|
| | | B.1.526.2 | 2.90% | 0.18% | V$^2$ | E$^2$ | S$^3$ | N$^2$ | A$^3$ | Q$^2$ | G$^1$ |
| | | B.1.596 | 1.70% | 1.04% | V$^2$ | E$^2$ | S$^3$ | N$^2$ | A$^3$ | Q$^2$ | G$^1$ |
| | | R.1 | 1.20% | 0.20% | V$^2$ | K$^1$ | S$^3$ | N$^2$ | A$^3$ | Q$^2$ | G$^1$ |
| | | B.1.575 | 1.10% | 0.19% | V$^2$ | E$^2$ | P | N$^2$ | A$^3$ | Q$^2$ | G$^1$ |
| | | B.1.243, B.1.1.207 | 0.60% | 0.84% | V$^2$ | E$^2$ | S$^3$ | N$^2$ | A$^3$ | Q$^2$ | G$^1$ |
| | US | B.1.375 | <1% | 0.03% | V$^2$ | E$^2$ | S$^3$ | N$^2$ | A$^3$ | Q$^2$ | G$^1$ |
| | | B.1.1.1, B.1.416, B.1.1.33, B.1.311, B.1.1.122 | <1% | 0.50% | V$^2$ | E$^2$ | S$^3$ | N$^2$ | A$^3$ | Q$^2$ | G$^1$ |
| | Brazil Original | B.1.1.28 | <1% | 0.10% | V$^2$ | E$^2$ | S$^3$ | N$^2$ | A$^3$ | Q$^2$ | G$^1$ |
| | Andhra Pradesh | B.1.36.29 | <1% | 0.08% | V$^2$ | E$^2$ | S$^3$ | N$^2$ | A$^3$ | Q$^2$ | G$^1$ |
| | | A.23.1 | <1% | 0.05% | V$^2$ | E/K$^1$ | S$^3$ | N$^2$ | A$^3$ | H$^1$ | D$^2$ |
| | | A.27 | <1% | 0.05% | V$^2$ | E$^2$ | S$^3$ | Y$^1$ | A$^3$ | Q$^2$ | D$^2$ |
| | | A.28 | <1% | 0.02% | V$^2$ | E$^2$ | S$^3$ | T | A$^3$ | Q$^2$ | D$^2$ |
| | Mink/ Cluster V | B.1.1.298 | <1% | 0.00% | V$^2$ | E$^2$ | S$^3$ | N$^2$ | A$^3$ | Q$^2$ | G$^1$ |
| | | B.1.1.318 | <1% | 0.01% | V$^2$ | K$^1$ | S$^3$ | N$^2$ | A$^3$ | Q$^2$ | G$^1$ |
| | | B.1.160 | <1% | 1.76% | V$^2$ | E$^2$ | S$^3$ | N$^2$ | A$^3$ | Q$^2$ | G$^1$ |
| | | B.1.177 | <1% | 3.19% | V$^2$ | E$^2$ | S$^3$ | N$^2$ | A$^3$ | Q$^2$ | G$^1$ |
| | | B.1.177.80 | <1% | 0.04% | V$^2$ | E$^2$ | S$^3$ | N$^2$ | A$^3$ | Q$^2$ | G$^1$ |
| | | B.1.258 | <1% | 1.15% | V$^2$ | E$^2$ | S$^3$ | N$^2$ | A$^3$ | Q$^2$ | G$^1$ |
| | | B.1.258.14 | <1% | 0.06% | V$^2$ | E$^2$ | S$^3$ | N$^2$ | A$^3$ | Q$^2$ | G$^1$ |
| | | B.1.258.17 | <1% | 1.02% | V$^2$ | E$^2$ | S$^3$ | N$^2$ | A$^3$ | Q$^2$ | G$^1$ |
| | | B.1.517 | <1% | 0.25% | V$^2$ | E$^2$ | S$^3$ | T | A$^3$ | Q/H$^1$ | G$^1$ |
| | WUHAN | WUHAN | — | — | V$^2$ | E$^2$ | S$^3$ | N$^2$ | A$^3$ | Q$^2$ | D$^2$ |
| PCR Amplimer length (bases) | | | | | | | (6) 151 | | | (7) 88 | |

| | | | | | H655Y | Q677P/H | P681H | I692V | A701V | T716I | G769V |
|---|---|---|---|---|---|---|---|---|---|---|---|
| | Street name | Pango lineage | CDC % Mar. 14-27, 2021 (US) | Incidence % Gisaid March 2021 | S2 subunit (686-1273) | | | | | | |
| VOC | UK | B.1.1.7 | 44.10% | 49.81% | H$^3$ | Q$^2$ | H$^1$ | I$^2$ | A$^2$ | I | G$^3$ |
| VOC | California L452R | B.1.427 | 6.90% | 2.08% | H$^3$ | Q$^2$ | P$^2$ | I$^2$ | A$^2$ | T$^3$ | G$^3$ |
| VOC | | B.1.429 | 2.90% | 0.90% | H$^3$ | Q$^2$ | P$^2$ | I$^2$ | A$^2$ | T$^3$ | G$^3$ |
| VOC | Brazil | P.1 | 1.40% | 0.39% | Y | Q$^2$ | P$^2$ | I$^2$ | A$^2$ | T$^3$ | G$^3$ |
| VOC | SA | B.1.351 | 0.70% | 1.13% | H$^3$ | Q$^2$ | P$^2$ | I$^2$ | V$^1$ | T$^3$ | G$^3$ |
| VOC | NYC (Ho et al.) | B.1.526 | 9.20% | 0.82% | H$^3$ | Q$^2$ | P$^2$ | I$^2$ | A/V$^1$ | T$^3$ | G$^3$ |
| VOC | NYC | B.1.525 | 0.50% | 0.10% | H$^3$ | H$^1$ | P$^2$ | I$^2$ | A$^2$ | T$^3$ | G$^3$ |
| VOC | Rio de Janeiro | P.2 | 0.30% | 0.36% | H$^3$ | Q$^2$ | P$^2$ | I$^2$ | A$^2$ | T$^3$ | G$^3$ |
| | | B.1.2 | 10.00% | 7.83% | H$^3$ | Q$^2$ | P$^2$ | I$^2$ | A$^2$ | T$^3$ | G$^3$ |
| | | B.1, B.1.1, B.1.234 | 2.4%/ 0.9%/ 0.5% | 2.6%/ 1.5%/ 0.5% | H$^3$ | Q$^2$ | P$^2$ | I$^2$ | A$^2$ | T$^3$ | G$^3$ |
| | | B.1.1.519 | 4.10% | 1.50% | H$^3$ | Q$^2$ | H$^1$ | I$^2$ | A$^2$ | T$^3$ | G$^3$ |
| | | B.1.526.1 | 3.90% | 0.35% | H$^3$ | Q$^2$ | P$^2$ | I$^2$ | A/V$^1$ | T$^3$ | G$^3$ |
| | | B.1.526.2 | 2.90% | 0.18% | H$^3$ | Q$^2$ | P$^2$ | I$^2$ | A$^2$ | T$^3$ | G$^3$ |
| | | B.1.596 | 1.70% | 1.04% | H$^3$ | Q/P$^1$ | P$^2$ | I$^2$ | A$^2$ | T$^3$ | G$^3$ |
| | | R.1 | 1.20% | 0.20% | H$^3$ | Q$^2$ | P$^2$ | I$^2$ | A$^2$ | T$^3$ | V |
| | | B.1.575 | 1.10% | 0.19% | H$^3$ | Q$^2$ | H$^1$ | I$^2$ | A$^2$ | I | G$^3$ |
| | | B.1.243, B.1.1.207 | 0.60% | 0.84% | H$^3$ | Q$^2$ | H$^1$ | I$^2$ | A$^2$ | T$^3$ | G$^3$ |
| | US | B.1.375 | <1% | 0.03% | H$^3$ | Q$^2$ | P$^2$ | I$^2$ | A$^2$ | T$^3$ | G$^3$ |
| | | B.1.1.1, B.1.416, B.1.1.33, B.1.311, B.1.1.122 | <1% | 0.50% | H$^3$ | Q$^2$ | P$^2$ | I$^2$ | A$^2$ | T$^3$ | G$^3$ |
| | Brazil Original | B.1.1.28 | <1% | 0.10% | H$^3$ | Q$^2$ | P$^2$ | I$^2$ | A$^2$ | T$^3$ | G$^3$ |
| | Andhra Pradesh | B.1.36.29 | <1% | 0.08% | H$^3$ | Q$^2$ | P$^2$ | I$^2$ | A$^2$ | T$^3$ | G$^3$ |
| | | A.23.1 | <1% | 0.05% | Y | Q$^2$ | R$^1$ | I$^2$ | A$^2$ | T$^3$ | G$^3$ |
| | | A.27 | <1% | 0.05% | Y | Q$^2$ | P$^2$ | I$^2$ | A$^2$ | T$^3$ | G$^3$ |
| | | A.28 | <1% | 0.02% | H$^3$ | Q$^2$ | P$^2$ | I$^2$ | A$^2$ | T$^3$ | G$^3$ |
| | Mink/ Cluster V | B.1.1.298 | <1% | 0.00% | H$^3$ | Q$^2$ | P$^2$ | I$^2$ | A$^2$ | T$^3$ | G$^3$ |
| | | B.1.1.318 | <1% | 0.01% | H$^3$ | Q$^2$ | H$^1$ | I$^2$ | A$^2$ | T$^3$ | G$^3$ |
| | | B.1.160 | <1% | 1.76% | H$^3$ | Q$^2$ | P$^2$ | I$^2$ | A$^2$ | T$^3$ | G$^3$ |

TABLE 19-continued

Spike Gene Target Region (Codon) Amino Acid Change

| | | | | | | | | | | | |
|---|---|---|---|---|---|---|---|---|---|---|---|
| | | B.1.177 | <1% | 3.19% | H[3] | Q[2] | P[2] | I[2] | A[2] | T[3] | G[3] |
| | | B.1.177.80 | <1% | 0.04% | H[3] | Q[2] | P[2] | I[2] | A[2] | T[3] | G[3] |
| | | B.1.258 | <1% | 1.15% | H[3] | Q[2] | P[2] | I[2] | A[2] | T[3] | G[3] |
| | | B.1.258.14 | <1% | 0.06% | H[3] | Q[2] | P[2] | I[2] | A[2] | T[3] | G[3] |
| | | B.1.258.17 | <1% | 1.02% | H[3] | Q[2] | P[2] | I[2] | A[2] | T[3] | G[3] |
| | | B.1.517 | <1% | 0.25% | H[3] | Q[2] | P[2] | I[2] | A[2] | T[3] | G[3] |
| | WUHAN | WUHAN | — | — | H[3] | Q[2] | P[2] | I[2] | A[2] | T[3] | G[3] |
| PCR Amplimer length (bases) | | | | | | | (8) 135 | | | | |

| | | | | | D796V | F888L | S982A | T1027I | D1118H | V1176F |
|---|---|---|---|---|---|---|---|---|---|---|
| | Street name | Pango lineage | CDC % Mar. 14-27, 2021 (US) | Incidence % Gisaid March 2021 | S2 subunit (686-1273) Fusion peptide (788-806) | | | | | |
| VOC | UK | B.1.1.7 | 44.10% | 49.81% | D[3] | F[3] | A | T[3] | H | V[3] |
| VOC | California L452R | B.1.427 | 6.90% | 2.08% | D[3] | F[3] | S[3] | T[3] | D[3] | V[3] |
| VOC | | B.1.429 | 2.90% | 0.90% | D[3] | F[3] | S[3] | T[3] | D[3] | V[3] |
| VOC | Brazil | P.1 | 1.40% | 0.39% | D[3] | F[3] | S[3] | I | D[3] | F |
| VOC | SA | B.1.351 | 0.70% | 1.13% | D[3] | F[3] | S[3] | T[3] | D[3] | V[3] |
| VOC | NYC (Ho et al.) | B.1.526 | 9.20% | 0.82% | D[3] | F[3] | S[3] | T[3] | D[3] | V[3] |
| VOC | NYC | B.1.525 | 0.50% | 0.10% | D[3] | L | S[3] | T[3] | D[3] | V[3] |
| VOC | Rio de Janeiro | P.2 | 0.30% | 0.36% | D[3] | F[3] | S[3] | T[3] | D[3] | F |
| | | B.1.2 | 10.00% | 7.83% | D[3] | F[3] | S[3] | T[3] | D[3] | V[3] |
| | | B.1, B.1.1, B.1.234 | 2.4%/ 0.9%/ 0.5% | 2.6%/ 1.5%/ 0.5% | D[3] | F[3] | S[3] | T[3] | D[3] | V[3] |
| | | B.1.1.519 | 4.10% | 1.50% | D[3] | F[3] | S[3] | T[3] | D[3] | V[3] |
| | | B.1.526.1 | 3.90% | 0.35% | D[3] | F[3] | S[3] | T[3] | D[3] | V[3] |
| | | B.1.526.2 | 2.90% | 0.18% | D[3] | F[3] | S[3] | T[3] | D[3] | V[3] |
| | | B.1.596 | 1.70% | 1.04% | D[3] | F[3] | S[3] | T[3] | D[3] | V[3] |
| | | R.1 | 1.20% | 0.20% | D[3] | F[3] | S[3] | T[3] | D[3] | V[3] |
| | | B.1.575 | 1.10% | 0.19% | D[3] | F[3] | S[3] | T[3] | D[3] | V[3] |
| | | B.1.243, B.1.1.207 | 0.60% | 0.84% | D[3] | F[3] | S[3] | T[3] | D[3] | V[3] |
| | US | B.1.375 | <1% | 0.03% | D[3] | F[3] | S[3] | T[3] | D[3] | V[3] |
| | | B.1.1.1, B.1.416, B.1.1.33, B.1.311, B.1.1.122 | <1% | 0.50% | D[3] | F[3] | S[3] | T[3] | D[3] | V[3] |
| | Brazil Original | B.1.1.28 | <1% | 0.10% | D[3] | F[3] | S[3] | T[3] | D[3] | F |
| | Andhra Pradesh | B.1.36.29 | <1% | 0.08% | D[3] | F[3] | S[3] | T[3] | D[3] | V[3] |
| | | A.23.1 | <1% | 0.05% | D[3] | F[3] | S[3] | T[3] | D[3] | V[3] |
| | | A.27 | <1% | 0.05% | Y | F[3] | S[3] | T[3] | D[3] | V[3] |
| | | A.28 | <1% | 0.02% | D[3] | F[3] | S[3] | T[3] | D[3] | V[3] |
| | Mink/ Cluster V | B.1.1.298 | <1% | 0.00% | D[3] | F[3] | S[3] | T[3] | D[3] | V[3] |
| | | B.1.1.318 | <1% | 0.01% | D[3] | F[3] | S[3] | T[3] | D[3] | V[3] |
| | | B.1.160 | <1% | 1.76% | D[3] | F[3] | S[3] | T[3] | D[3] | V[3] |
| | | B.1.177 | <1% | 3.19% | D[3] | F[3] | S[3] | T[3] | D[3] | V[3] |
| | | B.1.177.80 | <1% | 0.04% | D[3] | F[3] | S[3] | T[3] | D[3] | V[3] |
| | | B.1.258 | <1% | 1.15% | D[3] | F[3] | S[3] | T[3] | D[3] | V[3] |
| | | B.1.258.14 | <1% | 0.06% | D[3] | F[3] | S[3] | T[3] | D[3] | V[3] |
| | | B.1.258.17 | <1% | 1.02% | D[3] | F[3] | S[3] | T[3] | D[3] | V[3] |
| | | B.1.517 | <1% | 0.25% | D[3] | F[3] | S[3] | T[3] | D[3] | V[3] |
| | WUHAN | WUHAN | — | — | D[3] | F[3] | S[3] | T[3] | D[3] | V[3] |
| PCR Amplimer length (bases) | | | | | | | | | | |

[1]AA mutation - hybridizes to mutation specific probe

[2]AA identical to hCoV-19/Wuhan/WIV04/2019 (WIV04) - official reference sequence employed by GISAID (EPI_ISL_402124)

[3]Potential probe target

TABLE 20

Plate map, PCR recipe and Cycling conditions used in the analysis

| Plate Map | | | RT-PCR Mix | | RT-PCR conditions | | | |
|---|---|---|---|---|---|---|---|---|
| | 1 | 2 | Components | Per reaction (μL) | Steps | Temp (° C.) | Time | Cycles |
| A | 300 copies S. Africa | 300 copies UK | ACCESSQUICK ™ Mastermix | 25 | 1 | 55 | 20 min | 1 |
| B | 100 copies S. Africa | 100 copies UK | Primer | 2 | 2 | 94 | 2 min | 1 |
| C | 300 copies California | 300 copies Wuhan gRNA | Avian Myeloblastosis Virus (AMV) Enzyme mix | 1 | 3 | 94 | 30 s | 45 |
| D | 100 copies California | 100 copies Wuhan gRNA | Water | 17 | 4 | 55 | 30 s | |
| E | 300 copies India | NTC | Total | 45 | 5 | 68 | 30 s | |
| F | 100 copies India | NTC | | | 6 | 68 | 7 min | 1 |
| G | 300 copies Brazil | NTC | | | 7 | 4 | ∞ | |
| H | 100 copies Brazil | NTC | | | | | | |

Results

FIGS. 18A-18E and Table 21 show the results from analysis of synthetic clade variant standards at TriCore. The data shows that the raw data, i.e. the ratio of Mutant (open bars) to Wild Type signal (black bars) readily identifies the state of each of the ten (10) target domains. Spike target sites, which were expected to display a "Mutant" signal (i.e. open bars>black bars), are marked in square brackets. As shown, the Mutant vs Wild type signals obtained by TriCore on synthetic Clade variant standards were as expected. The data established that the DETECTX-Cv workflow is easily deployable in any high throughput COVID-19 clinical testing lab.

TABLE 21

DETECTX-Cv analysis of synthetic Clade variant standards at TriCore

Figure 18A:
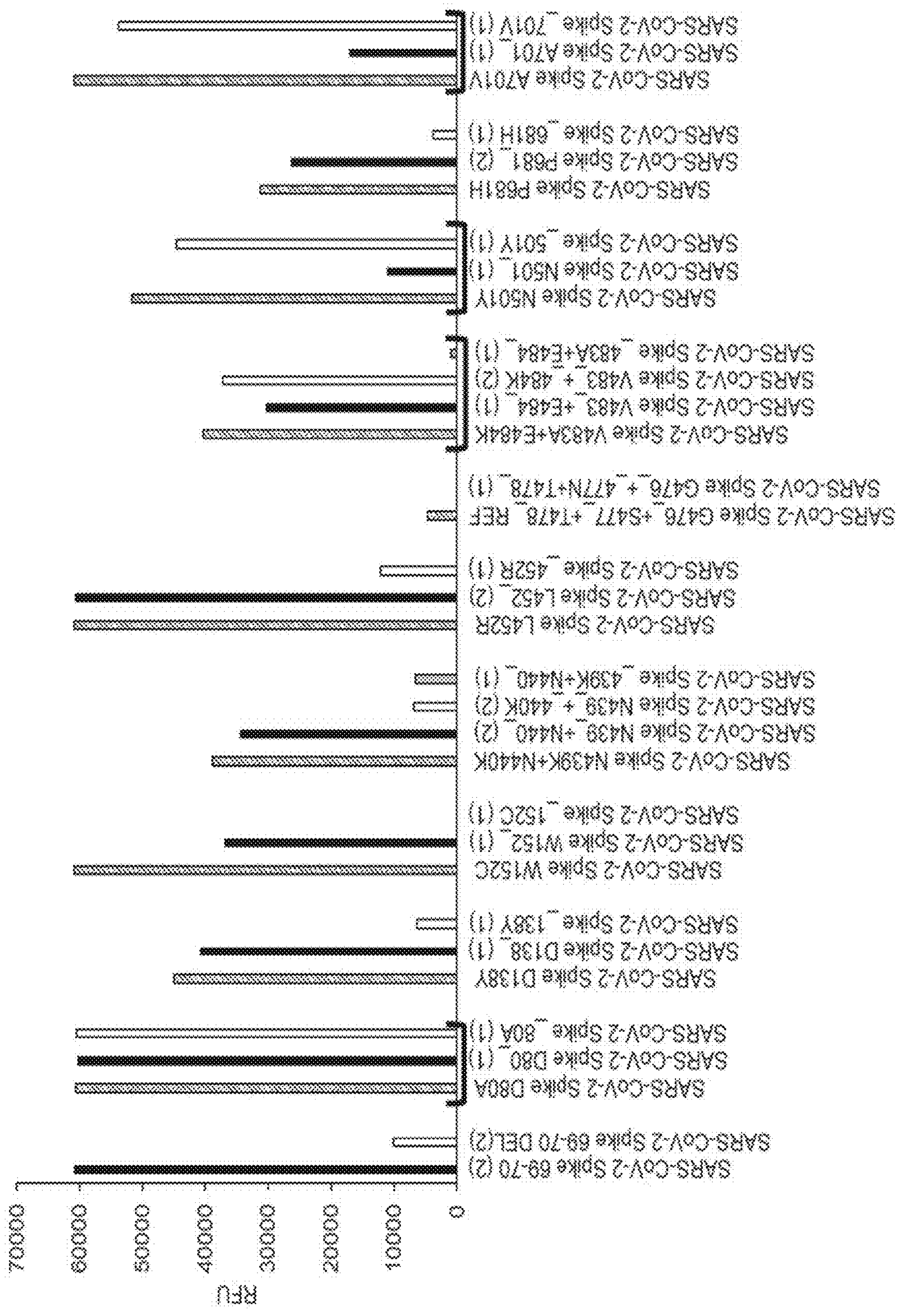
FIGS. 18A-18E shows representative DETECTX-Cv analysis of synthetic Clade variant standards.

Reference FIG. 18A

| Probe | Wild Type | Mutant Type | Confidence |
|---|---|---|---|
| HYBRIDIZED PROBES | | | |
| H/V69_ | ON | | 100.00% |
| _80A | | ON | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | | ON | 100.00% |
| _501Y | | ON | 100.00% |
| P681_ | ON | | 100.00% |
| _701V | | ON | 100.00% |

TABLE 21-continued

DETECTX-Cv analysis of synthetic Clade variant standards at TriCore

| | | | |
|---|---|---|---|
| UNHYBRIDIZED PROBES | | | |
| _152C | | OFF | 98.80% |
| _681H | | OFF | 100.00% |
| A701_ | OFF | | 97.40% |

Pattern consistent with S Africa (B.1.351)

Figure 18B:
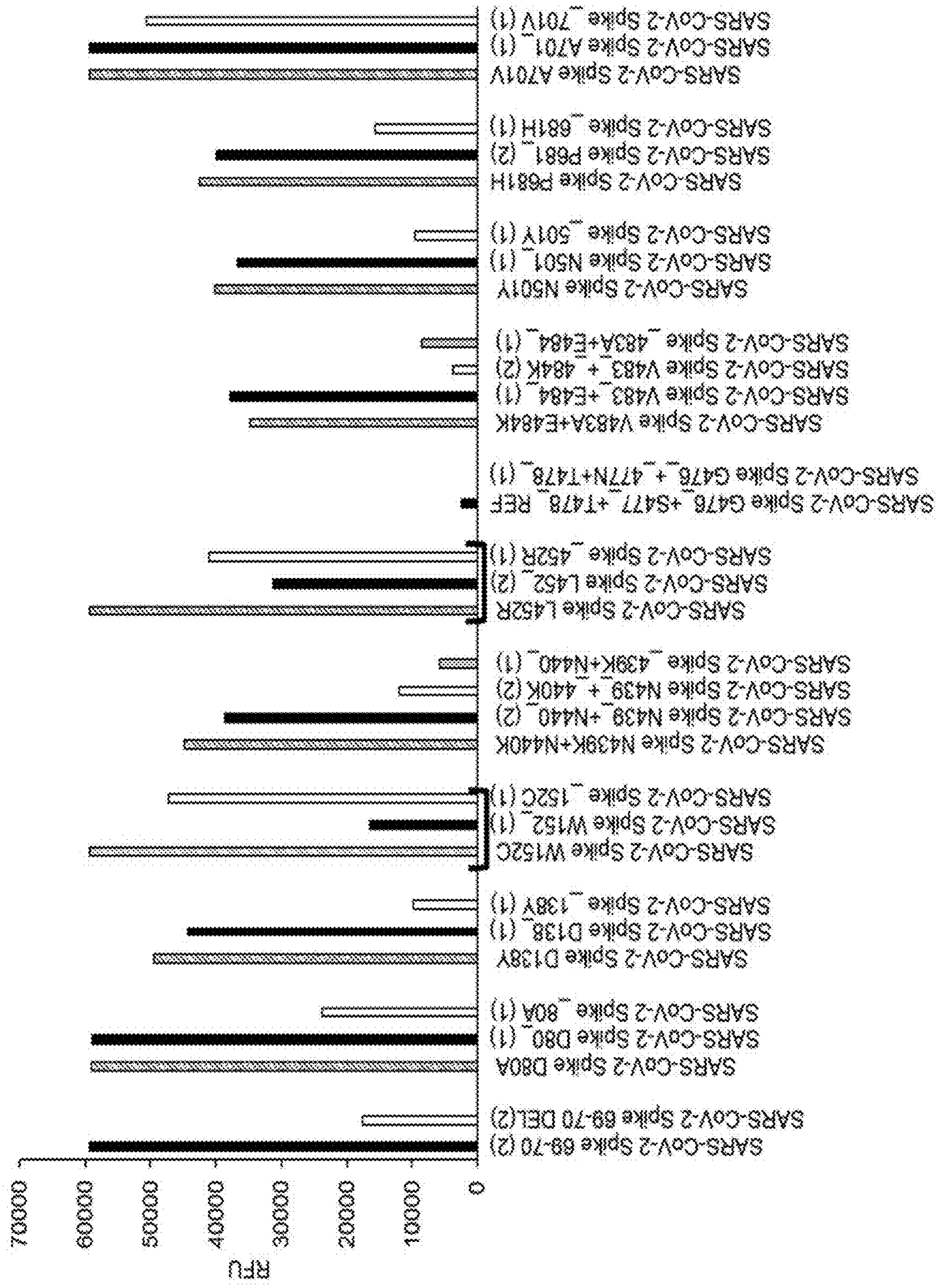

Reference FIG. 18B

| Probe | Wild Type | Mutant Type | Confidence |
|---|---|---|---|
| HYBRIDIZED PROBES | | | |
| H/V69_ | ON | | 100.00% |
| D80_ | ON | | 100.00% |
| D138_ | ON | | 100.00% |
| _152C | | ON | 100.00% |
| N439_ | ON | | 100.00% |
| N440_ | ON | | 100.00% |
| _452R | | ON | 100.00% |
| E484_ | ON | | 100.00% |
| N501_ | ON | | 100.00% |
| P681_ | ON | | 100.00% |
| A701_ | ON | | 100.00% |

TABLE 21-continued

DETECTX-Cv analysis of synthetic Clade variant standards at TriCore

| Probe | Wild Type | Mutant Type | Confidence |
|---|---|---|---|
| UNHYBRIDIZED PROBES | | | |
| _484K | | OFF | 100.00% |
| _501Y | | OFF | 99.80% |

Figure 18C:
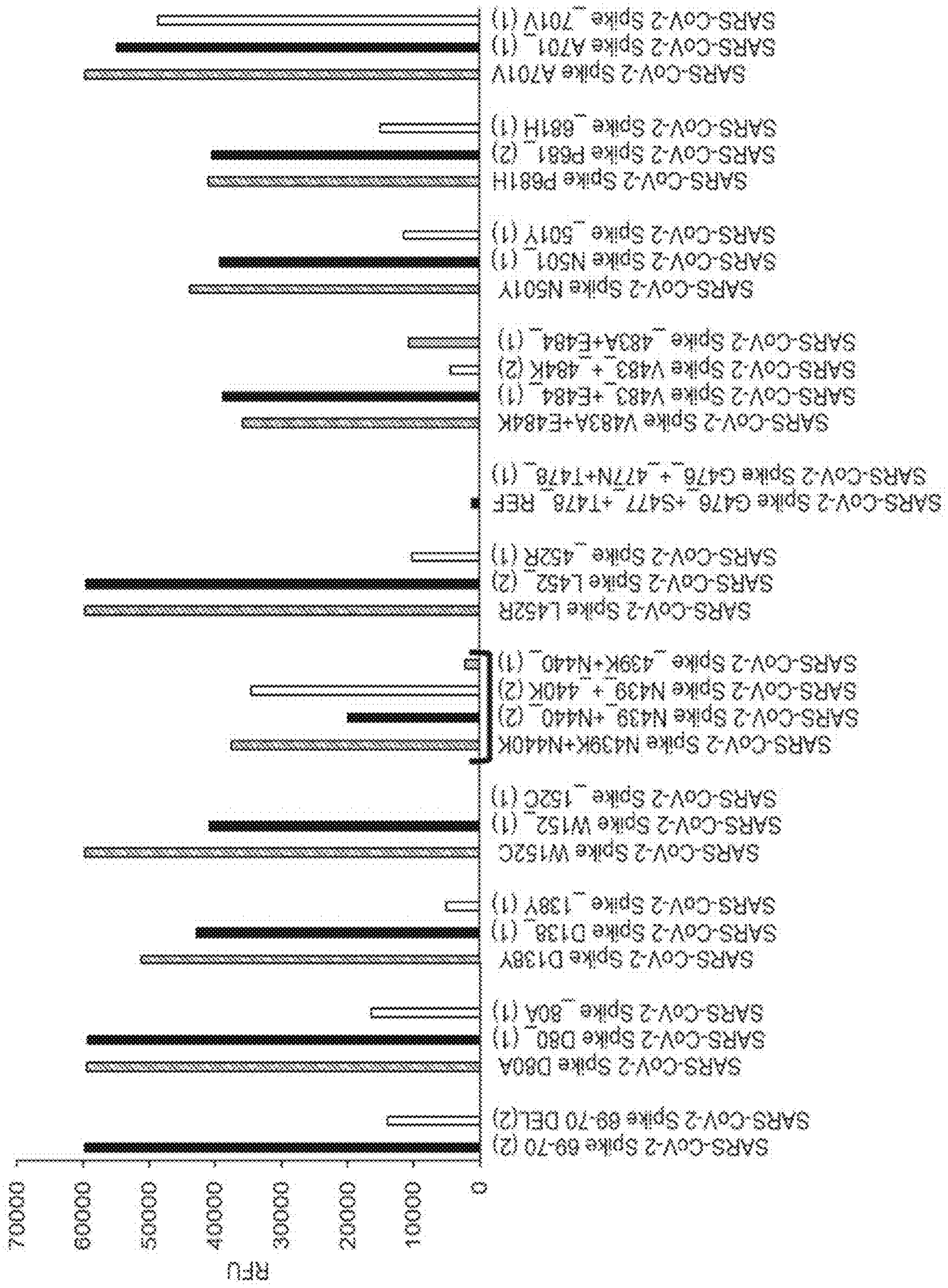

Pattern consistent with California (B.1.429/427)
Reference FIG. 18C

| Probe | Wild Type | Mutant Type | Confidence |
|---|---|---|---|
| HYBRIDIZED PROBES | | | |
| H/V69_ | ON | | 100.00% |
| D80_ | ON | | 100.00% |
| D138_ | ON | | 100.00% |
| W152_ | ON | | 100.00% |
| N439_ | ON | | 100.00% |
| _440K | | ON | 100.00% |
| L452_ | ON | | 100.00% |
| E484_ | ON | | 100.00% |
| N501_ | ON | | 100.00% |
| P681_ | ON | | 100.00% |
| A701_ | ON | | 100.00% |
| UNHYBRIDIZED PROBES | | | |
| _152C | | OFF | 98.80% |
| _484K | | OFF | 100.00% |
| _501Y | | OFF | 98.20% |

Figure 18D:
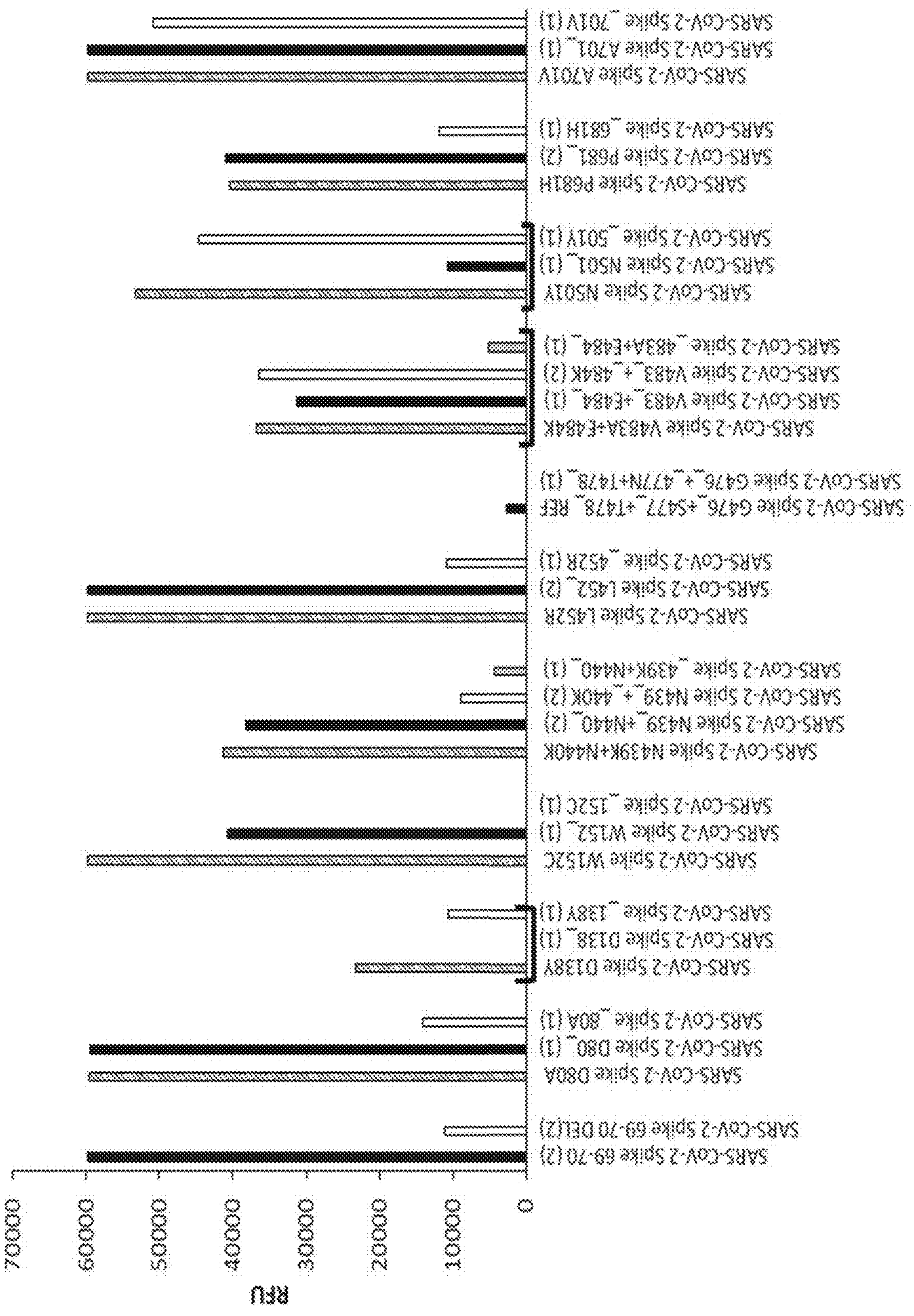

Pattern consistent with India (N440K)
Reference FIG. 18D

| Probe | Wild Type | Mutant Type | Confidence |
|---|---|---|---|
| HYBRIDIZED PROBES | | | |
| H/V69_ | ON | | 100.00% |
| D80_ | ON | | 100.00% |
| _138Y | | ON | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| _501Y | | ON | 100.00% |
| P681_ | ON | | 100.00% |
| A701_ | ON | | 100.00% |
| UNHYBRIDIZED PROBES | | | |
| D138_ | OFF | | 100.00% |
| _152C | | OFF | 98.80% |

Figure 18E:
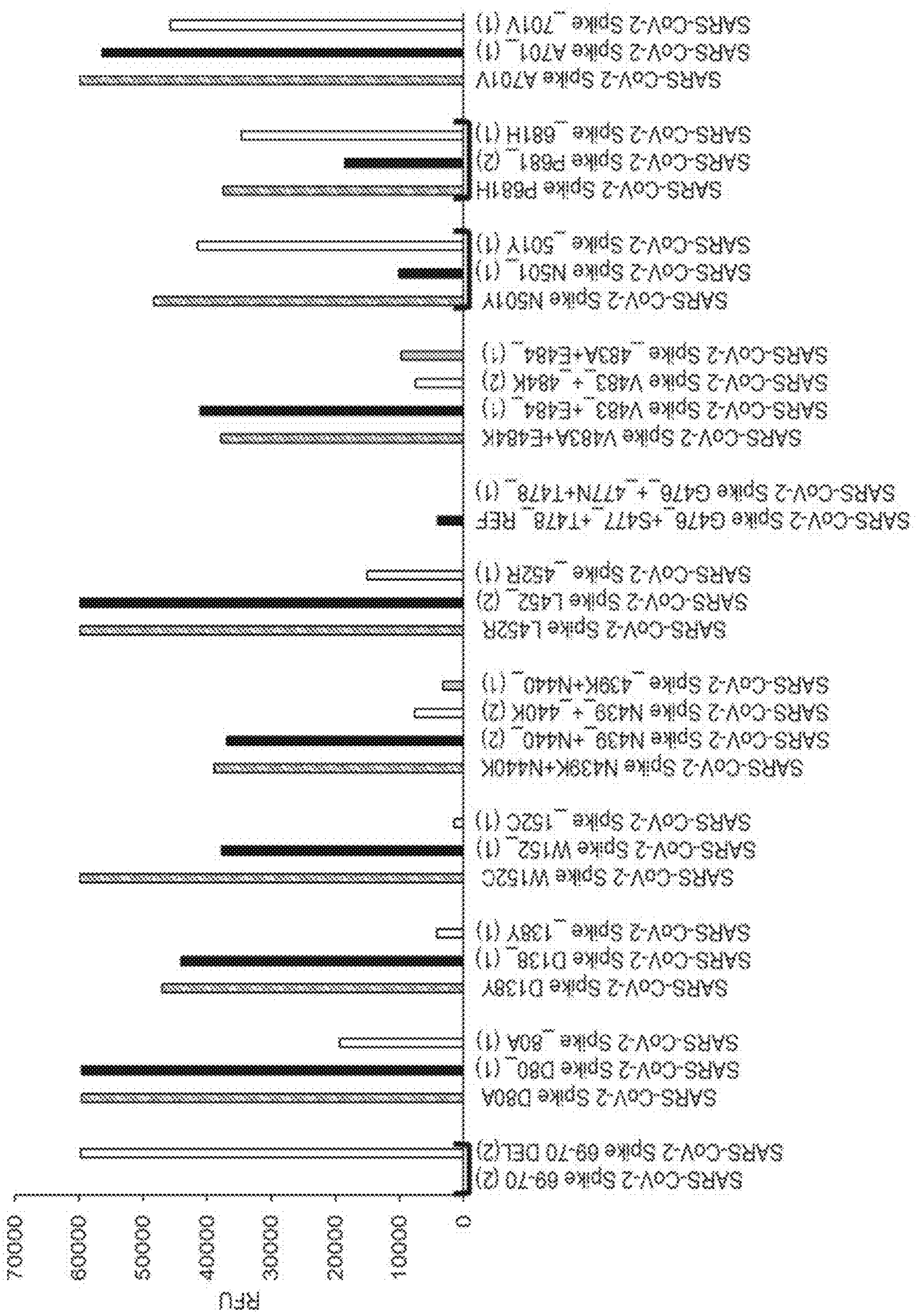

Pattern consistent with Brazil (P1)
Reference FIG. 18E

| Probe | Wild Type | Mutant Type | Confidence |
|---|---|---|---|
| HYBRIDIZED PROBES | | | |
| _69(del) | | ON | 100.00% |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| _501Y | | ON | 100.00% |
| _681H | | ON | 100.00% |
| A701_ | ON | | 100.00% |

TABLE 21-continued

DETECTX-Cv analysis of synthetic Clade variant standards at TriCore

| Probe | Wild Type | Mutant Type | Confidence |
|---|---|---|---|
| UNHYBRIDIZED PROBES | | | |
| H/V69_ | OFF | | 100.00% |
| _484K | | OFF | 100.00% |

Pattern consistent with UK (B.1.1.7)

TABLE 22

Hybridization plate map for 28 SARS-CoV-2 positive clinical samples

| | 3 | 4 | 5 | 6 |
|---|---|---|---|---|
| A | Sample 1 | Sample 9 | Sample 17 | Sample 25 |
| B | Sample 2 | Sample 10 | Sample 18 | Sample 26 |
| C | Sample 3 | Sample 11 | Sample 19 | Sample 27 |
| D | Sample 4 | Sample 12 | Sample 20 | Sample 28 |
| E | Sample 5 | Sample 13 | Sample 21 | |
| F | Sample 6 | Sample 14 | Sample 22 | |
| G | Sample 7 | Sample 15 | Sample 23 | |
| H | Sample 8 | Sample 16 | Sample 24 | |

DETECTX-Cv Analysis of Clinical Positive Samples Performed at Tricore

The Biomerieux EASYMAG® Magnetic Bead platform (bioMérieux, St. Louis, MO) was used to extract Covid-19 RNA from 28 clinical positive (NP-VTM) samples (positivity previously determined by Cobas 6800 analysis). The extracted RNA (5 L) was processed using the DETECTX-Cv method. Table 22 shows a plate map for 28 SARS-CoV-2 positive clinical samples. The PCR recipe and cycling conditions were as described in Table 20.

Results FIGS. 19A-19K and Table 23 show the results of the DETECTX-Cv analysis for the clinical samples. It was determined that 68% (19/28) of samples generated data that passed QA/QC in terms of Universal Probe signal strength and were therefore fit for manual or autonomous Augury Clade calls. These data thus demonstrate that high quality DETECTX-Cv data is obtainable with minimal training on clinical positive samples.

TABLE 23

DETECTX-Cv analysis of clinical positive samples performed at TriCore

Figure 19A:
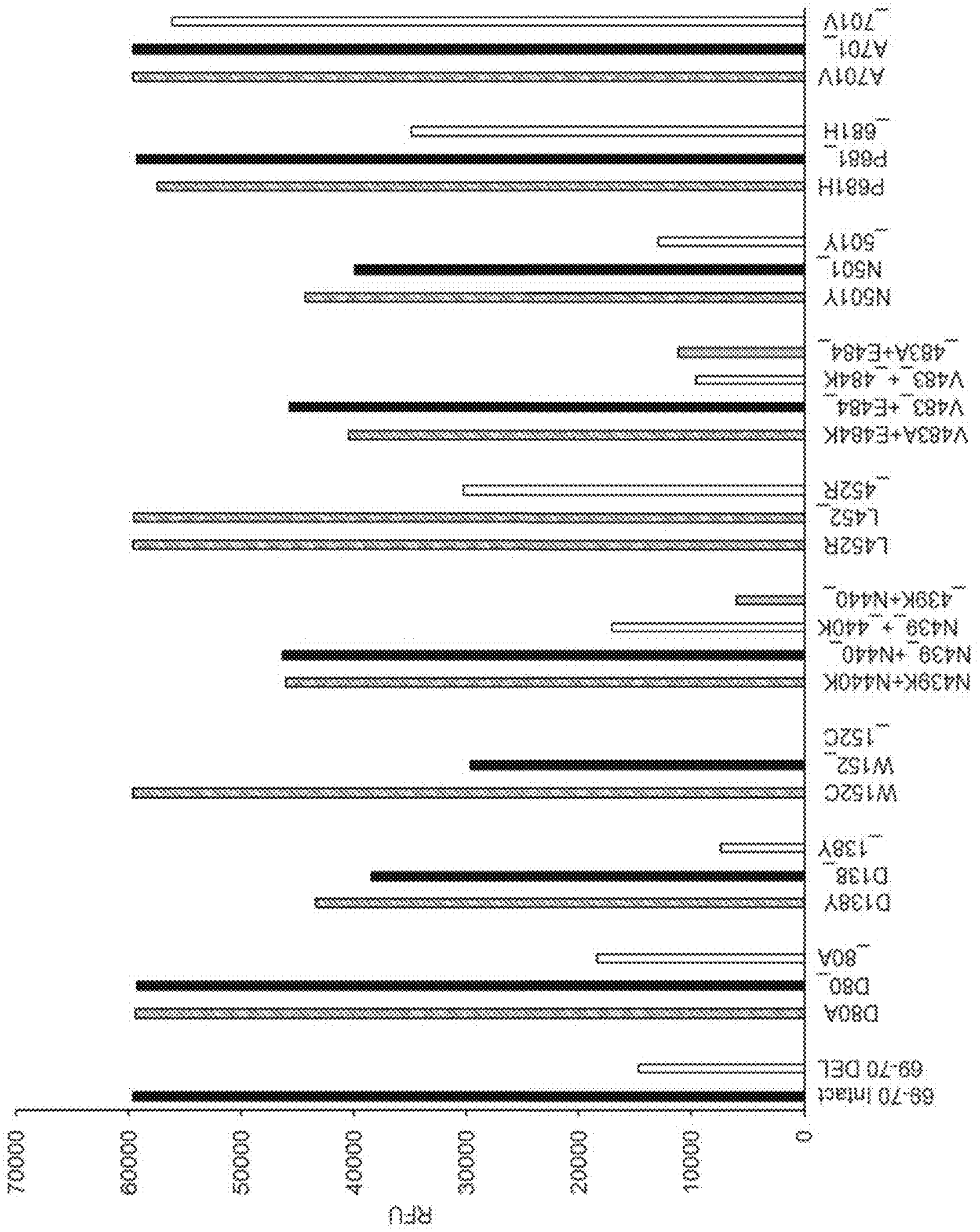
FIGS. 19A-19K show representative data for DETECTX-Cv analysis of clinical positive samples performed at TriCore.
Figure 19B:
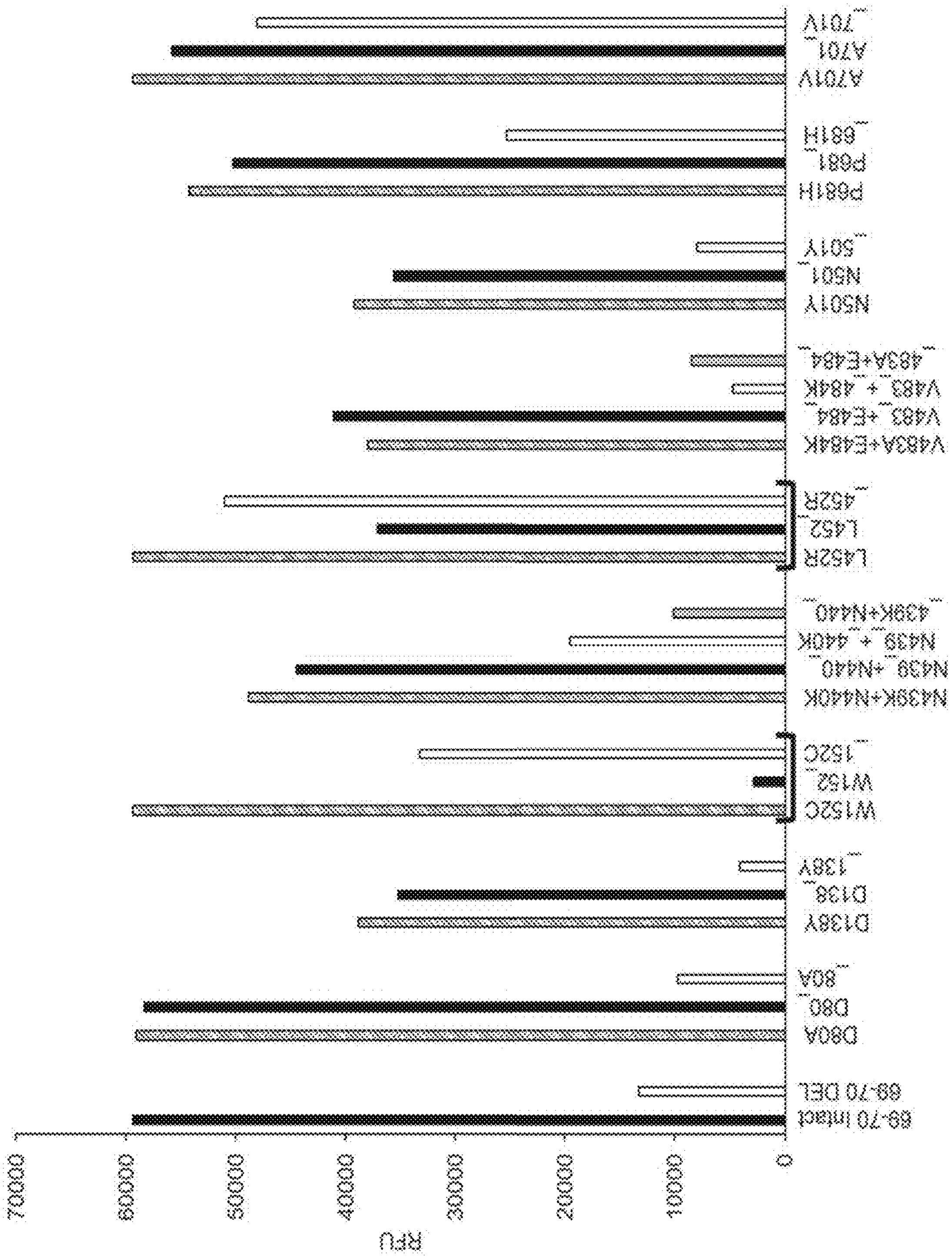
Figure 19C:
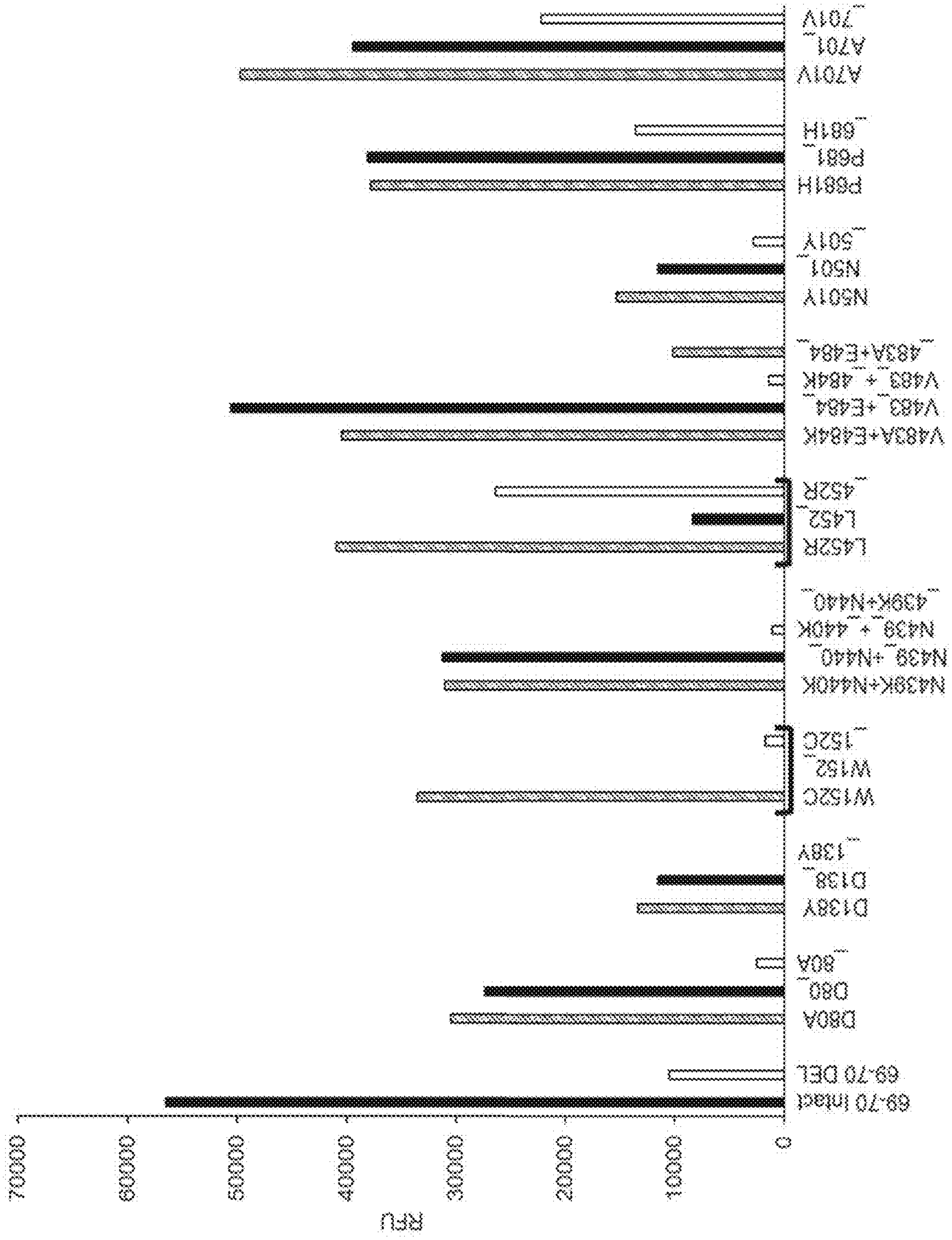
Figure 19D:
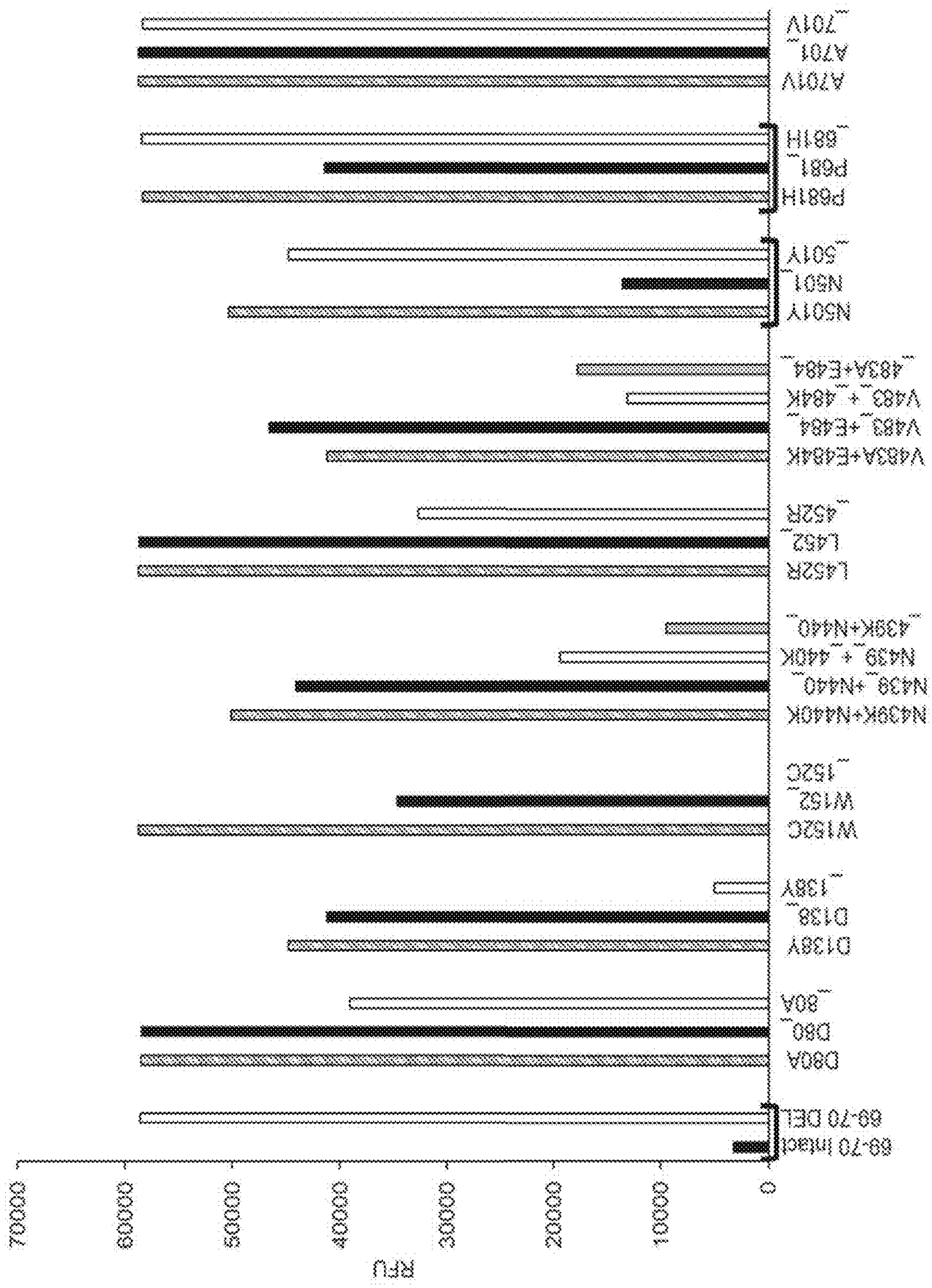
Figure 19E:
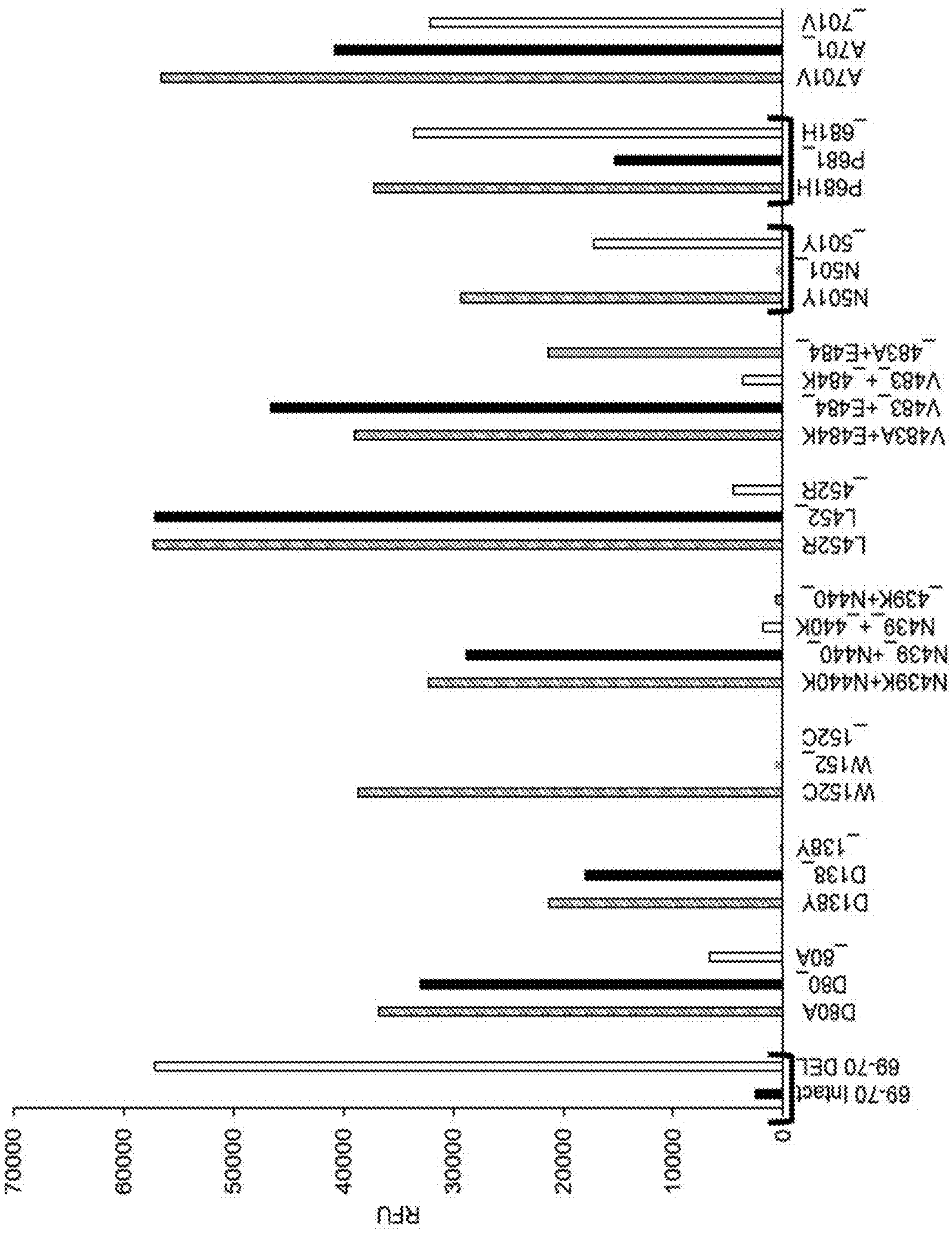
Figure 19F:
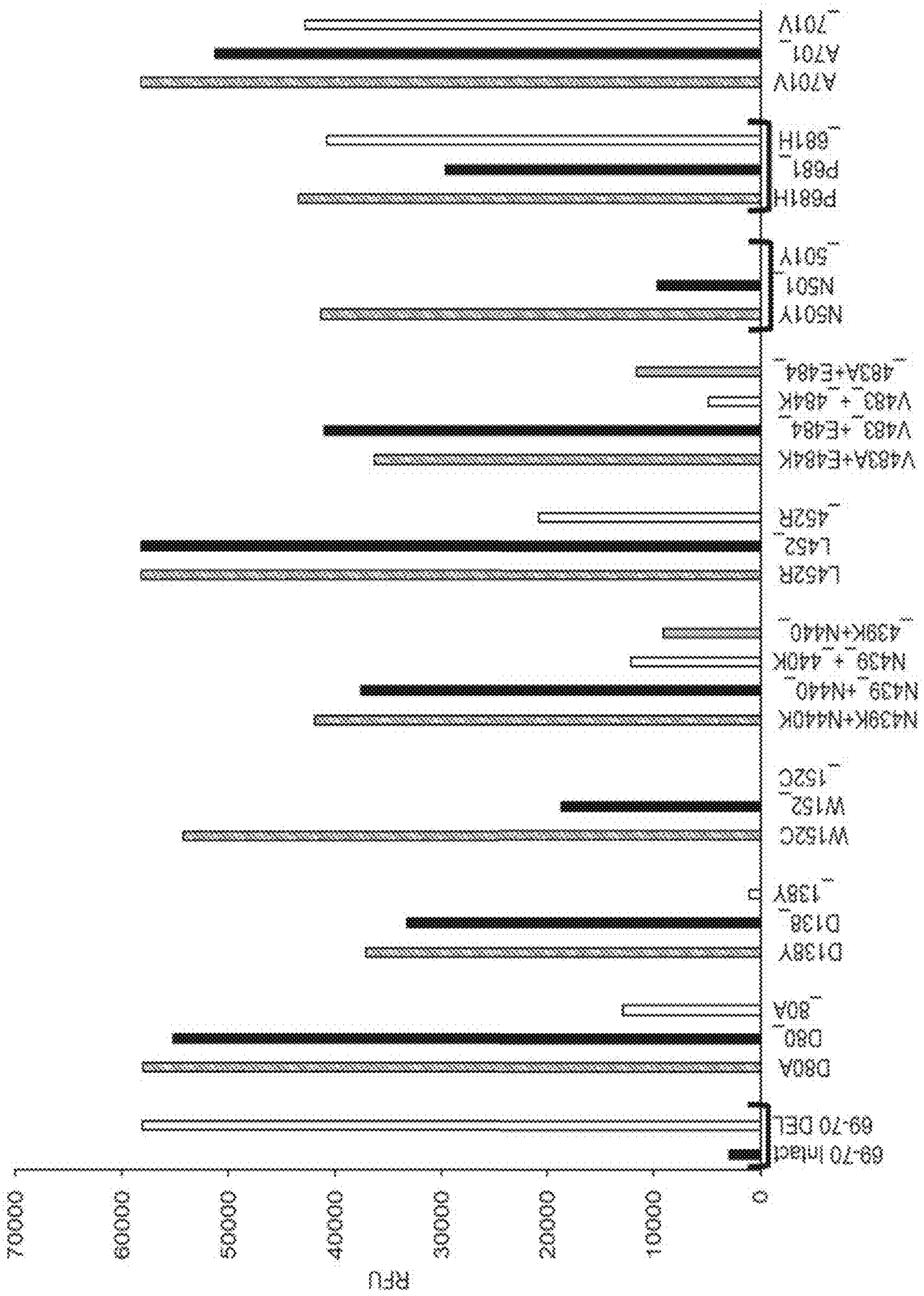
Figure 19G:
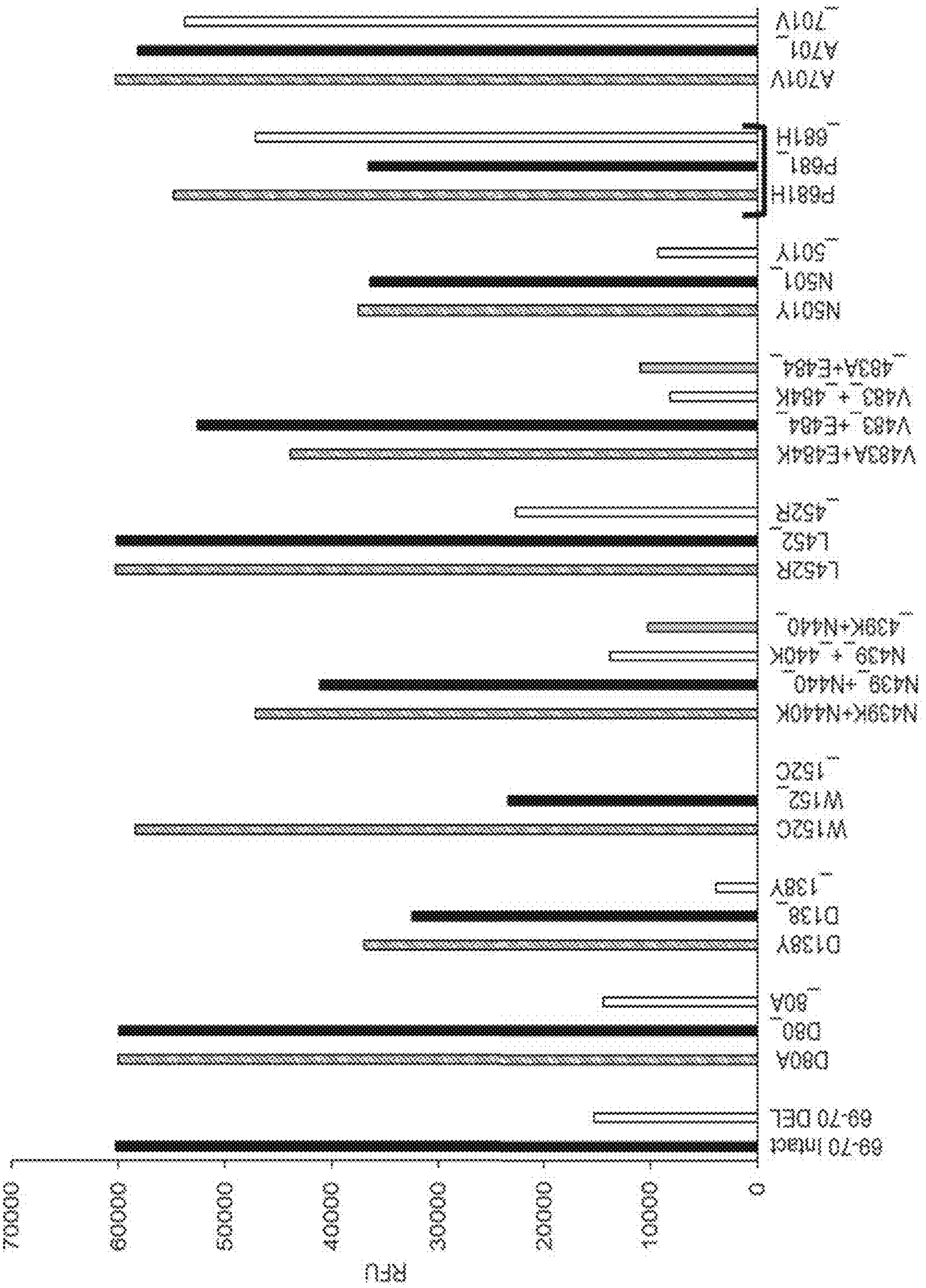

Reference FIG. 19A TriCore Sample 2-B

| Probe | Wild Type | Mutant Type | Confidence |
|---|---|---|---|
| HYBRIDIZED PROBES | | | |
| H/V69_ | ON | | 100.00% |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |

TABLE 23-continued

DETECTX-Cv analysis of clinical positive samples performed at TriCore

| | | | |
|---|---|---|---|
| N501_ | ON | | 100.00% |
| P681_ | ON | | 100.00% |
| A701_ | ON | | 100.00% |
| UNHYBRIDIZED PROBES | | | |
| _152C | | OFF | 98.80% |
| _484K | | OFF | 100.00% |
| _501Y | | OFF | 93.30% |

Pattern consistent with: Wuhan Progenitor
Reference FIG. 19B TriCore Sample 7-B

| Probe | Wild Type | Mutant Type | Confidence |
|---|---|---|---|
| HYBRIDIZED PROBES | | | |
| H/V69_ | ON | | 100.00% |
| D80_ | ON | | 100.00% |
| D138_ | ON | | 100.00% |
| _152C | | ON | 100.00% |
| N439_ | ON | | 100.00% |
| N440_ | ON | | 100.00% |
| _452R | | ON | 100.00% |
| E484_ | ON | | 100.00% |
| N501_ | ON | | 100.00% |
| P681_ | ON | | 100.00% |
| A701_ | ON | | 100.00% |
| UNHYBRIDIZED PROBES | | | |
| _80A | | OFF | 100.00% |
| _484K | | OFF | 100.00% |
| _501Y | | OFF | 100.00% |

Pattern consistent with: California (B.1.429/427)
Reference FIG. 19C TriCore Sample 9-B

| Probe | Wild Type | Mutant Type | Confidence |
|---|---|---|---|
| HYBRIDIZED PROBES | | | |
| H/V69_ | ON | | 100.00% |
| D80_ | ON | | 100.00% |
| D138_ | ON | | 100.00% |
| N439_ | ON | | 100.00% |
| N440_ | ON | | 100.00% |
| _452R | | ON | 100.00% |
| E484_ | ON | | 100.00% |
| N501_ | ON | | 69.70% |
| P681_ | ON | | 100.00% |
| A701_ | ON | | 100.00% |
| UNHYBRIDIZED PROBES | | | |
| _80A | | OFF | 100.00% |
| _138Y | | OFF | 100.00% |
| W152_ | OFF | | 100.00% |
| N439_/_440K | | OFF | 100.00% |
| L452_ | OFF | | 97.40% |
| _484K | | OFF | 100.00% |
| _501Y | | OFF | 100.00% |
| _701V | | OFF | 95.40% |

Pattern consistent with: California (B.1.429/427)
Reference FIG. 19D TriCore Sample 17-B

| Probe | Wild Type | Mutant Type | Confidence |
|---|---|---|---|
| HYBRIDIZED PROBES | | | |
| _69(del) | | ON | 100.00% |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| _501Y | | ON | 100.00% |

TABLE 23-continued

DETECTX-Cv analysis of clinical positive samples performed at TriCore

| | | | |
|---|---|---|---|
| _681H | | ON | 100.00% |
| A701_ | ON | | 100.00% |
| UNHYBRIDIZED PROBES | | | |
| H/V69_ | OFF | | 100.00% |
| _152C | | OFF | 98.80% |
| _484K | | OFF | 100.00% |

Pattern consistent with: UK (B.1.1.7)
Reference FIG. 19E TriCore Sample 18-B

| Probe | Wild Type | Mutant Type | Confidence |
|---|---|---|---|
| HYBRIDIZED PROBES | | | |
| _69(del) | | ON | 100.00% |
| D80_ | ON | | 100.00% |
| D138_ | ON | | 100.00% |
| N439_ | ON | | 100.00% |
| N440_ | ON | | 100.00% |
| L452_ | ON | | 100.00% |
| E484_ | ON | | 100.00% |
| 501Y | | ON | 100.00% |
| 681H | | ON | 100.00% |
| A701_ | ON | | 100.00% |
| UNHYBRIDIZED PROBES | | | |
| H/V69_ | OFF | | 100.00% |
| _80A | | OFF | 100.00% |
| _138Y | | OFF | 100.00% |
| _152C | | OFF | 98.80% |
| W152_ | OFF | | 98.30% |
| N439_/_440K | | OFF | 100.00% |
| _484K | | OFF | 100.00% |
| N501_ | OFF | | 100.00% |

Pattern consistent with: UK (B.1.1.7)
Reference FIG. 19F TriCore Sample 21-B

| Probe | Wild Type | Mutant Type | Confidence |
|---|---|---|---|
| HYBRIDIZED PROBES | | | |
| _69(del) | | ON | 100.00% |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| _501Y | | ON | 100.00% |
| _681H | | ON | 100.00% |
| A701_ | ON | | 100.00% |
| UNHYBRIDIZED PROBES | | | |
| H/V69_ | OFF | | 100.00% |
| _138Y | | OFF | 100.00% |
| _152C | | OFF | 98.80% |
| _484K | | OFF | 100.00% |

Pattern consistent with: UK (B.1.1.7)
Reference FIG. 19G TriCore Sample 22-B

| Probe | Wild Type | Mutant Type | Confidence |
|---|---|---|---|
| HYBRIDIZED PROBES | | | |
| H/V69_ | ON | | 100.00% |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| N501_ | ON | | 100.00% |

TABLE 23-continued

DETECTX-Cv analysis of clinical positive samples performed at TriCore

| Probe | Wild Type | Mutant Type | Confidence |
|---|---|---|---|
| _681H | | ON | 100.00% |
| A701_ | ON | | 100.00% |
| UNHYBRIDIZED PROBES | | | |
| _152C | | OFF | 98.80% |
| _484K | | OFF | 100.00% |
| _501Y | | OFF | 99.80% |

Pattern consistent with: B.1.1.207

Figure 19H:
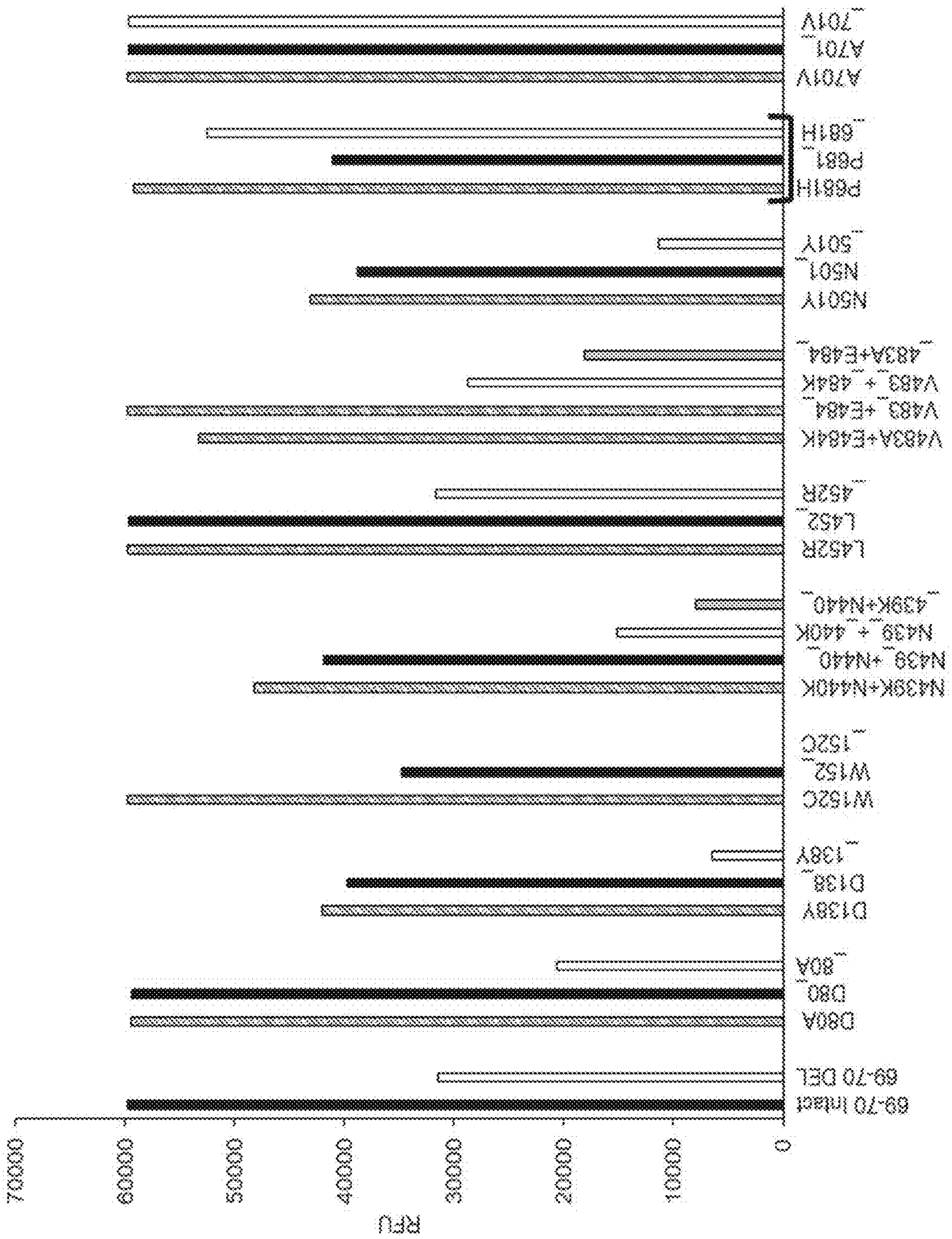

Reference FIG. 19H TriCore Sample 24-B

| Probe | Wild Type | Mutant Type | Confidence |
|---|---|---|---|
| HYBRIDIZED PROBES | | | |
| H/V69_ | ON | | 100.00% |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| N501_ | ON | | 100.00% |
| _681H | | ON | 100.00% |
| A701_ | ON | | 100.00% |
| UNHYBRIDIZED PROBES | | | |
| _152C | | OFF | 97.60% |
| _501Y | | OFF | 98.60% |

Pattern consistent with: B.1.1.207

Figure 19I:
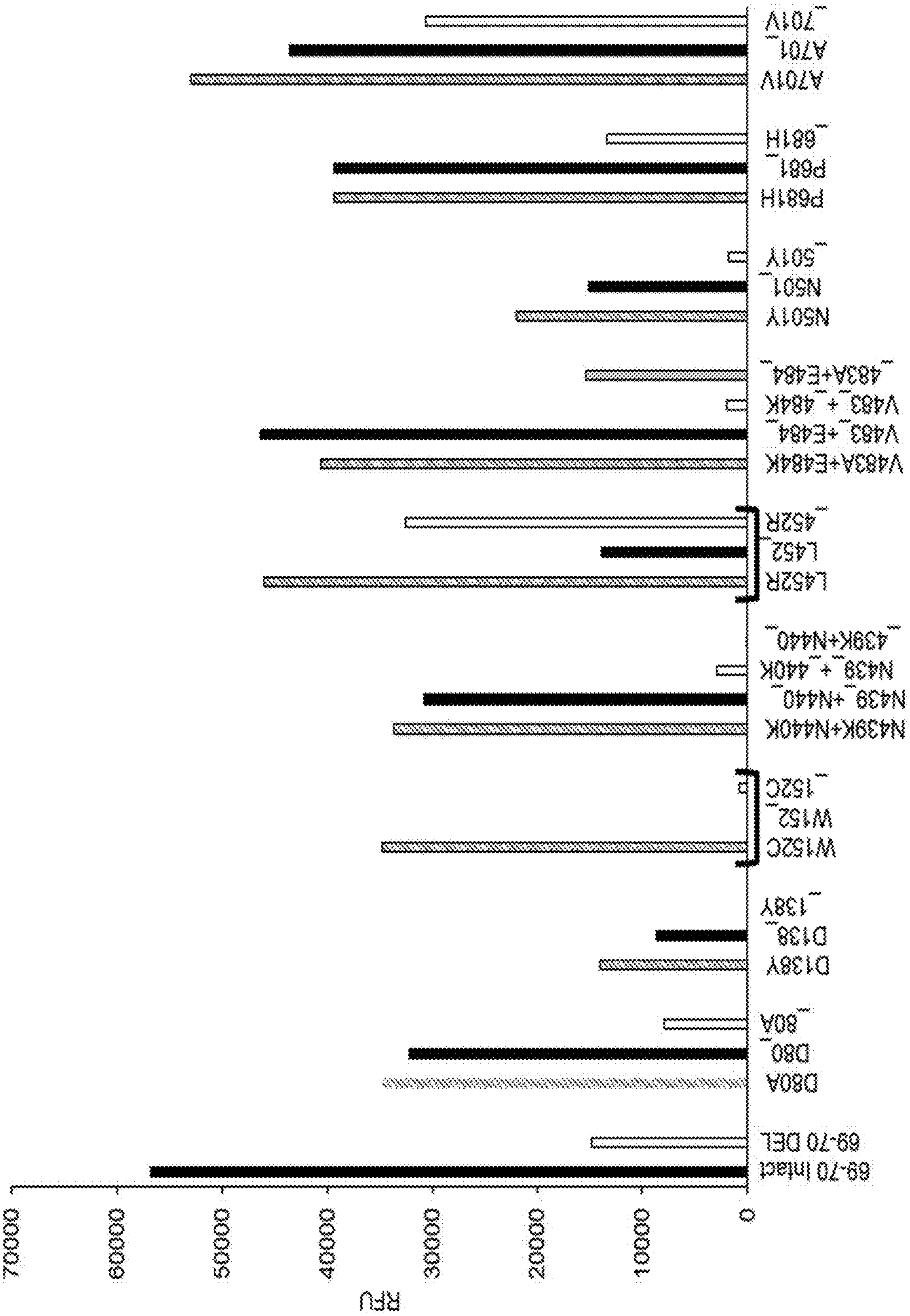

Reference FIG. 19I TriCore Sample 27-B

| Probe | Wild Type | Mutant Type | Confidence |
|---|---|---|---|
| HYBRIDIZED PROBES | | | |
| H/V69_ | ON | | 100.00% |
| D80_ | ON | | 100.00% |
| D138_ | ON | | 100.00% |
| 152C | | ON | 85.40% |
| N439_ | ON | | 100.00% |
| N440_ | ON | | 100.00% |
| _452R | | ON | 100.00% |
| E484_ | ON | | 100.00% |
| N501_ | ON | | 100.00% |
| P681_ | ON | | 100.00% |
| A701_ | ON | | 100.00% |
| UNHYBRIDIZED PROBES | | | |
| _80A | | OFF | 100.00% |
| _138Y | | OFF | 100.00% |
| _152C | | OFF | 69.40% |
| W152_ | OFF | | 100.00% |
| N439_/_440K | | OFF | 98.30% |

TABLE 23-continued

DETECTX-Cv analysis of clinical positive samples performed at TriCore

| Probe | Wild Type | Mutant Type | Confidence |
|---|---|---|---|
| _484K | | OFF | 100.00% |
| _501Y | | OFF | 100.00% |

Pattern consistent with: California (B.1.429/427)

Figure 19J:
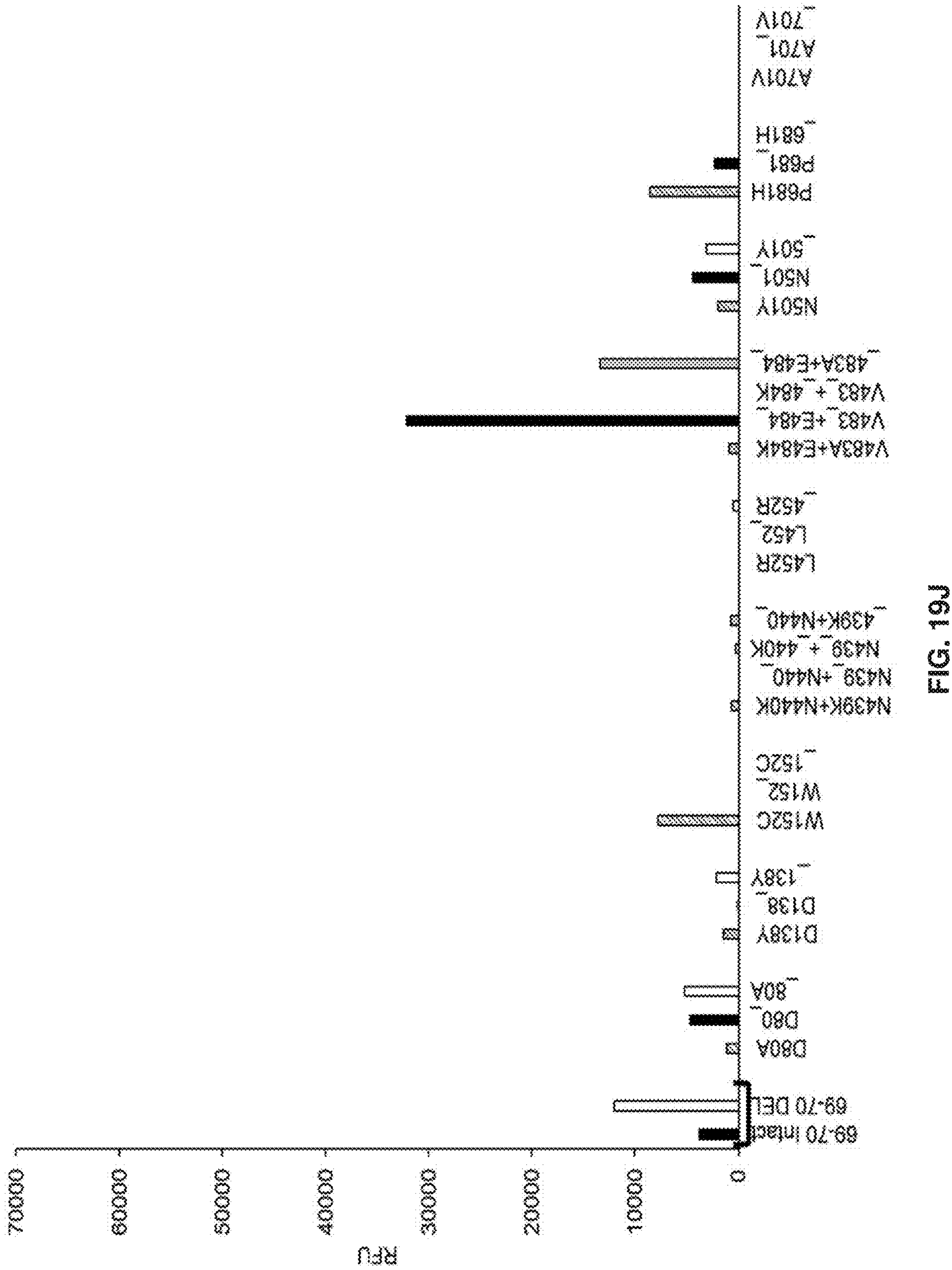

Reference FIG. 19J TriCore Sample 1-B

| Probe | Wild Type | Mutant Type | Confidence |
|---|---|---|---|
| HYBRIDIZED PROBES | | | |
| _69(del) | | ON | 87.50% |
| UNHYBRIDIZED PROBES | | | |
| H/V69_ | OFF | | 99.70% |

Pattern consistent with:

| | |
|---|---|
| 1 | UK (B.1.1.7) |
| 2 | B.1.525 |
| 3 | B.1.375 |
| 4 | Denmark |
| 5 | B.1.258 |

Figure 19K:
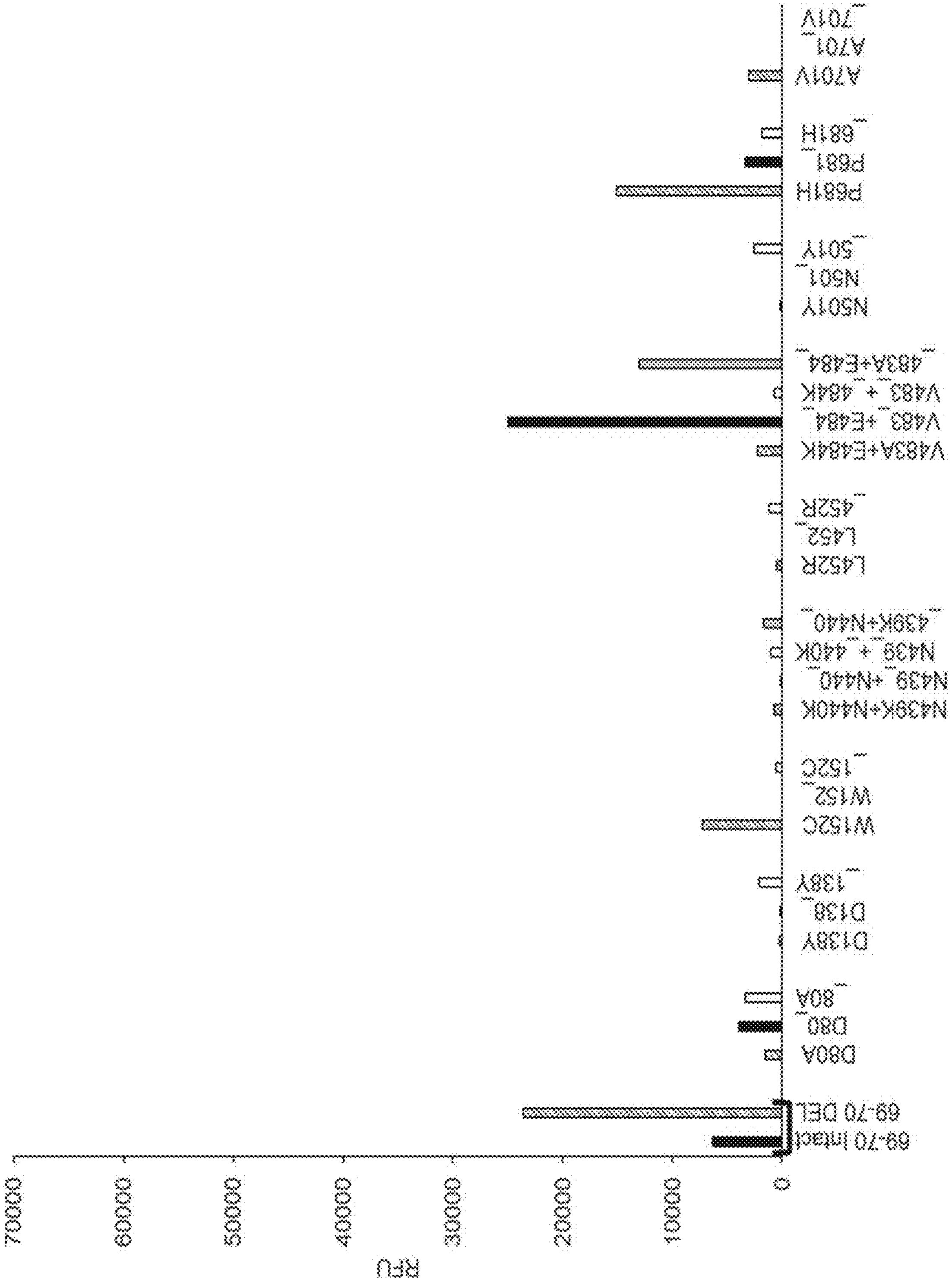

Reference FIG. 19K TriCore Sample 4-B
START_WELL_20
SPECIMEN_ID Sample #20

| Probe | Wild Type | Mutant Type | Confidence |
|---|---|---|---|
| HYBRIDIZED PROBES | | | |
| _69(del) | | ON | 100.00% |
| UNHYBRIDIZED PROBES | | | |

Pattern consistent with: NA
END_WELL_20

DETECTX-Cv Analysis of TriCore Clinical Positive Samples at Pathogen Dx

Sixty (60) clinical positive NP-VTM samples collected by TriCore were sent to PathogenDx for DETECTX-Cv analysis. RNA was extracted from these samples using the Zymo Magnetic Bead platform. The extracted RNA (5 L) was processed using the DETECTX-Cv method. The PCR recipe and cycling conditions were as described in Table 20.

Results

FIGS. 20A-20J and Table 24 show the results of this analysis. It was determined that 65% (39/60) of these samples generated data which passed QC/QA in terms of signal strength and were thus fit for manual or autonomous Augury Clade calls. The data shows all NP-VTM specimens which passed QA/QC and which displayed nonstandard clade variants (other than Wuhan) and representative data (2) for which QA/QC were inadequate either due to low RNA concentration or degraded RNA in the sample.

TABLE 24

DETECTX-Cv analysis of clinical positive samples performed at PathogenDx

Figure 20A:
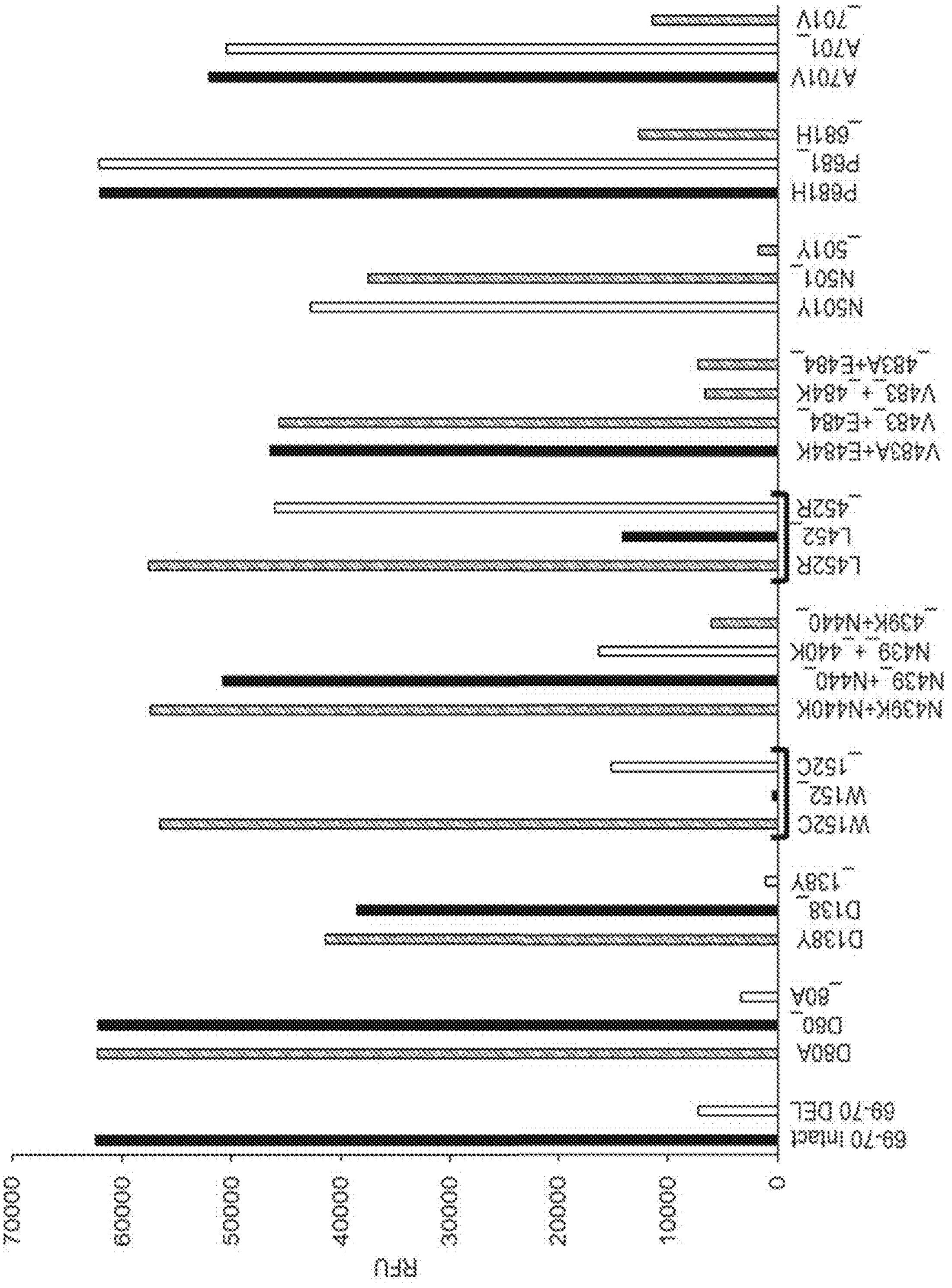
FIGS. 20A-20J show representative data for DETECTX-Cv analysis of clinical positive samples performed at PathogenDx.
Figure 20B:
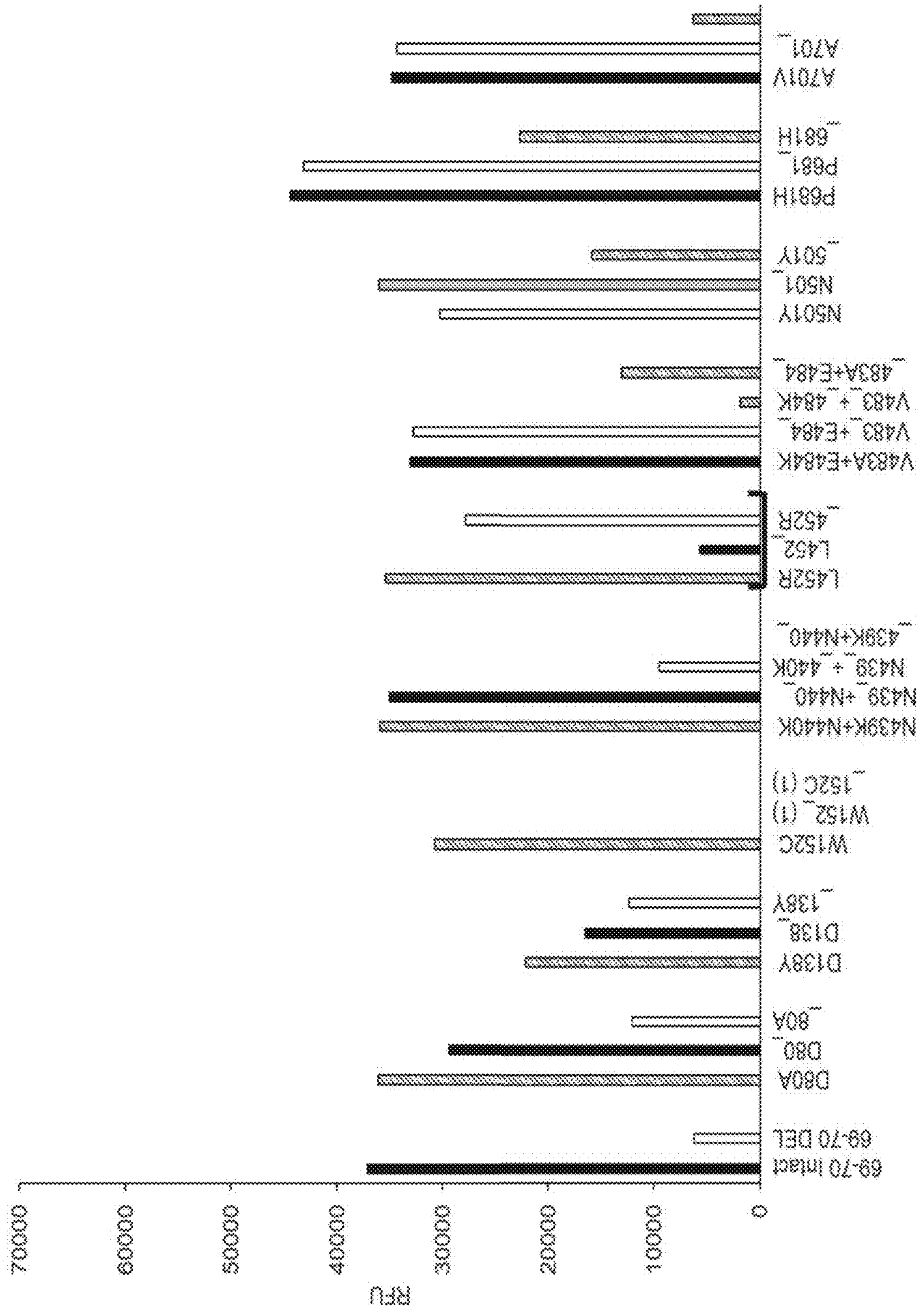
Figure 20C:
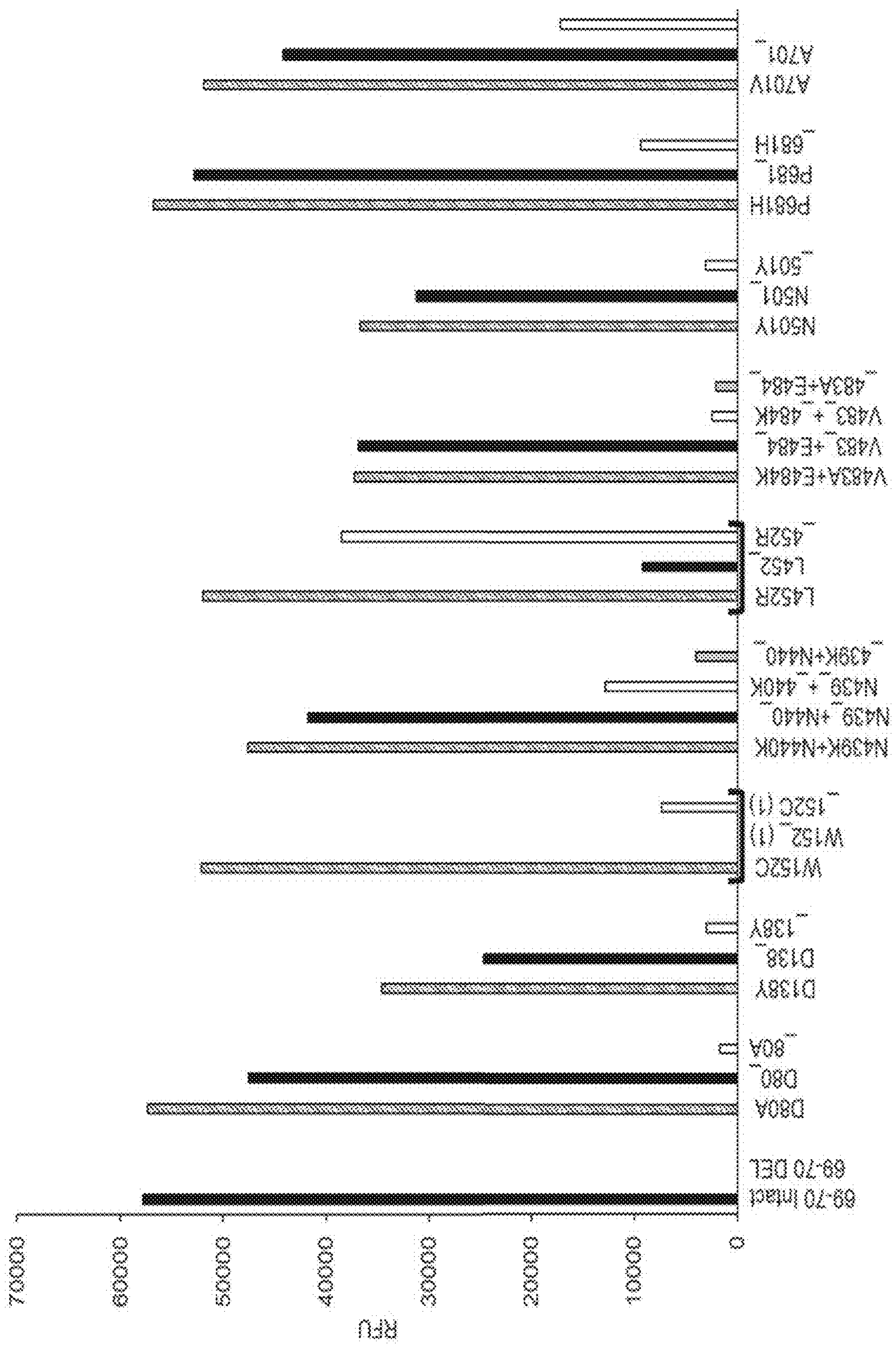
Figure 20D:
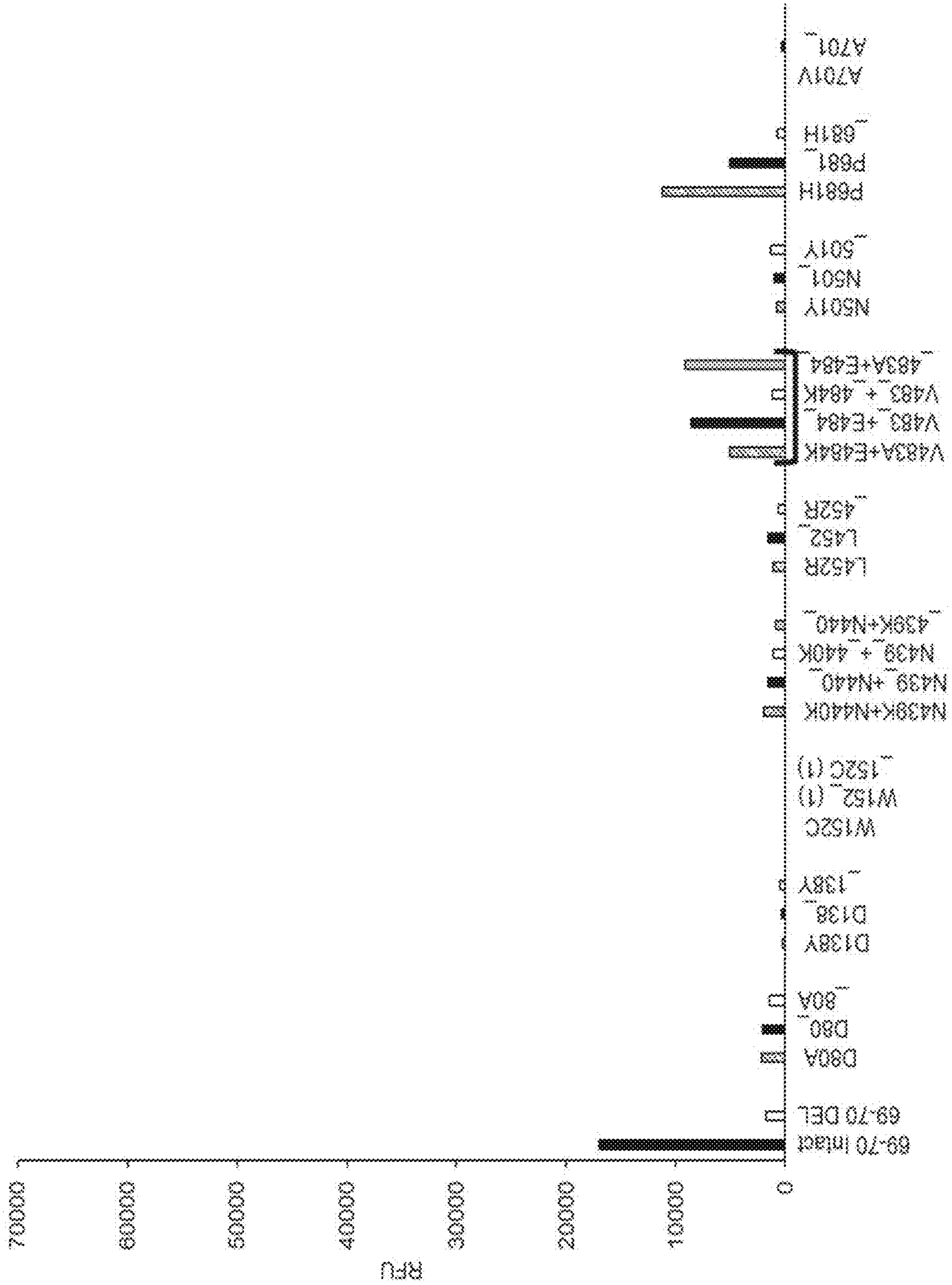
Figure 20E:
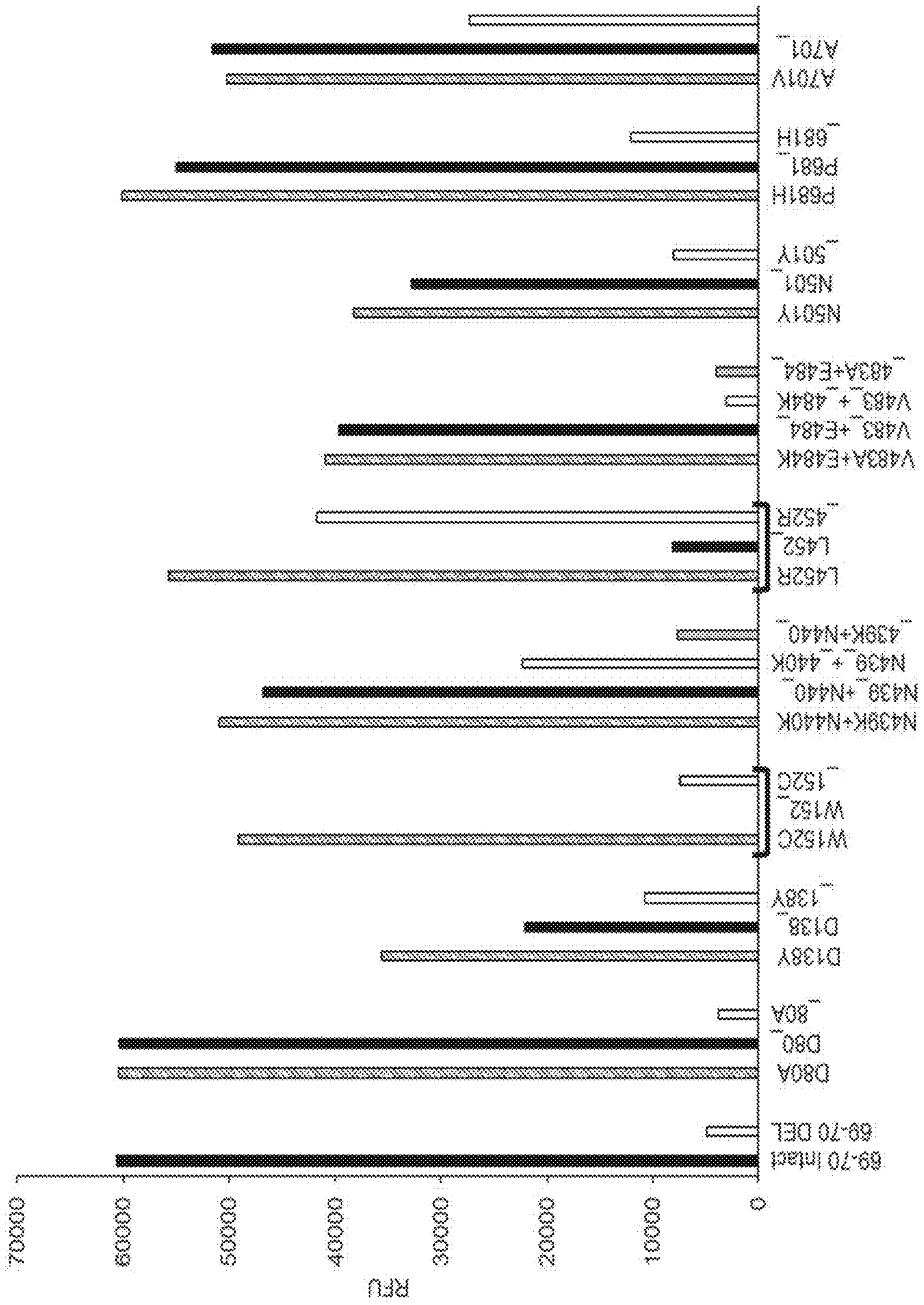
Figure 20F:
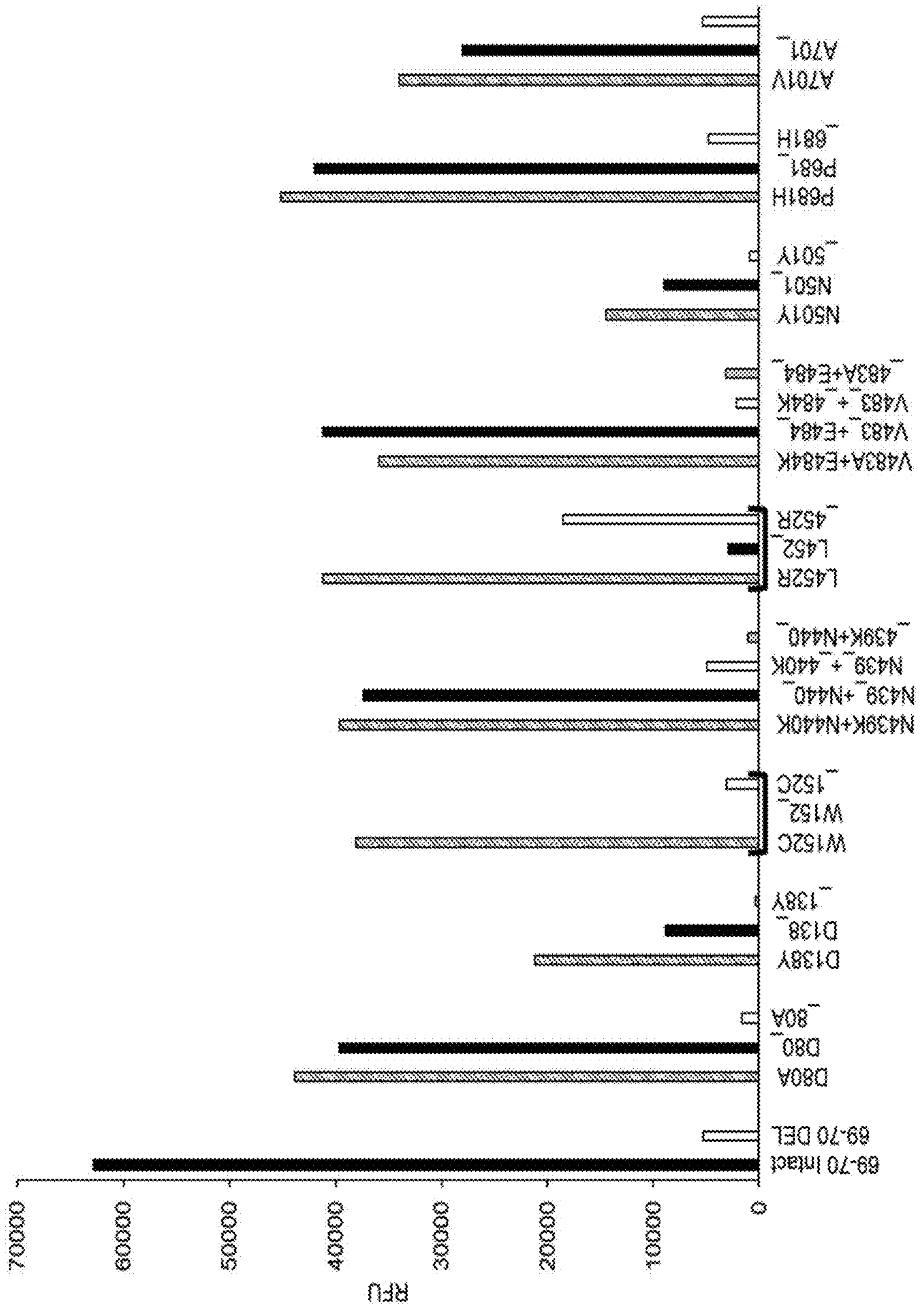
Figure 20G:
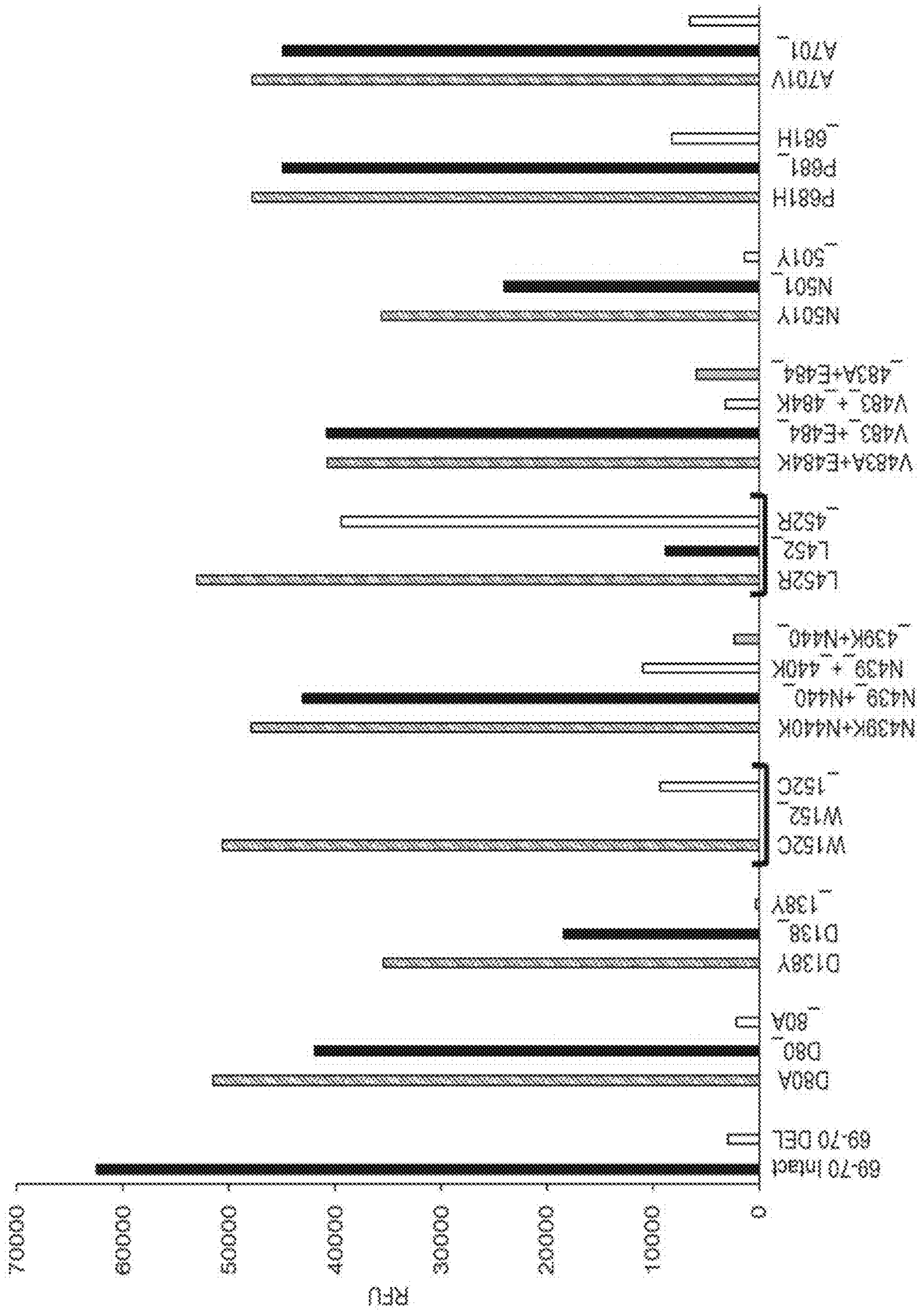
Figure 20H:
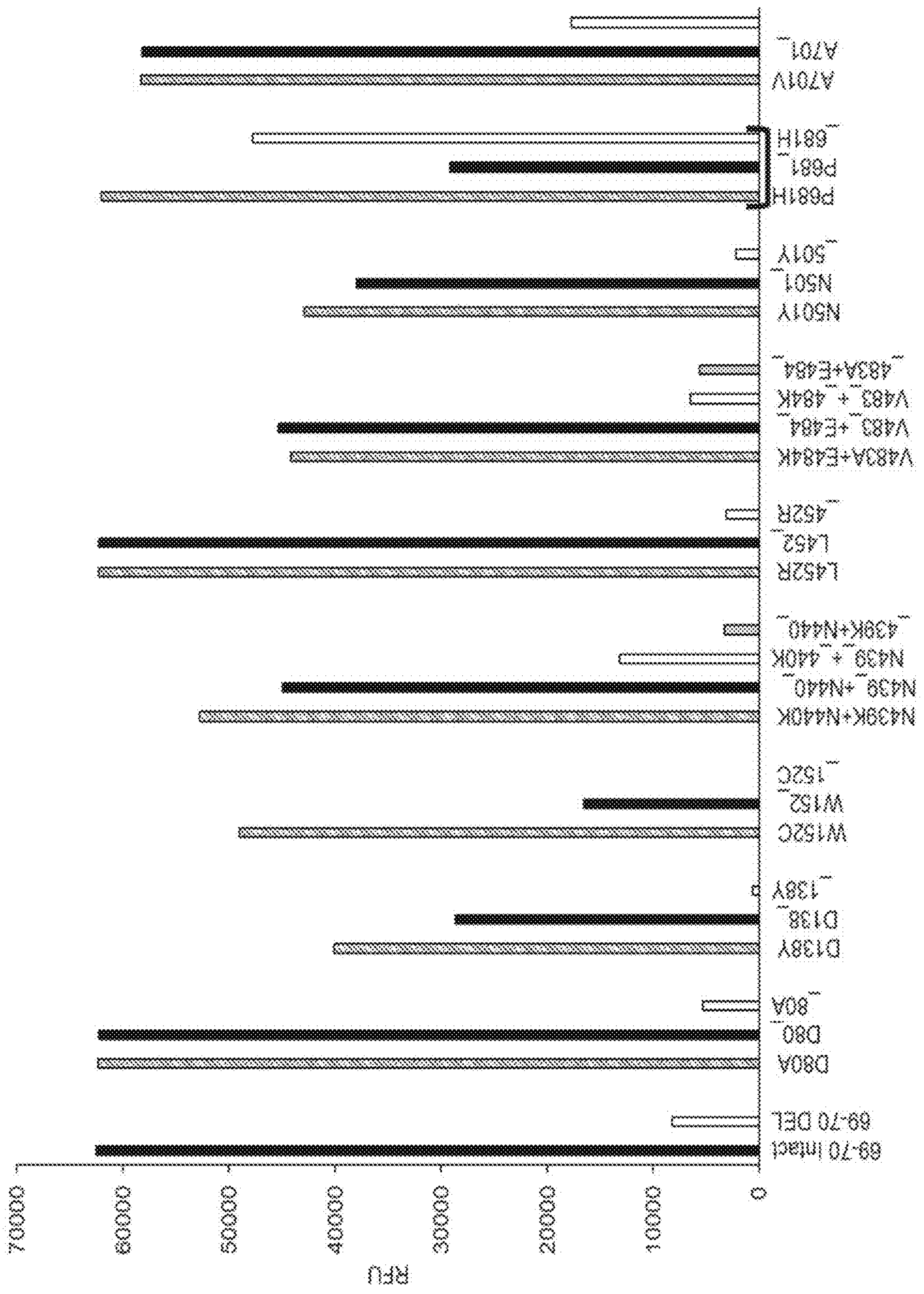
Figure 20I:
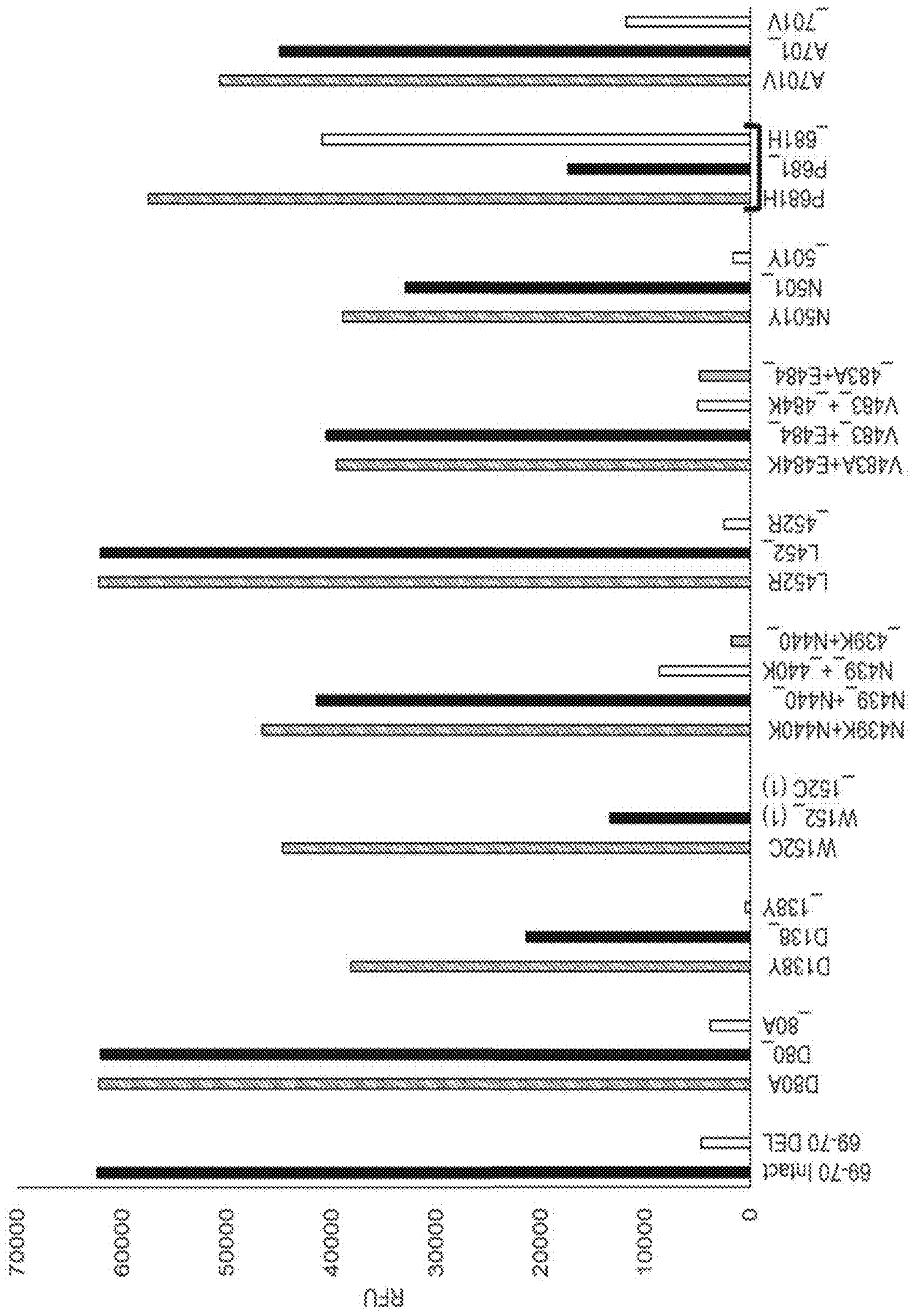
Figure 20J:
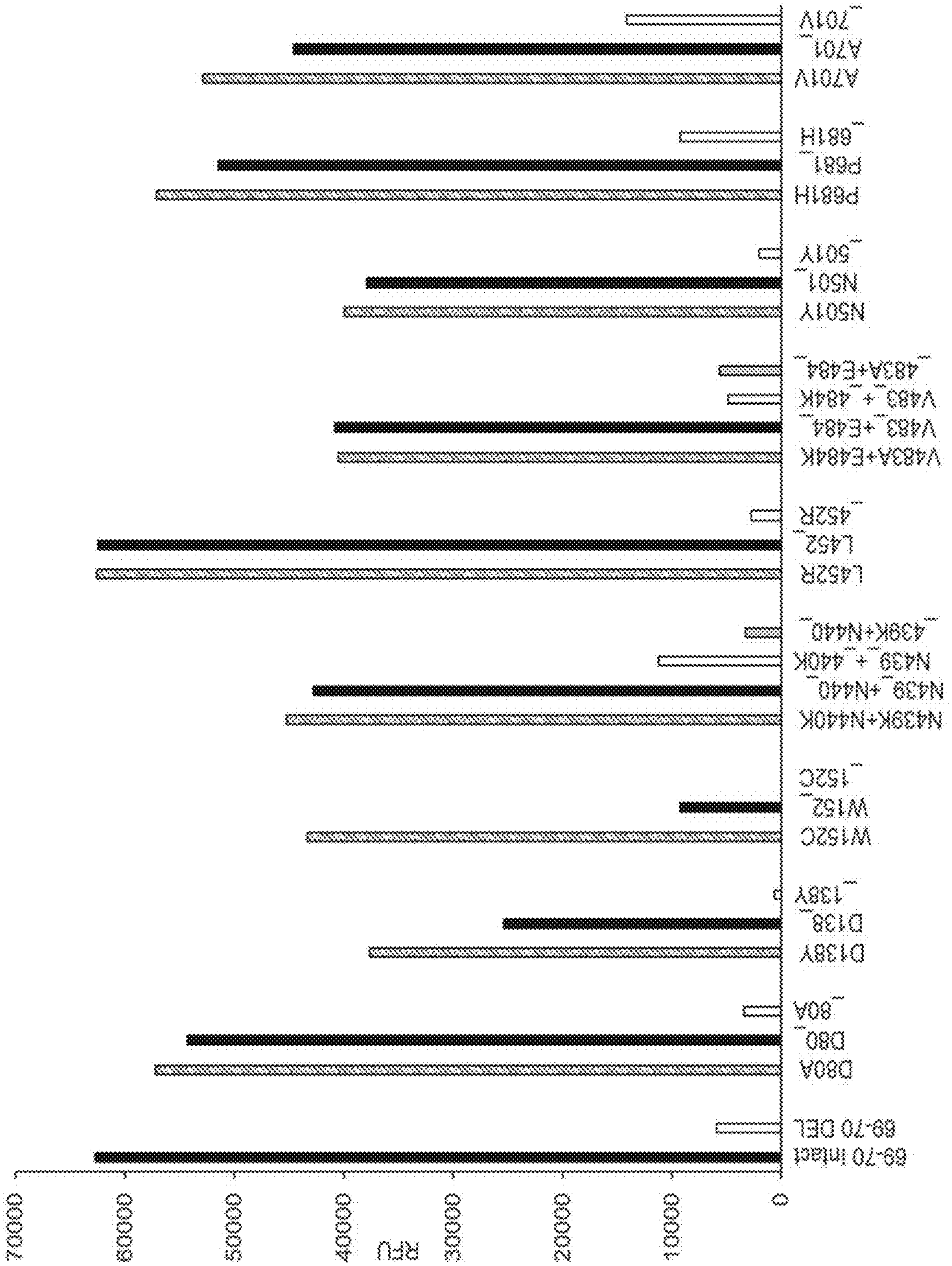

Reference FIG. 20A TriCore 238480-d Sample 1

| Probe | Wild Type | Mutant Type | Confidence |
|---|---|---|---|
| HYBRIDIZED PROBES | | | |
| D80_ | ON | | 100.00% |
| D138_ | ON | | 100.00% |
| W152_ | ON | | 100.00% |

TABLE 24-continued

DETECTX-Cv analysis of clinical positive samples performed at PathogenDx

| Probe | Wild Type | Mutant Type | Confidence |
|---|---|---|---|
| N439_ | ON | | 100.00% |
| N440_ | ON | | 100.00% |
| L452_ | ON | | 100.00% |
| E484_ | ON | | 100.00% |
| N501_ | ON | | 100.00% |
| P681_ | ON | | 100.00% |
| A701_ | ON | | 100.00% |
| UNHYBRIDIZED PROBES | | | |
| _69(del) | | OFF | 100.00% |
| _80A | | OFF | 100.00% |
| _138Y | | OFF | 100.00% |
| _152C | | OFF | 98.80% |
| _452R | | OFF | 98.00% |
| _484K | | OFF | 100.00% |
| _501Y | | OFF | 100.00% |
| _681H | | OFF | 87.00% |
| _701V | | OFF | 100.00% |

Pattern consistent with: Wuhan Progenitor
Reference FIG. 20B TriCore 238484-d Sample 4

| Probe | Wild Type | Mutant Type | Confidence |
|---|---|---|---|
| HYBRIDIZED PROBES | | | |
| D80_ | ON | | 100.00% |
| D138_ | ON | | 100.00% |
| N439_ | ON | | 100.00% |
| N440_ | ON | | 100.00% |
| _452R | | ON | 100.00% |
| E484_ | ON | | 100.00% |
| N501_ | ON | | 100.00% |
| P681_ | ON | | 100.00% |
| A701_ | ON | | 99.90% |
| UNHYBRIDIZED PROBES | | | |
| _69(del) | | OFF | 100.00% |
| _80A | | OFF | 89.00% |
| _152C | | OFF | 98.80% |
| W152_ | OFF | | 100.00% |
| L452_ | OFF | | 100.00% |
| _484K | | OFF | 100.00% |
| _701V | | OFF | 100.00% |

Pattern consistent with: No Clade Call, likely California
Reference FIG. 20C TriCore 238485-d Sample 5

| Probe | Wild Type | Mutant Type | Confidence |
|---|---|---|---|
| HYBRIDIZED PROBES | | | |
| D80_ | ON | | 100.00% |
| D138_ | ON | | 100.00% |
| _152C | | ON | 100.00% |
| N439_ | ON | | 100.00% |
| N440_ | ON | | 100.00% |
| _452R | | ON | 100.00% |
| E484_ | ON | | 100.00% |
| N501_ | ON | | 100.00% |
| P681_ | ON | | 100.00% |
| A701_ | ON | | 100.00% |
| UNHYBRIDIZED PROBES | | | |
| _69(del) | | OFF | 100.00% |
| _80A | | OFF | 100.00% |
| W152_ | OFF | | 100.00% |
| L452_ | OFF | | 90.50% |
| _484K | | OFF | 100.00% |
| _501Y | | OFF | 100.00% |

TABLE 24-continued

DETECTX-Cv analysis of clinical positive samples performed at PathogenDx

| Probe | Wild Type | Mutant Type | Confidence |
|---|---|---|---|
| _681H | | OFF | 83.60% |
| _701V | | OFF | 99.90% |

Pattern consistent with: California (B.1.429/427)
Reference FIG. 20D TriCore 238487-d Sample 6

| Probe | Wild Type | Mutant Type | Confidence |
|---|---|---|---|
| HYBRIDIZED PROBES | | | |
| UNHYBRIDIZED PROBES | | | |
| _69(del) | | OFF | 100.00% |

Pattern consistent with: NA
Reference FIG. 20E TriCore 238488-d Sample 7

| Probe | Wild Type | Mutant Type | Confidence |
|---|---|---|---|
| HYBRIDIZED PROBES | | | |
| D80_ | ON | | 100.00% |
| D138_ | ON | | 100.00% |
| _152C | | ON | 100.00% |
| N439_ | ON | | 100.00% |
| N440_ | ON | | 100.00% |
| _452R | | ON | 100.00% |
| E484_ | ON | | 100.00% |
| N501_ | ON | | 100.00% |
| P681_ | ON | | 100.00% |
| A701_ | ON | | 100.00% |
| UNHYBRIDIZED PROBES | | | |
| _69(del) | | OFF | 100.00% |
| _80A | | OFF | 100.00% |
| W152_ | OFF | | 100.00% |
| L452_ | OFF | | 98.50% |
| _484K | | OFF | 100.00% |
| _501Y | | OFF | 100.00% |

Pattern consistent with: California (B.1.429/427)
Reference FIG. 20F TriCore 238498-d Sample 12

| Probe | Wild Type | Mutant Type | Confidence |
|---|---|---|---|
| HYBRIDIZED PROBES | | | |
| D80_ | ON | | 100.00% |
| D138_ | ON | | 100.00% |
| _152C | | ON | 97.60% |
| N439_ | ON | | 100.00% |
| N440_ | ON | | 100.00% |
| _452R | | ON | 100.00% |
| E484_ | ON | | 100.00% |
| P681_ | ON | | 100.00% |
| A701_ | ON | | 78.60% |
| UNHYBRIDIZED PROBES | | | |
| _69(del) | | OFF | 100.00% |
| _80A | | OFF | 100.00% |
| _138Y | | OFF | 100.00% |
| W152_ | OFF | | 100.00% |
| L452_ | OFF | | 100.00% |
| _484K | | OFF | 100.00% |
| _501Y | | OFF | 100.00% |
| _681H | | OFF | 100.00% |
| _701V | | OFF | 100.00% |

Pattern consistent with: California (B.1.429/427)
Reference FIG. 20G TriCore 238499-d Sample 13

| Probe | Wild Type | Mutant Type | Confidence |
|---|---|---|---|
| HYBRIDIZED PROBES | | | |
| D80_ | ON | | 100.00% |
| D138_ | ON | | 100.00% |
| _152C | | ON | 100.00% |

TABLE 24-continued

DETECTX-Cv analysis of clinical positive samples performed at PathogenDx

| | | | |
|---|---|---|---|
| N439_ | ON | | 100.00% |
| N440_ | ON | | 100.00% |
| _452R | | ON | 100.00% |
| E484_ | ON | | 100.00% |
| N501_ | ON | | 100.00% |
| P681_ | ON | | 100.00% |
| A701_ | ON | | 100.00% |
| UNHYBRIDIZED PROBES | | | |
| _69(del) | | OFF | 100.00% |
| _80A | | OFF | 100.00% |
| _138Y | | OFF | 100.00% |
| W152_ | OFF | | 100.00% |
| L452_ | OFF | | 94.40% |
| _484K | | OFF | 100.00% |
| _501Y | | OFF | 100.00% |
| _681H | | OFF | 98.40% |
| _701V | | OFF | 100.00% |

Pattern consistent with: California (B.1.429/427)
Reference FIG. 20H TriCore 238504-d Sample 16

| Probe | Wild Type | Mutant Type | Confidence |
|---|---|---|---|
| HYBRIDIZED PROBES | | | |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| N501_ | ON | | 100.00% |
| _681H | | ON | 100.00% |
| A701_ | ON | | 100.00% |
| UNHYBRIDIZED PROBES | | | |
| _69(del) | | OFF | 99.70% |
| _80A | | OFF | 100.00% |
| _138Y | | OFF | 100.00% |
| _152C | | OFF | 97.40% |
| _452R | | OFF | 94.60% |
| _484K | | OFF | 100.00% |
| _501Y | | OFF | 100.00% |
| _701V | | OFF | 99.80% |

Pattern consistent with: B.1.1.207
Reference FIG. 20I TriCore 236310-P Sample 39

| Probe | Wild Type | Mutant Type | Confidence |
|---|---|---|---|
| HYBRIDIZED PROBES | | | |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| N501_ | ON | | 100.00% |
| _681H | | ON | 100.00% |
| A701_ | ON | | 100.00% |
| UNHYBRIDIZED PROBES | | | |
| _69(del) | | OFF | 100.00% |
| _80A | | OFF | 100.00% |
| _138Y | | OFF | 100.00% |
| _152C | | OFF | 98.80% |
| _452R | | OFF | 98.90% |
| _484K | | OFF | 100.00% |
| _501Y | | OFF | 100.00% |
| _701V | | OFF | 100.00% |

Pattern consistent with: B.1.1.207
Reference FIG. 20J TriCore 236315-P Sample 42

| Probe | Wild Type | Mutant Type | Confidence |
|---|---|---|---|
| HYBRIDIZED PROBES | | | |
| D80_ | ON | | 100.00% |
| D138_ | ON | | 100.00% |
| W152_ | ON | | 100.00% |
| N439_ | ON | | 100.00% |
| N440_ | ON | | 100.00% |
| L452_ | ON | | 100.00% |
| E484_ | ON | | 100.00% |
| N501_ | ON | | 100.00% |
| P681_ | ON | | 100.00% |
| A701_ | ON | | 100.00% |
| UNHYBRIDIZED PROBES | | | |
| _69(del) | | OFF | 100.00% |
| _80A | | OFF | 100.00% |
| _138Y | | OFF | 100.00% |
| _152C | | OFF | 98.80% |
| _452R | | OFF | 98.00% |
| _484K | | OFF | 100.00% |
| _501Y | | OFF | 100.00% |
| _681H | | OFF | 87.00% |
| _701V | | OFF | 100.00% |

Pattern consistent with: Wuhan Progenitor

Conclusion

Described here is a "DETECTX-Cv" technology designed to combine the practicality of field deployable Q-RT-PCR testing with the high-level information content of targeted NGS. Population scale deployment of DETECTX-Cv is enabled in a way that is simple enough that it can be "drop-shipped" with minimal set up cost and training into any laboratory performing conventional Q-RT-PCR based COVID-19 screening. Initial field deployment demonstrated the ability of DETECTX-Cv to identify clinical positives per shift per Q-RT-PCR screening and analysis without additional sample prep for a large panel of CoV-2 clade variants (UK, Denmark, South Africa, Brazil, US (CA, NY, Southern US) and Wuhan) incorporated into the content of the assay.

In conclusion, the technology encompassed in this invention enables DETECTX-Cv to perform very low-cost microarray analyses in a field-deployable format. DETECTX-Cv is based on proprietary technology of PathogenDx for designing DNA microarray probes and so, the resulting microarrays can be mass produced to deliver >24,000 tests/day. DETECTX-Cv also enables sequence-based testing on these microarrays via open-format room temperature hybridization and washing, much like the processing of ELISA assays. Like an ELISA plate, DETECTX-Cv is mass produced in a 96-well format, ready for manual or automated fluid handling and has the capability to handle up to 576 probe spots per well, at full production scale.

DETECTX-Cv is a combinatorial assay with several targets in the CoV-2 Spike gene comprising an exceptionally large set of gain-of-function Spike mutants, which are believed to be selected for enhanced infectivity or resistance to natural or vaccine induced host immunity. Based on analysis of the rapidly growing CoV-2 resequencing effort (600,000 genomes in GISAID, April 2021) "terminal differentiation" of the Spike gene marker "basis set" into a set of about thirty-five (35) informative Spike gene target sites is expected, which can be built into and mass produced into the same 96-well format described above. DETECTX-Cv is therefore expected to be beneficial as a true discovery tool that is capable of unbiased identification of new CoV-2 clade variants based on detection of novel combinations of the underlying Spike Variant "basis set". Thus, DETECTX-Cv is expected to become the basis for field deployed seasonal COVID testing with military and civilian applications The DETECTX-Cv test content comprises Spike Gene Target sequence analysis among eleven (11) discrete information-rich domains, produced as triplicate tests per array, with positive and negative controls, to produce core content that is deployed as about 140 independent hybridization tests (per well) on each sample. The DETECTX-Cv technology described here is based on multiplex (n=5) asymmetric, endpoint RT-PCR amplification of viral RNA purified as for Q-RT-PCR screening. The RT-PCR product resulting from amplification is fluorescently tagged and used as-is without cleanup for the subsequent steps of hybridization and washing, which are performed at room temperature (RT). Subsequent to hybridization and washing, the DETECTX-Cv plate is subjected to fluorescent plate reading, data processing and analysis that occurs automatically with no intervention by a human user to result in an output of detected CoV-2 clades which can be used locally for diagnosis and/or simultaneously uploaded to a secure, cloud-based portal for use by medical officials for military or public health tracking and epidemiology analysis.

What is claimed is:

1. A method for detecting Glade variants in a Coronavirus disease 2019 virus (COVID-19) in a sample, comprising:
obtaining the sample;
harvesting viruses from the sample;
isolating a total RNA from the harvested viruses;
performing a combined reverse transcription and first amplification reaction on the total RNA using at least one first primer pair selective for all COVID-19 viruses to generate COVID-19 virus cDNA amplicons;
performing a second amplification using the COVID-19 virus cDNA amplicons as template and at least one fluorescent labeled second primer pair selective for a target nucleotide sequence in the COVID-19 virus cDNA to generate at least one fluorescent labeled COVID-19 virus amplicon;
hybridizing the fluorescent labeled COVID-19 virus amplicons to a plurality of nucleic acid probes, each having a sequence corresponding to a sequence determinant that discriminates among the Glade variants of the COVID-19 virus, said nucleic acid probes attached to a solid microarray support;
washing the microarray at least once; and
imaging the microarray to detect at least one fluorescent signal from the hybridized fluorescent labeled COVID-19 virus amplicons, thereby detecting the Glade variants of the COVID-19 virus in the sample.

2. The method of claim 1, wherein prior to the harvesting step the method further comprises mixing the sample with an RNA stabilizer.

3. The method of claim 1, wherein one or more of the at least one fluorescent labeled second primer pair is selective for a panel of target nucleotide sequences within a target region of a gene in the COVID-19 virus; and
wherein the nucleic acid probes are specific to the target region of the gene, whereby the at least one fluorescent labeled COVID-19 virus amplicon generated is hybridized to the nucleic acid probe thereby discriminating the Glade variants of the COVID-19 virus in the sample.

4. The method of claim 3, further comprising:
detecting the at least one fluorescent signal from the hybridized at least one fluorescent labeled COVID-19 virus amplicons associated with the panel of target nucleotide sequences within the target region of the gene; and
generating an intensity distribution profile unique to each of the Glade variants, whereby each of the Glade variants is distinguishable from others.

5. The method of claim 3, where the gene is a Spike gene.

6. The method of claim 1, wherein the Glade variants of the COVID-19 virus are Denmark, UK (B.1.1.7), South African (B.1.351), Brazil/Japan (P1), Brazil(B1.1.28), California USA, L452R (1.429), India (N440K), or Wuhan, or a combination thereof.

7. The method of claim 1, wherein the first primer pair comprises at least one of the nucleotide sequence pairs of SEQ ID NO: 1 and SEQ ID NO: 2, SEQ ID NO: 3 and SEQ ID NO: 4, SEQ ID NO: 5 and SEQ ID NO: 6, or SEQ ID NO: 7 and SEQ ID NO: 8.

8. The method of claim 1, wherein the fluorescent labeled second primer pair comprises at least one of the nucleotide sequence pairs of SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, or SEQ ID NO: 29 and SEQ ID NO: 24.

9. The method of claim 1, wherein the nucleic acid probes comprise at least one nucleotide sequence selected from the group consisting of SEQ ID NOS: 30-129.

10. The method of claim 1, wherein the sample comprises at least one of a nasopharyngeal swab, a nasal swab, a mouth swab, a mouthwash, an aerosol, or a swab from a hard surface.

* * * * *

SEQUENCE LISTING

```
<160> NUMBER OF SEQ ID NOS: 136

<210> SEQ ID NO 1
<211> LENGTH: 28
<212> TYPE: DNA
<213> ORGANISM: Artificial Sequence
<220> FEATURE:
<223> OTHER INFORMATION: Forward primer sequence for SARS CoV-2 Spike
      gene

<400> SEQUENCE: 1

tttaacagag ttgttatttc tagtgatg                                          28


<210> SEQ ID NO 2
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike
      gene

<400> SEQUENCE: 2

ttttctaaag tagtaccaaa aatccagc                                          28


<210> SEQ ID NO 3
<211> LENGTH: 28
<212> TYPE: DNA
<213> ORGANISM: Artificial Sequence
<220> FEATURE:
<223> OTHER INFORMATION: Forward primer sequence for SARS CoV-2 Spike
      gene

<400> SEQUENCE: 3

tttccctact tattgttaat aacgctac                                          28


<210> SEQ ID NO 4
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike
      gene

<400> SEQUENCE: 4

tttagataac ccacataata agctgcag                                          28


<210> SEQ ID NO 5
<211> LENGTH: 28
<212> TYPE: DNA
```

-continued

<213> ORGANISM: Artificial Sequence
<220> FEATURE:
<223> OTHER INFORMATION: Forward primer sequence for SARS CoV-2 Spike
gene

<400> SEQUENCE: 5
tttatctctg ctttactaat gtctatgc 28

<210> SEQ ID NO 6
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike
gene

<400> SEQUENCE: 6
tttacaaaca gttgctggtg catgtaga 28

<210> SEQ ID NO 7
<211> LENGTH: 28
<212> TYPE: DNA
<213> ORGANISM: Artificial Sequence
<220> FEATURE:
<223> OTHER INFORMATION: Forward primer sequence for SARS CoV-2 Spike
gene

<400> SEQUENCE: 7
ttttggtgtc agtgttataa caccagga 28

<210> SEQ ID NO 8
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike
gene

<400> SEQUENCE: 8
ttttgtcttg gtcatagaca ctggtaga 28

<210> SEQ ID NO 9
<211> LENGTH: 28
<212> TYPE: DNA
<213> ORGANISM: Artificial Sequence
<220> FEATURE:
<223> OTHER INFORMATION: Forward primer sequence for SARS CoV-2 Spike
gene

<400> SEQUENCE: 9
acctttcttt tccaatgtta cttggttc 28

<210> SEQ ID NO 10
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike
gene
<220> FEATURE:
<221> NAME/KEY: modified_base
<222> LOCATION: 1
<223> OTHER INFORMATION: Thymidine at position 1 is modified with a
fluorescent Label

<400> SEQUENCE: 10
ttttatgtta gacttctcag tggaagca 28

<210> SEQ ID NO 11
<211> LENGTH: 28
<212> TYPE: DNA
<213> ORGANISM: Artificial Sequence
<220> FEATURE:
<223> OTHER INFORMATION: Forward primer sequence for SARS CoV-2 Spike gene

<400> SEQUENCE: 11
tttcttattg ttaataacgc tactaatg 28

<210> SEQ ID NO 12
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike gene
<220> FEATURE:
<221> NAME/KEY: modified_base
<222> LOCATION: 1
<223> OTHER INFORMATION: Thymidine at position 1 is modified with a fluorescent Label

<400> SEQUENCE: 12
tttcattcgc actagaataa actctgaa 28

<210> SEQ ID NO 13
<211> LENGTH: 25
<212> TYPE: DNA
<213> ORGANISM: Artificial Sequence
<220> FEATURE:
<223> OTHER INFORMATION: Forward primer sequence for SARS CoV-2 Spike gene

<400> SEQUENCE: 13
tgtaattaga ggtgatgaag tcaga 25

<210> SEQ ID NO 14
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike gene
<220> FEATURE:
<221> NAME/KEY: modified_base
<222> LOCATION: 1
<223> OTHER INFORMATION: Thymidine at position 1 is modified with a fluorescent Label

<400> SEQUENCE: 14
tttaaaggtt tgagattaga cttcctaa 28

<210> SEQ ID NO 15
<211> LENGTH: 28
<212> TYPE: DNA
<213> ORGANISM: Artificial Sequence
<220> FEATURE:
<223> OTHER INFORMATION: Forward primer sequence for SARS CoV-2 Spike gene

<400> SEQUENCE: 15
ttttatttca actgaaatyt atcaggcc 28

<210> SEQ ID NO 16
<211> LENGTH: 28
<212> TYPE: DNA

<213> ORGANISM: Artificial Sequence
<220> FEATURE:
<223> OTHER INFORMATION: Reverse primer sequence for SARS CoV-2 Spike gene
<220> FEATURE:
<221> NAME/KEY: modified_base
<222> LOCATION: 1
<223> OTHER INFORMATION: Thymidine at position 1 is modified with a fluorescent Label

<400> SEQUENCE: 16
tttaaagtac tactactctg tatggttg 28

<210> SEQ ID NO 17
<211> LENGTH: 28
<212> TYPE: DNA
<213> ORGANISM: Artificial Sequence
<220> FEATURE:
<223> OTHER INFORMATION: Forward primer sequence for SARS CoV-2 Spike gene

<400> SEQUENCE: 17
ttttatatgc gctagttatc agactcag 28

<210> SEQ ID NO 18
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike gene
<220> FEATURE:
<221> NAME/KEY: modified_base
<222> LOCATION: 1
<223> OTHER INFORMATION: Thymidine at position 1 is modified with a fluorescent Label

<400> SEQUENCE: 18
ttttggtatg gcaatagagt tattagag 28

<210> SEQ ID NO 19
<211> LENGTH: 28
<212> TYPE: DNA
<213> ORGANISM: Artificial Sequence
<220> FEATURE:
<223> OTHER INFORMATION: Forward primer sequence for SARS CoV-2 Spike gene

<400> SEQUENCE: 19
tttttttctt gttttattgc cactagtc 28

<210> SEQ ID NO 20
<211> LENGTH: 28
<212> TYPE: DNA
<213> ORGANISM: Artificial Sequence
<220> FEATURE:
<223> OTHER INFORMATION: Reverse primer sequence for SARS CoV-2 Spike gene
<220> FEATURE:
<221> NAME/KEY: modified_base
<222> LOCATION: 1
<223> OTHER INFORMATION: Thymidine at position 1 is modified with a fluorescent Label

<400> SEQUENCE: 20
tttttgtcag ggtaataaac accacgtg 28

<210> SEQ ID NO 21
<211> LENGTH: 28

```
<212> TYPE: DNA
<213> ORGANISM: Artificial Sequence
<220> FEATURE:
<223> OTHER INFORMATION: Forward primer sequence for SARS CoV-2 Clade
      variant Spike gene

<400> SEQUENCE: 21

ttttaagcac acgcctatta atttagtg                                          28


<210> SEQ ID NO 22
<211> LENGTH: 28
<212> TYPE: DNA
<213> ORGANISM: Artificial Sequence
<220> FEATURE:
<223> OTHER INFORMATION: Reverse primer sequence for SARS CoV-2 Clade
      variant Spike gene
<220> FEATURE:
<221> NAME/KEY: modified_base
<222> LOCATION: 1
<223> OTHER INFORMATION: Thymidine at position 1 is modified with a
      fluorescent Label

<400> SEQUENCE: 22

tttccacata ataagctgca gcaccagc                                          28


<210> SEQ ID NO 23
<211> LENGTH: 28
<212> TYPE: DNA
<213> ORGANISM: Artificial Sequence
<220> FEATURE:
<223> OTHER INFORMATION: Forward primer sequence for SARS CoV-2 Clade
      variant Spike gene

<400> SEQUENCE: 23

tttagtgtta taacaccagg aacaaata                                          28


<210> SEQ ID NO 24
<211> LENGTH: 28
<212> TYPE: DNA
<213> ORGANISM: Artificial Sequence
<220> FEATURE:
<223> OTHER INFORMATION: Reverse primer sequence for SARS CoV-2 Clade
      variant Spike gene
<220> FEATURE:
<221> NAME/KEY: modified_base
<222> LOCATION: 1
<223> OTHER INFORMATION: Thymidine at position 1 is modified with a
      fluorescent Label

<400> SEQUENCE: 24

ttttgcatga atagcaacag ggacttct                                          28


<210> SEQ ID NO 25
<211> LENGTH: 28
<212> TYPE: DNA
<213> ORGANISM: Artificial Sequence
<220> FEATURE:
<223> OTHER INFORMATION: Forward primer sequence for SARS CoV-2 Clade
      variant Spike gene

<400> SEQUENCE: 25

ttcttttcca atgttacttg gttccatg                                          28


<210> SEQ ID NO 26
<211> LENGTH: 28
<212> TYPE: DNA
<213> ORGANISM: Artificial Sequence
<220> FEATURE:
<223> OTHER INFORMATION: Reverse primer sequence for SARS CoV-2 Clade
```

variant Spike gene
<220> FEATURE:
<221> NAME/KEY: modified_base
<222> LOCATION: 1
<223> OTHER INFORMATION: Thymidine at position 1 is modified with a fluorescent Label

<400> SEQUENCE: 26
tttcaaaata aacaccatca ttaaatgg 28

<210> SEQ ID NO 27
<211> LENGTH: 28
<212> TYPE: DNA
<213> ORGANISM: Artificial Sequence
<220> FEATURE:
<223> OTHER INFORMATION: Forward primer sequence for SARS CoV-2 Clade variant Spike gene

<400> SEQUENCE: 27
tttgatgaag tcagacaaat cgctccag 28

<210> SEQ ID NO 28
<211> LENGTH: 28
<212> TYPE: DNA
<213> ORGANISM: Artificial Sequence
<220> FEATURE:
<223> OTHER INFORMATION: Reverse primer sequence for SARS CoV-2 Clade variant Spike gene
<220> FEATURE:
<221> NAME/KEY: modified_base
<222> LOCATION: 1
<223> OTHER INFORMATION: Thymidine at position 1 is modified with a fluorescent Label

<400> SEQUENCE: 28
tttctctcaa aaggtttgag attagact 28

<210> SEQ ID NO 29
<211> LENGTH: 28
<212> TYPE: DNA
<213> ORGANISM: Artificial Sequence
<220> FEATURE:
<223> OTHER INFORMATION: Forward primer sequence for SARS CoV-2 Clade variant Spike gene

<400> SEQUENCE: 29
tttcaaatac ttctaaccag gttgctgt 28

<210> SEQ ID NO 30
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 30
tttttctagt ctctaktcag tgtgtttttt 30

<210> SEQ ID NO 31
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 31
tttttcccat gctatacatg tctctgtttt tt 32

<210> SEQ ID NO 32
<211> LENGTH: 32
<212> TYPE: DNA
<213> ORGANISM: Artificial Sequence
<220> FEATURE:
<223> OTHER INFORMATION: Probe sequence for SARS CoV-2 Clade variant
<400> SEQUENCE: 32
tttttttttc catgctatct ctgggatttt tt 32

<210> SEQ ID NO 33
<211> LENGTH: 32
<212> TYPE: DNA
<213> ORGANISM: Artificial Sequence
<220> FEATURE:
<223> OTHER INFORMATION: Probe sequence for SARS CoV-2 Clade variant
<400> SEQUENCE: 33
tttttcagag gtttgmtaac cctgtctttt tt 32

<210> SEQ ID NO 34
<211> LENGTH: 30
<212> TYPE: DNA
<213> ORGANISM: Artificial Sequence
<220> FEATURE:
<223> OTHER INFORMATION: Probe sequence for SARS CoV-2 Clade variant
<400> SEQUENCE: 34
tttttttggt ttgataaccc tgcttttttt 30

<210> SEQ ID NO 35
<211> LENGTH: 30
<212> TYPE: DNA
<213> ORGANISM: Artificial Sequence
<220> FEATURE:
<223> OTHER INFORMATION: Probe sequence for SARS CoV-2 Clade variant
<400> SEQUENCE: 35
tttttttggt ttgctaaccc tgcttttttt 30

<210> SEQ ID NO 36
<211> LENGTH: 30
<212> TYPE: DNA
<213> ORGANISM: Artificial Sequence
<220> FEATURE:
<223> OTHER INFORMATION: Probe sequence for SARS CoV-2 Clade variant
<400> SEQUENCE: 36
ttttattttg taatkatcca tttttgtttt 30

<210> SEQ ID NO 37
<211> LENGTH: 30
<212> TYPE: DNA
<213> ORGANISM: Artificial Sequence
<220> FEATURE:
<223> OTHER INFORMATION: Probe sequence for SARS CoV-2 Clade variant
<400> SEQUENCE: 37
tttttctttg taatgatcca ttttcttttt 30

<210> SEQ ID NO 38
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 38
tttttttttg taattatcca ttttcttttt 30

<210> SEQ ID NO 39
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 39
tttttagttg katggaaagt gagttctttt 30

<210> SEQ ID NO 40
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 40
tttctctaaa agttggatgg aaactcttct 30

<210> SEQ ID NO 41
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 41
tttcttcaaa gttgtatgga aagccttctt 30

<210> SEQ ID NO 42
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 42
tttttaattc taamaakctt gattctaatt tt 32

<210> SEQ ID NO 43
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 43
tttttaattc taacaatctt gatttctttt 30

<210> SEQ ID NO 44
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 44
ttttttattc taacaagctt gatttttttt 30

<210> SEQ ID NO 45

<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 45
ttttctattc taaaaatctt gatttctttt 30

<210> SEQ ID NO 46
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 46
tttctataat tacctgtata gattgtcttt 30

<210> SEQ ID NO 47
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 47
tttttttaat tacctgtata gatttctttt 30

<210> SEQ ID NO 48
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 48
tttttcataa ttactggtat agatcttttt 30

<210> SEQ ID NO 49
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 49
ttttttcgcc ggtagcacac ctcttttttt 30

<210> SEQ ID NO 50
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 50
ttttcttccg gtaacacacc tttttttttt 30

<210> SEQ ID NO 51
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 51 tttttaatg gtgttraagg ttttaatttt tt 32

<210> SEQ ID NO 52
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 52 tttttctgg tgttgaaggt tttacttttt 30

<210> SEQ ID NO 53
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 53
tttttttatg gtgttaaagg ttttcttttt 30

<210> SEQ ID NO 54
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 54
tttttttatg gtgctgaagg ttcttttttt 30

<210> SEQ ID NO 55
<211> LENGTH: 33
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 55
ttttttttcc aacccactwa tggtgttttt ttt 33

<210> SEQ ID NO 56
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 56
ttttttttac ccactaatgg tgtctttttt 30

<210> SEQ ID NO 57
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 57
ttttttttac ccacttatgg tgtctttttt 30

<210> SEQ ID NO 58
<211> LENGTH: 30
<212> TYPE: DNA

-continued

<213> ORGANISM: Artificial Sequence
<220> FEATURE:
<223> OTHER INFORMATION: Probe sequence for SARS CoV-2 Clade variant

<400> SEQUENCE: 58 tttttcaga ctaattctcm tcggcttttt 30

<210> SEQ ID NO 59
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 59
tttttttcta attctcctcg gcgttttttt 30

<210> SEQ ID NO 60
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 60
ttttttttta attctcatcg gcgttttttt 30

<210> SEQ ID NO 61
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 61
ttttcacttg gtgyagaaaa ttcagttttt 30

<210> SEQ ID NO 62
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 62
tcttcttctt ggtgcagaaa attattcttt 30

<210> SEQ ID NO 63
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 63
tcttcttctt ggtgtagaaa attattcttt 30

<210> SEQ ID NO 64
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 64
tttttttgtc tctagtcagt gttttttttt 30

<210> SEQ ID NO 65
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 65 ttttttagt ctctagtcag tgtttttttt 30

<210> SEQ ID NO 66
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 66 tttttagtc tctattcagt gttttttttt 30

<210> SEQ ID NO 67
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 67 ttttttagt ctctattcag tgtttttttt 30

<210> SEQ ID NO 68
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 68 tttttaaty ttacaamcag aactcttttt 30

<210> SEQ ID NO 69
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 69 ttttttatc ttacaaccag aacctttttt 30

<210> SEQ ID NO 70
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 70 ttttttatc ttacaaccag aactttttttt 30

<210> SEQ ID NO 71
<211> LENGTH: 30
<212> TYPE: DNA
<213> ORGANISM: Artificial Sequence
<220> FEATURE:

<223> OTHER INFORMATION: Probe sequence for SARS CoV-2 Clade variant

<400> SEQUENCE: 71 tttttattt tacaaacaga acttttttt 30

<210> SEQ ID NO 72
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 72
tttttcaatt ttacaaacag aacttttttt 30

<210> SEQ ID NO 73
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 73
ttttttatgc tatacatgtc tctgtttttt 30

<210> SEQ ID NO 74
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 74
ttttttacca tgctatctct gggatttttt 30

<210> SEQ ID NO 75
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 75
tttttctagg tttgataacc ctgctttttt 30

<210> SEQ ID NO 76
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 76
tttttttagg tttgctaacc ctcttttttt 30

<210> SEQ ID NO 77
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 77
ttttttcttt gtaatgatcc atttcttttt 30

<210> SEQ ID NO 78
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 78
tttttctttg taattatcca ttttcttttt 30

<210> SEQ ID NO 79
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 79
ttttcttcaa agttggatgg aaactctttt 30

<210> SEQ ID NO 80
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 80
tttctctaaa agttgtatgg aaactcttct 30

<210> SEQ ID NO 81
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 81
ttttttagtg cgtgrtctcc ctcatttttt 30

<210> SEQ ID NO 82
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 82
ttttttctgc gtgatctccc tcattttttt 30

<210> SEQ ID NO 83
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 83
tttttttctg cgtgatctcc ctcttttttt 30

<210> SEQ ID NO 84
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 84 tttttttgc gtggtctccc tcttttttt 30

<210> SEQ ID NO 85
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 85 ttttttttg cgtggtctcc ctttttttt 30

<210> SEQ ID NO 86
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 86
ttttaactgg aaakattgct gattattttt 30

<210> SEQ ID NO 87
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 87
tttcttctct ggaaagattg ctgctttttt 30

<210> SEQ ID NO 88
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 88
ttcttctctg gaaagattgc tgactttttt 30

<210> SEQ ID NO 89
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 89
tttttctctg gaaatattgc tgactttttt 30

<210> SEQ ID NO 90
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 90
ttttctctgg aaatattgct gatctttttt 30

<210> SEQ ID NO 91
<211> LENGTH: 30

<212> TYPE: DNA
<213> ORGANISM: Artificial Sequence
<220> FEATURE:
<223> OTHER INFORMATION: Probe sequence for SARS CoV-2 Clade variant

<400> SEQUENCE: 91
tttttttact ggaacgattg cttttttttt 30

<210> SEQ ID NO 92
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 92
ttttttcctg gaacgattgc tgtttttttt 30

<210> SEQ ID NO 93
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 93
ttttttattc taacaatctt gatttctttt 30

<210> SEQ ID NO 94
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 94
tttttttttc taacaagctt gatttttttt 30

<210> SEQ ID NO 95
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 95
ttcttaattc taaaaatctt gatttctttt 30

<210> SEQ ID NO 96
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 96
tttttcataa ttacctgtat agactttctt 30

<210> SEQ ID NO 97
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 97 tttttcaat taccggtata gatcttttt 30

<210> SEQ ID NO 98
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 98
ttttttttgg tagcatacct tgttttttt 30

<210> SEQ ID NO 99
<211> LENGTH: 29
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 99
tttttttcgg tagcatacct tgtttttt 29

<210> SEQ ID NO 100
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 100
ttttttcgcc ggtaacacac ctcttttttt 30

<210> SEQ ID NO 101
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 101
ttttttttca ggccagtagc acttttttt 30

<210> SEQ ID NO 102
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 102
tttttctggt gttgaaggtt ttatcttttt 30

<210> SEQ ID NO 103
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 103
ttttttctgg tgttaaaggt tttacttttt 30

<210> SEQ ID NO 104
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 104 tttttcaat ggtgctgaag gttcttttt 30

<210> SEQ ID NO 105
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 105
tttttttaac ccactaatgg tgtctttttt 30

<210> SEQ ID NO 106
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 106
tttttttaac ccacttatgg tgtctttttt 30

<210> SEQ ID NO 107
<211> LENGTH: 34
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 107
tttttctctt tatcargrtg ttaactgctt tttt 34

<210> SEQ ID NO 108
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 108
tttttcttat caggatgtta actttttttt 30

<210> SEQ ID NO 109
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 109
ttttttccta tcagggtgtt aacttttttt 30

<210> SEQ ID NO 110
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 110
ttttttccta tcaaggtgtt aacttttttt 30

<210> SEQ ID NO 111
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 111 tttttccta tcarggtgtt aacttttttt 30

<210> SEQ ID NO 112
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 112 tttttttaa ttctcctcgg cgtttttttt 30

<210> SEQ ID NO 113
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 113
tttttttcta attctcatcg gcgttttttt 30

<210> SEQ ID NO 114
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 114
ttcttctact tggtgcagaa aattattctt 30

<210> SEQ ID NO 115
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 115
tttctttctt ggtgtagaaa attctttttt 30

<210> SEQ ID NO 116
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 116
ttttttacaa tttgccccca gcgtcttttt 30

<210> SEQ ID NO 117
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 117
tttttttttg ctccragtgc ctcttttttt 30

<210> SEQ ID NO 118
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 118
ttttttttca aactttactt gctttactct tt 32

<210> SEQ ID NO 119
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 119
ttttttttca aactttacat agaagccttt tt 32

<210> SEQ ID NO 120
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 120
ttttctacat agaagttatt tgactccctt tt 32

<210> SEQ ID NO 121
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 121
ttttctgctt tacatatgac tcctggtttt tt 32

<210> SEQ ID NO 122
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 122
tttctactcc tggtgrttct tcttcatttt 30

<210> SEQ ID NO 123
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 123
ttttttccct ggtgattctt ctttcttttt 30

<210> SEQ ID NO 124

-continued

<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 124 tttttccct ggtggttctt cttttttttt 30

<210> SEQ ID NO 125
<211> LENGTH: 32
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 125 tttttatca gactcmgact aattctcttt tt 32

<210> SEQ ID NO 126
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 126
ttttttccag actcagacta atttcttttt 30

<210> SEQ ID NO 127
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 127
tttttcttca gactccgact aatctttttt 30

<210> SEQ ID NO 128
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 128
ttttttccag actcatacta atttcttttt 30

<210> SEQ ID NO 129
<211> LENGTH: 30
<212> TYPE: DNA
<213> ORGANISM: Artificial Sequence
<220> FEATURE:
<223> OTHER INFORMATION: Probe sequence for SARS CoV-2 Clade variant

<400> SEQUENCE: 129
ttttttccag actcacacta atttcttttt 30

<210> SEQ ID NO 130
<211> LENGTH: 28
<212> TYPE: DNA
<213> ORGANISM: Artificial Sequence
<220> FEATURE:
<223> OTHER INFORMATION: Primer sequence for human RNAse P control

<400> SEQUENCE: 130
tttacttcag catggcggtg tttgcaga 28

<210> SEQ ID NO 131
<211> LENGTH: 28
<212> TYPE: DNA
<213> ORGANISM: Artificial Sequence
<220> FEATURE:
<223> OTHER INFORMATION: Primer sequence for human RNAse P control

<400> SEQUENCE: 131
ttttgatagc aacaactgaa tagccaag 28

<210> SEQ ID NO 132
<211> LENGTH: 28
<212> TYPE: DNA
<213> ORGANISM: Artificial Sequence
<220> FEATURE:
<223> OTHER INFORMATION: Primer sequence for human RNAse P control

<400> SEQUENCE: 132
tttgtttgca gatttggacc tgcgagcg 28

<210> SEQ ID NO 133
<211> LENGTH: 28
<212> TYPE: DNA
<213> ORGANISM: Artificial Sequence
<220> FEATURE:
<223> OTHER INFORMATION: Primer sequence for human RNAse P control

<400> SEQUENCE: 133
tttaaggtga gcggctgtct ccacaagt 28

<210> SEQ ID NO 134
<211> LENGTH: 34
<212> TYPE: DNA
<213> ORGANISM: Artificial Sequence
<220> FEATURE:
<223> OTHER INFORMATION: Probe sequence for human RNAse P control

<400> SEQUENCE: 134 tttttttct gacctgaagg ctctgcgcgt tttt 34

<210> SEQ ID NO 135
<211> LENGTH: 30
<212> TYPE: DNA
<213> ORGANISM: Artificial Sequence
<220> FEATURE:
<223> OTHER INFORMATION: Probe sequence for human RNAse P control

<400> SEQUENCE: 135
tttttcttga cctgaaggct ctgctttttt 30

<210> SEQ ID NO 136
<211> LENGTH: 34
<212> TYPE: DNA
<213> ORGANISM: Artificial Sequence
<220> FEATURE:
<223> OTHER INFORMATION: Probe sequence for Negative Control

<400> SEQUENCE: 136
ttttttctac tacctatgct gattcactct tttt 34